US008158647B2

(12) United States Patent
Blaney et al.

(10) Patent No.: US 8,158,647 B2
(45) Date of Patent: Apr. 17, 2012

(54) SUBSTITUTED PYRROLOPYRIDINES AND PYRAZOLOPYRIDINES AS KINASE MODULATORS

(75) Inventors: Jeffrey M. Blaney, San Diego, CA (US); Andreas Gosberg, San Diego, CA (US); Stefan N. Gradl, San Diego, CA (US); Gavin Hirst, San Diego, CA (US); Stephanie A. Hopkins, San Diego, CA (US); Paul A. Sprengeler, San Diego, CA (US); Ruo W. Steensma, San Diego, CA (US); Johnny Uy, San Diego, CA (US)

(73) Assignee: SGX Pharmaceuticals, Inc., San Diego, CA (US)

( * ) Notice: Subject to any disclaimer, the term of this patent is extended or adjusted under 35 U.S.C. 154(b) by 938 days.

(21) Appl. No.: 12/129,546

(22) Filed: May 29, 2008

(65) Prior Publication Data
US 2009/0005356 A1 Jan. 1, 2009

Related U.S. Application Data

(60) Provisional application No. 60/940,589, filed on May 29, 2007.

(51) Int. Cl.
| | |
|---|---|
| *A61K 31/437* | (2006.01) |
| *A61K 31/5377* | (2006.01) |
| *A61K 31/497* | (2006.01) |
| *A61P 35/00* | (2006.01) |
| *C07D 491/147* | (2006.01) |
| *C07D 471/04* | (2006.01) |

(52) U.S. Cl. ........ 514/300; 546/113; 546/64; 546/119; 514/210.18; 514/303; 514/234.5; 514/255.05; 514/187; 544/127; 544/405

(58) Field of Classification Search ................ 546/113; 514/300
See application file for complete search history.

(56) References Cited

U.S. PATENT DOCUMENTS

| 3,755,340 A | 8/1973 | Hoehn et al. |
| 5,643,734 A | 7/1997 | Henderson |
| 6,589,950 B1 | 7/2003 | Hayler et al. |

FOREIGN PATENT DOCUMENTS

| WO | WO-03-87816 A1 | 10/2003 |
| WO | WO-2004-024895 A2 | 3/2004 |
| WO | 2005/062795 | * 7/2005 |
| WO | WO-2005-062795 | 7/2005 |
| WO | WO-2006-124863 A2 | 11/2006 |
| WO | WO-2008-075007 | 6/2008 |

OTHER PUBLICATIONS

West, Anthony R., Solid State Chemistry and its Applications, Wiley, New York, 1988, pp. 358 & 365.*
PCT/US08/65150 Search Report dated Aug. 21, 2008.
U.S. Appl. No. 10/139,775, filed May 3, 2002, Klingler.
Alterman, M. and Hallberg, A., "Fast Microwave-Assisted Preparation of Aryl and Vinyl Nitriles and the Corresponding Tetrazoles from Organo-halides," J. Org. Chem. 65:7984-7989 (2000).
Altschul et al., "Gapped BLAST and PSI-BLAST: a new generation of protein database search programs," Nucl. Acids Res. 24:3389-3402 (1997).
Alvarez, M. et al., "Synthesis of 3-Aryl-and 3-Heteroaryl-7-azaindoles," Synthesis 4:615-620 (1999).
Berge et al., "Pharmaceutical Salts," J. Pharma. Sci. 66:1-19 (1977).
Blaney, J.M. and Dixon, J.S., "A good ligand is hard to find: Automated docking methods," Perspectives in Drugt Discovery and Design 1:301-319 (1993).
Boudier et al., "New Applications of Polyfunctional Organometallic Compounds in Organic Synthesis," Angew. Chem. Int. Ed. 39: 4414-4435 (2000).
Buchwald, S.L. et al., "A General, Efficient, and Inexpensive Catalyst System for the Coupling of Aryl Iodides and Thiols," Org. Lett. 4:3517-3520 (2002).
Bundgaard, H. Chapter 5: Design and application of prodrugs. A Textbook of Drug Design and Development. Krosgaard-Larsen, et al., eds., pp. 113-191, 1991.
Bundgaard, H., "Means to enhance penetration: Prodrugs as a means to improve the delivery of peptide drugs," Advanced Drug Delivery Reviews 8: 1-38, 1992.
Charifson, P.S. et al., "Consensus Scoring: A Method for Obtaining Improved Hit Rates from Docking Databases of Three-Dimensional Structures into Proteins," J. Med. Chem. 42:5100-5109 (1999).
Crabtree, S. and Cronan, J.E., "Facile and Gentle Method for Quantitative Lysis of *Escherichia coli* and *Salmonella typhimurium*," J. Bacteriol. 158(1):354-356 (1984).
Deininger, M. et al., "The development of imatinib as a therapeutic agent for chronic myeloid leukemia," Blood 105(7):2640-2653 (2005).
Ellis, G.P. and Romney-Alexander, T.M., "Cyanation of Aromatic Halides," Chem. Rev. 87:779-794 (1987). Fedorak et al., "A novel colon-specific steroid prodrug enhances sodium chloride absorption in rat colitis," Am J Physiol 269(2 Pt 1): G210-8, 1995.
Fleisher et al., "Improved oral drug delivery: solubility limitations overcome by the use of prodrugs," Advanced Drug Delivery Reviews 19(2): 115-30, 1996.
Garg. N.K. et al., "The First Total Synthesis of Dragmacidin D," J. Am. Chem. Soc. 124:13179-13184 (2002).
Goodsell and Olsen: "Automated Docking of Substrates to Proteins by Simulated Annealing," Proteins: Structure, Function and Genetics 8:195-202 (1990).

(Continued)

*Primary Examiner* — Janet Andres
*Assistant Examiner* — Niloofar Rahmani
(74) *Attorney, Agent, or Firm* — Wilson, Sonsini, Goodrich & Rosati

(57) ABSTRACT

Provided herein are substituted pyrrolopyridine heterocycles and substituted pyrazolopyridine heterocycles, pharmaceutical compositions comprising said heterocycles and methods of using said heterocycles in the treatment of disease. The heterocycles disclosed herein function as kinase modulators and have utility in the treatment of diseases such as cancer, allergy, asthma, inflammation, obstructive airway disease, autoimmune diseases, metabolic disease, infection, CNS disease, brain tumor, obesity, asthma, hematological disorder, degenerative neural disease, cardiovascular disease, or disease associated with angiogenesis, neovascularization, or vasculogenesis.

35 Claims, 1 Drawing Sheet

OTHER PUBLICATIONS

Gouet et al., "ESPript: analysis of multiple sequence alignments in PostScript," Bioinformatics 15:305-308 (1999).

Hartwig, J.F., "Carbon-Heteroatom Bond-Forming Reductive Eliminations of Amines, Ethers, and Sulfides," Acc. Chem. Res. 31:852-860 (1998).

Hochhaus et al. "A selective HPLC/RIA for dexamethasone and its prodrug dexamethasone-21-sulphobenzoate sodium in biological fluids," Biomed Chromatogr. 1992; 6(6):283-286 (1992).

Ishiyama et al., "Paladium (0)-Catalyzed Cross-Coupling Reaction of Alkoxydiboron with Haloarenes: A Direct Procedure for Arylvoboronic Esters," J. Org. Chem. 60:7508-7510 (1995).

Jones et al., "Molecular Recognition of Receptor Sites using a Genetic Algorithm with a Description of Desolvation," J. Mol. Biol. 245:43-53 (1995).

Kuntz et al., "A Geometric Approach to Macromolecule-Ligand Interactions," J. Mol. Biol. 161:269-288 (1982).

Larsen, et al., "Prodrug forms for the sulfonamide group. I. Evaluation of N-acyl derivative, N-sulfonylamidines, N-sulfonylsulfilimines and sulfonylureas as possible prodrug derivatives," Int J Pharmaceutics 37(1-2): 87-95, 1987.

Larsen et al., "Prodrug forms for the sulfonamide group. II. Water-soluble amino acid derivatives of N-methylsulfonamides as possible prodrugs," Int J Pharmaceutics 47(1-3): 103-10, 1988.

Ley, S. et al., "Modern Synthetic: Methods for Copper-Mediated C(Aryl)-O-, C(Aryl)-N- und C(Aryl)-S Bond Formation," Angew. Chem. 115:5558-5607 (2003).

L'Heureux et al., "Synthesis of functionalized 7-azaindoles via directed *ortho*-metalations," Tetrahedron Lett. 45:2317-2319 (2004).

McLeod et al., "A glucocorticoid prodrug facilitates normal mucosal function in rat colitis without adrenal suppression," Gastroenterology 106(2): 405-13, 1994.

Meng et al., "Automated Docking with Grid-Based Energy Evaluation," J. Comp. Chem. 13(4):505-524 (1992).

Misra, R.N. et al., "1*H*-Pyrazolo[3,4-*b*]pyridine Inhibitors of Cyclin-Dependent Kinases. Highly Potent 2,6-Difluorophenacyl Analogues," Bioorg. Med. Chem. Lett. 13(14):2405-2408 (2003).

Molander et al., "Palladium-Catalyzed Suzuki-Miyaura Cross-Coupling Reactions of Potassium Aryl-and Heteroarylatrifluoroborates," J. Org. Chem. 68:4302-4314 (2003).

Molander et al., "*B*-Alkyl Suzuki-Miyaura Cross-Coupling Reactions with Air-Stable Potassium Alkyltrifluoroborates," J. Org. Chem. 68:5534-5539 (2003).

Mongin et al., "Advances in the directed metallation of azines and diazines (pyridines, pyrmimidines, pyrazines, pyrizadines, quinolines, benzodiazines and carbolines). Part 1: Metallation of pyridines, quinolines and carbolines," Tetrahedron 57:4059-4090 (2001).

Nahm et al., "N-Methoxy-N-Methylamides as Effective Acylating Agents," Tetrahedron Lett. 22(39):3815-3818 (1981).

Rarey, M. et al., "A Fast Flexible Docking Method using an Incremental Construction Algorithm," J. Mol. Biol. 261:470-489 (1996).

Robinson et al., "Discovery of the hemifumarate and (alpha-L-alanyloxy)methyl ether as prodrugs of an antirheumatic oxindole: prodrugs for the enolic OH group," J Med Chem 39(1): 10-8, 1996.

Sakamoto et al., "Condensed Heteroaromatic Ring Systems. XXII.[1] Simple and General Synthesis of 1*H*-Pyrrolo-Pyridines," Heterocycles 34(12): 2379-84 (1992).

Sapountzis et al., "A New General Preparation of Polyfunctional Diarylamines by the Addition of Functionalized Arylmagnesium Compounds to Nitroarenes," J. Am. Chem. Soc. 124:9390-9391 (2002).

Saulnier et al., "An efficient method for the synthesis of guanidino prodrugs," Bioorganic & Medicinal Chemistry Letters 4(16): 1985-90, 1994.

Saulnier, M.G. and Gribble, G.W., "Generation and Reactions of 3-Lithio-1-(phenylsulfonyl)indole," J. Org. Chem. 47(5):757-761 (1982).

Simpson, W.G., "The Calcium Channel Blocker Verapamil and Cancer Therapy," Cell Calcium. 6:449-467 (1985).

Sinkula et al., "Rationale for design of biologically reversible drug derivatives: prodrugs," J Pharm Sci 64(2): 181-210, 1975.

Song, J.J. et al., "Organometallic methods for the synthesis and functionalization of azaindoles," Chem. Soc. Rev. 36:1120-1132 (2007).

Thompson et al. "DbClustal: rapid and reliable global multiple alignments of protein sequences detected by database searches," Nucl. Acids Res. 28:2919-2926 (2000).

Travis, "Proteins and Organic Solvents Make an Eye-Opening Mix," Science 262:1374 (1993).

Turck et al., Advances in the directed metallation of azines and diazines (pyridines, pyrimidines, pyrazines, pyridazines, quinolines, benzodiazines and carbolines). Part 2. Metallation of pyrimidines, pyrazines, pyridazines and benzodiazines,) Tetrahedron 57:4489-4905 (2001).

Wannberg, J. and Larhed, M., "Increasing Rates and Scope of Reactions: Sluggish Amines in Microwave-Heated Aminocarbonylation Reactions under Air," J. Org. Chem. 68:5750-5753 (2003).

Weiner et al., "A New Force Field for Molecular Mechanical Simulation of Nucelic Acids and Proteins," J. Am. Chem. Soc. 106:765-784 (1984).

Widder, K. et al., "Theory and Practice of Prodrug Kinetics," Methods in Enzymology vol. 42 (1985), pp. 309-396.

Wolfe, J. et al., "Rational Development of Practical Catalysts for Aromatic Carbon—Nitrogen Bond Formation," Acc. Chem. Res. 31:805-818 (1998).

Supplementary EP Search Report EP08780716 dated Aug. 6, 2009.

* cited by examiner

```
   1 MLEICLKLVGCKSKKGLSSSSSCYLEEALQRPVASDFEPQGLSEAARWNS   50
  51 KENLLAGPSENDPNLFVALYDFVASGDNTLSITKGEKLRVLGYNHNGEWC  100
 101 EAQTKNGQGWVPSNYITPVNSLEKHSWYHGPVSRNAAEYLLSSGINGSFL  150
 151 VRESESSPGQRSISLRYEGRVYHYRINTASDGKLYVSSESRFNTLAELVH  200
 201 HHSTVADGLITTLHYPAPKRNKPTVYGVSPNYDKWEMERTDITMKHKLGG  250
 251 GQYGEVYEGVWKKYSLTVAVKTLKEDTMEVEEFLKEAAVMKEIKHPNLVQ  300
 301 LLGVCTREPPFYIITEFMTYGNLLDYLRECNRQEVNAVVLLYMATQISSA  350
 351 MEYLEKKNFIHRDLAARNCLVGENHLVKVADFGLSRLMTGDTYTAHAGAK  400
 401 FPIKWTAPESLAYNKFSIKSDVWAFGVLLWEIATYGMSPYPGIDLSQVYE  450
 451 LLEKDYRMERPEGCPEKVYELMRACWQWNPSDRPSFAEIHQAFETMFQES  500
 501 SISDEVEKELGKQGVRGAVSTLLQAPELPTKTRTSRRAAEHRDTTDVPEM  550
 551 PHSKGQGESDPLDHEPAVSPLLPRKERGPPEGGLNEDERLLPKDKKTNLF  600
 601 SALIKKKKKTAPTPPKRSSSFREMDGQPERRGAGEEEGRDISNGALAFTP  650
 651 LDTADPAKSPKPSNGAGVPNGALRESGGSGFRSPHLWKKSSTLTSSRLAT  700
 701 GEEEGGGSSSKRFLRSCSASCVPHGAKDTEWRSVTLPRDLQSTGRQFDSS  750
 751 TFGGHKSEKPALPRKRAGENRSDQVTRGTVTPPPRLVKKNEEAADEVFKD  800
 801 IMESSPGSSPPNLTPKPLRRQVTVAPASGLPHKEEAEKGSALGTPAAAEP  850
 851 VTPTSKAGSGAPGGTSKGPAEESRVRRHKHSSESPGRDKGKLSRLKPAPP  900
 901 PPPAASAGKAGGKPSQSPSQEAAGEAVLGAKTKATSLVDAVNSDAAKPSQ  950
 951 PGEGLKKPVLPATPKPQSAKPSGTPISPAPVPSTLPSASSALAGDQPSST 1000
1001 AFIPLISTRVSLRKTRQPPERIASGAITKGVVLDSTEALCLAISRNSEQM 1050
1051 ASHSAVLEAGKNLYTFCVSYVDSIQQMRNKFAFREAINKLENNLRELQIC 1100
1101 PATAGSGPAATQDFSKLLSSVKEISDIVQR    1130
```

SUBSTITUTED PYRROLOPYRIDINES AND PYRAZOLOPYRIDINES AS KINASE MODULATORS

CROSS-REFERENCE

This application claims the benefit of U.S. Provisional Application No. 60/940,589, filed May 29, 2007, which is incorporated herein by reference in its entirety.

INCORPORATION BY REFERENCE

This application contains references to amino acid sequences and nucleotide sequences which have been submitted concurrently herewith as the sequence listing text file "20268-720.201_ST25.txt", file size 13 KiloBytes (KB), created on May 16, 2008. The aforementioned sequence listing is hereby incorporated by reference in its entirety pursuant to 37 CFR §1.52(e)(5).

All publications and patent applications mentioned in this specification are herein incorporated by reference to the same extent as if each individual publication or patent application was specifically and individually indicated to be incorporated by reference.

BACKGROUND OF THE INVENTION

Mammalian protein kinases are important regulators of cellular functions. Because dysfunctions in protein kinase activity have been associated with several diseases and disorders, protein kinases are targets for drug development.

The tyrosine kinase receptor, FMS-like tyrosine kinase 3 (FLT3), is implicated in cancers, including leukemia, such as acute myeloid leukemia (AML), acute lymphoblastic leukemia (ALL), and myelodysplasia. About one-quarter to one-third of AML patients have FLT3 mutations that lead to constitutive activation of the kinase and downstream signaling pathways. Although in normal humans, FLT3 is expressed mainly by normal myeloid and lymphoid progenitor cells, FLT3 is expressed in the leukemic cells of 70-80% of patients with AML and ALL. Inhibitors that target FLT3 have been reported to be toxic to leukemic cells expressing mutated and/or constitutively-active FLT3. Thus, there is a need to develop potent FLT3 inhibitors that may be used to treat diseases and disorders such as leukemia.

The Abelson non-receptor tyrosine kinase (c-Abl) is involved in signal transduction, via phosphorylation of its substrate proteins. In the cell, c-Abl shuttles between the cytoplasm and nucleus, and its activity is normally tightly regulated through a number of diverse mechanisms. Abl has been implicated in the control of growth-factor and integrin signaling, cell cycle, cell differentiation and neurogenesis, apoptosis, cell adhesion, cytoskeletal structure, and response to DNA damage and oxidative stress.

The c-Abl protein contains approximately 1150 amino-acid residues, organized into a N-terminal cap region, an SH3 and an SH2 domain, a tyrosine kinase domain, a nuclear localization sequence, a DNA-binding domain, and an actin-binding domain.

Chronic myelogenous leukemia (CML) is associated with the Philadelphia chromosomal translocation, between chromosomes 9 and 22. This translocation generates an aberrant fusion between the bcr gene and the gene encoding c-Abl. The resultant Bcr-Abl fusion protein has constitutively active tyrosine-kinase activity. The elevated kinase activity is reported to be the primary causative factor of CML, and is responsible for cellular transformation, loss of growth-factor dependence, and cell proliferation.

The 2-phenylaminopyrimidine compound imatinib (also referred to as STI-571, CGP 57148, or Gleevec) has been identified as a specific and potent inhibitor of Bcr-Abl, as well as two other tyrosine kinases, c-kit and platelet-derived growth factor receptor. Imatinib blocks the tyrosine-kinase activity of these proteins. Imatinib has been reported to be an effective therapeutic agent for the treatment of all stages of CML. However, the majority of patients with advanced-stage or blast crisis CML suffer a relapse despite continued imatinib therapy, due to the development of resistance to the drug. Frequently, the molecular basis for this resistance is the emergence of imatinib-resistant variants of the kinase domain of Bcr-Abl. The most commonly observed underlying amino-acid substitutions include Glu255Lys, Thr315Ile, Tyr293Phe, and Met351Thr.

MET was first identified as a transforming DNA rearrangement (TPR-MET) in a human osteosarcoma cell line that had been treated with N-methyl-N'-nitro-nitrosoguanidine (Cooper et al. 1984). The MET receptor tyrosine kinase (also known as hepatocyte growth factor receptor, HGFR, MET or c-Met) and its ligand hepatocyte growth factor ("HGF") have numerous biological activities including the stimulation of proliferation, survival, differentiation and morphogenesis, branching tubulogenesis, cell motility and invasive growth. Pathologically, MET has been implicated in the growth, invasion and metastasis of many different forms of cancer including kidney cancer, lung cancer, ovarian cancer, liver cancer and breast cancer. Somatic, activating mutations in MET have been found in human carcinoma metastases and in sporadic cancers such as papillary renal cell carcinoma. The evidence is growing that MET is one of the long-sought oncogenes controlling progression to metastasis and therefore a very interesting target. In addition to cancer there is evidence that MET inhibition may have value in the treatment of various indications including: *Listeria* invasion, Osteolysis associated with multiple myeloma, Malaria infection, diabetic retinopathies, psoriasis, and arthritis.

The tyrosine kinase RON is the receptor for the macrophage stimulating protein and belongs to the MET family of receptor tyrosine kinases. Like MET, RON is implicated in growth, invasion and metastasis of several different forms of cancer including gastric cancer and bladder cancer.

The Aurora family of serine/threonine kinases is essential for mitotic progression. Expression and activity of the Aurora kinases are tightly regulated during the cell cycle. A variety of proteins having roles in cell division have been identified as Aurora kinase substrates. Based on the known function of the Aurora kinases, inhibition of their activity is believed to disrupt the cell cycle and block proliferation and therefore tumor cell viability. Harrington et al., Nature Medicine (2004).

3-phosphoinositide-dependent kinase 1 (PDK1) is a Ser/Thr protein kinase that can phosphorylate and activate a number of kinases in the AGC kinase super family, including Akt/PKB, protein kinase C(PKC), PKC-related kinases (PRK1 and PRK2), p70 ribosomal S6-kinase (S6K1), and serum and glucocorticoid-regulated kinase (SGK). The first identified PDK1 substrate is the proto-oncogene Akt. Numerous studies have found a high level of activated Akt in a large percentage (30-60%) of common tumor types, including melanoma and breast, lung, gastric, prostate, hematological and ovarian cancers. The PDK1/Akt signaling pathway thus represents an attractive target for the development of small molecule inhibitors that may be useful in the treatment of cancer.

Because kinases have been implicated in numerous diseases and conditions, such as cancer, there is a need to develop new and potent protein kinase modulators that can be used for treatment. The present invention fulfills these and other needs in the art. Although certain protein kinases are specifically named herein, the present invention is not limited to modulators of these kinases, and, includes, within its scope, modulators of related protein kinases, and modulators of homologous proteins.

SUMMARY OF THE INVENTION

In one aspect, the invention relates to compounds having formula I:

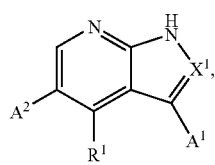

(I)

or an enantiomer, diastereomer, racemate, or pharmaceutically acceptable salt or solvate thereof, wherein:

$A^1$ is independently halogen, cyano, nitro, hydroxyl, perfluoroalkyl, difluoromethyl, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted aralkyl, substituted or unsubstituted heteroaryl; substituted or unsubstituted heteroaralkyl, $-(CH_2)_j C(=Z)R^3$, $-(CH_2)_j OR^3$, $-(CH_2)_j C(O)R^3$, $-(CH_2)_j C(O)OR^3$, $-(CH_2)_j NR^4R^5$, $-(CH_2)_j C(O)NR^4R^5$, $-(CH_2)_j OC(O)NR^4R^5$, $-(CH_2)_j NR^6C(O)R^3$, $-(CH_2)_j NR^6C(O)OR^3$, $-(CH_2)_j NR^6C(O)NR^4R^5$, $-(CH_2)_j S(O)_m R^7$, $-(CH_2)_j NR^6S(O)_2R^7$, or $-(CH_2)_j S(O)_2NR^4R^5$; wherein each j is independently an integer from 0 to 6; and m is independently an integer from 0 to 2; with the proviso when $A^1$ is $-S(O)_m R^7$, m is not 2;

Z is O, S or $NR^8$; or $X^1$ is independently $-CR^2=$ or $-N=$;

$A^2$ is independently nitro, hydroxyl, perfluoroalkyl, difluoromethyl, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted aralkyl, substituted or unsubstituted heteroaryl; substituted or unsubstituted heteroaralkyl, $-(CH_2)_j C(=Z)R^3$, $-(CH_2)_j OR^3$, $-(CH_2)_j C(O)R^3$, $-(CH_2)_j C(O)OR^3$, $-(CH_2)_j NR^4R^5$, $-(CH_2)_j C(O)NR^4R^5$, $-(CH_2)_j OC(O)NR^4R^5$, $-(CH_2)_j NR^6C(O)R^3$, $-(CH_2)_j NR^6C(O)OR^3$, $-(CH_2)_j NR^6C(O)NR^4R^5$, $-(CH_2)_j S(O)_m R^7$, $-(CH_2)_j NR^6S(O)_2R^7$, or $-(CH_2)_j S(O)_2NR^4R^5$; wherein each j is independently an integer from 0 to 6; and m is independently an integer from 0 to 2;

Z is O, S or $NR^8$; or $R^1$ is independently halogen, cyano, nitro, hydroxyl, perfluoroalkyl, difluoromethyl, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted aralkyl, substituted or unsubstituted heteroaryl; substituted or unsubstituted heteroaralkyl, $-(CH_2)_j C(=Z)R^3$, $-(CH_2)_j OR^3$, $-(CH_2)_j C(O)R^3$, $-(CH_2)_j C(O)OR^3$, $-(CH_2)_j NR^4R^5$, $-(CH_2)_j C(O)NR^4R^5$, $-(CH_2)_j OC(O)NR^4R^5$, $-(CH_2)_j NR^6C(O)R^3$, $-(CH_2)_j NR^6C(O)OR^3$, $-(CH_2)_j NR^6C(O)NR^4R^5$, $-(CH_2)_j S(O)_m R^7$, $-(CH_2)_j N^6RS(O)_2R^7$, or $-(CH_2)_j S(O)_2NR^4R^5$; wherein each j is independently an integer from 0 to 6; and m is independently an integer from 0 to 2;

Z is O, S or $NR^8$; or $R^1$ and $A^1$ are joined together to form substituted or unsubstituted 6- to 9-membered cycloalkyl, or substituted or unsubstituted 6- to 9-membered heterocycloalkyl;

$R^2$ is independently hydrogen, halogen, cyano, nitro, perfluoroalkyl, difluoromethyl, or substituted or unsubstituted alkyl;

$R^3$ is independently hydrogen, perfluoroalkyl, difluoromethyl, substituted or unsubstituted alkyl; substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$, $R^5$, $R^6$ and $R^7$ are each independently hydrogen, substituted or unsubstituted alkyl, substituted or unsubstituted alkyl-$NR^9R^{10}$, substituted or unsubstituted alkyl-$CONR^9R^{10}$, substituted or unsubstituted heteroalkyl, substituted or unsubstituted cycloalkyl, substituted or unsubstituted heterocycloalkyl, substituted or unsubstituted aryl; or substituted or unsubstituted heteroaryl, substituted or unsubstituted aralkyl, substituted or unsubstituted heteroaralkyl, or $R^4$ and $R^5$ are joined together with the nitrogen to which they are attached, to form substituted or unsubstituted 3- to 7-membered heterocycloalkyl, or substituted or unsubstituted 5-membered heteroaryl:

$R^8$ is independently hydrogen, substituted or unsubstituted alkyl, or substituted or unsubstituted heteroalkyl;

$R^9$ and $R^{10}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, substituted or unsubstituted aralkyl, or substituted or unsubstituted heteroaralkyl, or $R^9$ and $R^{10}$ are joined together with the nitrogen to which they are attached, to form substituted or unsubstituted 3- to 7-membered heterocycloalkyl, or substituted or unsubstituted 5-membered heteroaryl; and wherein any of the groups listed for $R^1$, $R^2$, $R^3$, $R^4$, $R^5$, $R^6$, $R^7$, $R^8$, $R^9$ and $R^{10}$ are each optionally independently substituted with 1 to 3 groups, each group independently selected from halogen, hydroxyl, amino, aminomonoalkyl, aminodialkyl, cyano, nitro, trifluoromethyl, difluoromethyl, oxo, alkyl, —O-alkyl, and —S-alkyl.

In another aspect, the invention relates to methods for modulating the activity of a protein kinase, methods for treating diseases modulated by protein kinases, and pharmaceutical compositions having the compound of formula I.

In one embodiment is the compound having formula A:

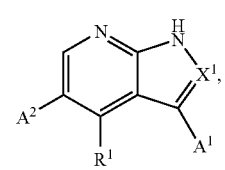

Formula (A)

or an enantiomer, diastereomer, racemate, or pharmaceutically acceptable salt or solvate thereof, wherein:

$A^1$ is independently halogen, cyano, nitro, hydroxyl, substituted or unsubstituted alkyl, substituted or unsubstituted alkene, substituted or unsubstituted alkyne, substituted or unsubstituted haloalkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, —$(CH_2)_j$C(=Z)$R^3$, —$(CH_2)_j$O$R^3$, —$(CH_2)_j$C(O)$R^3$, —$(CH_2)_j$C(O)O$R^3$, —$(CH_2)_j$N$R^4R^5$, —$(CH_2)_j$C(O)N$R^4R^5$, —$(CH_2)_j$OC(O)N$R^4R^5$, —$(CH_2)_j$N$R^6$C(O)$R^3$, —$(CH_2)_j$N$R^6$C(O)O$R^3$, —$(CH_2)_j$N$R^6$C(O)N$R^4R^5$, —$(CH_2)_j$S(O)$_m$$R^7$, —$(CH_2)_j$ N$R^6$S(O)$_2$$R^7$, or —$(CH_2)_j$S(O)$_2$N$R^4R^5$; wherein each j is independently an integer from 0 to 6; and m is independently an integer from 0 to 2 and Z is O, S or N$R^8$; with the proviso when $A^1$ is —S(O)$_m$$R^7$, m is not 2;

$X^1$ is independently —CH— or —N—;

$A^2$ is independently nitro, hydroxyl, haloalkyl, substituted or unsubstituted alkyl, substituted or unsubstituted alkene, substituted or unsubstituted alkyne, substituted or unsubstituted cycloalkyl, substituted or unsubstituted heteroalkyl, substituted or unsubstituted heterocycloalkyl, substituted or unsubstituted aryl, substituted or unsubstituted aralkyl, substituted or unsubstituted heteroaryl; substituted or unsubstituted heteroaralkyl, —$(CH_2)_j$C(=Z)$R^3$, —$(CH_2)_j$O$R^3$, —$(CH_2)_j$C(O)$R^3$, —$(CH_2)_j$C(O)O$R^3$, —$(CH_2)_j$N$R^4R^5$, —$(CH_2)_j$C(O)N$R^4R^5$, —$(CH_2)_j$OC(O)N$R^4R^5$, —$(CH_2)_j$N$R^6$C(O)$R^3$, —$(CH_2)_j$N$R^6$C(O)O$R^3$, —$(CH_2)_j$N$R^6$C(O)N$R^4R^5$, —$(CH_2)_j$S(O)$_m$$R^7$, —$(CH_2)_j$N$R^6$S(O)$_2$$R^7$, or —$(CH_2)_j$S(O)$_2$N$R^4R^5$; wherein each j is independently an integer from 0 to 6; and m is independently an integer from 0 to 2; and Z is O, S or N$R^8$; with the proviso that when $A^1$ is methyl, $A^2$ is not heteroaryl, —C(O)OEt, or —C(O)phenyl, and with the proviso that $A^2$ is not —C(O)H, —C(O)NH$_2$, or —C(O)NHMe;

$R^1$ is independently halogen, cyano, nitro, hydroxyl, substituted or unsubstituted alkyl, substituted or unsubstituted haloalkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, —$(CH_2)_j$C(=Z)$R^3$, —$(CH_2)_j$O$R^3$, —$(CH_2)_j$C(O)$R^3$, —$(CH_2)_j$C(O)O$R^3$, —$(CH_2)_j$N$R^4R^5$, —$(CH_2)_j$C(O)N$R^4R^5$, —$(CH_2)_j$OC(O)N$R^4R^5$, —$(CH_2)_j$N$R^6$C(O)$R^3$, —$(CH_2)_j$N$R^6$C(O)O$R^3$, —$(CH_2)_j$N$R^6$C(O)N$R^4R^5$, —$(CH_2)_j$S(O)$_m$$R^7$, —$(CH_2)_j$N$^6$RS(O)$_2$$R^7$, or —$(CH_2)_j$S(O)$_2$N$R^4R^5$; wherein each j is independently an integer from 0 to 6; and m is independently an integer from 0 to 2; and Z is O, S or N$R^8$; or $R^1$ and $A^1$ are joined together to form substituted or unsubstituted 6- to 12-membered cycloalkyl, or substituted or unsubstituted 6- to 12-membered heterocycloalkyl;

$R^2$ is independently hydrogen, bromine, chlorine, fluorine, cyano, nitro, substituted or unsubstituted alkyl, or substituted or unsubstituted haloalkyl;

$R^3$ is independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$, $R^5$, $R^6$ and $R^7$ are each independently hydrogen, substituted or unsubstituted alkyl, substituted or unsubstituted alkyl-N$R^9R^{10}$, substituted or unsubstituted alkyl-CON$R^9R^{10}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl, substituted or unsubstituted aralkyl, substituted or unsubstituted heteroaralkyl, or $R^4$ and $R^5$ are joined together with the nitrogen to which they are attached, to form substituted or unsubstituted 3- to 7-membered heterocycloalkyl, or substituted or unsubstituted 5-membered heteroaryl;

$R^8$ is independently hydrogen, substituted or unsubstituted alkyl, substituted or unsubstituted haloalkyl, substituted or unsubstituted heteroalkyl, substituted or unsubstituted aryl, substituted or unsubstituted heteroaryl, substituted or unsubstituted heterocycloalkyl, or substituted or unsubstituted cycloalkyl;

$R^9$ and $R^{10}$ are joined together with the nitrogen to which they are attached, to form substituted or unsubstituted 3- to 7-membered heterocycloalkyl, or substituted or unsubstituted 5-membered heteroaryl;

wherein any of the groups listed for $R^1$, $R^2$, $R^3$, $R^4$, $R^5$, $R^6$, $R^7$, $R^8$, $R^9$ and $R^{10}$ are each optionally independently substituted with 1 to 3 groups, each group independently selected from halogen, hydroxyl, amino, aminomonoalkyl, aminodialkyl, cyano, nitro, haloalkyl, alkyl, heteroalkyl, oxo, —O-alkyl, and —S-alkyl.

In another embodiment is a compound of formula A, wherein: $A^1$ is an aryl or heteroaryl group each optionally substituted with 1 to 5 $R^{11}$ groups; each $R^{11}$ is independently hydrogen, halogen, cyano, nitro, hydroxyl, perfluoroalkyl, difluoromethyl, substituted or unsubstituted alkyl, substituted or unsubstituted heteroalkyl, substituted or unsubstituted heterocycloalkyl, substituted or unsubstituted aryl, substituted or unsubstituted heteroaryl, —$(CH_2)_j$C(=Z)$R^2$, —$(CH_2)_j$O$R^2$, —$(CH_2)_j$C(O)$R^{12}$, —$(CH_2)_j$C(O)O$R^2$, —$(CH_2)_j$N$R^3R^4$, —$(CH_2)_j$C(O)N$R^{13}R^{14}$, —$(CH_2)_j$OC(O)N$R^{13}R^{14}$, —$(CH_2)_j$N$R^{15}$C(O)$R^{12}$, —$(CH_2)_j$N$R^{15}$C(O)O$R^{12}$, —$(CH_2)_j$N$R^{15}$C(O)N$R^{13}R^{14}$, —$(CH_2)_j$S(O)$_m$$R^{16}$, —$(CH_2)_j$N$R^{15}$S(O)$_2$$R^{16}$, or —$(CH_2)_j$S(O)$_2$N$R^{13}R^{14}$, wherein each j is independently an integer from 0 to 6; m is independently an integer from 0 to 2; and Z is O, S or N$R^{17}$; $R^{12}$ is independently hydrogen, substituted or unsubstituted haloalkyl, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{13}$, $R^{14}$, $R^{15}$ and $R^{16}$ are each independently hydrogen, substituted or unsubstituted alkyl, substituted or unsubstituted alkyl-N$R^{18}R^{19}$, substituted or unsubstituted alkyl-CON$R^{18}R^{19}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or $R^{13}$ and $R^{14}$ are joined together with the nitrogen to which they are attached, to form substituted or unsubstituted 3- to 7-membered heterocycloalkyl, or substituted or unsubstituted 5-membered heteroaryl; $R^{17}$ is independently hydrogen, substituted or unsubstituted alkyl, substituted or unsubstituted heteroalkyl, substituted or unsubstituted aryl, substituted or unsubstituted heteroaryl, substituted or unsubstituted heterocycloalkyl, or substituted or unsubstituted cycloalkyl; $R^{18}$ and $R^{19}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or $R^{18}$ and $R^{19}$ are joined together with the nitrogen to which they are attached, to form substituted or unsubstituted 3- to 7-membered heterocycloalkyl, or substituted or unsubstituted 5-membered heteroaryl; and wherein any of the groups listed for $R^{11}$, $R^{12}$, $R^{13}$, $R^{14}$, $R^{15}$, $R^{16}$, $R^{17}$, $R^{18}$ and $R^{19}$ are each optionally independently substituted with 1 to 3 groups, each group independently selected from halogen, hydroxyl, amino, aminomonoalkyl, aminodialkyl, cyano, nitro, haloalkyl, heteroalkyl, oxo, alkyl, —O-alkyl, and —S-alkyl.

In another embodiment is a compound of formula A, wherein: $A^2$ is an aryl or heteroaryl group each optionally substituted with 1 to 5-$(CR^{20}R^{21})_n R^{22}$ groups; n is an integer from 0 to 2; $R^{20}$, $R^{21}$ and $R^{22}$ are each independently hydrogen, halogen, cyano, nitro, hydroxyl, substituted or unsubstituted haloalkyl, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —$(CH_2)_j C(Z)R^{23}$, —$(CH_2)_j OR^{23}$, —$(CH_2)_j C(O)R^{23}$, —$(CH_2)_j C(O)OR^{23}$, —$(CH_2)_j NR^{24}R^{25}$, —$(CH_2)_j C(O)NR^{24}R^{25}$, —$(CH_2)_j OC(O)NR^{24}R^{25}$, —$(CH_2)_j NR^{26}C(O)R^{23}$, —$(CH_2)_j NR^{26}C(O)OR^{23}$, —$(CH_2)_j NR^{26}C(O)NR^{24}R^{25}$, —$(CH_2)_j S(O)_m R^{27}$, —$(CH_2)_j NR^{26}S(O)_2 R^{27}$, or —$(CH_2)_j S(O)_2 NR^{24}R^{25}$, wherein each j is independently an integer from 0 to 6; m is independently an integer from 0 to 2; and Z is O, S or $NR^{28}$; or $R^{20}$ and $R^{21}$ together form oxo, or $R^{21}$ and $R^{22}$ are joined together to form substituted or unsubstituted cycloalkyl or substituted or unsubstituted heterocycloalkyl; $R^{23}$ is independently hydrogen, substituted or unsubstituted haloalkyl, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{24}$, $R^{25}$, $R^{26}$ and $R^{27}$ are each independently hydrogen, substituted or unsubstituted alkyl, substituted or unsubstituted alkyl-$NR^{29}R^{30}$, substituted or unsubstituted alkyl-$CONR^{29}R^{30}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or $R^{24}$ and $R^{25}$ are joined together with the nitrogen to which they are attached, to form substituted or unsubstituted 3- to 7-membered heterocycloalkyl, or substituted or unsubstituted 5-membered heteroaryl; $R^{28}$ is independently hydrogen, substituted or unsubstituted alkyl, or substituted or unsubstituted heteroalkyl, substituted or unsubstituted aryl, substituted or unsubstituted heteroaryl, substituted or unsubstituted heterocycloalkyl, or substituted or unsubstituted cycloalkyl; $R^{29}$ and $R^{30}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or $R^{29}$ and $R^{30}$ are joined together with the nitrogen to which they are attached, to form substituted or unsubstituted 3- to 7-membered heterocycloalkyl, or substituted or unsubstituted 5-membered heteroaryl; and wherein any of the groups listed for $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are each optionally independently substituted with 1 to 3 groups, each group independently selected from halogen, hydroxyl, amino, aminomonoalkyl, aminodialkyl, cyano, nitro, haloalkyl, heteroalkyl, oxo, alkyl, —O-alkyl, and —S-alkyl.

In another embodiment is a compound of formula A wherein, $A^1$ is substituted 6-membered aryl, substituted 6-membered heteroaryl, or substituted 5-membered heteroaryl.

In another embodiment is a compound of formula A, wherein $A^1$ is:

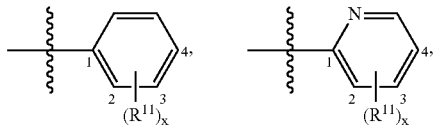

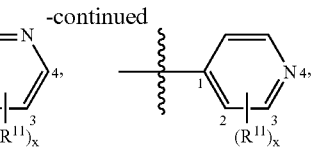

wherein x is independently an integer from 1 to 3.

In another embodiment is a compound of formula A, wherein two $R^{11}$ groups are combined to form a substituted or unsubstituted ring with the carbons to which they are attached, wherein the substituted or unsubstituted ring is substituted or unsubstituted heterocycloalkyl or substituted or unsubstituted heteroaryl.

In another embodiment is a compound of formula A, wherein $R^{11}$ is independently halogen, —$OR^{12}$, —$NR^{13}R^{14}$, substituted or unsubstituted alkyl, substituted or unsubstituted haloalkyl, or substituted or unsubstituted heteroalkyl; wherein $R^{12}$, $R^{13}$ and $R^{14}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another embodiment is a compound of formula A, wherein $R^{12}$, $R^{13}$ and $R^{14}$ are each independently hydrogen, unsubstituted $(C_1-C_6)$alkyl, or unsubstituted $(C_1-C_6)$haloalkyl.

In another embodiment is a compound of formula A, wherein x is 1 or 2 and $R^{11}$ is attached at position 2 or position 3.

In another embodiment is a compound of formula A, wherein $A^2$ is:

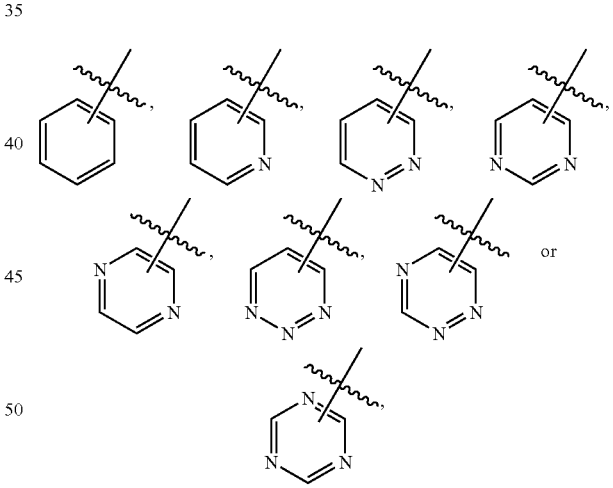

wherein any of the above groups are each independently optionally substituted with 1 to 5—$R^{22}$ groups.

In another embodiment is a compound of formula A, wherein: $R^{22}$ is substituted or unsubstituted haloalkyl, substituted or unsubstituted alkyl, —$(C_0-C_3)OR^{23}$, —$NR^{24}R^{25}$, —$(C_0-C_3)C(O)C(O)NR^{24}R^{25}$, —$(C_0-C_3)CH(OH)C(O)NR^{24}R^{25}$, or —$(C_0-C_3)C(O)NR^{24}R^{25}$; $R^{23}$, $R^{24}$ and $R^{25}$ are each independently hydrogen, $(C_1-C_6)$alkoxy, or $(C_1-C_6)$alkyl; or where $R^{24}$ and $R^{25}$ cyclize with the nitrogen they are attached to form a 3- to 7-membered heterocycloalkyl, or substituted or unsubstituted 5- to 6-membered heteroaryl.

In another embodiment is a compound of formula A, wherein $R^{22}$ is —$(C_1-C_3)OR^{23}$, —$(C_1-C_3)C(O)C(O)R^{23}$, —$(C_0-C_3)CH(OH)R^{23}$, —$(C_0-C_3)CH(OH)C(O)R^{23}$ or —$(C_0-C_3)C(O)R^{23}$; wherein $R^{23}$ is substituted or unsubstituted cycloalkyl, substituted or unsubstituted heterocycloalkyl, substituted or unsubstituted aryl, or substituted or unsubstituted heteroaryl.

In another embodiment is a compound of formula A, wherein: n is 1; $R^{20}$ is hydrogen; and $R^{21}$ is —$OR^{23}$, wherein $R^{23}$ is hydrogen or substituted or unsubstituted alkyl.

In another embodiment is a compound of formula A, wherein: $R^{22}$ is independently substituted or unsubstituted heterocycloalkyl, substituted or unsubstituted cycloalkyl, substituted or unsubstituted aryl, substituted or unsubstituted heteroaryl, —$OR^{23}$, —$NR^{24}R^{25}$ or —$C(O)NR^{24}R^{25}$; wherein $R^{24}$ and $R^{25}$ are each independently hydrogen, substituted or unsubstituted alkyl, substituted or unsubstituted alkyl-$NR^{29}R^{30}$, substituted or unsubstituted alkyl-$C(O)NR^{29}R^{30}$, wherein $R^{29}$ and $R^{30}$ are each independently hydrogen or substituted or unsubstituted alkyl.

In some embodiments, $R^1$ is chlorine, —$(C_0-C_3)$alkylCN—$(C_1-C_3)$alkyl, —$(C_1-C_3)$haloalkyl, —$(C_1-C_3)$alkene, —$(C_1-C_3)$alkyne, —$(C_0-C_3)NH_2$, —$(C_0-C_3)OH$, —$(C_1-C_3)SH$, —$(C_0-C_3)NH(C_1-C_3)$alkyl, —$(C_0-C_3)N(C_1-C_3)_2$alkyl, —$(C_0-C_3)O(C_1-C_3)$alkyl, —$(C_0-C_3)S(C_1-C_3)$alkyl, —$(C_0-C_3)NH(C_1-C_3)$haloalkyl, —$(C_0-C_3)N(C_1-C_3)_2$haloalkyl, —$(C_0-C_3)O(C_1-C_3)$haloalkyl, —$(C_0-C_3)S(C_1-C_3)$haloalkyl.

In another embodiment is the compound of formula A, having formulae:

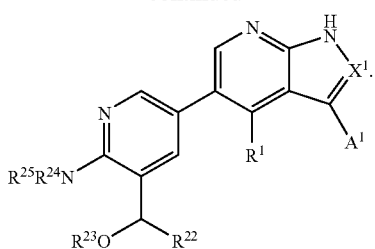

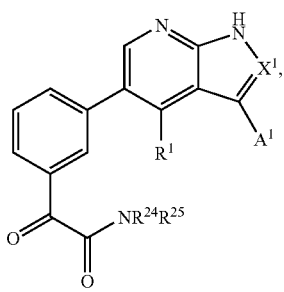

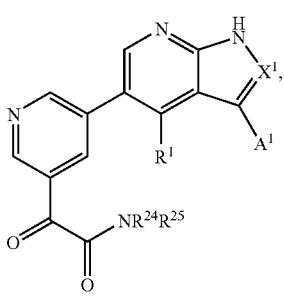

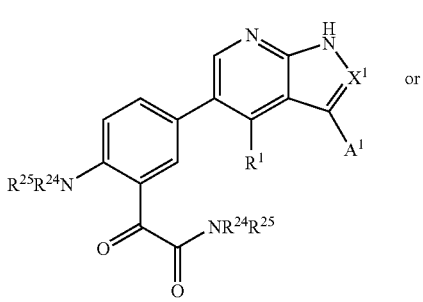

In another embodiment is the compound of formula A, having formulae:

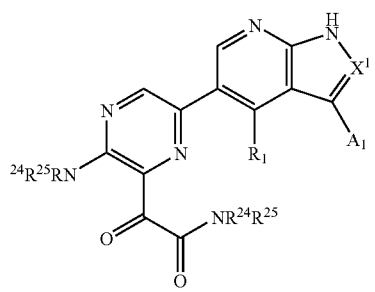

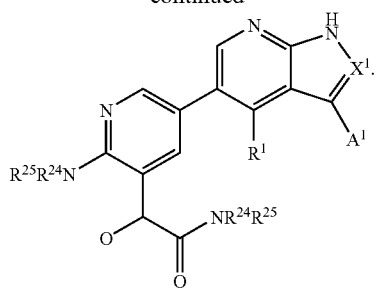
In another embodiment is the compound of formula A, having formulae:
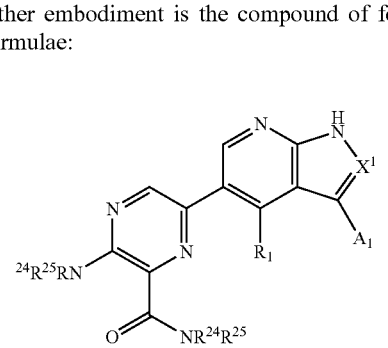
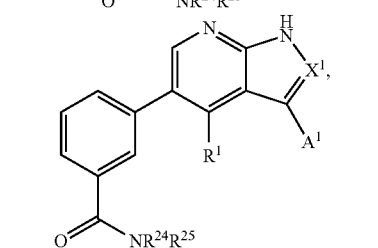

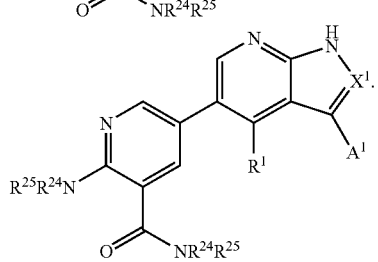
In another embodiment is a compound of formula A, having formulae:
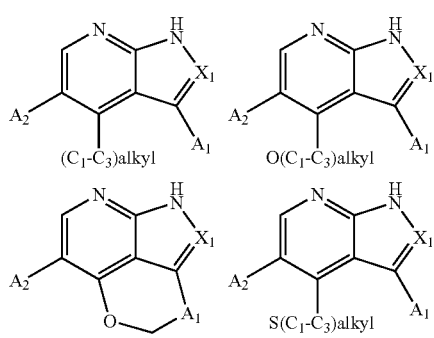
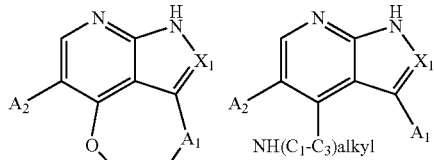
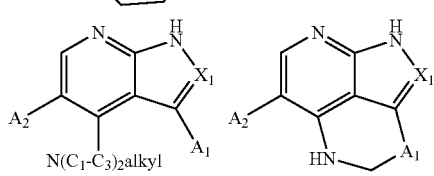
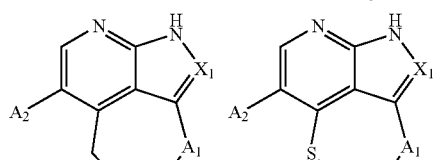
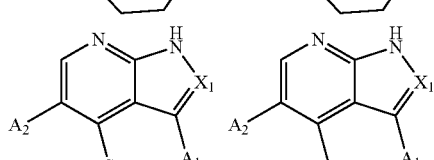
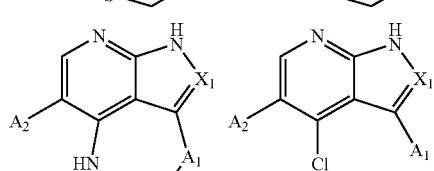
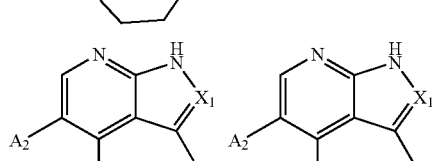
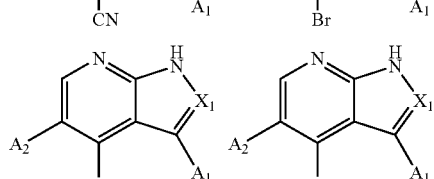
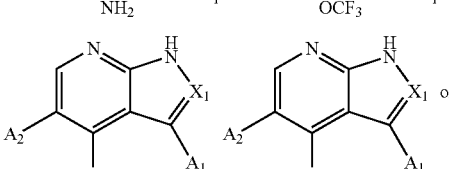

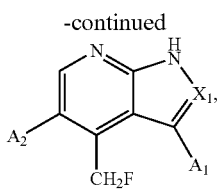

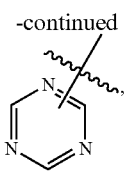

wherein each S is optionally substituted with one or two oxygen atoms.

In another embodiment is a compound of formula A, wherein $A^1$ is substituted 6-membered aryl, substituted 6-membered heteroaryl, or substituted 5-membered heteroaryl.

In another embodiment is a compound of formula A, wherein $A^1$ is:

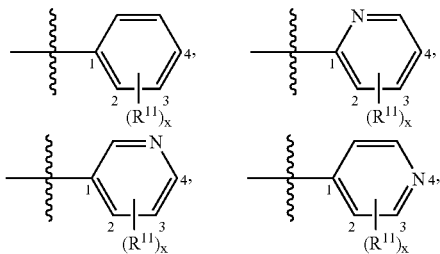

wherein x is independently an integer from 1 to 3.

In another embodiment is a compound of formula A, wherein two $R^{11}$ groups are combined to form a substituted or unsubstituted ring with the carbons to which they are attached, wherein the substituted or unsubstituted ring is substituted or unsubstituted heterocycloalkyl or substituted or unsubstituted heteroaryl.

In another embodiment is a compound of formula A, wherein $R^{11}$ is independently halogen, —$OR^{12}$, —$NR^{13}R^{14}$, substituted or unsubstituted alkyl, substituted or unsubstituted haloalkyl, or substituted or unsubstituted heteroalkyl; wherein $R^{12}$, $R^{13}$ and $R^{14}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

In another embodiment is a compound of formula A, wherein $R^{12}$, $R^{13}$ and $R^{14}$ are each independently hydrogen, unsubstituted $(C_1-C_6)$alkyl, or unsubstituted $(C_1-C_6)$haloalkyl.

In another embodiment is a compound of formula A, wherein $A^2$ is:

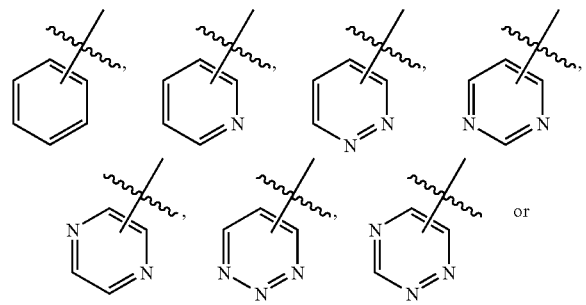

wherein any of the above groups are each independently optionally substituted with 1 to 5—$R^{22}$ groups.

In another embodiment is a compound of formula A, wherein:

$R^{22}$ is substituted or unsubstituted haloalkyl, substituted or unsubstituted alkyl, —$(C_0-C_3)OR^{23}$, —$NR^{24}R^{25}$, —$(C_0-C_3)C(O)C(O)NR^{24}R^{25}$, —$(C_0-C_3)CH(OH)C(O)NR^{24}R^{25}$, or —$(C_0-C_3)C(O)NR^{24}R^{25}$;

$R^{23}$, $R^{24}$ and $R^{25}$ are each independently hydrogen, $(C_1-C_6)$alkoxy, or $(C_1-C_6)$alkyl; or where $R^{24}$ and $R^{25}$ cyclize with the nitrogen they are attached to form a 3- to 7-membered heterocycloalkyl, or substituted or unsubstituted 5- to 6-membered heteroaryl.

In another embodiment is a compound of formula A, wherein $R^{22}$ is —$(C_0-C_3)OR^{23}$, —$(C_0-C_3)C(O)C(O)R^{23}$, —$(C_0-C_3)CH(OH)R^{23}$, —$(C_0-C_3)CH(OH)C(O)R^{23}$, or —$(C_0-C_3)C(O)R^{23}$; wherein $R^{23}$ is substituted or unsubstituted cycloalkyl, substituted or unsubstituted heterocycloalkyl, substituted or unsubstituted aryl, or substituted or unsubstituted heteroaryl.

In another embodiment is a compound of formula A, wherein: $R^{22}$ is independently substituted or unsubstituted heterocycloalkyl, substituted or unsubstituted cycloalkyl, substituted or unsubstituted aryl, substituted or unsubstituted heteroaryl, —$OR^{23}$, —$NR^{24}R^{25}$ or —$C(O)NR^{24}R^{25}$; wherein $R^{24}$ and $R^{25}$ are each independently hydrogen, substituted or unsubstituted alkyl, substituted or unsubstituted alkyl-$NR^{29}R^{30}$, substituted or unsubstituted alkyl-$C(O)NR^{29}R^{30}$, wherein $R^{29}$ and $R^{30}$ are each independently hydrogen or substituted or unsubstituted alkyl.

In another embodiment are compounds of formula A having the following structure:

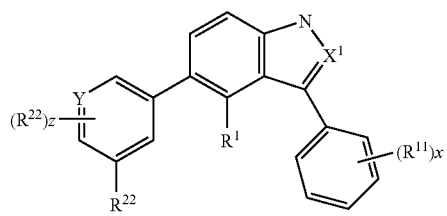

wherein: $X^1$ N or CH; Y is N or CH; each $R^{11}$ is independently halogen, —$OR^{12}$, —$NR^{13}R^{14}$, substituted or unsubstituted alkyl, substituted or unsubstituted haloalkyl, or substituted or unsubstituted heteroalkyl; wherein $R^{12}$, $R^{13}$ and $R^{14}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and x is a whole integer between 1 and 3; and each $R^{22}$ is substituted or unsubstituted haloalkyl, substituted or unsubstituted alkyl, —$(C_0-C_3)OR^{23}$, —$NR^{24}R^{25}$, —$(C_0-C_3)C(O)C(O)NR^{24}R^{25}$, —$(C_0-C_3)CH(OH)C(O)NR^{24}R^{25}$, or —$(C_0-C_3)C(O)NR^{24}R^{25}$; $R^{23}$, $R^{24}$ and $R^{25}$ are each independently hydrogen, $(C_1-C_6)$alkoxy, or ($C_1$-$C_6$)alkyl; or where $R^{24}$ and $R^{25}$ cyclize with the nitrogen they are attached to form a 3- to 7-membered heterocycloalkyl, or substituted or unsubstituted 5- to 6-membered heteroaryl; and z is a whole integer between 0 and 2.

In some embodiments, $R^1$ is chlorine, —($C_0$-$C_3$)alkylCN —($C_1$-$C_3$)alkyl, —($C_1$-$C_3$)haloalkyl, —($C_1$-$C_3$)alkene, —($C_1$-$C_3$)alkyne, —($C_0$-$C_3$)$NH_2$, —($C_0$-$C_3$)OH, —($C_0$-$C_3$)SH, —($C_0$-$C_3$)NH($C_1$-$C_3$)alkyl, —($C_0$-$C_3$)N($C_1$-$C_3$)$_2$alkyl, —($C_0$-$C_3$)O($C_1$-$C_3$)alkyl, —($C_0$-$C_3$)S($C_1$-$C_3$)alkyl, —($C_0$-$C_3$)NH($C_1$-$C_3$)haloalkyl, —($C_0$-$C_3$)N($C_1$-$C_3$)$_2$haloalkyl, —($C_0$-$C_3$)O($C_1$-$C_3$)haloalkyl, —($C_0$-$C_3$)S($C_1$-$C_3$)haloalkyl.

In some embodiments, $R^{22}$ is —($C_0$-$C_3$)$OR^{23}$, —($C_0$-$C_3$)C(O)C(O)$R^{23}$, —($C_0$-$C_3$)CH(OH)$R^{23}$, —($C_0$-$C_3$)CH(OH)C(O)$R^{23}$, or —($C_1$-$C_3$)C(O)$R^{23}$; wherein $R^{23}$ is substituted or unsubstituted cycloalkyl, substituted or unsubstituted heterocycloalkyl, substituted or unsubstituted aryl, or substituted or unsubstituted heteroaryl.

In some embodiments, $R^{22}$ is independently substituted or unsubstituted heterocycloalkyl, substituted or unsubstituted cycloalkyl, substituted or unsubstituted aryl, substituted or unsubstituted heteroaryl, —$OR^{23}$, —$NR^{24}R^{25}$ or —C(O)$NR^{24}R^{25}$; wherein $R^{24}$ and $R^{25}$ are each independently hydrogen, substituted or unsubstituted alkyl, substituted or unsubstituted alkyl-$NR^{29}R^{30}$, substituted or unsubstituted alkyl-C(O)$NR^{29}R^{30}$, wherein $R^{29}$ and $R^{30}$ are each independently hydrogen or substituted or unsubstituted alkyl.

In some embodiments, $R^{12}$, $R^{13}$ and $R^{14}$ are each independently hydrogen, unsubstituted ($C_1$-$C_6$)alkyl, or unsubstituted ($C_1$-$C_6$)haloalkyl.

In another embodiment is a method of modulating the activity of a protein kinase comprising contacting the protein kinase with the compound of formula A. In another embodiment is the method of modulating the activity of a protein kinase comprising contacting the protein kinase with the compound of formula A, wherein the protein kinase is Abelson tyrosine kinase, Ron receptor tyrosine kinase, Met receptor tyrosine kinase, Fms-like tyrosine kinase-3, Aurora kinases, p21-activated kinase-4 or 3-phosphoinositide-dependent kinase-1 and Janus kinase family. In another embodiment is the method described therein, wherein the protein kinase is a Bcr-Abl kinase having one or more mutations selected from the group consisting of M244V, L248V, G250E, G250A, Q252H, Q252R, Y253F, Y253H, E255K, E255V, D276G, F311L, T315I, T315N, T315A, F317V, F317L, M343T, M351T, E355G, F359A, F359V, V379I, F382L, L387M, H396P, H396R, S417Y, E459K and F486S. In another embodiment is the method described therein, wherein the protein kinase has a T315I mutation.

In another embodiment is a method for treating cancer in a subject in need of such treatment, the method comprising administering to the subject a therapeutically effective amount of a compound of formula A.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 shows the wild-type ABL numbering according to ABL exon Ia (SEQ ID NO: 11).

DETAILED DESCRIPTION OF THE INVENTION

Definitions

Abbreviations used herein have their conventional meaning within the chemical and biological arts.

Where substituent groups are specified by their conventional chemical formulae, written from left to right, they equally encompass the chemically identical substituents that would result from writing the structure from right to left, e.g., —$CH_2O$— is equivalent to —$OCH_2$—.

The term "alkyl," by itself or as part of another substituent, means, unless otherwise stated, a straight (i.e., unbranched) or branched chain, or cyclic hydrocarbon radical, or combination thereof, which may be fully saturated, mono- or poly-unsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, N-propyl, isopropyl, N-butyl, t-butyl, isobutyl, sec-butyl, cyclohexyl, (cyclohexyl)methyl, cyclopropylmethyl, homologs and isomers of, for example, N-pentyl, N-hexyl, N-heptyl, N-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. Alkyl groups which are limited to hydrocarbon groups are termed "homoalkyl".

The term "alkylene" by itself or as part of another substituent means a divalent radical derived from an alkyl, as exemplified, but not limited, by —$CH_2CH_2CH_2CH_2$—, —$CH_2CH$=$CHCH_2$—, —$CH_2C$≡$CCH_2$—, —$CH_2CH_2CH(CH_2CH_2CH_3)CH_2$—. Typically, an alkyl (or alkylene) group will have from 1 to 24 carbon atoms, while other alkyl (or alkylene) groups will have 10 or fewer carbon atoms. A "lower alkyl" or "lower alkylene" is a shorter chain alkyl or alkylene group, generally having eight or fewer carbon atoms.

The term "heteroalkyl," by itself or in combination with another term, means, unless otherwise stated, a stable straight or branched chain, or cyclic hydrocarbon radical, or combinations thereof, consisting of at least one carbon atoms and at least one heteroatom selected from the group consisting of O, N, P, Si and S, and wherein the nitrogen, phosphorus, and sulfur atoms may optionally be oxidized and the nitrogen heteroatom may optionally be quaternized. The heteroatom(s) O, N, P and S and Si may be placed at any interior position of the heteroalkyl group or at the position at which alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$.

Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxo, alkylenedioxo, alkyleneamino, alkylenediamino, and the like). Still further, for alkylene and heteroalkylene linking groups, no orientation of the linking group is implied by the direction in which the formula of the linking group is written. For example, the formula —C(O)OR'— represents both —C(O) OR'— and —R'OC(O)—. As described above, heteroalkyl groups, as used herein, include those groups that are attached to the remainder of the molecule through a heteroatom, such as —C(O)R', —C(O)NR', —NR'R", —OR'—, —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. The terms "cycloalkylene" and "heterocycloalkylene" refer to the divalent derivatives of cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent which can be a single ring or multiple rings (usually from 1 to 3 rings) which are fused together or linked covalently. The term "heteroaryl" refers to aryl groups (or rings) that contain from one to four heteroatoms (in each separate ring in the case of multiple rings) selected from N, O, and S, wherein the nitrogen and sulfur atoms are optionally oxidized, and the nitrogen atom(s) are optionally quaternized. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of above noted aryl and heteroaryl ring systems are selected from the group of acceptable substituents described below. The terms "arylene" and "heteroarylene" refer to the divalent radicals of aryl and heteroaryl, respectively.

For brevity, the term "aryl" when used in combination with other terms (e.g., aryloxo, arylthioxo, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like). However, the term "haloaryl," as used herein is meant to cover only aryls substituted with one or more halogens.

Where a heteroalkyl, heterocycloalkyl, or heteroaryl includes a specific number of members (e.g., "3 to 7 membered"), the term "member" referrers to a carbon or heteroatom.

The term "oxo" as used herein means an oxygen that is double bonded to a carbon atom.

Each of above terms (e.g., "alkyl," "heteroalkyl," "cycloalkyl, and "heterocycloalkyl", "aryl," "heteroaryl" as well as their divalent radical derivatives) are meant to include both substituted and unsubstituted forms of the indicated radical. Examples of substituents for each type of radical are provided below.

Substituents for alkyl, heteroalkyl, cycloalkyl, heterocycloalkyl monovalent and divalent derivative radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 4-, 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O) CH$_3$, —C(O)CF$_3$, —C(O)CH$_2$OCH$_3$, and the like).

Similar to the substituents described for alkyl radicals above, exemplary substituents for aryl and heteroaryl groups (as well as their divalent derivatives) are varied and are selected from, for example: halogen, —OR', —NR'R", —SR', -halogen, —SiR'R"R'", —OC(O)R', —C(O)R', —CO$_2$R', —C(O)NR'R", —OC(O)NR'R", —NR"C(O)R', —NR'—C(O)NR"R'", —NR"C(O)OR', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro($C_1$-$C_4$)alkoxo, and fluoro ($C_1$-$C_4$)alkyl, in a number ranging from zero to the total number of open valences on aromatic ring system; and where R', R", R'" and R"" are independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present.

Two of the substituents on adjacent atoms of aryl or heteroaryl ring may optionally form a ring of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of aryl or heteroaryl ring may optionally be replaced with a substituent of the formula -A-(CH$_2$)$_r$—B—, wherein A and B are independently CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R" and R'" are independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the term "heteroatom" or "ring heteroatom" is meant to include oxygen (O), nitrogen (N), sulfur (S), phosphorus (P), and silicon (Si).

An "aminoalkyl" as used herein refers to an amino group covalently bound to an alkylene linker. The amino group is —NR'R", wherein R' and R" are typically selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

The compounds of the present invention may exist as salts. The present invention includes such salts. Examples of applicable salt forms include hydrochlorides, hydrobromides, sulfates, methanesulfonates, nitrates, maleates, acetates, citrates, fumarates, tartrates (eg (+)-tartrates, (−)-tartrates or mixtures thereof including racemic mixtures, succinates, benzoates and salts with amino acids such as glutamic acid. These salts may be prepared by methods known to those skilled in art. Also included are base addition salts such as sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C— or $^{14}$C-enriched carbon are within the scope of this invention.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

The term "pharmaceutically acceptable salts" is meant to include salts of active compounds which are prepared with relatively nontoxic acids or bases, depending on the particular substituent moieties found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science*, 66:1-19 (1977)). Certain specific compounds of the present invention contain both basic and acidic functionalities that allow the compounds to be converted into either base or acid addition salts.

In addition to salt forms, the present invention provides compounds, which are in a prodrug form Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

The terms "a," "an," or "a(n)", when used in reference to a group of substituents herein, mean at least one. For example, where a compound is substituted with "an" alkyl or aryl, the compound is optionally substituted with at least one alkyl and/or at least one aryl. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The symbol ⌇ denotes the point of attachment of a moiety to the remainder of the molecule.

Certain Pharmaceutical Terminology

The term "subject", "patient" or "individual" as used herein in reference to individuals suffering from a disorder, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "treating" or "treatment" in reference to a particular disease includes prevention of the disease.

The terms "treat," "treating" or "treatment," and other grammatical equivalents as used herein, include alleviating, abating or ameliorating a disease or condition symptoms, preventing additional symptoms, ameliorating or preventing the underlying metabolic causes of symptoms, inhibiting the disease or condition, e.g., arresting the development of the disease or condition, relieving the disease or condition, causing regression of the disease or condition, relieving a condition caused by the disease or condition, or stopping the symptoms of the disease or condition, and are intended to include prophylaxis. The terms further include achieving a therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. In some embodiments, for prophylactic benefit, the compositions are administered to a patient at risk of developing a particular disease, or to a patient reporting one or more of the physiological symptoms of a disease, even though a diagnosis of this disease may not have been made.

As used herein, the terms "cancer treatment" "cancer therapy" and the like encompasses treatments such as surgery, radiation therapy, administration of chemotherapeutic agents and combinations of any two or all of these methods. In some embodiments, combination treatments occur sequentially or concurrently. Treatment(s), such as radiation therapy and/or chemotherapy, that is administered prior to surgery, is referred to as neoadjuvant therapy. Treatments(s), such as radiation therapy and/or chemotherapy, administered after surgery is referred to herein as adjuvant therapy.

In some embodiments, examples of surgeries that are used for cancer treatment include, but are not limited to radical prostatectomy, cryotherapy, mastectomy, lumpectomy, transurethral resection of the prostate, and the like.

Many chemotherapeutic agents are known and are discussed in greater detail herein. In some embodiments, they operate via a wide variety of modes of action such as, though not limited to, cytotoxic agents, antiproliferatives, targeting agents (such as monoclonal antibodies), and the like. The nature of a combination therapy involving administration of a chemotherapeutic agent will depend upon the type of agent being used.

In some embodiments, the compounds described herein are administered in combination with surgery, as an adjuvant, or as a neoadjuvant agent. In other embodiments, the compounds described herein are useful in instances where radiation and chemotherapy are indicated, to enhance the therapeutic benefit of these treatments, including induction chemotherapy, primary (neoadjuvant) chemotherapy, and both adjuvant radiation therapy and adjuvant chemotherapy. Radiation and chemotherapy frequently are indicated as adjuvants to surgery in the treatment of cancer. For example, in some embodiments, radiation is used both pre- and post-surgery as components of the treatment strategy for rectal carcinoma. In further embodiments, the compounds described herein are useful following surgery in the treatment of cancer in combination with radio- and/or chemotherapy.

Where combination treatments are contemplated, it is not intended that the compounds described herein be limited by the particular nature of the combination. For example, in some embodiments, the compounds described herein are administered in combination as simple mixtures as well as chemical hybrids. An example of the latter is where the compound is covalently linked to a targeting carrier or to an active pharmaceutical. In some embodiments, covalent binding is accomplished in many ways, such as, though not limited to, the use of a commercially available cross-linking compound.

As used herein, the terms "pharmaceutical combination", "administering an additional therapy", "administering an additional therapeutic agent" and the like refer to a pharmaceutical therapy resulting from the mixing or combining of more than one active ingredient and includes both fixed and non-fixed combinations of the active ingredients. The term "fixed combination" means that at least one of the compounds described herein, and at least one co-agent, are both administered to a patient simultaneously in the form of a single entity or dosage. The term "non-fixed combination" means that at least one of the compounds described herein, and at least one co-agent, are administered to a patient as separate entities either simultaneously, concurrently or sequentially with variable intervening time limits, wherein such administration provides effective levels of the two or more compounds in the body of the patient. These also apply to cocktail therapies, e.g. the administration of three or more active ingredients.

As used herein, the terms "co-administration", "administered in combination with" and their grammatical equivalents or the like are meant to encompass administration of the selected therapeutic agents to a single patient, and are intended to include treatment regimens in which the agents are administered by the same or different route of administration or at the same or different times. In some embodiments the compounds described herein is co-administered with other agents. These terms encompass administration of two or more agents to an animal so that both agents and/or their metabolites are present in the animal at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

The terms "effective amount", "therapeutically effective amount" or "pharmaceutically effective amount" as used herein, refer to a sufficient amount of at least one agent or compound being administered which will relieve to some extent one or more of the symptoms of the disease or condition being treated. In some embodiments, the result is a reduction and/or alleviation of the signs, symptoms, or causes of a disease, or any other desired alteration of a biological system. For example, an "effective amount" for therapeutic uses is the amount of the composition comprising the compound as disclosed herein required to provide a clinically significant decrease in a disease. In some embodiments, an appropriate "effective" amount in any individual case is determined using techniques, such as a dose escalation study.

In some embodiments, the terms "administer," "administering", "administration," and the like, as used herein, refer to the methods that are used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. In some embodiments, the administration techniques are employed with the compounds and methods described herein, e.g., as discussed in Goodman and Gilman, The Pharmacological Basis of Therapeutics, current ed.; Pergamon; and Remington's, Pharmaceutical *Sciences* (current edition), Mack Publishing Co., Easton, Pa. In other embodiments, the compounds and compositions described herein are administered orally.

The term "acceptable" as used herein, with respect to a formulation, composition or ingredient, means having no persistent detrimental effect on the general health of the subject being treated.

The term "pharmaceutically acceptable" as used herein, refers to a material, such as a carrier or diluent, which does not abrogate the biological activity or properties of the compounds described herein, and is relatively nontoxic, i.e., in other embodiments, the material is administered to an individual without causing undesirable biological effects or interacting in a deleterious manner with any of the components of the composition in which it is contained.

The term "pharmaceutical composition," as used herein, refers to a biologically active compound, optionally mixed with at least one pharmaceutically acceptable chemical component, such as, though not limited to carriers, stabilizers, diluents, dispersing agents, suspending agents, thickening agents, and/or excipients.

The term "carrier" as used herein, refers to relatively non-toxic chemical compounds or agents that facilitate the incorporation of the compound into cells or tissues.

The term "agonist," as used herein, refers to a molecule such as the compound, a drug, an enzyme activator or a hormone modulator which enhances the activity of another molecule or the activity of a receptor site.

The term "antagonist," as used herein, refers to a molecule such as the compound, a drug, an enzyme inhibitor, or a hormone modulator, which diminishes, or prevents the action of another molecule or the activity of a receptor site.

The term "modulate," as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator," as used herein, refers to a molecule that interacts with a target either directly or indirectly. The interactions include, but are not limited to, the interactions of an agonist and an antagonist.

The term "pharmaceutically acceptable derivative or prodrug" as used herein, refers to any pharmaceutically acceptable salt, ester, salt of an ester or other derivative of the compound of Formula I, which, upon administration to a recipient, is capable of providing, either directly or indirectly, the compound disclosed herein or a pharmaceutically active metabolite or residue thereof. Particularly favored derivatives or prodrugs are those that increase the bioavailability of the compounds described herein when such compounds are administered to a patient (e.g., by allowing orally administered compound to be more readily absorbed into blood) or which enhance delivery of the parent compound to a biological compartment (e.g., the brain or lymphatic system).

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "metabolite," as used herein, refers to a derivative of the compound which is formed when the compound is metabolized.

The term "active metabolite," as used herein, refers to a biologically active derivative of the compound that is formed when the compound is metabolized.

The term "metabolized," as used herein, refers to the sum of the processes (including, but not limited to, hydrolysis reactions and reactions catalyzed by enzymes) by which a particular substance is changed by an organism. Thus, in some embodiments, enzymes produce specific structural alterations to the compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Further information on metabolism may be obtained from *The Pharmacological Basis of Therapeutics,* 9th Edition, McGraw-Hill (1996).

4-Substituted Pyrrolopyridines and Pyrazolopyridines

In one aspect, the invention relates to compounds having formula I:

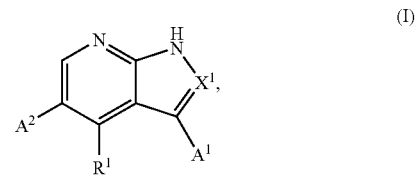

(I)

or an enantiomer, diastereomer, racemate, or pharmaceutically acceptable salt or solvate thereof, wherein:

$A^1$ is independently halogen, cyano, nitro, hydroxyl, perfluoroalkyl, difluoromethyl, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted aralkyl, substituted or unsubstituted heteroaryl; substituted or unsubstituted heteroaralkyl, —$(CH_2)_j$C(=Z)$R^3$, —$(CH_2)_j$O$R^3$, —$(CH_2)_j$C(O)$R^3$, —$(CH_2)_j$C(O)O$R^3$, —$(CH_2)_j$N$R^4R^5$, —$(CH_2)_j$C(O)N$R^4R^5$, —$(CH_2)_j$OC(O)N$R^4R^5$, —$(CH_2)_j$N$R^6$C(O)$R^3$, —$(CH_2)_j$N$R^6$C(O)O$R^3$, —$(CH_2)_j$N$R^6$C(O)N$R^4R^5$, —$(CH_2)_j$S(O)$_m$$R^7$, —$(CH_2)_j$N$R^6$S(O)$_2$$R^7$, or —$(CH_2)_j$S(O)$_2$N$R^4R^5$; wherein each j is independently an integer from 0 to 6; and m is independently an integer from 0 to 2; with the proviso when $A^1$ is —S(O)$_m$$R^7$, m is not 2; Z is O, S or N$R^8$; or $X^1$ is independently —C$R^2$= or —N=;

$A^2$ is independently nitro, hydroxyl, perfluoroalkyl, difluoromethyl, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted aralkyl, substituted or unsubstituted heteroaryl; substituted or unsubstituted heteroaralkyl, —$(CH_2)_j$C(=Z)$R^3$, —$(CH_2)_j$O$R^3$, —$(CH_2)_j$C(O)$R^3$, —$(CH_2)_j$C(O)O$R^3$, —$(CH_2)_j$N$R^4R^5$, —$(CH_2)_j$C(O)N$R^4R^5$, —$(CH_2)_j$OC(O)N$R^4R^5$, —$(CH_2)_j$N$R^6$C(O)$R^3$, —$(CH_2)_j$N$R^6$C(O)O$R^3$, —$(CH_2)_j$N$R^6$C(O)N$R^4R^5$, —$(CH_2)_j$S(O)$_m$$R^7$, —$(CH_2)_j$N$R^6$S(O)$_2$$R^7$, or —$(CH_2)_j$S(O)$_2$N$R^4R^5$; wherein each j is independently an integer from 0 to 6; and m is independently an integer from 0 to 2; Z is O, S or N$R^8$;]

$R^1$ is independently halogen, cyano, nitro, hydroxyl, perfluoroalkyl, difluoromethyl, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted aralkyl, substituted or unsubstituted heteroaryl; substituted or unsubstituted heteroaralkyl, —$(CH_2)_j$C(=Z)$R^3$, —$(CH_2)_j$O$R^3$, —$(CH_2)_j$C(O)$R^3$, —$(CH_2)_j$C(O)O$R^3$, —$(CH_2)_j$N$R^4R^5$, —$(CH_2)_j$C(O)N$R^4R^5$, —$(CH_2)_j$OC(O)N$R^4R^5$, —$(CH_2)_j$N$R^6$C(O)$R^3$, —$(CH_2)_j$N$R^6$C(O)O$R^3$, —$(CH_2)_j$N$R^6$C(O)N$R^4R^5$, —$(CH_2)_j$S(O)$_m$$R^7$, —$(CH_2)_j$N$^6$RS(O)$_2$$R^7$, or —$(CH_2)_j$S(O)$_2$N$R^4R^5$; wherein each j is independently an integer from 0 to 6; and m is independently an integer from 0 to 2; Z is O, S or $NR^8$; or $R^1$ and $A^1$ are joined together to form substituted or unsubstituted 6- to 9-membered cycloalkyl, or substituted or unsubstituted 6- to 9-membered heterocycloalkyl;

$R^2$ is independently hydrogen, halogen, cyano, nitro, perfluoroalkyl, difluoromethyl, or substituted or unsubstituted alkyl;

$R^3$ is independently hydrogen, perfluoroalkyl, difluoromethyl, substituted or unsubstituted alkyl; substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$, $R^5$, $R^6$ and $R^7$ are each independently hydrogen, substituted or unsubstituted alkyl, substituted or unsubstituted alkyl-$NR^9R^{10}$, substituted or unsubstituted alkyl-$CONR^9R^{10}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl, substituted or unsubstituted aralkyl, substituted or unsubstituted heteroaralkyl, or $R^4$ and $R^5$ are joined together with the nitrogen to which they are attached, to form substituted or unsubstituted 3- to 7-membered heterocycloalkyl, or substituted or unsubstituted 5-membered heteroaryl;

$R^8$ is independently hydrogen, substituted or unsubstituted alkyl, or substituted or unsubstituted heteroalkyl;

$R^9$ and $R^{10}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, substituted or unsubstituted aralkyl, substituted or unsubstituted heteroaralkyl, or $R^9$ and $R^{10}$ are joined together with the nitrogen to which they are attached, to form substituted or unsubstituted 3- to 7-membered heterocycloalkyl, or substituted or unsubstituted 5-membered heteroaryl; and wherein any of the groups listed for $R^1$, $R^2$, $R^3$, $R^4$, $R^5$, $R^6$, $R^7$, $R^8$, $R^9$ and $R^{10}$ are each optionally independently substituted with 1 to 3 groups, each group independently selected from halogen, hydroxyl, amino, aminomonoalkyl, aminodialkyl, cyano, nitro, trifluoromethyl, difluoromethyl, oxo, alkyl, —O-alkyl, and —S-alkyl.

In another aspect, the invention relates to compounds having formula I, wherein: $A^1$ is optionally substituted with 1 to 5 $R^{11}$ groups; wherein each $R^{11}$ is independently hydrogen, halogen, cyano, nitro, hydroxyl, perfluoroalkyl, difluoromethyl, substituted or unsubstituted alkyl, substituted or unsubstituted heteroalkyl, substituted or unsubstituted heterocycloalkyl, substituted or unsubstituted aryl, substituted or unsubstituted aralkyl, substituted or unsubstituted heteroaryl; substituted or unsubstituted heteroaralkyl, —$(CH_2)_jC(=Z)R^{12}$, —$(CH_2)_jOR^2$, —$(CH_2)_jC(O)R^{12}$, —$(CH_2)_jC(O)OR^{12}$, —$(CH_2)_jNR^{13}R^{14}$, —$(CH_2)_jC(O)NR^{13}R^{14}$, —$(CH_2)_jOC(O)NR^{13}R^{14}$, —$(CH_2)_jNR^{15}C(O)R^{12}$, —$(CH_2)_jNR^{15}C(O)OR^{12}$, —$(CH_2)_jNR^{15}C(O)NR^{13}R^{14}$, —$(CH_2)_jS(O)_mR^{16}$, —$(CH_2)_jN^{15}RS(O)_2R^{16}$, or —$(CH_2)_jS(O)_2NR^{13}R^{14}$, wherein each j is independently an integer from 0 to 6; and m is independently an integer from 0 to 2; Z is O, S or $NR^{17}$; $R^{12}$ is independently hydrogen, perfluoroalkyl, difluoromethyl, substituted or unsubstituted alkyl; substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{13}$, $R^{14}$, $R^{15}$ and $R^{16}$ are each independently hydrogen, substituted or unsubstituted alkyl, substituted or unsubstituted alkyl-$NR^{18}R^{19}$, substituted or unsubstituted alkyl-$CONR^{15}R^{19}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl, substituted or unsubstituted aralkyl, substituted or unsubstituted heteroaralkyl, or $R^{13}$ and $R^{14}$ are joined together with the nitrogen to which they are attached, to form substituted or unsubstituted 3- to 7-membered heterocycloalkyl, or substituted or unsubstituted 5-membered heteroaryl; $R^{17}$ is independently hydrogen, substituted or unsubstituted alkyl, or substituted or unsubstituted heteroalkyl; $R^{18}$ and $R^{19}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, substituted or unsubstituted aralkyl, substituted or unsubstituted heteroaralkyl, or $R^{18}$ and $R^{19}$ are joined together with the nitrogen to which they are attached, to form substituted or unsubstituted 3- to 7-membered heterocycloalkyl, or substituted or unsubstituted 5-membered heteroaryl; and wherein any of the groups listed for $R^{11}$, $R^{12}$, $R^{13}$, $R^{14}$, $R^{15}$, $R^{16}$, $R^{17}$, $R^{18}$, and $R^{19}$ are each optionally independently substituted with 1 to 3 groups, each group independently selected from halogen, hydroxyl, amino, aminomonoalkyl, aminodialkyl, cyano, nitro, trifluoromethyl, difluoromethyl, oxo, alkyl, —O-alkyl, and —S-alkyl.

In another aspect, the invention relates to compounds having formula I, wherein: $A^2$ is optionally substituted with 1 to 5-$(CR^{20}R^{21})_nR^{22}$ groups; n is an integer from 0 to 2; $R^{20}$, $R^{21}$ and $R^{22}$ are each independently hydrogen, halogen, cyano, nitro, hydroxyl, perfluoroalkyl, difluoromethyl, substituted or unsubstituted alkyl, substituted or unsubstituted cycloalkyl, substituted or unsubstituted heteroalkyl, substituted or unsubstituted heterocycloalkyl, substituted or unsubstituted aryl, substituted or unsubstituted aralkyl, substituted or unsubstituted heteroaryl; substituted or unsubstituted heteroaralkyl, —$(CH_2)_jC(Z)R^{23}$, —$(CH_2)_jOR^{23}$, —$(CH_2)_jC(O)R^{23}$, —$(CH_2)_jC(O)OR^{23}$, —$(CH_2)_jNR^{24}R^{25}$, —$(CH_2)_jC(O)NR^{24}R^{25}$, $(CH_2)_jOC(O)NR^{24}R^{21}$, —$(CH_2)_jNR^6C(O)R^{23}$, $(CH_2)_jNR^{26}C(O)OR^{23}$, $(CH_2)_jNR^{26}C(O)NR^{24}R^{25}$, —$(CH_2)_jS(O)_mR^{27}$, —$(CH_2)_jNR^{26}S(O)_2R^{27}$, or —$(CH_2)_jS(O)_2NR^{24}R^{25}$, wherein each j is independently an integer from 0 to 6; and m is independently an integer from 0 to 2, or $R^{20}$ and $R^{21}$ together form oxo, or $R^{21}$ and $R^{22}$ are joined together to form substituted or unsubstituted cycloalkyl, or substituted or unsubstituted heterocycloalkyl; Z is O, S or $NR^{28}$; $R^{23}$ is independently hydrogen, perfluoroalkyl, difluoromethyl, substituted or unsubstituted alkyl; substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{24}$, $R^{25}$, $R^{26}$ and $R^{27}$ are each independently hydrogen, substituted or unsubstituted alkyl, substituted or unsubstituted alkyl-$NR^{29}R^{30}$, substituted or unsubstituted alkyl-$CONR^{29}R^{30}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl, substituted or unsubstituted aralkyl, substituted or unsubstituted heteroaralkyl, or $R^{24}$ and $R^{25}$ are joined together with the nitrogen to which they are attached, to form substituted or unsubstituted 3- to 7-membered heterocycloalkyl, or substituted or unsubstituted 5-membered heteroaryl; $R^{29}$ is independently hydrogen, substituted or unsubstituted alkyl or substituted or unsubstituted heteroalkyl; $R^{29}$ and $R^{30}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, substituted or unsubstituted aralkyl, substituted or unsubstituted heteroaralkyl, or $R^{29}$ and $R^{30}$ are joined together with the nitrogen to which they are attached, to form substituted or unsubstituted 3- to 7-membered heterocycloalkyl, or substituted or unsubstituted 5-membered heteroaryl; and wherein any of the groups listed for $R^{20}$, $R^{21}$, $R^{22}$, $R^{23}$, $R^{24}$, $R^{25}$, $R^{26}$, $R^{27}$, $R^{28}$, $R^{29}$ and $R^{30}$ are each optionally independently substituted with 1 to 3 groups, each group independently selected from halogen, hydroxyl, amino, aminomonoalkyl, aminodialkyl, cyano, nitro, trifluoromethyl, difluoromethyl, oxo, alkyl, —O-alkyl, and —S-alkyl.

In another aspect, the invention relates to compounds having formula I, wherein:

$A^1$ is substituted 6-membered aryl, substituted 6-membered heteroaryl, or substituted 5-membered heteroaryl.

In another aspect, the invention relates to compounds having formula I, wherein:

$A^1$ is substituted or unsubstituted phenyl, substituted or unsubstituted pyridinyl, substituted or unsubstituted pyridinyl N-oxide, substituted or unsubstituted pyrimidinyl, substituted or unsubstituted benzodioxolyl, substituted or unsubstituted benzimidazolyl, or substituted or unsubstituted indolyl, substituted or unsubstituted furyl, substituted or unsubstituted thiophenyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted isoxazolyl, substituted or unsubstituted isothiazolyl, substituted or unsubstituted pyridinyl, substituted or unsubstituted pyridazinyl, substituted or unsubstituted pyrazinyl, substituted or unsubstituted indolizinyl, substituted or unsubstituted isoindolyl, substituted or unsubstituted indolinyl, substituted or unsubstituted benzo[b]furanyl, substituted or unsubstituted benzo[b]thiophenyl, substituted or unsubstituted indazolyl, substituted or unsubstituted benzimidazolyl, substituted or unsubstituted benzthiazolyl, substituted or unsubstituted purinyl, substituted or unsubstituted quinolizinyl, substituted or unsubstituted quinolinyl, substituted or unsubstituted isoquinolinyl, substituted or unsubstituted cinnolinyl, substituted or unsubstituted phthalazinyl, substituted or unsubstituted quinazolinyl, substituted or unsubstituted quinoxalinyl, substituted or unsubstituted naphthyridinyl, or substituted or unsubstituted pteridinyl.

In another aspect, the invention relates to compounds having formula I, wherein $A^1$ is substituted with halogen or $(C_1$-$C_6)$ alkyl.

In another aspect, the invention relates to compounds having formula I, wherein $A^1$ is substituted phenyl.

In another aspect, the invention relates to compounds having formula I, wherein $A^1$ has anyone of formulae:

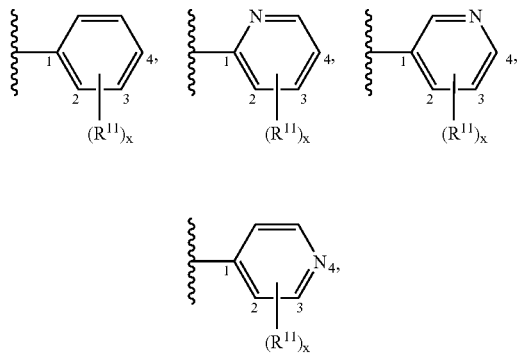

wherein:

x is independently an integer from 1 to 3, or
two $R^{11}$ groups form a substituted or unsubstituted ring.

In another aspect, the invention relates to compounds having formula I, wherein an $R^{11}$ attached at position 2 is combined with an $R^{11}$ attached at position 3 to form a substituted or unsubstituted ring.

In another aspect, the invention relates to compounds having formula I, wherein an $R^{11}$ attached at position 3 is combined with an $R^{11}$ attached at position 4 to form a substituted or unsubstituted ring.

In another aspect, the invention relates to compounds having formula I, wherein two $R^{11}$ groups are optionally combined to form a substituted or unsubstituted ring with the carbons to which they are attached, wherein the substituted or unsubstituted ring is substituted or unsubstituted heterocycloalkyl or substituted or unsubstituted heteroaryl.

In another aspect, the invention relates to compounds having formula I, wherein $R^{11}$ is independently halogen, —$OR^{12}$, —$NR^{13}R^{14}$, or substituted or unsubstituted alkyl.

In another aspect, the invention relates to compounds having formula I, wherein:

$R^{12}$, $R^{13}$ and $R^{14}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or $R^{13}$ and $R^{14}$ are optionally joined together with the nitrogen to which they are attached, to form substituted or unsubstituted heterocycloalkyl, or substituted or unsubstituted 5-membered heteroaryl.

In another aspect, the invention relates to compounds having formula I, wherein $R^{12}$, $R^{13}$ and $R^{14}$ are each independently hydrogen, or substituted or unsubstituted alkyl.

In another aspect, the invention relates to compounds having formula I, wherein $R^{12}$, $R^{13}$ and $R^{14}$ are each independently hydrogen, or substituted or unsubstituted $(C_1$-$C_6)$ alkyl.

In another aspect, the invention relates to compounds having formula I, wherein x is 1; and $R^{11}$ is attached at position 2.

In another aspect, the invention relates to compounds having formula I, wherein x is 1; and $R^{11}$ is attached at position 3.

In another aspect, the invention relates to compounds having formula I, wherein at least one $R^{11}$ is attached at position 2.

In another aspect, the invention relates to compounds having formula I, wherein at least one $R^{11}$ is attached at position 3.

In another aspect, the invention relates to compounds having formula I, wherein $A^1$ has formulae:

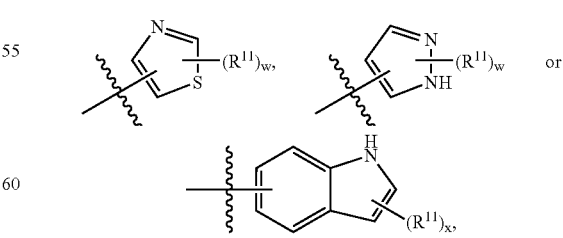

wherein:
w is independently an integer from 0 to 2; and
x is independently an integer from 0 to 3; or
two $R^{11}$ groups form a substituted or unsubstituted ring.

In another aspect, the invention relates to compounds having formula I, wherein $A^1$ has anyone of formulae:

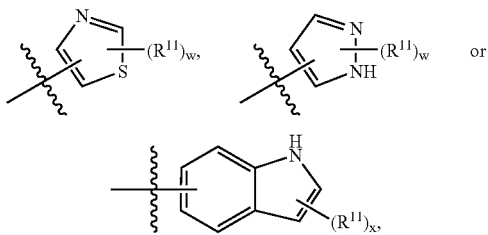

wherein:

$R^{11}$ is independently halogen, $-OR^{12}$, $-NR^{13}R^{14}$, or substituted or unsubstituted alkyl; and $R^{12}$, $R^{13}$ and $R^{14}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or $R^{13}$ and $R^{14}$ are optionally joined with together with the nitrogen to which they are attached to form substituted or unsubstituted heterocycloalkyl, or substituted or unsubstituted 5-membered heteroaryl.

In another aspect, the invention relates to compounds having formula I, wherein $A^1$ is independently

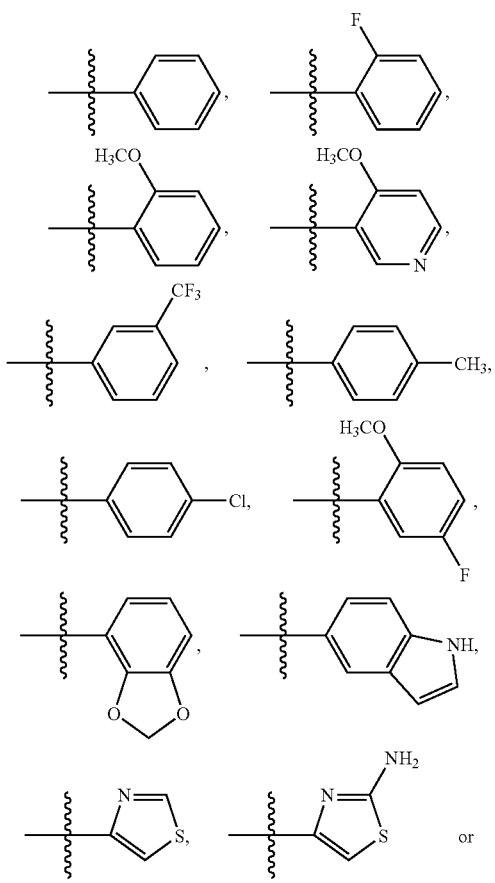

wherein:

$X^1$ is independently $-N-$; and $A^2$ is independently substituted or unsubstituted phenyl, substituted or unsubstituted pyridinyl, or substituted or unsubstituted pyrazinyl.-

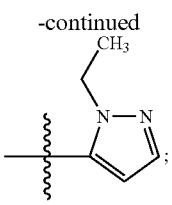

wherein:

$X^1$ is independently $-CR^2=$;

$R^2$ is independently hydrogen; and $A^2$ is independently substituted or unsubstituted phenyl, substituted or unsubstituted pyridinyl, or substituted or unsubstituted pyrazinyl.

In another aspect, the invention relates to compounds having formula I, wherein $A^1$ is independently

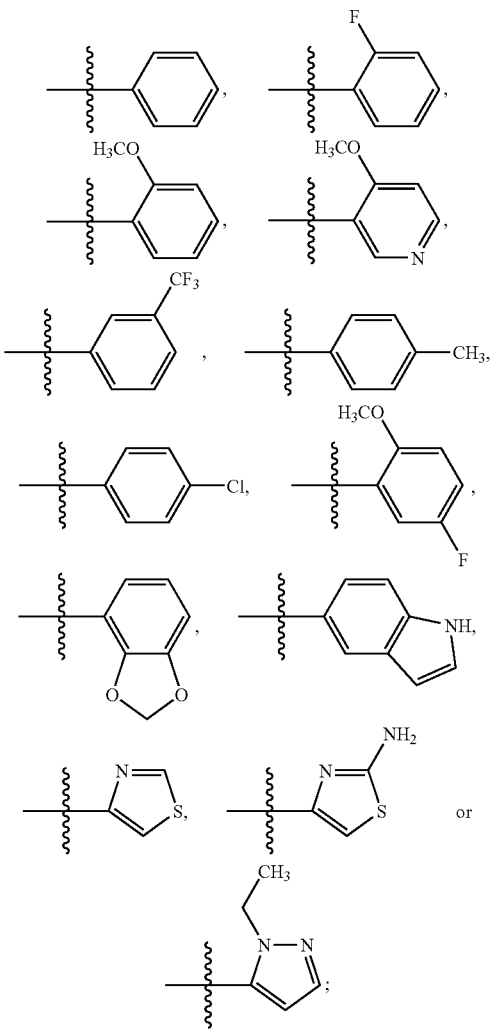

In another aspect, the invention relates to compounds having formula I, wherein:

$A^2$ is substituted or unsubstituted phenyl, substituted or unsubstituted pyridinyl, substituted or unsubstituted pyridinyl N-oxide, substituted or unsubstituted pyrimidinyl, substituted or unsubstituted pyrazinyl, substituted or unsubstituted heteroaryl is substituted or unsubstituted furyl, substituted or unsubstituted thiophenyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted isoxazolyl, substituted or unsubstituted isothiazolyl, substituted or unsubstituted pyridazinyl, substituted or unsubstituted pyrazinyl, substituted or unsubstituted indolizinyl, substituted or unsubstituted indolyl, substituted or unsubstituted isoindolyl, substituted or unsubstituted indolinyl, substituted or unsubstituted benzo[b]furanyl, substituted or unsubstituted benzo[b]thiophenyl, substituted or unsubstituted indazolyl, substituted or unsubstituted benzimidazolyl, substituted or unsubstituted benzthiazolyl, substituted or unsubstituted purinyl, substituted or unsubstituted quinolizinyl, substituted or unsubstituted quinolinyl, substituted or unsubstituted isoquinolinyl, substituted or unsubstituted cinnolinyl, substituted or unsubstituted phthalazinyl, substituted or unsubstituted quinazolinyl, substituted or unsubstituted quinoxalinyl, substituted or unsubstituted naphthyridinyl, or substituted or unsubstituted pteridinyl.

In another aspect, the invention relates to compounds having formula I, wherein $A^2$ has formulae:

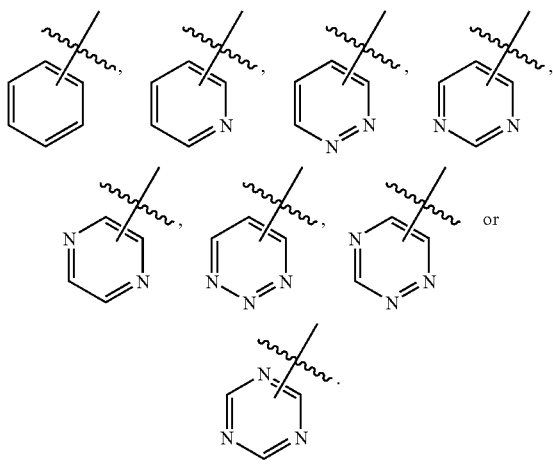

wherein any of the above groups are each independently optionally substituted with 1 to 1 to 5-$(CR^{20}R^{21})_nR^{22}$ groups.

In another aspect, the invention relates to compounds having formula I, wherein $A^2$ has formulae:

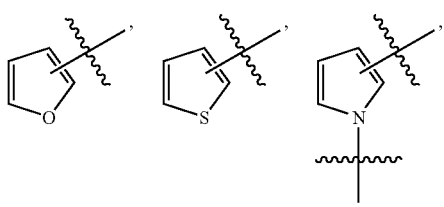

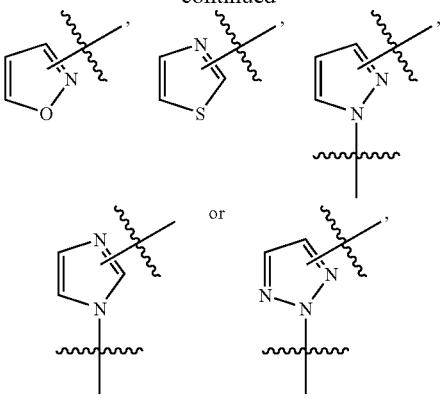

wherein any of the above groups are each independently optionally substituted with 1 to 3-$(CR^{20}R^{21})_nR^{22}$ groups.

In another aspect, the invention relates to compounds having formula I, wherein:

$R^{20}$ and $R^{21}$ are each independently hydrogen, halogen, cyano, nitro, trifluormethyl, difluoromethyl, substituted or unsubstituted alkyl, —$OR^{23}$, —$NR^{24}R^{25}$, or —$CONR^{24}R^{25}$;

$R^{23}$ is independently hydrogen or $(C_1$-$C_6)$alkyl; and $R^{24}$ and $R^{25}$ are each independently hydrogen or $(C_1$-$C_6)$alkyl.

In another aspect, the invention relates to compounds having formula I, wherein:

$R^{20}$ and $R^{21}$ are each independently hydrogen, —$NR^{24}R^{25}$ or —$CONR^{24}R^{25}$; and $R^{24}$ and $R^{25}$ are each independently joined together with the nitrogen to which they are attached, to form substituted or unsubstituted 3- to 7-membered heterocycloalkyl, or substituted or unsubstituted 5-membered heteroaryl.

In another aspect, the invention relates to compounds having formula I, wherein:

$R^{20}$ and $R^{21}$ are each independently hydrogen, —$NR^{24}R^{25}$ or —$CONR^{24}R^{25}$; and $R^{24}$ and $R^{25}$ are each independently joined together with the nitrogen to which they are attached, to form substituted or unsubstituted 3- to 7-membered heterocycloalkyl, wherein the substituted or unsubstituted 3- to 7-membered heterocycloalkyl is substituted or unsubstituted pyrrolidinyl, substituted or unsubstituted imidazolidinyl, substituted or unsubstituted pyrazolidinyl, substituted or unsubstituted piperidinyl, substituted or unsubstituted morpholinyl, substituted or unsubstituted thiomorpholinyl, substituted or unsubstituted thiomorpholinyl sulfone, or substituted or unsubstituted piperazinyl.

In another aspect, the invention relates to compounds having formula I, wherein:

$R^{20}$ and $R^{21}$ are each independently hydrogen, —$NR^{24}R^{25}$ or —$CONR^{24}R^{25}$; and $R^{24}$ and $R^{25}$ are each independently joined together with the nitrogen to which they are attached, to form substituted or unsubstituted 5-membered heteroaryl, wherein the substituted or unsubstituted 5-membered heteroaryl is substituted or unsubstituted pyrrolyl, substituted or unsubstituted imidazolyl, substituted or unsubstituted pyrazolyl.

In another aspect, the invention relates to compounds having formula I, wherein:

$R^{20}$ is hydrogen;

$R^{21}$ is —$OR^{23}$; and $R^{23}$ is hydrogen.

In another aspect, the invention relates to compounds having formula I, wherein:

$R^{22}$ is independently hydrogen, halogen, substituted or unsubstituted alkyl, substituted or unsubstituted heteroalkyl, substituted or unsubstituted heterocycloalkyl, substituted or unsubstituted aryl, substituted or unsubstituted aralkyl, substituted or unsubstituted heteroaryl; substituted or unsubstituted heteroaralkyl, —$OR^{23}$, —$NR^{24}R^{25}$ or —$CONR^{24}R^{25}$;

$R^{23}$ is hydrogen, or substituted or unsubstituted alkyl; and $R^{24}$ and $R^{25}$ are each independently hydrogen, substituted or unsubstituted alkyl, substituted or unsubstituted alkyl-$NR^{29}R^{30}$, substituted or unsubstituted alkyl-$CONR^{29}R^{30}$; and $R^{29}$ and $R^{30}$ are each independently hydrogen, or substituted or unsubstituted alkyl.

In another aspect, the invention relates to compounds having formula I, wherein:

$R^{22}$ is independently —$NR^{24}R^{25}$ or —$CONR^{24}R^{25}$; and $R^{24}$ and $R^{25}$ are each independently joined together with the nitrogen to which they are attached, to form substituted or unsubstituted 3- to 7-membered heterocycloalkyl, or substituted or unsubstituted 5-membered heteroaryl.

In another aspect, the invention relates to compounds having formula I, wherein:

$R^{22}$ is independently —$NR^{24}R^{25}$ or —$CONR^{24}R^{25}$; and $R^{24}$ and $R^{25}$ are each independently joined together with the nitrogen to which they are attached, to form substituted or unsubstituted 3- to 7-membered heterocycloalkyl, wherein the substituted or unsubstituted 3- to 7-membered heterocycloalkyl is substituted or unsubstituted pyrrolidinyl, substituted or unsubstituted imidazolidinyl, substituted or unsubstituted pyrazolidinyl, substituted or unsubstituted piperidinyl, substituted or unsubstituted morpholinyl, substituted or unsubstituted thiomorpholinyl, substituted or unsubstituted thiomorpholinyl sulfone, or substituted or unsubstituted piperazinyl.

In another aspect, the invention relates to compounds having formula I, wherein:

$R^{22}$ is independently —$NR^{24}R^{25}$ or —$CONR^{24}R^{25}$; and $R^{24}$ and $R^{25}$ are each independently joined together with the nitrogen to which they are attached, to form substituted or unsubstituted 5-membered heteroaryl, wherein the substituted or unsubstituted 5-membered heteroaryl is substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted isoxazolyl, substituted or unsubstituted isothiazolyl.

In another aspect, the invention relates to compounds having formula I, wherein:

$R^{22}$ is independently substituted or unsubstituted heterocycloalkyl, substituted or unsubstituted aryl, substituted or unsubstituted aralkyl, substituted or unsubstituted heteroaryl; or substituted or unsubstituted heteroaralkyl.

In another aspect, the invention relates to compounds having formula I, wherein:

$R^{22}$ is independently substituted or unsubstituted heterocycloalkyl, wherein the substituted or unsubstituted heterocycloalkyl is substituted or unsubstituted pyrrolidinyl, substituted or unsubstituted dioxolanyl, substituted or unsubstituted imidazolidinyl, substituted or unsubstituted pyrazolidinyl, substituted or unsubstituted piperidinyl, substituted or unsubstituted morpholinyl, substituted or unsubstituted dithianyl, substituted or unsubstituted thiomorpholinyl, substituted or unsubstituted thiomorpholinyl sulfone, or substituted or unsubstituted piperazinyl.

In another aspect, the invention relates to compounds having formula I, wherein:

$R^{22}$ is independently substituted or unsubstituted aryl, substituted or unsubstituted aralkyl, wherein the substituted or unsubstituted aryl is substituted or unsubstituted phenyl, and the substituted or unsubstituted aralkyl is substituted or unsubstituted benzyl.

In another aspect, the invention relates to compounds having formula I, wherein:

$R^{22}$ is substituted or unsubstituted heteroaryl, wherein the substituted or unsubstituted heteroaryl is substituted or unsubstituted furyl, substituted or unsubstituted thiophenyl, substituted or unsubstituted pyrrolyl, substituted or unsubstituted oxazolyl, substituted or unsubstituted thiazolyl, substituted or unsubstituted imidazolyl, substituted or unsubstituted pyrazolyl, substituted or unsubstituted isoxazolyl, substituted or unsubstituted isothiazolyl, substituted or unsubstituted pyridinyl, substituted or unsubstituted pyridazinyl, substituted or unsubstituted pyrimidinyl, substituted or unsubstituted pyrazinyl, substituted or unsubstituted indolizinyl, substituted or unsubstituted indolyl, substituted or unsubstituted isoindolyl, substituted or unsubstituted indolinyl, substituted or unsubstituted benzo[b]furanyl, substituted or unsubstituted benzo[b]thiophenyl, substituted or unsubstituted indazolyl, substituted or unsubstituted benzimidazolyl, substituted or unsubstituted benzthiazolyl, substituted or unsubstituted purinyl, substituted or unsubstituted quinolizinyl, substituted or unsubstituted quinolinyl, substituted or unsubstituted isoquinolinyl, substituted or unsubstituted cinnolinyl, substituted or unsubstituted phthalazinyl, substituted or unsubstituted quinazolinyl, substituted or unsubstituted quinoxalinyl, substituted or unsubstituted naphthyridinyl, or substituted or unsubstituted pteridinyl.

In another aspect, the invention relates to compounds having formula I, wherein:

$R^{21}$ and $R^{22}$ are joined together with the carbon atom to which they are attached, to form substituted or unsubstituted heterocycloalkyl.

In another aspect, the invention relates to compounds having formula I, wherein:

$R^{21}$ and $R^{22}$ are joined together with the carbon atoms to which they are attached, to form substituted or unsubstituted dioxolanyl or substituted or unsubstituted pyrimidone.

In another aspect, the invention relates to compounds of formula I, having formulae:

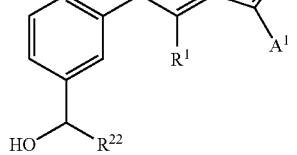

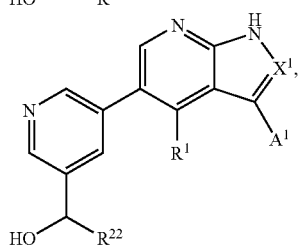

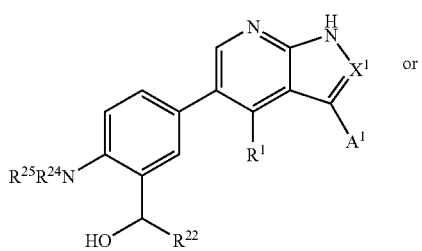
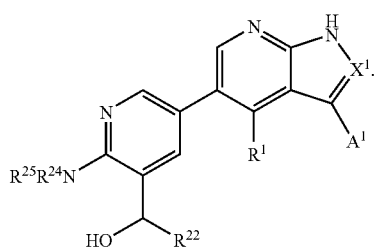
In another aspect, the invention relates to compounds of formula I, having formulae:
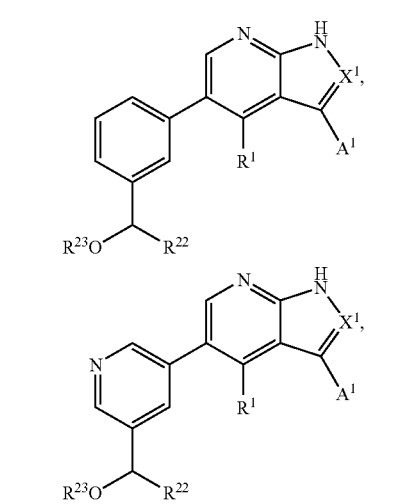
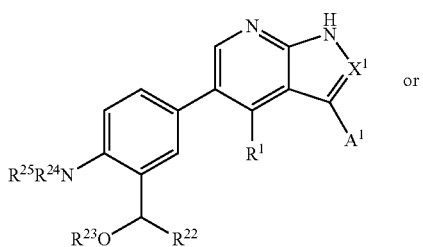
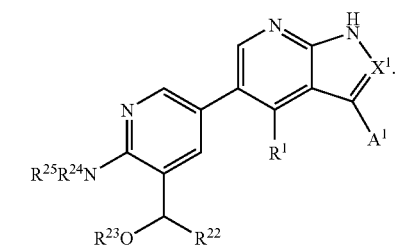
In another aspect, the invention relates to compounds of formula I, having formulae:
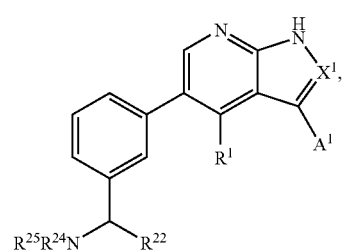
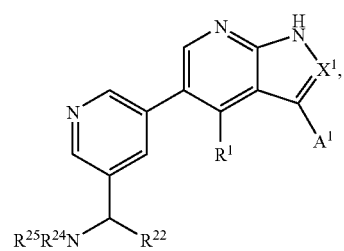
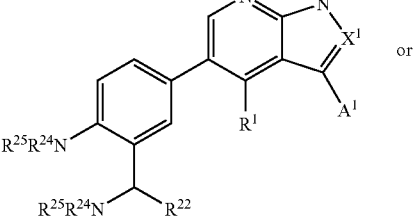
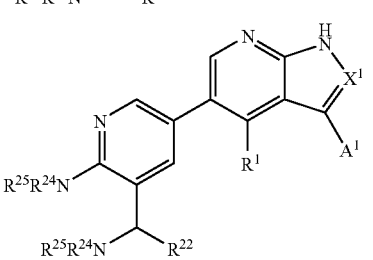
In another aspect, the invention relates to compounds of formula I, having formulae:
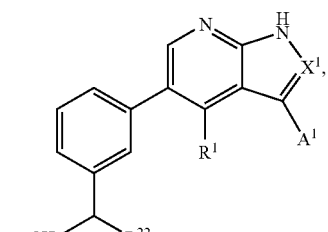
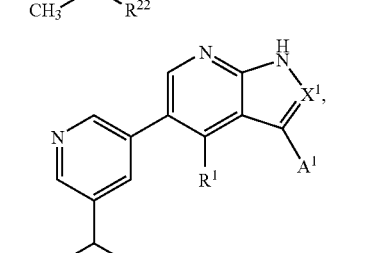

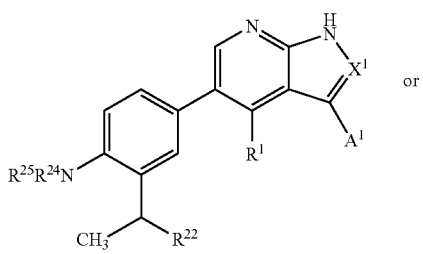 or
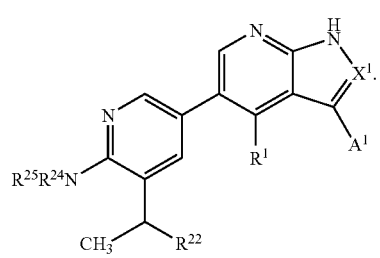
In another aspect, the invention relates to compounds of formula I, having formulae:
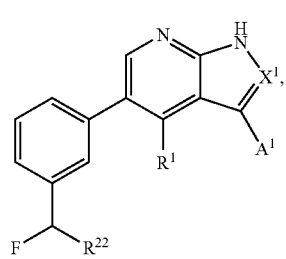
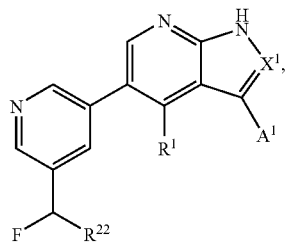
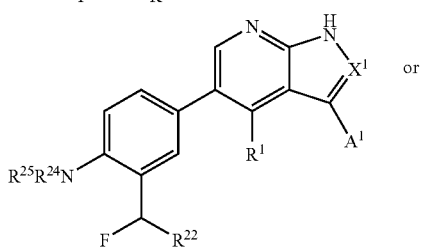 or
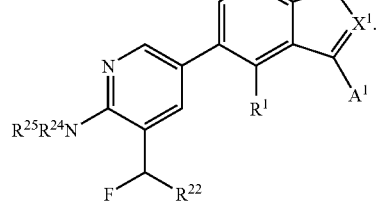
In another aspect, the invention relates to compounds of formula I, having formulae:
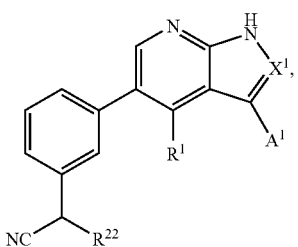
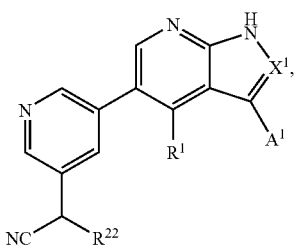
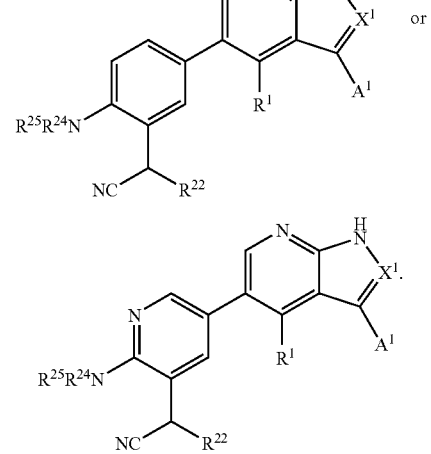 or
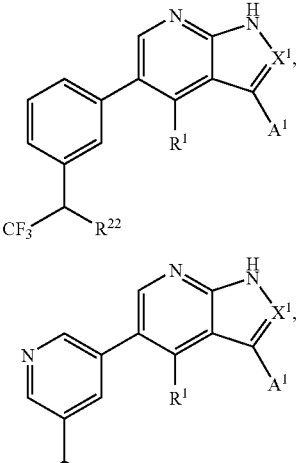
In another aspect, the invention relates to compounds of formula I, having formulae:

-continued
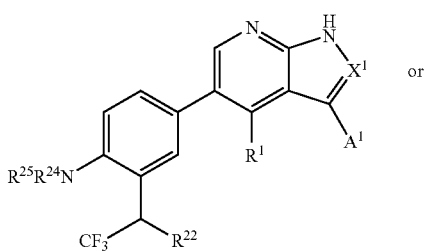 or
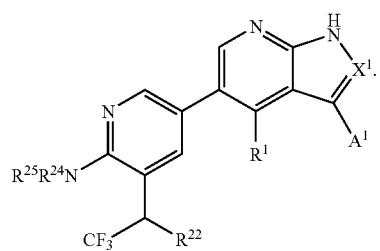
In another aspect, the invention relates to compounds of formula I, having formulae:
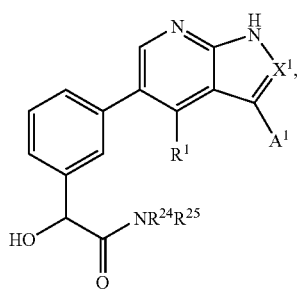
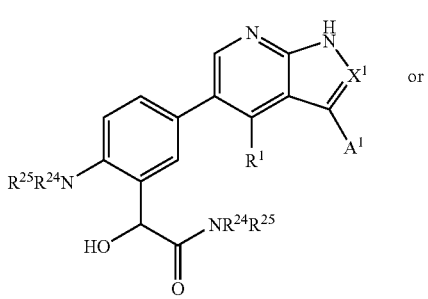 or
-continued
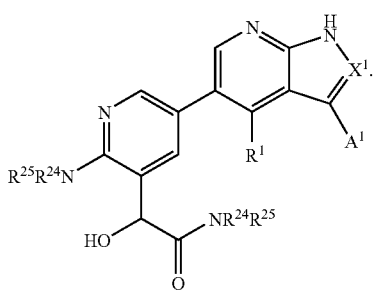
In another aspect, the invention relates to compounds of formula I, having formulae:
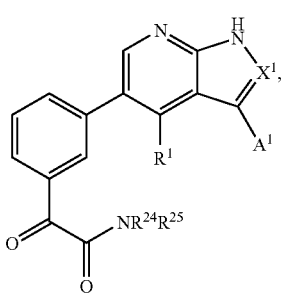
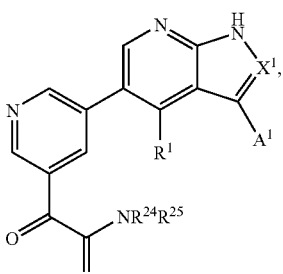
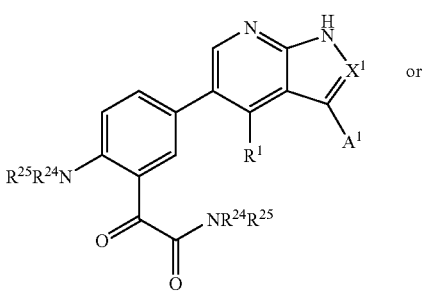 or
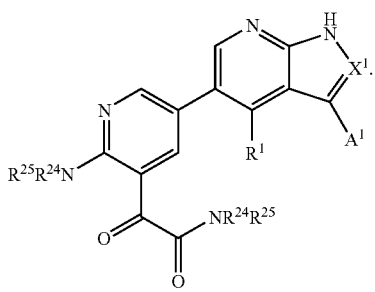

In another aspect, the invention relates to compounds of formula I, having formulae:
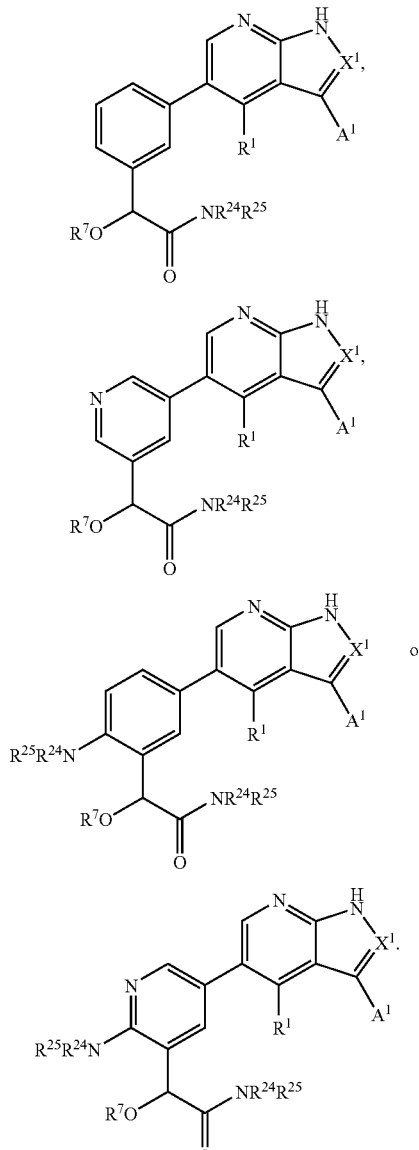
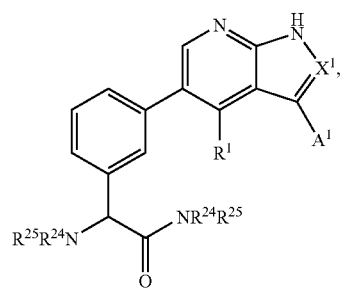
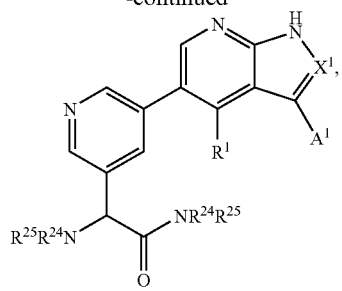
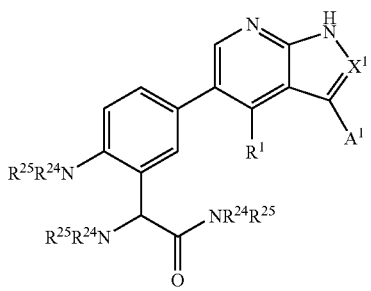
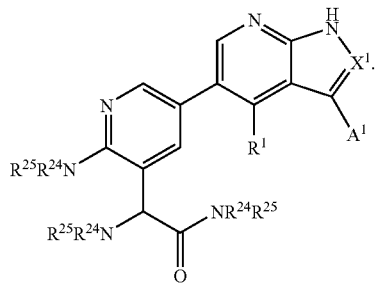
In another aspect, the invention relates to compounds of formula I, having formulae:
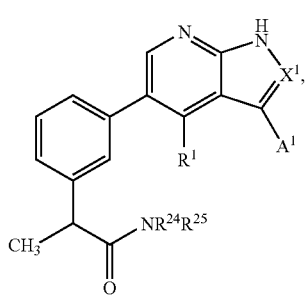
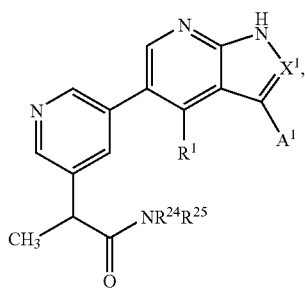

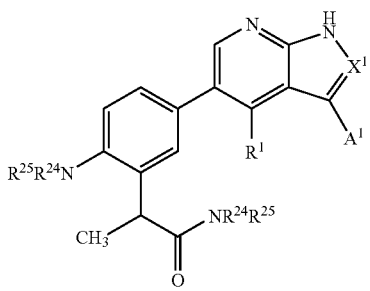 or
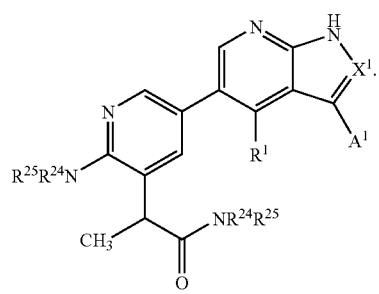
In another aspect, the invention relates to compounds of formula I, having formulae:
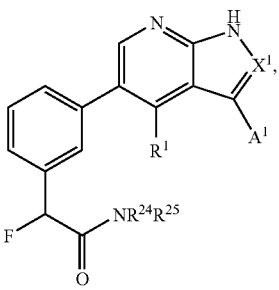
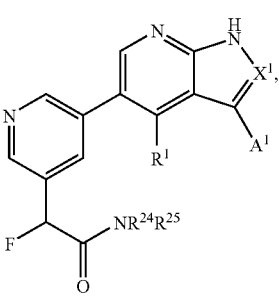
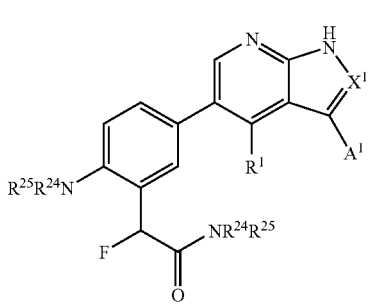 or
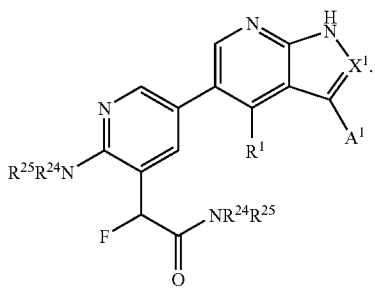
In another aspect, the invention relates to compounds of formula I, having formulae:
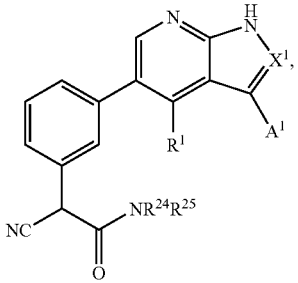
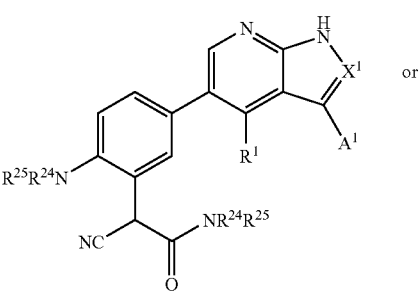 or
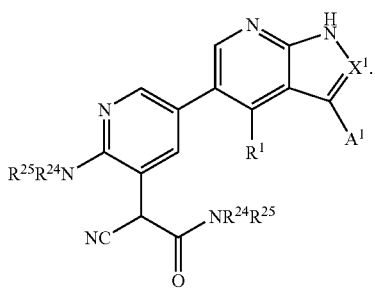

In another aspect, the invention relates to compounds of formula I, having formulae:
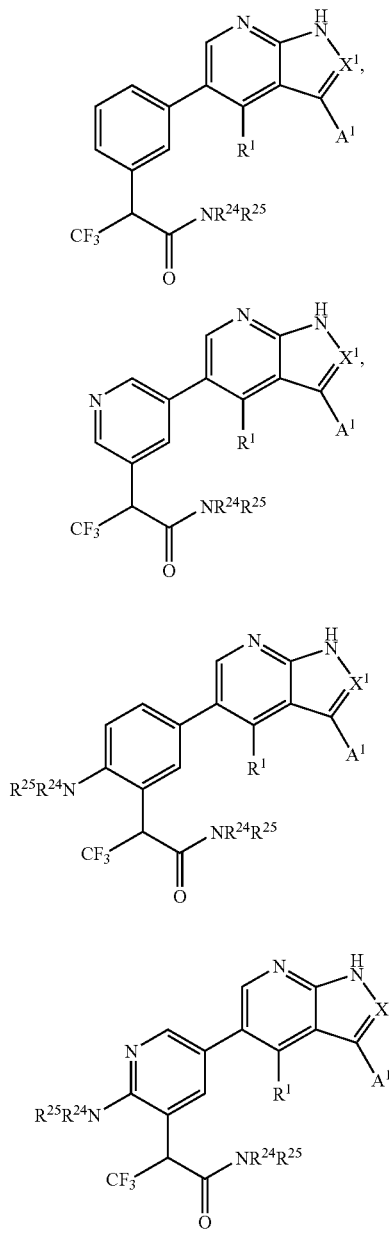
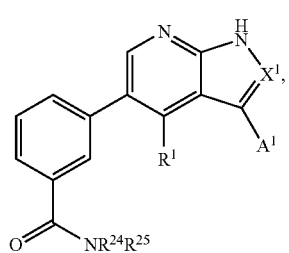
In another aspect, the invention relates to compounds of formula I, having formulae:
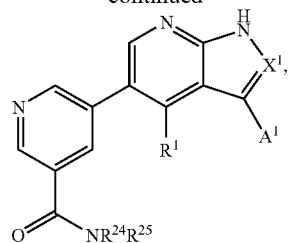
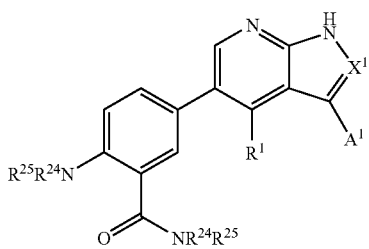
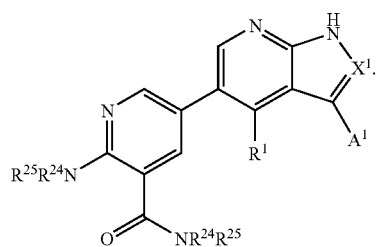
In another aspect, the invention relates to compounds of formula I, having formulae:
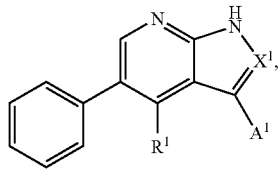
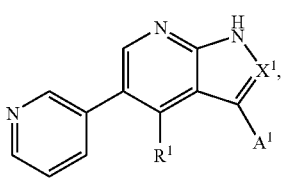
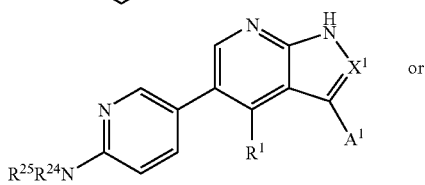
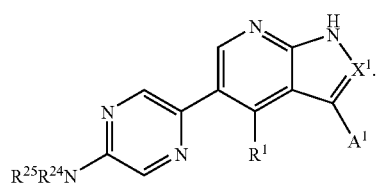

In another aspect, the invention relates to compounds of formula I, having formulae:
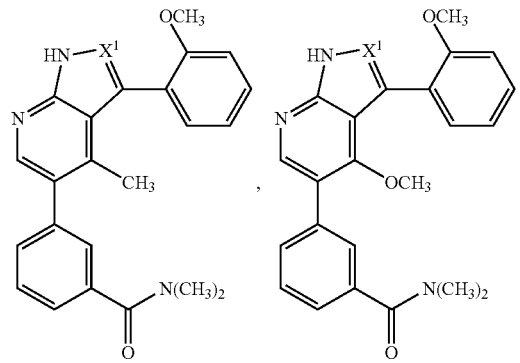
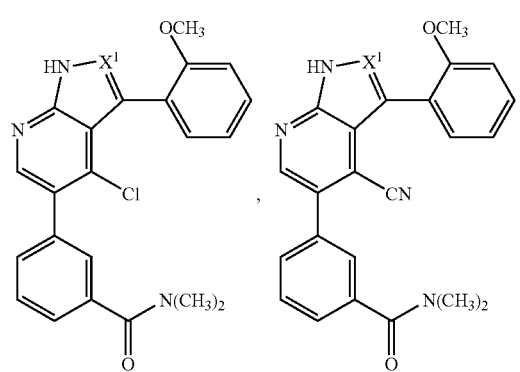
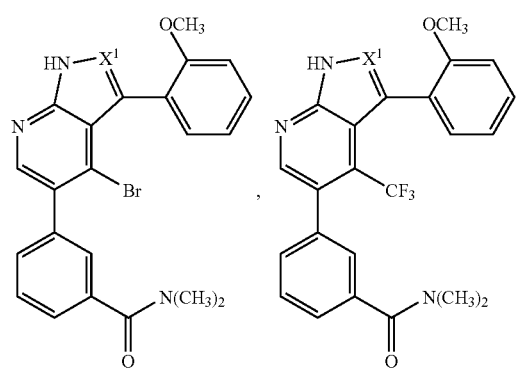
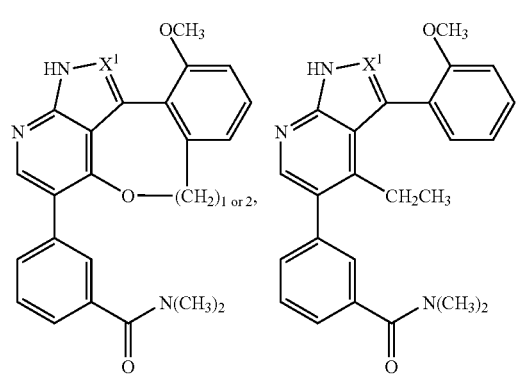
-continued
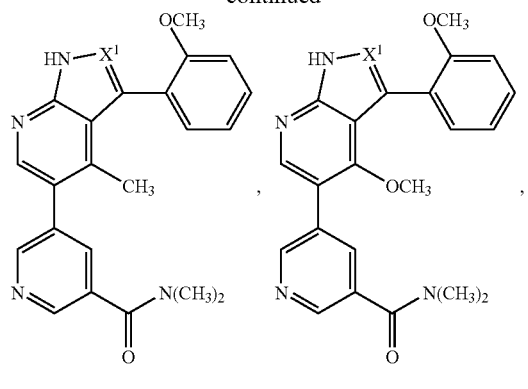
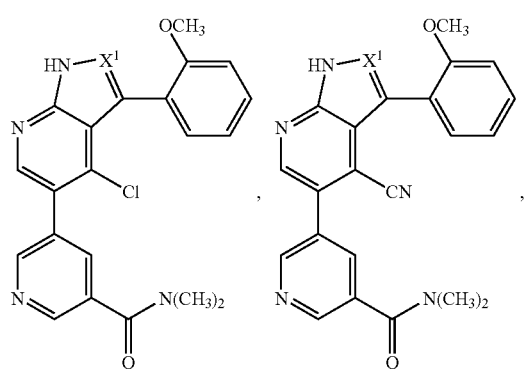
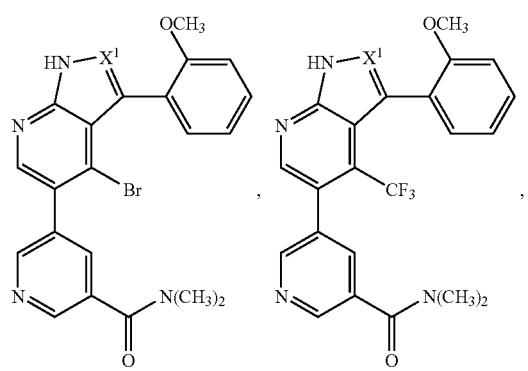
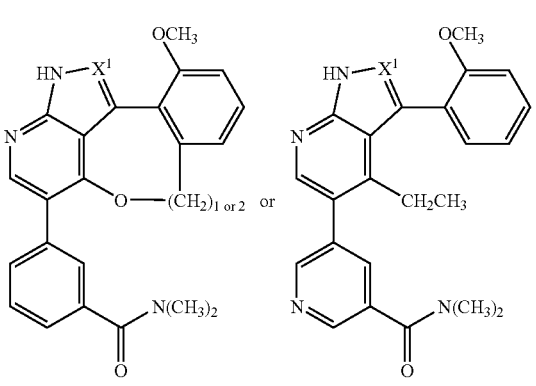

In another aspect, the invention relates to compounds of formula I, having formulae:
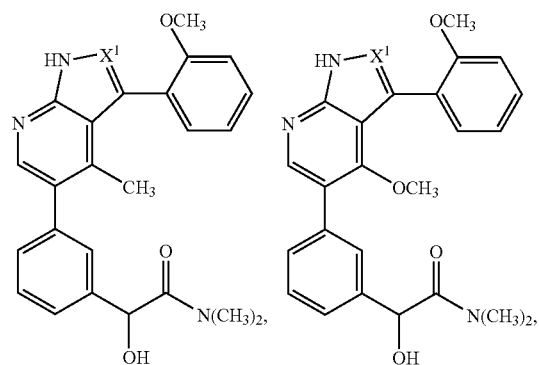
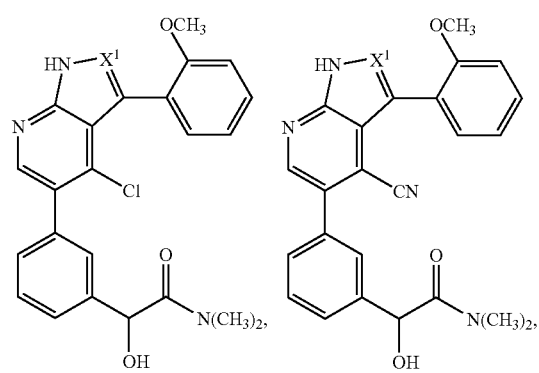
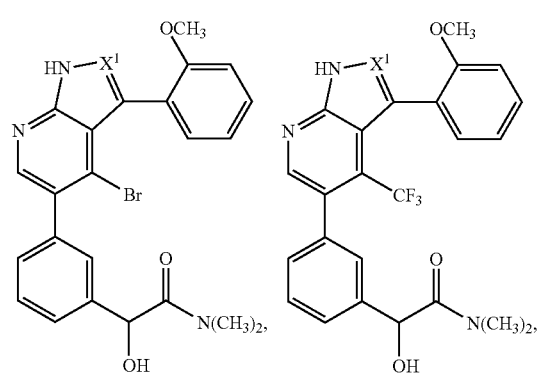
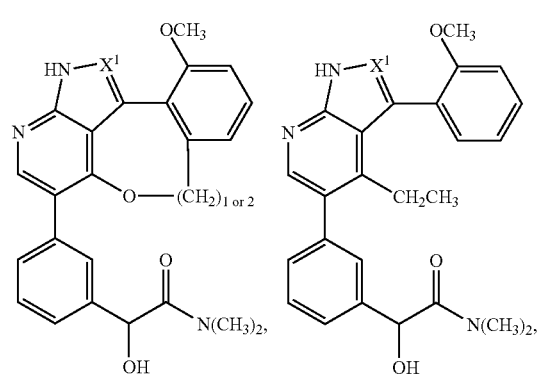
-continued
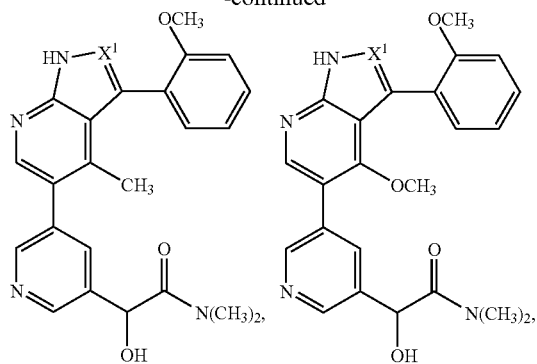
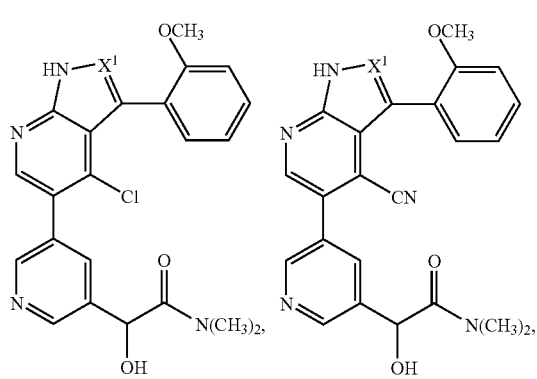
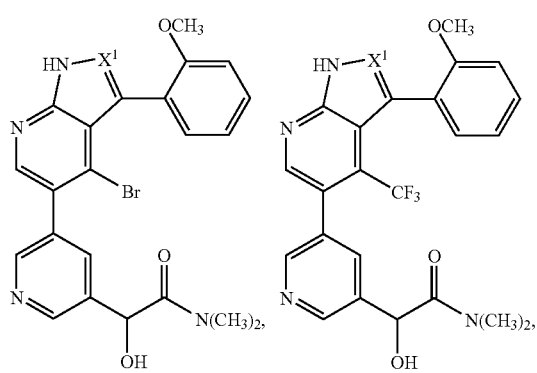
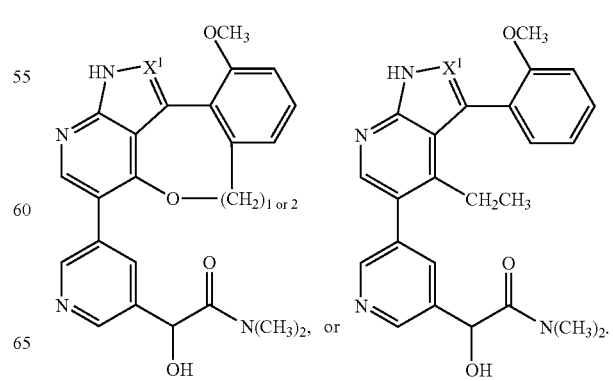

In another aspect, the invention relates to compounds of formula I, having formulae:
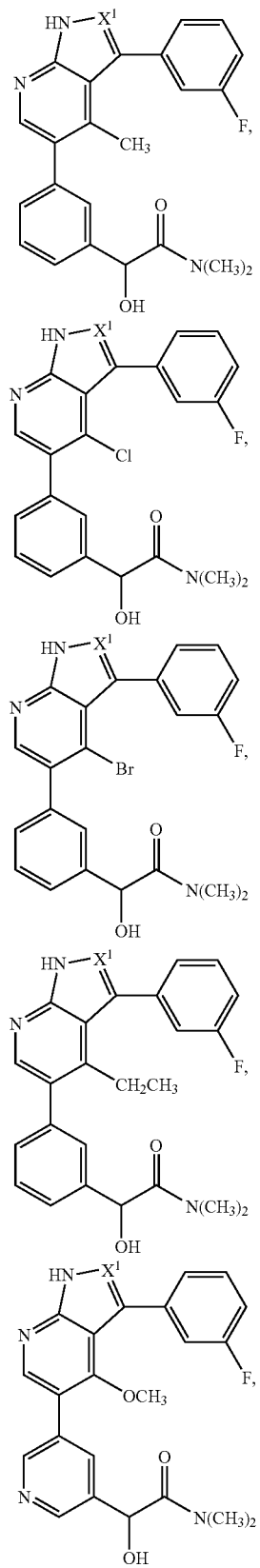
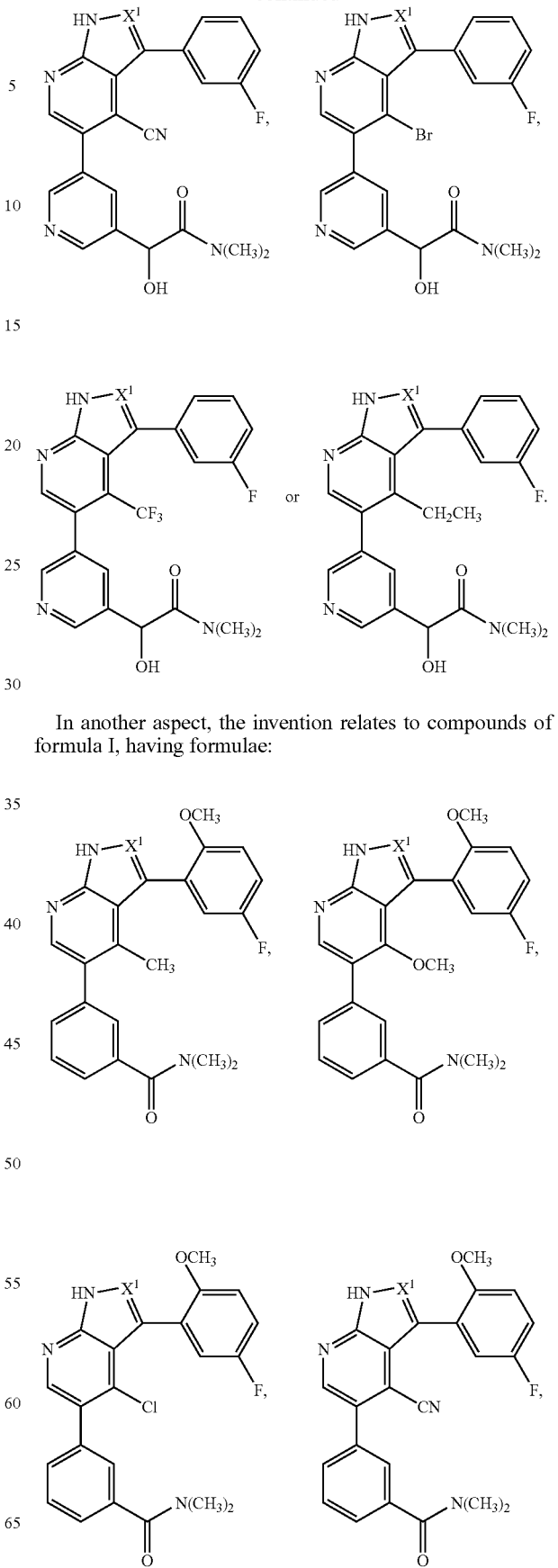
In another aspect, the invention relates to compounds of formula I, having formulae:

-continued
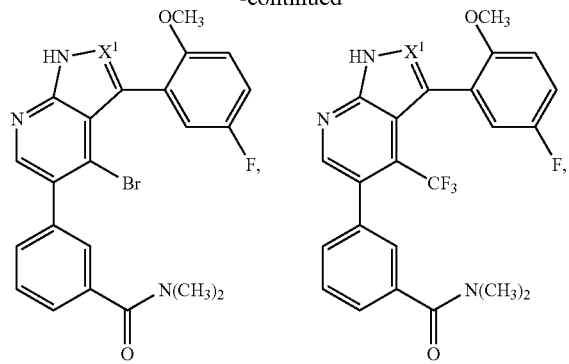
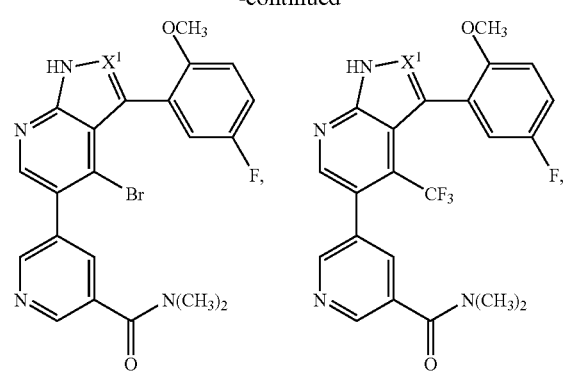
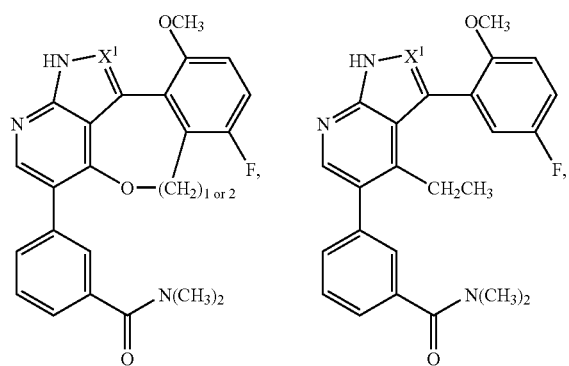
or
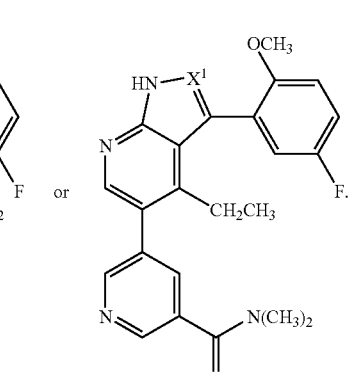
In another aspect, the invention relates to compounds of formula I, having formulae:
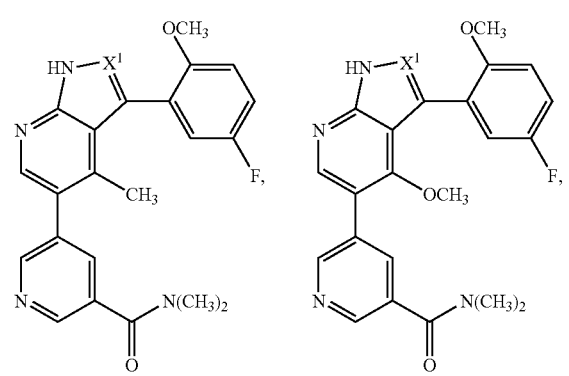
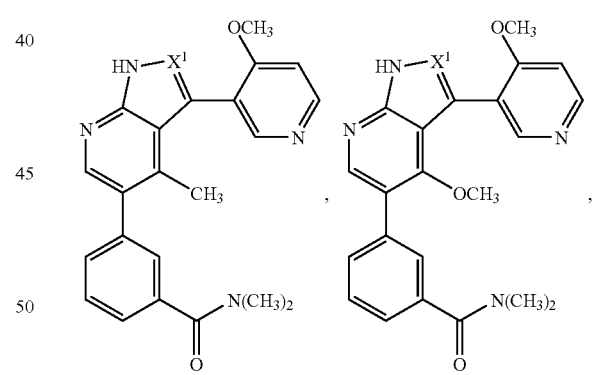
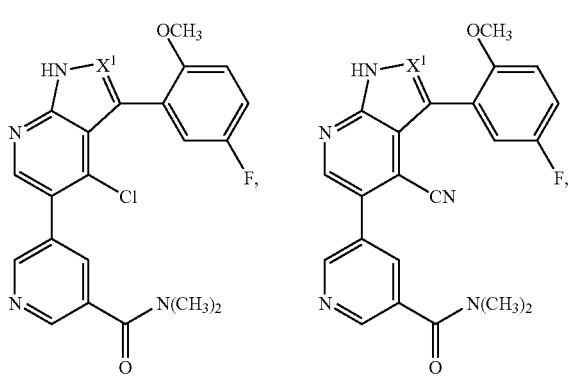
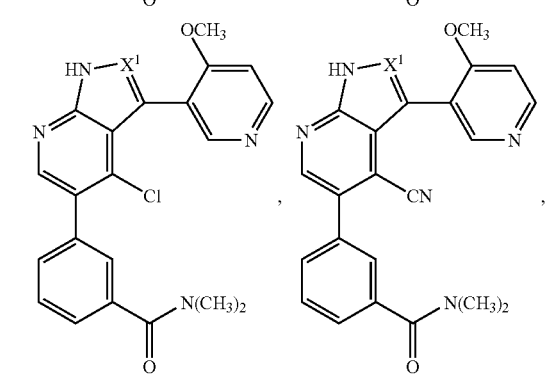

-continued
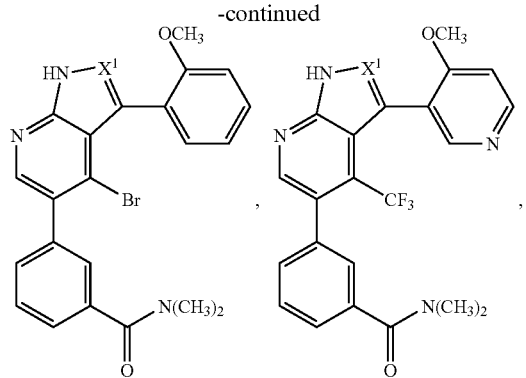
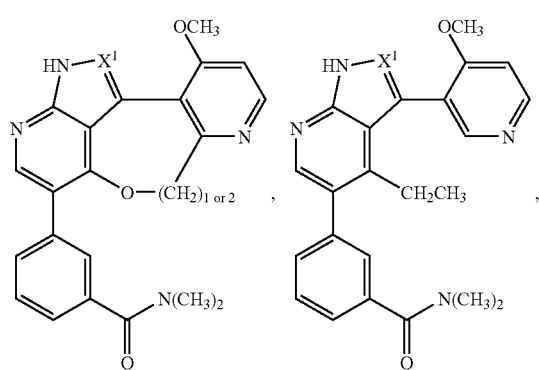
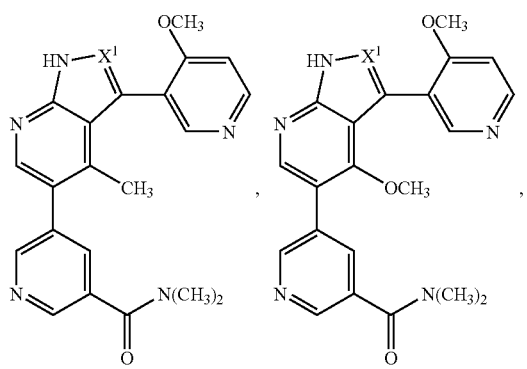
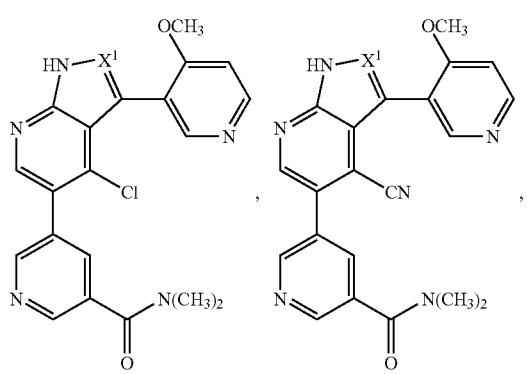
-continued
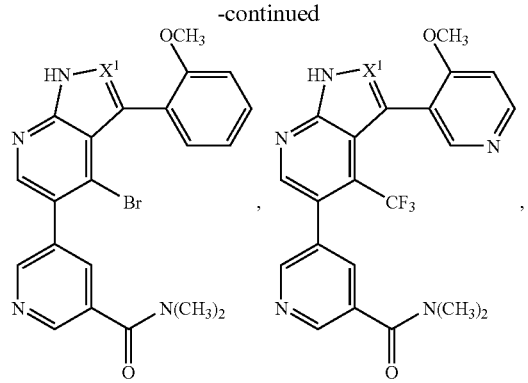
In another aspect, the invention relates to compounds of formula I, having formulae:
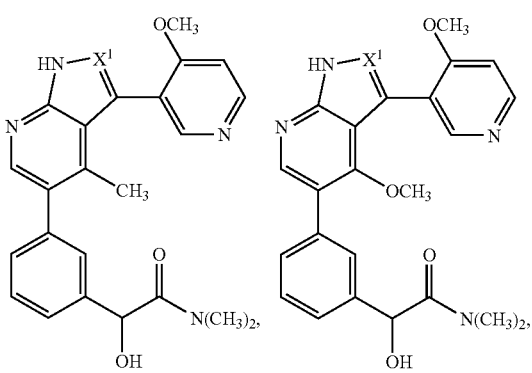
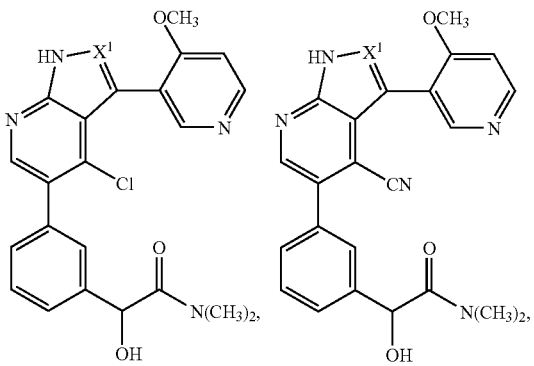

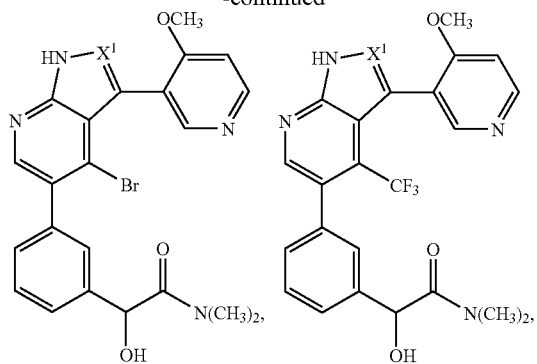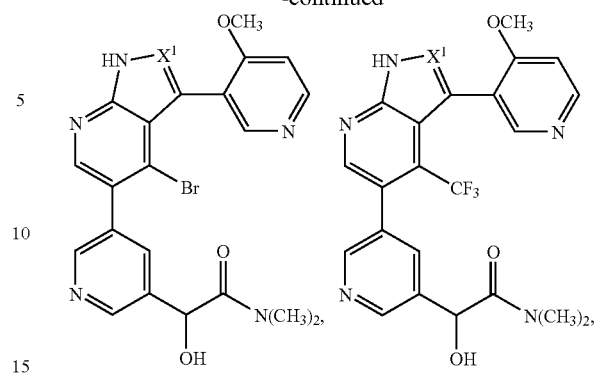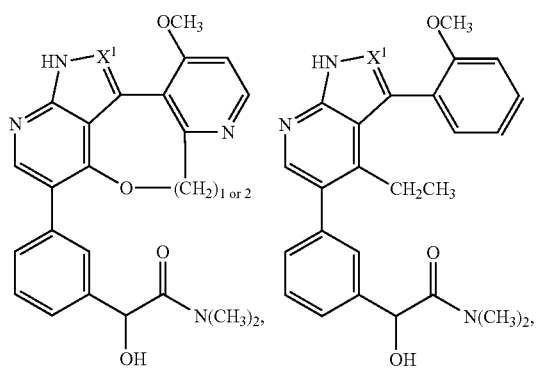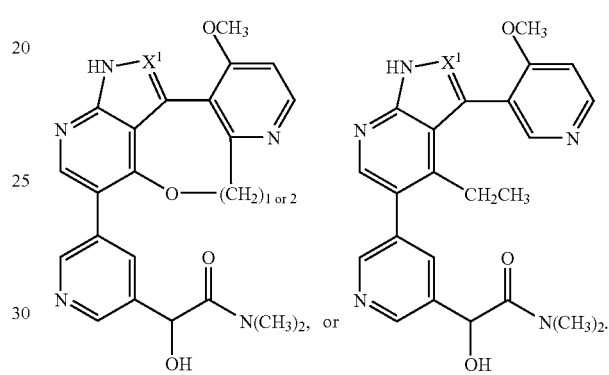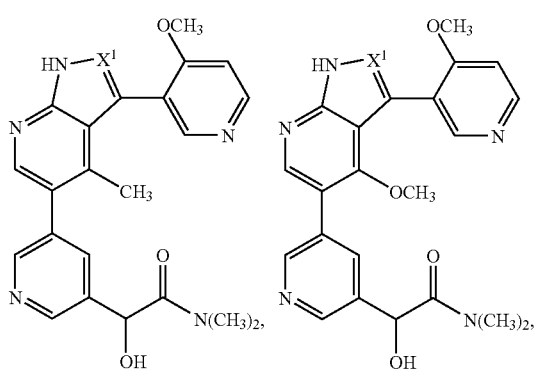
In another aspect, the invention relates to compounds of formula I, having formulae:
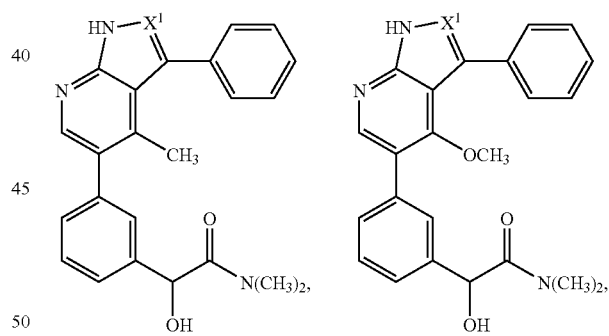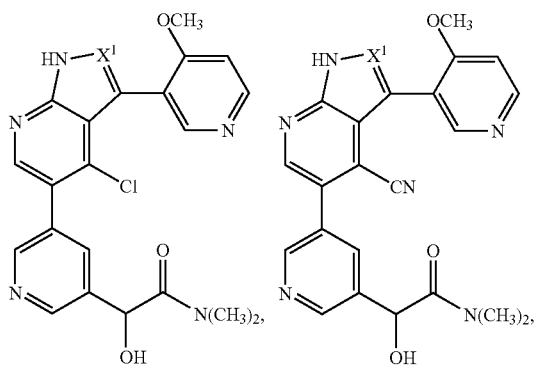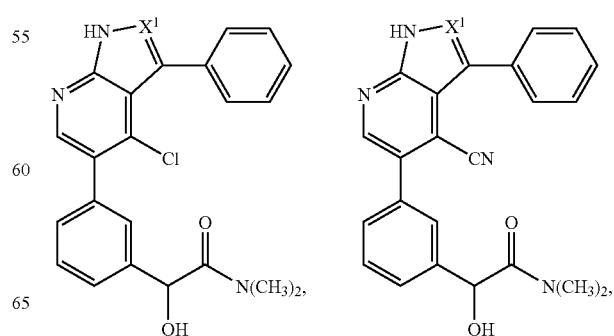

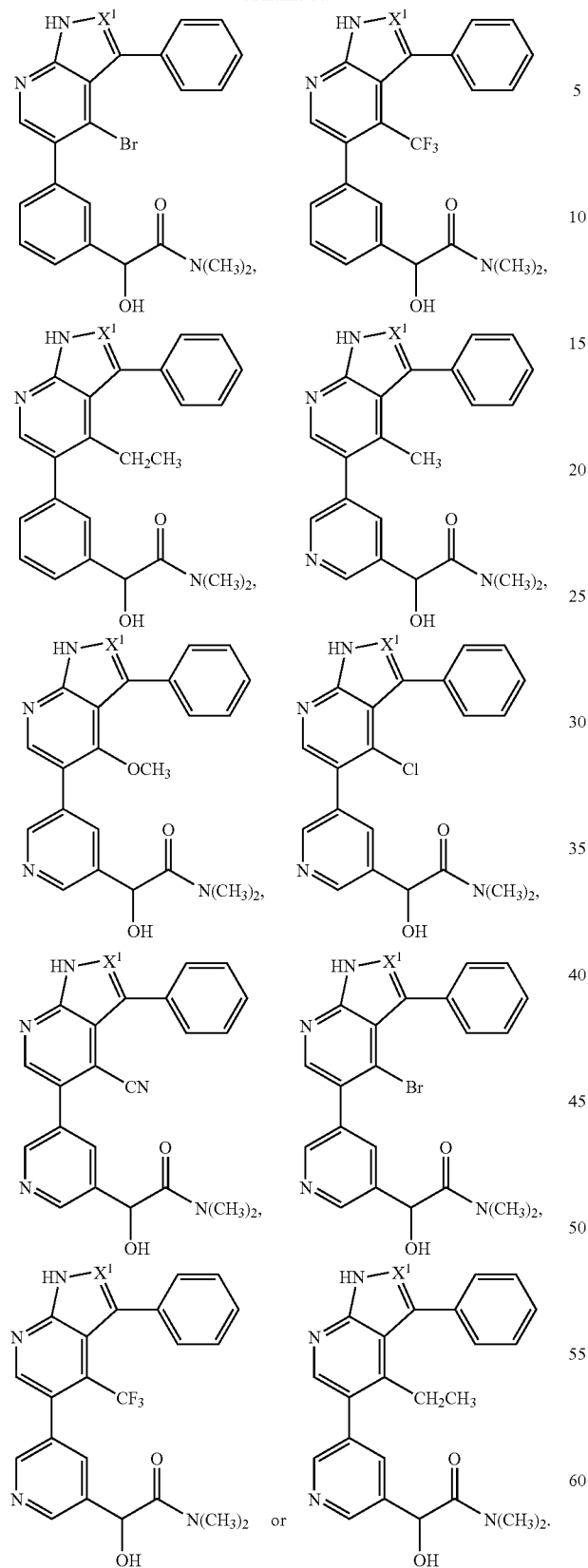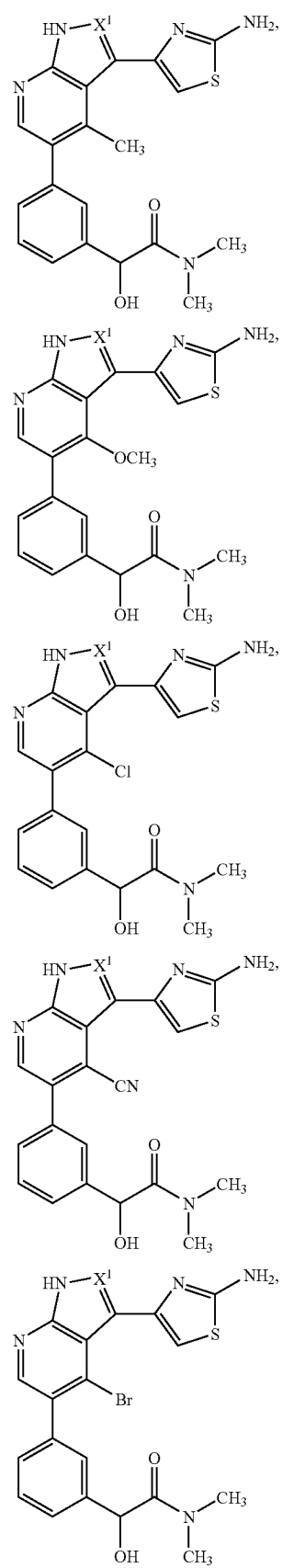
In another aspect, the invention relates to compounds of formula I, having formulae:

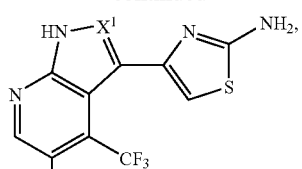
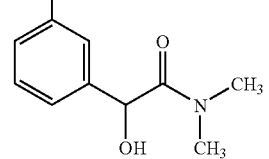
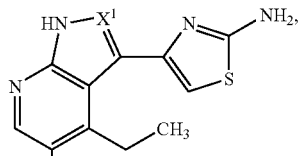
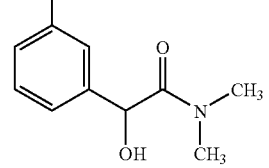
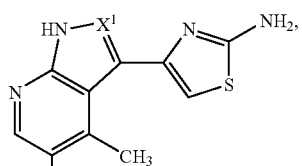
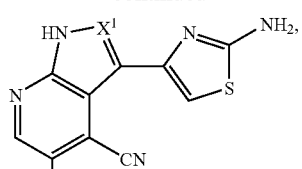
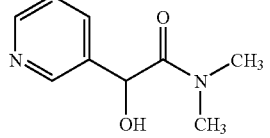
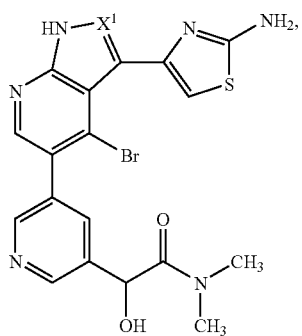
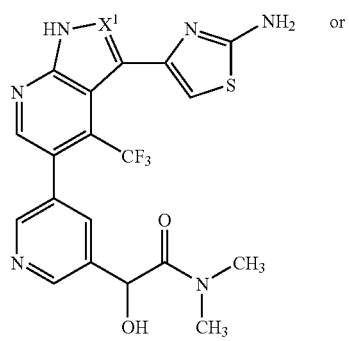 or
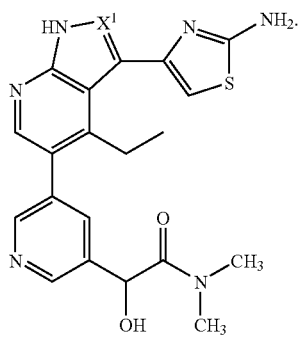

In another aspect, the invention relates to compounds of formula I, having formulae:
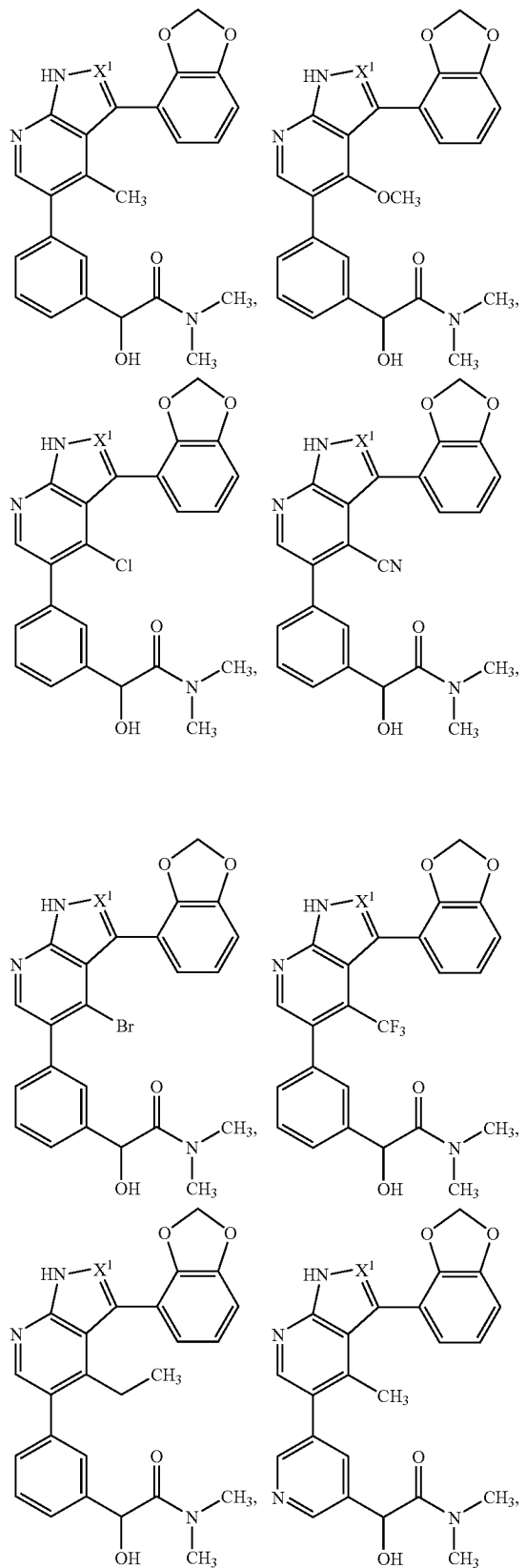
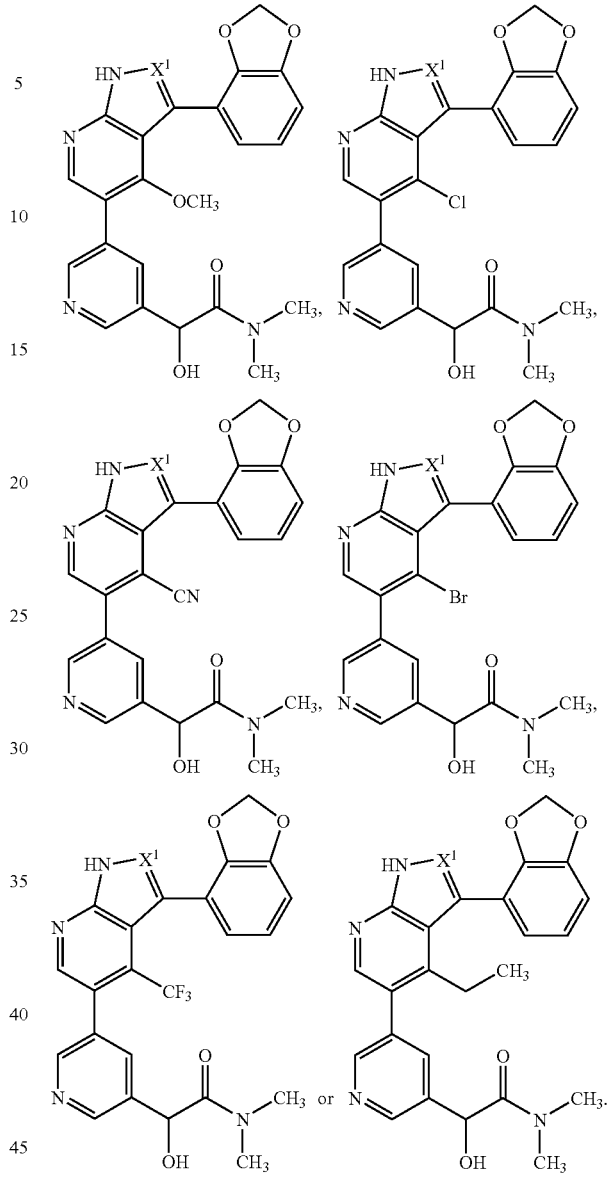
In another aspect, the invention relates to compounds of formula I, having formulae:
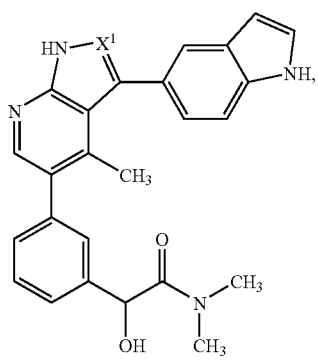

67
-continued

68
-continued

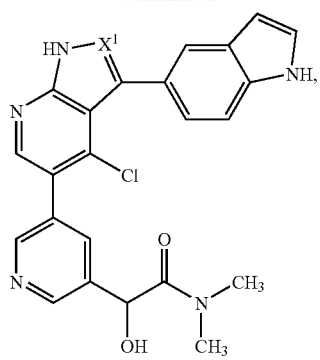
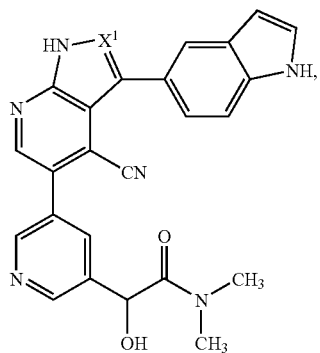
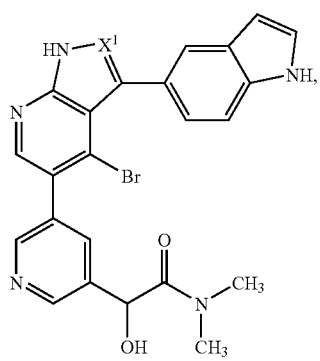
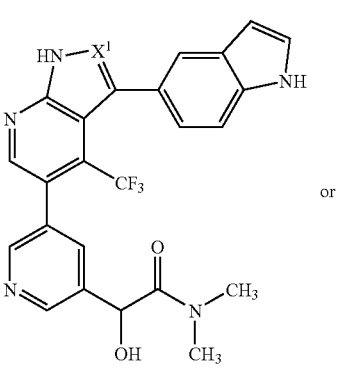
or
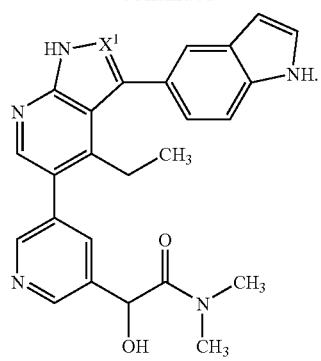
In another aspect, the invention relates to compounds of formula I, having formulae:
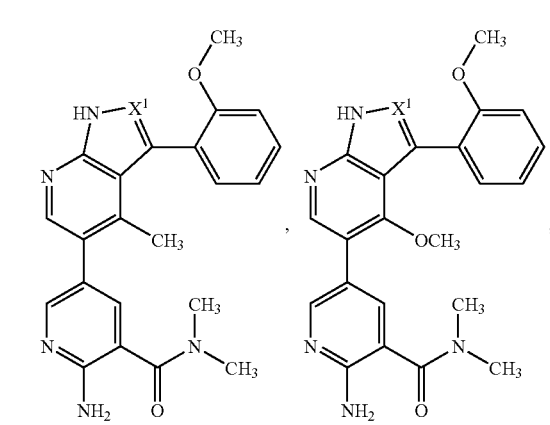
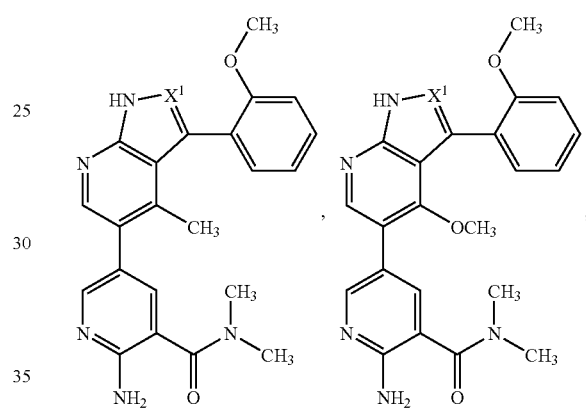
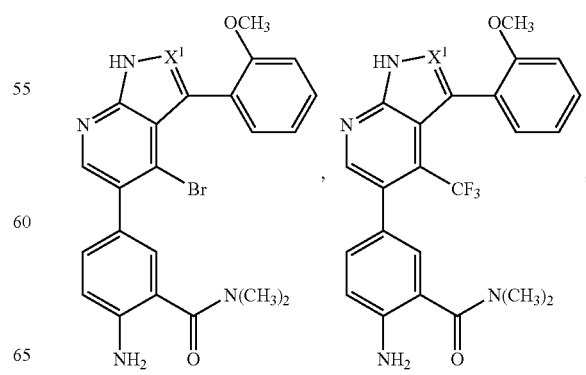

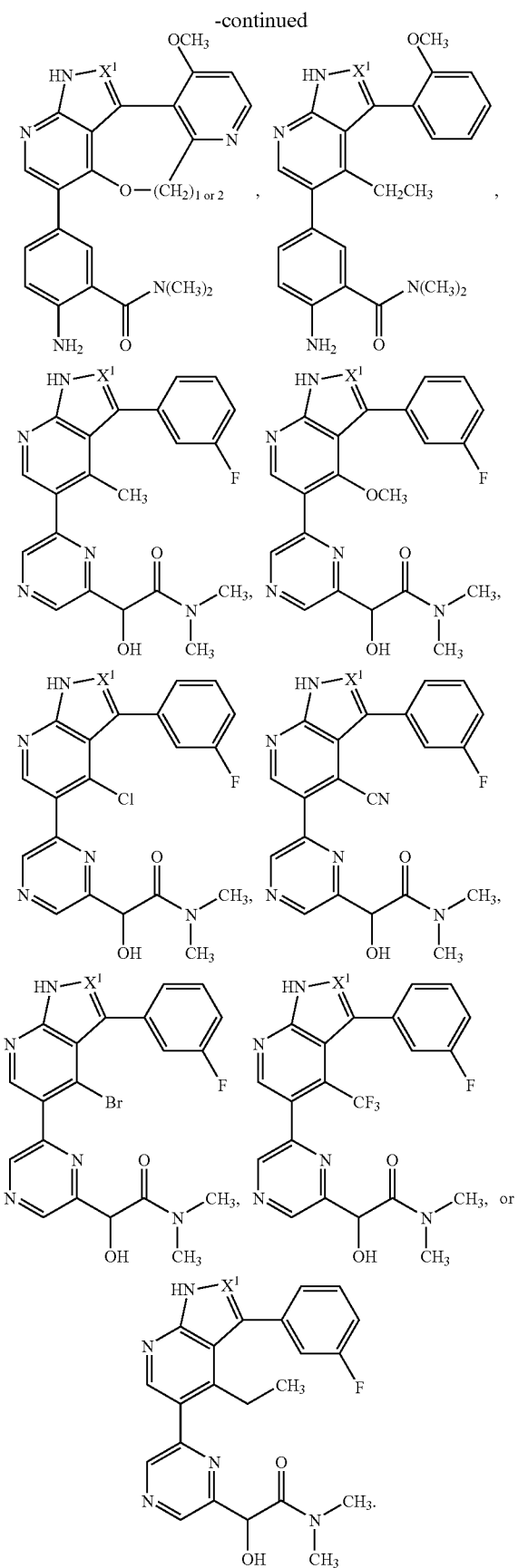

In another aspect, the invention relates methods for modulating the activity of a protein kinase by contacting the protein kinase with a compound described herein.

In another aspect, the invention relates methods for modulating the activity of a protein kinase by contacting the protein kinase with a compound described herein wherein the protein kinase is Abelson tyrosine kinase, Ron receptor tyrosine kinase, Met receptor tyrosine kinase, Fms-like tyrosine kinase-3, Aurora kinases, p21-activated kinase-4 or 3-phosphoinositide-dependent kinase-1 and Janus kinase family.

In another aspect, the invention relates methods for modulating the activity of a protein kinase by contacting the protein kinase with a compound described herein, wherein the protein kinase is a Bcr-Abl kinase having a mutation selected from the group consisting of M244V, L248V, G250E, G250A, Q252H, Q252R, Y253F, Y253H, E255K, E255V, D276G, F311L, T315I, T315N, T315A, F317V, F317L, M343T, M351T, E355G, F359A, F359V, V379I, F382L, L387M, H396P, H396R, S417Y, E459K and F486S.

In another aspect, the invention relates methods for modulating the activity of a protein kinase by contacting the protein kinase with a compound described herein, wherein the protein kinase has a T315I mutation.

In another aspect, the invention relates methods for treating cancer, allergy, asthma, inflammation, obstructive airway disease, autoimmune diseases, metabolic disease, infection, CNS disease, brain tumor, obesity, asthma, hematological disorder, degenerative neural disease, cardiovascular disease, or disease associated with angiogenesis, neovascularization, or vasculogenesis in a subject in need of such treatment, by administering to the subject a therapeutically effective amount of a compound described herein.

In another aspect, the invention relates methods for treating cancer in a subject in need of such treatment, by administering to the subject a therapeutically effective amount of a compound described herein, wherein the cancer is leukemia or myeloproliferative disorder.

In another aspect, the invention relates to pharmaceutical compositions having a pharmaceutically acceptable excipient and a compound described herein.

Synthetic Procedures

In one aspect, methods for synthesizing the compounds described herein are provided. In some embodiments, the compounds described herein can be prepared by the methods described below. The procedures and examples below are intended to illustrate those methods. Neither the procedures nor the examples should be construed as limiting the scope of the present disclosure in any way. Compounds described herein may also be synthesized using standard synthetic techniques known to those of skill in the art or using methods known in the art in combination with methods described herein. In additions, solvents, temperatures and other reaction conditions presented herein may vary according to the practice and knowledge of those of skill in the art.

The starting materials used for the synthesis of the compounds as described herein can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March, ADVANCED ORGANIC CHEMISTRY 4th Ed., (Wiley 1992); Carey and Sundberg, ADVANCED ORGANIC CHEMISTRY $4^{th}$ Ed., Vols. A and B (Plenum 2000, 2001), and Green and Wuts, PROTECTIVE GROUPS IN ORGANIC SYNTHESIS 3d Ed., (Wiley 1999) (all of which are incorporated by reference in their entirety). General methods for the preparation of compounds as disclosed herein may be derived from known reactions in the field, and the reactions may be modified by the use of appropriate reagents and conditions, as would be recognized by the skilled person, for the introduction of the various moieties found in the formulae as provided herein. As a guide the following synthetic methods may be utilized.

Formation of Covalent Linkages by Reaction of an Electrophile with a Nucleophile The compounds described herein can be modified using various electrophiles or nucleophiles to form new functional groups or substituents. The table below entitled "Examples of Covalent Linkages and Precursors Thereof" lists selected examples of covalent linkages and precursor functional groups which yield and can be used as guidance toward the variety of electrophiles and nucleophiles combinations available. Precursor functional groups are shown as electrophilic groups and nucleophilic groups.

| Covalent Linkage Product | Electrophile | Nucleophile |
|---|---|---|
| Carboxamides | Activated esters | Amines/anilines |
| Carboxamides | Acyl azides | Amines/anilines |
| Carboxamides | Acyl halides | Amines/anilines |
| Esters | Acyl halides | Alcohols/phenols |
| Esters | Acyl nitriles | Alcohols/phenols |
| Carboxamides | Acyl nitriles | Amines/anilines |
| Imines | Aldehydes | Amines/anilines |
| Hydrazones | Aldehydes or ketones | Hydrazines |
| Oximes | Aldehydes or ketones | Hydroxylamines |
| Alkyl amines | Alkyl halides | Amines/anilines |
| Esters | Alkyl halides | Carboxylic acids |
| Thioethers | Alkyl halides | Thiols |
| Ethers | Alkyl halides | Alcohols/phenols |
| Thioethers | Alkyl sulfonates | Thiols |
| Esters | Alkyl sulfonates | Carboxylic acids |

-continued

| Covalent Linkage Product | Electrophile | Nucleophile |
|---|---|---|
| Ethers | Alkyl sulfonates | Alcohols/phenols |
| Esters | Anhydrides | Alcohols/phenols |
| Carboxamides | Anhydrides | Amines/anilines |
| Thiophenols | Aryl halides | Thiols |
| Aryl amines | Aryl halides | Amines |
| Thioethers | Aziridines | Thiols |
| Boronate esters | Boronates | Glycols |
| Carboxamides | Carboxylic acids | Amines/anilines |
| Esters | Carboxylic acids | Alcohols |
| Hydrazines | Hydrazides | Carboxylic acids |
| N-acylureas or Anhydrides | Carbodiimides | Carboxylic acids |
| Esters | Diazoalkanes | Carboxylic acids |
| Thioethers | Epoxides | Thiols |
| Thioethers | Haloacetamides | Thiols |
| Ammotriazines | Halotriazines | Amines/anilines |
| Triazinyl ethers | Halotriazines | Alcohols/phenols |
| Amidines | Imido esters | Amines/anilines |
| Ureas | Isocyanates | Amines/anilines |
| Urethanes | Isocyanates | Alcohols/phenols |
| Thioureas | Isothiocyanates | Amines/anilines |
| Thioethers | Maleimides | Thiols |
| Phosphite esters | Phosphoramidites | Alcohols |
| Silyl ethers | Silyl halides | Alcohols |
| Alkyl amines | Sulfonate esters | Amines/anilines |
| Thioethers | Sulfonate esters | Thiols |
| Esters | Sulfonate esters | Carboxylic acids |
| Ethers | Sulfonate esters | Alcohols |
| Sulfonamides | Sulfonyl halides | Amines/anilines |
| Sulfonate esters | Sulfonyl halides | Phenols/alcohols |

Examples of Covalent Linkages and Precursors Thereof

Exemplary Synthesis

Synthesis of Trisubstituted Pyrrolo[2,3-b]pyridines

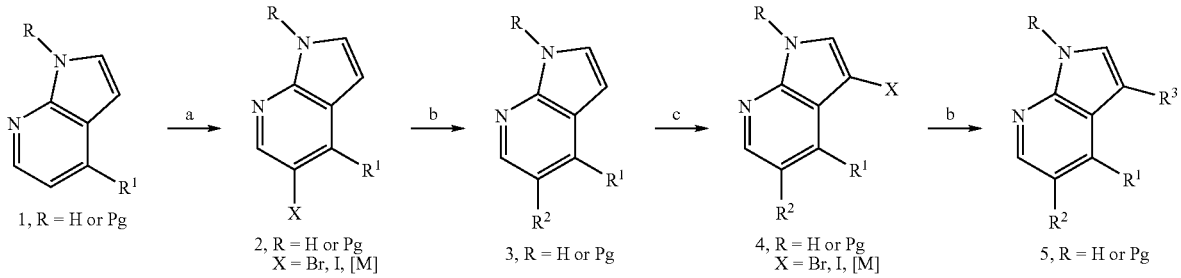

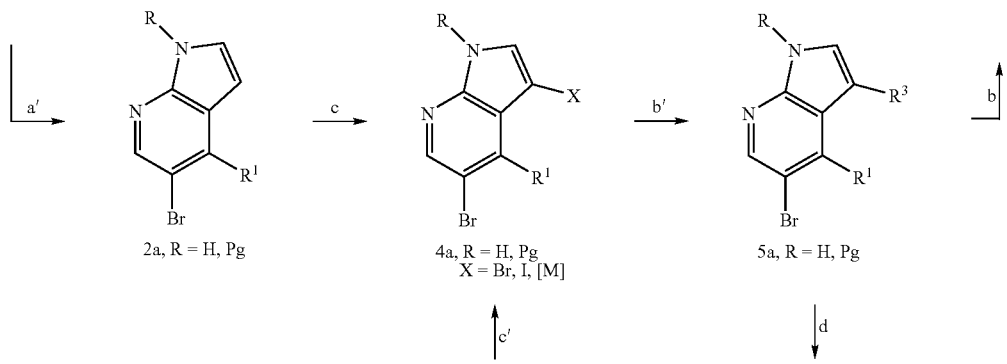

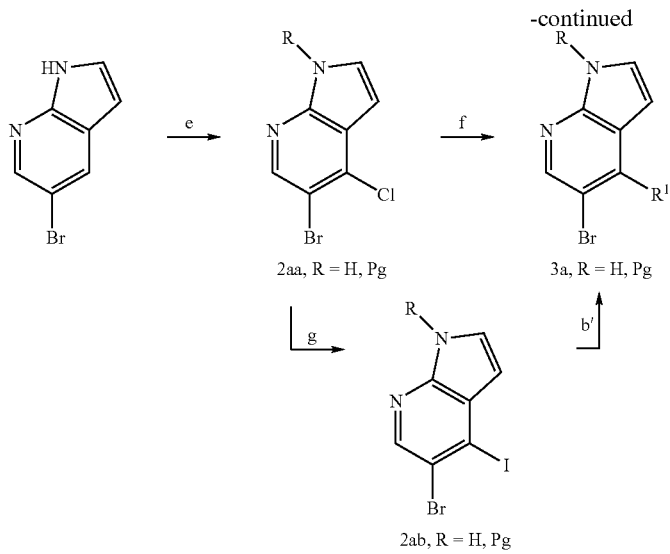
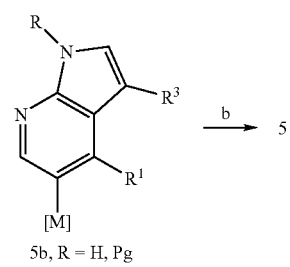

The synthesis of certain compounds of the present invention is outlined in Scheme 1. Many of these compounds can be synthesized conveniently from commercially available 4-substituted pyrrolo[2,3-b]pyridines. Treatment of a 4-substituted pyrrolo[2,3-b]pyridine (1, where $R^1$ is an electron withdrawing substituent, such as chloro, fluoro, or trifluoromethyl, and Pg is a suitable protecting group, typically a triisopropylsilyl group, cf. T. W. Greene, P. G. M. Wuts—*Protective Groups in Organic Synthesis*, 3rd ed., John Wiley & Sons, 1999) with strong base, such as, but not limited to organolithium compounds (e.g. sec-butyl lithium), or lithium amides (e.g. lithium diisopropyl amide or lithium 2,2,6,6-tetramethylpiperidide) and quenching of the resulting anion with electrophiles as outlined in L'Heureux et al. (*Tetrahedron Lett.* 2004, 45, p. 2317), such as, but not limited to N-iodosuccinimide, carbon tetrabromide, or triisopropoxyborane produces 4-substituted pyrrolo[2,3-b]pyridines with suitable synthetic handles in the 5-position [step a in Scheme 1].

Someone skilled in the art will recognize that these synthetic handles allow the introduction of aromatic, olefin, alkyne, or an aliphatic substituents at the 5-position of compound 2 to afford compounds of the general formula 3 [step b in Scheme 1] can be achieved via standard halogen cross-coupling methodologies (cf. F. Diederich, P. J. Stang (eds.)—*Metal-catalyzed Cross-coupling Reactions*, Wiley-VCH, 1998; J. Tsuji—*Palladium Reagents and Catalysts*, John Wiley & Sons, 1995). Couplings of the bromide 2a or iodide (2, X=I) with suitable reagents such as, but not limited to, boronic acids and boronates, organoboranes, trifluoroborate salts (e.g. G. A. Molander, G.-S. Yun, M. Ribagorda, B. Biolatto—*J. Org. Chem.* (2003) 68, 5534; G. A. Molander, B. Biolatto—*J. Org. Chem.* (2003) 68, 4302, organostannanes, organozinc compounds, organomagnesium compounds, olefins or terminal alkynes, either purchased or obtained via protocols well known in the chemical literature and familiar to someone skilled in the art, are carried out in the presence of a suitable transition metal catalyst, for example, but not limited to, suitable palladium compounds, either in the presence of ligands such as, but not limited to, phosphines, diphosphines or arsines or without and, as necessary, organic or inorganic bases, such as tertiary or secondary amines, alkaline carbonates, bicarbonates or phosphates and, as needed, other additives that are known in the chemical literature to assist or accelerate such transformations, such as lithium chloride, copper halides or silver salts. These cross coupling reactions are carried out in suitable solvents such as, but not limited to, THF, dioxane, dimethoxyethane, diglyme, dichloromethane, dichloroethane, acetonitrile, DMF, N-methylpyrrolidone, ethanol, or water, or mixtures of these at temperatures ranging from 25° C. to 200° C. using either no heating, conventional heating or microwave irradiation.

This methodology may be extended to the incorporation of non-carbon based nucleophiles such as, but not limited to alcohols, thiols, primary or secondary amines, heterocyclic rings containing hydrogen attached to a nitrogen atom, that may or may not contain groups which are known in the chemical literature to be suitable protecting groups (examples of such groups can be found in T. W. Greene, P. G. M. Wuts—*Protective Groups in Organic Synthesis*, 3rd ed., John Wiley & Sons, 1999) of alcohols, thiols or amines by methods well known in the chemical literature such as, by way of example, those mentioned in S. V. Ley, A. W. Thomas—*Angew. Chem.* (2003) 115, 5558; J. P. Wolfe, S. Wagaw, J.-F. Marcoux, S. L. Buchwald—*Acc. Chem. Res.* (1998) 31, 805 and J. F. Hartwig—*Acc. Chem. Res.* (1998) 31, 852. As will be apparent to someone with skill in the art, the compounds obtained by such methods can be further elaborated by methods well known in the chemical literature to other compounds claimed under this invention.

In some cases it may be advantageous to achieve cross-couplings to carbon or non-carbon atoms such as all those mentioned above, by first converting a halide 2 (X=Br, I) into an organometallic derivative 2, (X=[M]) such as, by means of example and not limitation, a boronic acid or ester, trifluoroborate salt, organomagnesium, organozinc or an organotin compound. Such compounds are accessible by means of substituting the halide moiety with an appropriate metal or metalloid in which case any functional group present in derivative 2, most notably the ring nitrogen in position 1 of the pyrrolo[2,3-b]pyridine (2, R=Pg), may be protected by a suitable protecting group (examples of such groups can be found in T. W. Greene, P. G. M. Wuts—*Protective Groups in Organic Synthesis*, 3rd ed., John Wiley & Sons, 1999). Introduction of such metals or metalloids can be achieved in a number of ways, such as for example via reductive metallation using metals such alkaline or alkaline earth metals or activated forms of such metals such as, for example, lithium, magnesium or lithium naphthalide or via a metal-halogen exchange reactions using suitable organolithium or organomagnesium compounds such as, but not limited to, n-butyllithium, tert-butyllithium or iso-propylmagnesium chloride or bromide and, as needed, subsequent transmetalation reactions of the organometallic intermediate with a suitable soluble and reactive metal compound such as, by means of example and not limitation, magnesium chloride, magnesium bromide, tri-n-butyltin chloride, trimethyltin chloride, trimethyl borate, triethyl borate, tri-iso-propyl borate, zinc triflate or zinc chloride. Introduction of a boronic acid pinacol ester can also most conveniently be achieved by reacting the halide derivative 2 directly with bis(pinacolato)diboron in the presence of dichloro[1,1'-bis(diphenylphosphino)ferrocene]palladium (II) and suitable bases such as potassium or sodium acetate in solvents such as DMSO, DMF, DMA or N-METHYLPYRROLIDONE at temperatures ranging from 80-160° C. either using conventional heating or microwave irradiation (literature precedent for similar transformations can be found in T. Ishiyama, M. Murata, N. Miyaura—*J. Org. Chem.* (1995) 60, 7508. Methods for conversion of the boronic acid pinacol ester obtained by this method into other boronic acid derivatives such as boronic acids, boronates, or trifluoroborate salts are known in the literature and familiar to the skilled artisan.

In one embodiment of the invention, treatment of a 4-substituted pyrrolo[2,3-b]pyridine (1, where $R^1$ is an electron withdrawing substituent, such as chloro, fluoro, or trifluoromethyl, and R is a suitable protecting group (R=Pg), typically a triisopropylsilyl group, cf. T. W. Greene, P. G. M. Wuts—*Protective Groups in Organic Synthesis,* 3rd ed., John Wiley & Sons, 1999) with strong base, such as, but not limited to organolithium compounds (e.g. sec-butyl lithium), or lithium amides (e.g. lithium diisopropyl amide or lithium 2,2,6,6-tetramethylpiperidide) and quenching of the resulting anion with electrophiles as outlined in L'Heureux et al. (*Tetrahedron Lett.* 2004, 45, p. 2317), such as, but not limited to magnesium chloride, magnesium bromide, tri-n-butyltin chloride, trimethyltin chloride, trimethyl borate, triethyl borate, tri-iso-propyl borate, zinc triflate or zinc chloride, directly lead to a metallated species 2 (X=[M]).

Cross-couplings of the metallated derivatives 2 (X=[M]) with suitable reagents such as, but not limited to, aromatic, heteroaromatic, or olefinic chlorides, bromides, iodides, triflates or acyl halides either purchased or obtained via protocols well known in the chemical literature and familiar to someone skilled in the art, are carried out in the presence of a suitable transition metal catalyst, for example, but not limited to suitable palladium compounds, either in the presence of ligands such as, but not limited to, phosphines, diphosphines, or arsines, or without and, as necessary, organic or inorganic bases, such as tertiary or secondary amines, alkaline carbonates, bicarbonates, or phosphates and, as needed, other additives that are known in the chemical literature to assist or accelerate such transformations, such as lithium chloride, copper halides or silver salts. These cross coupling reactions are carried out in suitable solvents such as, but not limited to, THF, dioxane, dimethoxyethane, diglyme, dichloromethane, dichloroethane, acetonitrile, DMF, N-methylpyrrolidone, or mixtures of these at temperatures ranging from 25° C. to 200° C. using either no heating, conventional heating or microwave irradiation.

More reactive organic nucleophiles 2 that are organometallic compounds containing alkaline or alkaline earth metals, such as, for example, organolithium, organomagnesium or organozinc compounds, can also be coupled to a range of other electrophilic coupling partners such as, by means of example and not limitation, activated olefins (Michael-acceptors), aldehydes, nitriles, aromatic nitro compounds (see, for example, I. Sapountzis, P. Knochel, *J. Am. Chem. Soc.* (2002) 124, 9390, carboxylic acid derivatives, organic disulfides or organic halides. Such couplings can be achieved using either no catalyst or a suitable transition metal catalyst, such as, by means of example and not limitation, a suitable copper, cobalt or iron compound in suitable solvents such as, but not limited to, ether, THF, dioxane, dimethoxyethane, or diglyme, or mixtures of these at temperatures ranging from −100° C. to 100° C. either in the presence of other additives that are known in the chemical literature to assist or accelerate such transformations, such as, for example, lithium halides, amines or diamines or their derivatives or without.

In another embodiment of this invention 2 may be converted into the corresponding acid, either by converting it to a nitrile using cuprous cyanide (cf. G. P. Ellis, T. M. Romney-Alexander, *Chem. Rev.* (1987) 87, 779or using zinc(II)-cyanide in the presence of a suitable palladium catalyst (cf. M. Alternan, M. Hallberg, *J. Org. Chem.* (2000) 65, 7984) and subsequent hydrolysis of the nitrile under acid catalysis or basic conditions in water or a mixture of water and organic solvent(s) such as methanol, ethanol, or acetone by methods that are well known to someone skilled in the art, or by metallation in 5-position by either direct insertion of magnesium under standard Grignard-reaction conditions, transmetallation with iso-propylmagnesium chloride or lithium-bromine exchange with n- or tert-butyllithium and subsequent reaction with dry carbon dioxide, either using 2 directly bearing a suitable protecting group, for example a sulfonamide, on the nitrogen atom in 1-position, again by methods that are well known in the chemical literature.

Formation of amide 5 ($R^2$=—C(O)NR'R") can be achieved using standard methods for amide-formation, either by prior activation of the acid or in situ or via a direct condensation, methods and reagents for which are described in the chemical literature and known to someone skilled in the art. Amide formation may, for example, be achieved by a direct method using suitable coupling reagents such as, but not limited to DCC, PyBOP, HBTU or HATU either in the presence of DMAP or a polymer bound form of DMAP or without.

Alternatively, a bromo derivative 5a ($R^2$=Br) may be directly converted to an amide 5 ($R^2$=—C(O)NR'R") by a procedure analogous or identical to one published by J. Warnberg and M. Larhed (*J. Org. Chem.* (2003) 68, 5750). Treatment of 5a (X=Br) with an amine in the presence of a metal carbonyl, for example, but not limited to, molybdenum hexacarbonyl, a strong organic base, for example, but not limited to, 1,8-diaza[5.4.0]undec-7-ene and a suitable palladium catalyst, for example, but not limited to, trans-di(μ-acetato)bis[ortho-(di-ortho-tolylphosphino)-benzyl]dipalladium(II) (HERRMANN's catalyst) in an aprotic solvent such as, but not limited to THF, acetonitrile, DMF or N-methylpyrrolidone, at temperatures ranging from 80° C. to 180° C. either using conventional heating or microwave irradiation.

Intermediate 3 offers the possibility for functionalization of the 3-position of the pyrrolo[2,3-b]pyridine core. Introduction of various functional groups that are either compounds claimed under this invention or show utility in the synthesis of compounds claimed under this invention can be achieved by methods described in the literature for systems that are reasonably similar as will be immediately apparent to someone with skill in the art, such as, for example structurally related indoles. Such transformations include, by means of example and not limitation, the introduction of iodine and bromine at the 3-position by reacting 3 with a suitable reagent known in the chemical literature to introduce an iodine or bromine atom such as, for example bromine, iodine, N-iodosuccinimide, N-bromosuccinimide, iodine monochloride, phosphorus(v)-bromide in a suitable solvent such as, for example chloroform, acetic acid, ethanol, dichloromethane, dichloroethane, DMF, DMA or N-methylpyrrolidone at temperatures ranging from −50° C. to 200° C. to give rise to the corresponding iodide or bromide 4 (X=I, Br, R=H) (cf M. M. Robinson, B. L. Robinson—*J. Am. Chem. Soc.* (1956) 78, 1247.

Other transformations include the deprotonation of derivatives of 3 bearing, as needed, a suitable protecting group on the nitrogen atom at position 1 (for examples of suitable groups cf. T. W. Greene, P. G. M. Wuts, *Protective Groups in Organic Synthesis,* 3rd ed., John Wiley & Sons, 1999) by means of a sufficiently strong base such as, by means of example, lithium N,N-diisopropylamide, lithium 2,2,6,6-tetramethylpiperidide or organolithium compounds or generation of equivalent metallated derivatives via metal-iodine exchange of the protected iodo compound 4 (X=I) using suitable organomagnesium or organolithium compounds such as, but not limited to, n-butyllithium, tert-butyllithium or iso-propylmagnesium chloride or bromide (transformations similar to those described in M. G. Saulnier, G. W. Gribble, *J. Org. Chem.* (1982) 47, 757 for indole derivatives) and subsequent reaction with a suitable electrophile such as by means of example and not limitation, activated olefins (Michael-acceptors), aldehydes, nitriles, aromatic nitro compounds (see for example I. Sapountzis, P. Knochel, *J. Am. Chem. Soc.* (2002) 124, 9390, carboxylic acid derivatives, organic disulfides or organic halides. Such transformations affording compounds of the general formula 5 can be achieved using either no catalyst or a suitable transition metal catalyst, such as, by means of example and not limitation, a suitable copper, cobalt or iron compound in suitable solvents such as, but not limited to, ether, THF, dioxane, dimethoxyethane, or diglyme, or mixtures of these at temperatures ranging from −100° C. to 100° C. either in the presence of other additives that are known in the chemical literature to assist or accelerate such transformations, such as, for example, lithium halides, amines or diamines or their derivatives or without.

Other transformations include the deprotonation of derivatives of 3 bearing, as needed, a suitable protecting group on the nitrogen atom at position 1 (for examples of suitable groups cf. T. W. Greene, P. G. M. Wuts, *Protective Groups in Organic Synthesis,* 3rd ed., John Wiley & Sons, 1999) by means of a sufficiently strong base such as, by means of example, lithium N,N-diisopropylamide, lithium 2,2,6,6-tetramethylpiperidide or organolithium compounds or generation of equivalent metallated derivatives via metal-iodine exchange of the protected iodo compound 4 (X=I) using suitable organomagnesium or organolithium compounds such as, but not limited to, n-butyllithium, tert-butyllithium or iso-propylmagnesium chloride or bromide (transformations similar to those described in M. G. Saulnier, G. W. Gribble, *J. Org. Chem.* (1982) 47, 757 for indole derivatives) and subsequent transmetalation of the organometallic intermediate with a suitable soluble and reactive metal compound such as, by means of example and not limitation, magnesium chloride, magnesium bromide, tri-n-butyltin chloride, trimethyltin chloride, trimethyl borate, triethyl borate, tri-iso-propyl borate, zinc triflate or zinc chloride. Methods for the conversion of boronic acid derivatives obtained by such methods into other boronic acid derivatives such as boronic acids, boronates, or trifluoroborate salts are known in the literature and familiar to the skilled artisan. Alternatively, a suitably protected derivative of 3 can be converted into the boronic acid derivative 4 (X=B(OH)$_2$) via the corresponding organomercury compound by methods described in N. K. Garg, R. Sarpong, B. M. Stoltz, *J. Am. Chem. Soc.* (2002) 124, 13179. In an extension of this methodology the metallated intermediates obtained from 3 or 4, which may contain a nitrogen protecting group as needed, by the methods described above may also be utilized in reactions with suitable disulfides to give rise to the corresponding thioether 5 ($R^3$=SR).

Alternatively, similar boronic acid derivatives 4 can be obtained from 3 by introduction of iodine at the 3-position as described above and subsequent reaction of the iodo derivative obtained with bis(pinacolato)diboron in the presence of dichloro[1,1'-bis(diphenylphosphino)ferrocene]palladium (II) and suitable bases such as potassium or sodium acetate in solvents such as DMSO, DMF, DMA or N-methylpyrrolidone at temperatures ranging from 50-120° C. either using conventional heating or microwave irradiation (literature precedent for similar transformations can be found in T. Ishiyama, M. Murata, N. Miyaura, *J. Org. Chem.* (1995) 60, 7508. As needed the nitrogen atom in 1-position may be protected by means of a suitable protecting group (for examples of suitable groups cf. T. W. Greene, P. G. M. Wuts, *Protective Groups in Organic Synthesis,* 3rd ed., John Wiley & Sons, 1999), for example as a sulfon-amide, such as, for example, a 4-toluoylsulfonamide.

The organomagnesium, organozinc, organoboron or organotin compounds 4 obtained by any one of such methods can be coupled with suitable reagents such as, but not limited to aromatic, heteroaromatic or olefinic chlorides, bromides, iodides or triflates, either purchased or obtained via protocols well known in the chemical literature and familiar to someone skilled in the art via standard cross-coupling methodologies (cf. F. Diederich, P. J. Stang (eds.), *Metal-catalyzed Cross-coupling Reactions,* Wiley-VCH, 1998; J. Tsuji, *Palladium Reagents and Catalysts,* John Wiley & Sons, 1995). Such coupling reactions are precedented in the chemical literature (cf. M. Alvarez, D. Fernández, J. A. Joule, *Synthesis* (1999) 615) and are carried out in the presence of a suitable transition metal catalyst, for example, but not limited to suitable palladium compounds, either in the presence of ligands such as, but not limited to, phosphines, diphosphines or arsines or without and, as necessary, organic or inorganic bases, such as tertiary or secondary amines, alkaline carbonates, bicarbonates or phosphates and, as needed, other additives that are known in the chemical literature to assist or accelerate such transformations, such as lithium chloride, copper halides or silver salts. These cross coupling reactions are carried out in suitable solvents such as, but not limited to, THF, dioxane, dimethoxyethane, diglyme, dichloromethane, dichloroethane, acetonitrile, DMF, N-methylpyrrolidone, ethanol, or water, or mixtures of these at temperatures ranging from 25° C. to 200° C. using either no heating, conventional heating or microwave irradiation. Such methodologies give access to compounds of the general formula 5.

Other transformations well known in the chemical literature and familiar to the skilled artisan include Friedel-Crafts-acylations that can be followed By Baeyer-Villiger-type oxidations giving rise to ketones and esters, respectively. Esters obtained in such manners can be hydrolized to afford the corresponding 3-hydroxy-pyrrolo[2,3-b]pyridine. 3-hydroxy-pyrrolo[2,3-b]pyridines which may, as needed, bear a suitable protecting group on the nitrogen atom at position 1 (for examples of suitable groups cf. T. W. Greene, P. G. M. Wuts, *Protective Groups in Organic Synthesis,* 3rd ed., John Wiley & Sons, 1999) can be utilized in the formation of compounds claimed under this invention in which Q is oxygen by methods known in the chemical literature, such as for example alkylation using an organic halide in the presence of a sufficiently strong base such as, for example, sodium hydride either in the presence of silver salts or without. 3-Hydroxy-pyrrolo[2,3-b]pyridines are also accessible utilizing the corresponding organoboron compounds 4 utilizing methods well known in the chemical literature, such as, for example treatment with oxidants such as hydrogen peroxide, or reaction with suitable oxygen based nucleophiles in the presence of suitable copper compounds such methods as, by way of example, those mentioned in S. V. Ley, A. W. Thomas—*Angew. Chem.* (2003) 115, 5558.

A variety of $R^1$ groups can be accessed at any stage of the synthesis from common precursors containing leaving groups in the 4-position of pyrrolo[2,3-b]pyridines, such as, but not limited to fluoro, chloro, bromo, methoxy, and methylsulfonyl substituents. Nucleophilic aromatic substitution may be affected under acidic or basic conditions in suitable solvents such as, but not limited to, THF, dioxane, dimethoxyethane, diglyme, dichloromethane, dichloroethane, acetonitrile, DMF, N-methylpyrrolidone, ethanol, or water, or mixtures of these at temperatures ranging from 25° C. to 200° C. using either no heating, conventional heating or microwave irradiation. Commercially available or synthesized building blocks such as amines, alkoxides, alcohols, thiols, carbon based nucleophiles such as malonates may be used to access a wide range of pyrrolo[2,3-b]pyridines 5. The skilled artisan will recognize that depending on the nature of the $R^1$ substituent it may be advantageous to introduce substituents at different stages utilizing intermediates 1 through 5.

Alternatively $R^1$ may be iodine which can be utilized as a functional handle. Interconversion of a chloro substituent to an iodo substituent may be achieved at any suitable stage of the synthesis. Treatment of I a ($R^1$=Cl) or 2aa with hydroiodic acid or sodium iodide in the presence of acid (such as sulfuric acid) may furnish 4-iodopyrrolo[2,3-b]pyridines 1b ($R^1$=I) or 2ab.

Someone skilled in the art will recognize that 4-iodopyrrolo[2,3-b]pyridines 1b ($R^1$=I) or 2ab allow the introduction of aromatic, olefin, alkyne, or an aliphatic substituents at the 4-position of compounds 1 or 2 to afford compounds of the general formula I or 2 which can be achieved via standard halogen cross-coupling methodologies (cf. F. Diederich, P. J. Stang (eds.)—*Metal-catalyzed Cross-coupling Reactions*, Wiley-VCH, 1998; J. Tsuji—*Palladium Reagents and Catalysts*, John Wiley & Sons, 1995). Couplings of the iodide 1b or iodide 2ab with suitable reagents such as, but not limited to, boronic acids and boronates, organoboranes, trifluoroborate salts (e.g. G. A. Molander, G.-S. Yun, M. Ribagorda, B. Biolatto—*J. Org. Chem.* (2003) 68, 5534; G. A. Molander, B. Biolatto—*J. Org. Chem.* (2003) 68, 4302), organostannanes, organozinc compounds, organomagnesium compounds, olefins or terminal alkynes, either purchased or obtained via protocols well known in the chemical literature and familiar to someone skilled in the art, are carried out in the presence of a suitable transition metal catalyst, for example, but not limited to, suitable palladium compounds, either in the presence of ligands such as, but not limited to, phosphines, diphosphines or arsines or without and, as necessary, organic or inorganic bases, such as tertiary or secondary amines, alkaline carbonates, bicarbonates or phosphates and, as needed, other additives that are known in the chemical literature to assist or accelerate such transformations, such as lithium chloride, copper halides or silver salts. These cross coupling reactions are carried out in suitable solvents such as, but not limited to, THF, dioxane, dimethoxyethane, diglyme, dichloromethane, dichloroethane, acetonitrile, DMF, N-methylpyrrolidone, ethanol, or water, or mixtures of these at temperatures ranging from 25° C. to 200° C. using either no heating, conventional heating or microwave irradiation.

This methodology may be extended to the incorporation of non-carbon based nucleophiles such as, but not limited to alcohols, thiols, primary or secondary amines, heterocyclic rings containing hydrogen attached to a nitrogen atom, that may or may not contain groups which are known in the chemical literature to be suitable protecting groups (examples of such groups can be found in T. W. Greene, P. G. M. Wuts—*Protective Groups in Organic Synthesis,* 3rd ed., John Wiley & Sons, 1999) of alcohols, thiols or amines by methods well known in the chemical literature such as, by way of example, those mentioned in S. V. Ley, A. W. Thomas— *Angew. Chem.* (2003) 115, 5558; J. P. Wolfe, S. Wagaw, J.-F. Marcoux, S. L. Buchwald—*Acc. Chem. Res.* (1998) 31, 805 and J. F. Hartwig—*Acc. Chem. Res.* (1998) 31, 852. As will be apparent to someone with skill in the art, the compounds obtained by such methods can be further elaborated by methods well known in the chemical literature to other compounds claimed under this invention.

In some cases it may be advantageous to achieve cross-couplings to carbon or non-carbon atoms such as all those mentioned above, by first converting iodides 1b or iodide 2ab into an organometallic derivative 1 or 2, ($R^1$=[M]) such as, by means of example and not limitation, a boronic acid or ester, trifluoroborate salt, organomagnesium, organozinc or an organotin compound. Such compounds are accessible by means of substituting the iodide moiety with an appropriate metal or metalloid in which case any functional group present in derivative 1 or 2, most notably the ring nitrogen in position 1 of the pyrrolo[2,3-b]pyridine, may be protected by a suitable protecting group (examples of such groups can be found in T. W. Greene, P. G. M. Wuts—*Protective Groups in Organic Synthesis,* 3rd ed., John Wiley & Sons, 1999). Introduction of such metals or metalloids can be achieved in a number of ways, such as for example via reductive metallation using metals such alkaline or alkaline earth metals or activated forms of such metals such as, for example, lithium, magnesium or lithium naphthalide or via a metal-halogen exchange reactions using suitable organolithium or organomagnesium compounds such as, but not limited to, n-butyllithium, tert-butyllithium or iso-propylmagnesium chloride or bromide and, as needed, subsequent transmetalation reactions of the organometallic intermediate with a suitable soluble and reactive metal compound such as, by means of example and not limitation, magnesium chloride, magnesium bromide, tri-n-butyltin chloride, trimethyltin chloride, trimethyl borate, triethyl borate, tri-iso-propyl borate, zinc triflate or zinc chloride. Introduction of a boronic acid pinacol ester can also most conveniently be achieved by reacting the halide derivative 1 or 2 directly with bis(pinacolato)diboron in the presence of dichloro[1,1'-bis(diphenylphosphino)ferrocene] palladium(II) and suitable bases such as potassium or sodium acetate in solvents such as DMSO, DMF, DMA or N-METHYLPYRROLIDONE at temperatures ranging from 80-160° C. either using conventional heating or microwave irradiation (literature precedent for similar transformations can be found in T. Ishiyama, M. Murata, N. Miyaura—*J. Org. Chem.* (1995) 60, 7508.). Methods for conversion of the boronic acid pinacol ester obtained by this method into other boronic acid derivatives such as boronic acids, boronates, or trifluoroborate salts are known in the literature and familiar to the skilled artisan.

The skilled artisan will recognize that depending on the nature of the $R^1$ substituent it may be advantageous to introduce substituents at different stages utilizing 4-iodo-pyrrolo [2,3-b]pyridines 1 through 5.

Building blocks such as 2 can be obtained by treatment of pyrrolo[2,3-b]pyridines with oxidants, such as, but not limited to 3-chloroperbenzoic acid, peracetic acid, and hydrogen peroxide to generate pyrrolo[2,3-b]pyridine-7-oxides. The oxides can be treated with phosphorus oxychloride in suitable solvents, such as NMP, at temperatures below −20° C. to afford 4-chloro-pyrrolo[2,3-b]pyridines. The skilled artisan will recognize that depending on the nature of the $R^2$ and $R^3$ substituent it may be advantageous to introduce a 4-chloro-substituent at different stages of the synthesis utilizing 3,5-disubstituted-pyrrolo[2,3-b]pyridines (5, $R^1$=H).

under standard conditions well known to someone skilled in the art. Coupling of iodide 9 with ethynyltrimethylsilane to afford alkyne 10 can be achieved via standard halogen cross-coupling methodologies (cf. F. Diederich, P. J. Stang (eds.), *Metal-catalyzed Cross-coupling Reactions*, Wiley-VCH, 1998; J. Tsuji, *Palladium Reagents and Catalysts*, John Wiley & Sons, 1995) such as using suitable palladium compounds, such as dichlorobis-(triphenylphosphino)palladium(II) or dichloro[1,1'-bis(diphenylphosphino)ferrocene]palladium (II) as a catalyst in the presence of copper(I)-salts, such as cuprous iodide in the presence of organic bases, such as Scheme 2.

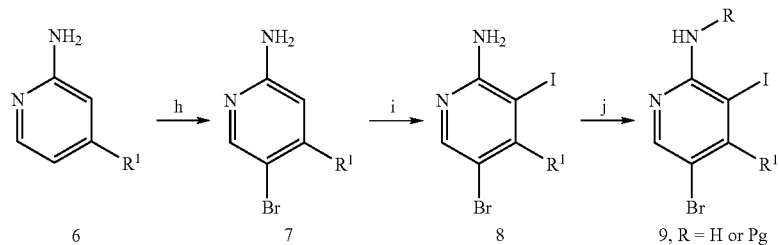

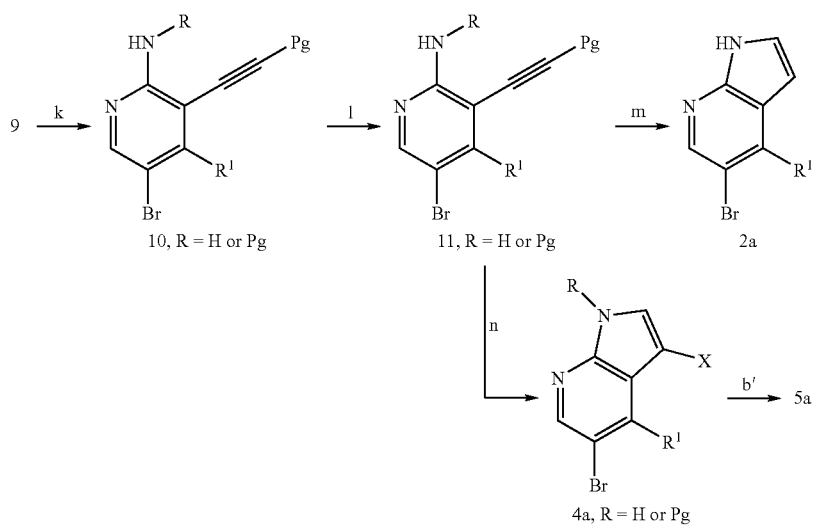

3,4,5-trisubstituted pyrrolo[2,3-b]pyridines can also be accessed via another method outlined in Scheme 4 (see also WO 2004/032874). Bromination of 4-substituted 2-aminopyridines (6) can be achieved by reacting it with electrophilic bromine sources such as bromine, N-bromosuccinimide, or hydrobromic acid and an oxidant (such as hydrogen peroxide) in a suitable solvent such as acetic acid, dichloromethane, chloroform, alcohols, aqueous base (such as sodium carbonate or sodium acetate solution). Iodination of 4-substituted 2-amino-5-bromopyridine (7) can be achieved by reacting it with iodine and sodium periodate in a suitable solvent such as DMF, DMA or N-methylpyrrolidone at elevated temperatures of 100-200° C. to afford intermediate 8. Alternatively N-iodosuccinimide in acetic acid may be used. This intermediate 8 can be protected (e.g. as the N-acetate or N-tosylate)

triethyl amine, in suitable solvents, such as dichloromethane at temperatures of 25° C. or above. Cyclization of the resulting alkynylpyridine 10 can be most conveniently achieved by exposure to soluble fluorides, such as tetrabutylammonium fluoride, in suitable solvents such as THF or dioxane at temperatures of 25-110° C. to afford 4-substituted 5-bromo-pyrrolo[2,3-b]pyridines (2a).

Intermediate 11 can be cyclized as outlined in Amjad and Knight, Tet. Lett. 45 (2004) p. 539. Treatment of a suitably protected 3-alkynyl-aminopyridine with iodine has been shown to yield N-protected-3-iodo-pyrrolo[2,3-b]pyridines analogous to 4a.

Scheme 3.

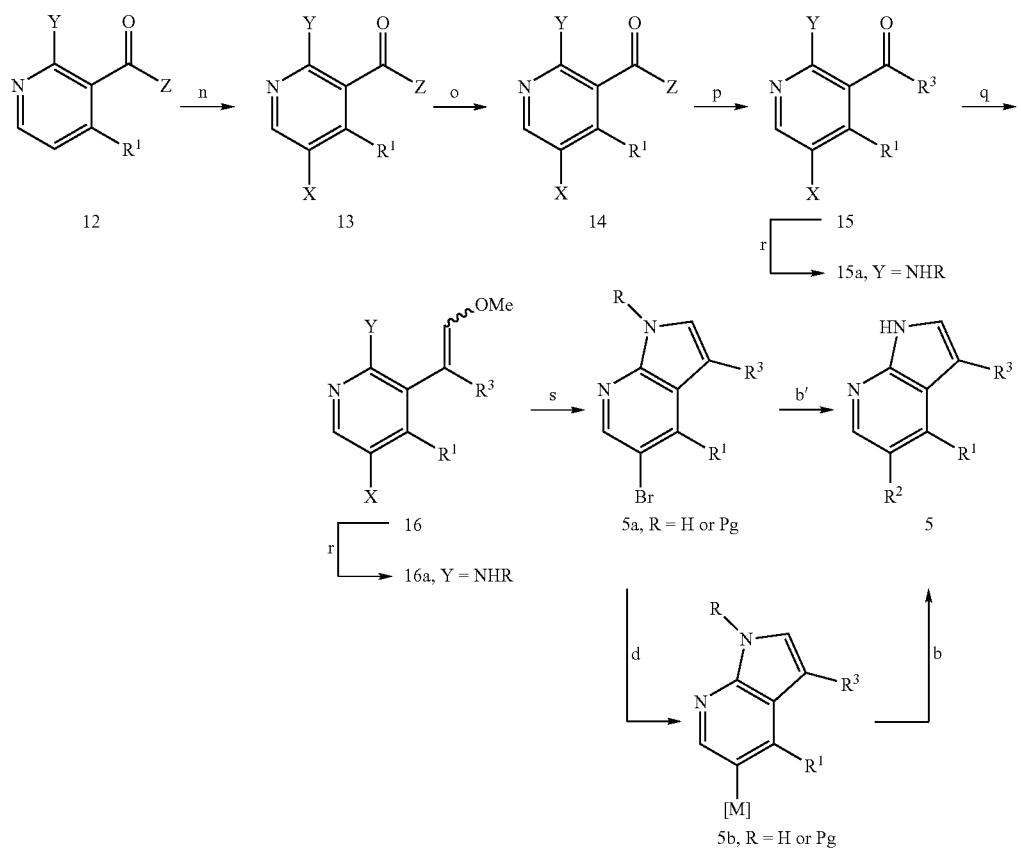

An alternative synthesis of certain compounds of the present invention is outlined in Scheme 3. Many of these compounds can be synthesized from commercially available nicotinic acids 12. Substituent $R^1$ can be a variety of moieties, including but not limited to alkyl, alkenyl, cycloalkyl, cycloalkenyl, cycloheteroalkyl, cycloheteroalkenyl, aryl, heteroaryl, alkynyl, fused rings, amino, oxy, carboxy, thio, cyano, sulfoxy, sulfenyl, sulfonyl, carbamino, amido, and halogens. Each of these moieties can be optionally substituted with one or more groups, $Z_1$, in which acidic protons such as for example the hydrogen atoms attached to nitrogen or oxygen may, as needed, be protected by a suitable protecting group by methods well known in the chemical literature (cf. T. W. Greene, P. G. M. Wuts—*Protective Groups in Organic Synthesis*, 3rd ed., John Wiley & Sons, 1999). The skilled artisan will recognize that some of these moieties may act as functional handles for further transformation during the course of the synthesis as outlined above.

Substituent Y will typically be a nitrogen moiety, either as the free amino substituent or a suitably protected amine, such as benzyl, toluenesulfonyl, or acyl (Y=NHR' or NR'R"). The skilled artisan will recognize that it may be necessary to change the protecting group in the course of the synthesis. Alternatively, substituent Y may be a moiety which can act as a functional handle to introduce an amino substituent via nucleophilic aromatic substitution at a later stage, most commonly a fluoride or a chloride substituent (Y=F,Cl), but may also be a bromide, methanesulfonyl, or methoxy substituent. It may be convenient to use a 2-hydroxy substituent (Or a suitably protected version thereof: Y=OR) or a 2-thio substituent (or a suitably protected version thereof: Y=SR) which may be converted into a 2-aminosubstituent in the course of the synthesis using methods well established in the art.

Starting from a suitable nicotinic acid (Z=OH) or ester (Z=OMe or OEt), bromination in the 5-position leading to 13 (X=Br) can be achieved by various methods known to someone skilled in the art, such as, but not limited to reactions using elemental bromine, N-bromosuccinimide, phosphorus (v)-bromide or pyridinium tribromide [step n in Scheme 3].

Synthesis of a ketone intermediate of general formula 14 (X=Br) can be achieved by treating the corresponding Weinreb-amide 14a (Z=N(Me)OMe) or its hydrochloride salt with a suitable organometallic species, for example, using an organomagnesium or organolithium compound [step p in Scheme 3]. (for examples of the use of N-methoxy-N-methylamides (Weinreb Amides) in ketone synthesis, see S. Nam, S. M. Weinreb—*Tetrahedron Lett.* 1981, 22, 3815.) The Weinreb-amide 14aa (X=Br) is accessible by condensation of the parent acid 13a (Z=OH) with N O-dimethylhydroxylamine using standard methods for amide-formation, either by prior activation of the acid or in situ or via a direct condensation. Methods and reagents for both transformations are described in the chemical literature and well known to someone skilled in the art [step o in Scheme 3]. Amide formation is achieved by direct methods using suitable coupling reagents such as, but not limited to, PyBOP, HBTU or HATU.

The organometallic reagents required for the introduction of a ketone residue $R^2$ in 15 (X=Br) [step p in Scheme 3] can be obtained either commercially or synthesized by various methods described in the literature, such as, but not limited to the Grignard-reaction of organic chlorides, bromides, or iodides, with magnesium (cf. J. March—*Advanced Organic Chemistry*, 3rd ed., John Wiley & Sons, 1992), metal-halogen exchange reactions of organic bromides or iodides using suitable organolithium or organomagnesium compounds such as, but not limited to, n-butyllithium, tert-butyllithium or iso-propylmagnesium chloride or bromide (e.g. J. Clayden—*Organolithiums: Selectivity for Synthesis*, Pergamon, 2002; A. Boudier, L. O. Bromm, M. Lotz, P. Knochel—*Angew. Chem. Int. Ed.* (2000) 39, 4414or deprotonation of sufficiently acidic compounds, such as for example pyrimidines, pyrazines, 2-chloro- or 2-fluoropyridines using a suitable base, such as for example lithium N,N-diisopropylamide or lithium 2,2,6,6-tetramethylpiperidide (cf. J. Clayden—*Organolithiums: Selectivity for Synthesis*, Pergamon, 2002; A. Turcko, N. Plé, F. Mongin, G. Quéguiner—*Tetrahedron* (2001) 57, 4489; F. Mongin, G. Quéguiner—*Tetrahedron* (2001) 57, 4059). The aforementioned group $R^2$ can be a variety of moieties, including but not limited to alkyl, alkenyl, cycloalkyl, cycloalkenyl, cycloheteroalkyl, cycloheteroalkenyl, aryl, heteroaryl, alkynyl, and fused rings. Each of these moieties can be optionally substituted with one or more groups, $Pg^2$, in which acidic protons such as for example the hydrogen atoms attached to nitrogen or oxygen may, as needed, be protected by a suitable protecting group by methods well known in the chemical literature (cf. T. W. Greene, P. G. M. Wuts—*Protective Groups in Organic Synthesis*, 3rd ed., John Wiley & Sons, 1999).

Olefination of the resulting ketones 15 [step q in Scheme 3] can be achieved by several methods known to those skilled in the art but is most conveniently carried out via a Wittig-reaction (cf. B. E. Maryanoff, A. B. Reitz—*Chem. Rev.* (1989) 89, 863) using an ylid generated from commercially available methoxymethyltriphenylphosphonium chloride and a suitable base, for example, but not limited to, a strong organometallic base such as, but not limited to, a non-nucleophilic amide such as the lithium, sodium or potassium salt of bis(trimethylsilyl)amine.

Subsequent cyclization of the resulting olefin 16, [step s in Scheme 3] which can be utilized in either the E- or Z form or a mixture of these both forms, can be achieved under general acid catalysis conditions using strong inorganic or organic acids, such as, but not limited to sulfuric acid, perchloric acid, hydrochloric acid, trifluoromethane-sulfonic acid or trifluoroacetic acid in suitable solvents such as, but not limited to THF, dioxane, diethyl ether, dimethoxyethane, diglyme, dichloromethane, dichloroethane or chloroform, water, methanol, or ethanol, or mixtures thereof at temperatures ranging from 0° C. to 160° C. A similar cyclization has been described by Sakamoto et al., *Heterocycles* (1992), 34(12), 2379-84. There the authors describe the conversion of 2-nitro-3-(2-ethoxyvinyl)pyridine to the parent pyrrolo[2,3-b]pyridine. Formation of the vinyl group is achieved via a STILLE-coupling of the 3-bromo analog with tributyl-2-ethoxyvinylstannane.

Such transformations lead, in the case of 2-aminonicotinic acids (Y=$NH_2$), directly to the intermediate 5a. In those cases in which a protecting group Pg is employed the removal of the protecting group to liberate the intermediate 5a (R=H) can be achieved by suitable methods well known in the chemical literature (cf. T. W. Greene, P. G. M. Wuts, *Protective Groups in Organic Synthesis*, 3rd ed., John Wiley & Sons, 1999) and depending on the actual substituent Pg. As will be evident to a person skilled in the art from the above description, the intermediate 5a may be used as a key intermediate for the synthesis of the pyrrolo[2,3-b]pyridines claimed under this invention.

Alternative methods of obtaining this intermediate from commercially available 4-substituted-2-hydroxynicotinic acids (12, Y=OH, Z=OH) follow the outline in Scheme 3. Starting from 2-hydroxynicotinic acids, bromination in the 5-position to afford (13, Y=OH, Z=OH) can be achieved (via step n in Scheme 3) by various methods, but most conveniently by treating the starting material with bromine in a suitable solvent such as acetic acid.

Nicotinic acid derivatives (13, Y=OH, Z=OH) can then be converted into 5-bromo-2-chloronicotinoyl chloride (13, Y=Cl, Z=Cl) under conditions that are well known in the chemical literature, for example, by treating 11 with either phosphorus oxychloride or a solution of phosphorus(v)-chloride in phosphorus oxychloride either in the presence of pyridine or without at temperatures ranging from 25° C. to 165° C. 5-bromo-2-chloronicotinoyl chloride (13, Y=Cl, Z=Cl) can either be used after purification by crystallization from a suitable solvent or distillation at pressures of $10^{-3}$ mbar or below or as a crude product directly after removal of the excess phosphorus oxychloride.

5-bromo-2-chloronicotinoyl chloride (13, Y=Cl, Z=Cl) may be converted into a corresponding ketone 15 (Y=Cl) by reaction (step p in Scheme 3) with an organocopper compound generated in situ from an organomagnesium or organolithium compound and a suitable copper(I)-compound (cf. B. H. Lipshutz in M. Schlosser (ed.)—*Organometallics in Synthesis*, John Wiley & Sons, 2002, pp. 665-816), for example, but not limited to, where the organocopper reagent is generated in situ from an organomagnesium compound and copper(I)-bromide in the presence of lithium bromide.

In one embodiment of the invention, a ketone 15 (Y=F, Cl, OMe, —$SO_2R$, etc.) is first treated with either ammonia, a suitable ammonia salt of a weak acid, such as, but not limited to, ammonium acetate or ammonium carbonate or a primary amine containing a residue Pg that is known in the chemical literature to be an easily removed group (protecting group, cf. T. W. Greene, P. G. M. Wuts, *Protective Groups in Organic Synthesis*, 3rd ed., John Wiley & Sons, 1999) such as, but not limited to allyl, benzyl or substituted benzyl, for example 4-methoxybenzyl in a suitable solvent such as, but not limited to dichloroethane, toluene, DMF, acetonitrile, ethanol, isopropanol or pentanol at temperatures ranging from 25° C. to 185° C. either in the presence of molecular sieves or without and subsequent hydrolysis of any imine (Schiff-base) formed under such conditions by methods well known in the chemical literature and known to someone skilled in the art, for example, but not limited to, by hydrolysis in aqueous solvent using strong mineral acids such as, but not limited to hydrochloric acid or sulfuric acid (step r in Scheme 3). The product of such a sequence of transformations is a ketone of general formula 15a (Y=NHR), and conversion to the central pyrolo [2,3-b]pyridine 5 can be achieved in the same way by olefination and subsequent cyclization as outlined above.

Another ketone derivative 15 ($R^1$=H) of similar utility containing a 2-fluoro substituent (Y=F) can be accessed starting from commercial 5-bromo-2-fluoropyridine via ortho-metallation by means of a sufficiently strong base such as, by means of example, lithium N,N-diisopropylamide or lithium 2,2,6,6-tetramethylpiperidide and reacting the resulting metallated pyridine, as for example the corresponding lithiated derivative, with a suitable acyl halide, such as for example a suitable acyl chloride, in the presence of a suitable transition metal catalyst, such as, for example a suitable copper salt, such as, for example copper(I)-bromide and, as needed, other additives known in the chemical literature to facilitate or assist such transformations, such as, for example, lithium bromide, in suitable aprotic solvents, such as for example ether, THF, dioxane, or mixtures thereof at temperatures ranging from −100° C. to 25° C. Conversion of ketone 15 to intermediate 5 (via sequential steps q and s in Scheme 3) can be accomplished by introducing ammonia or a suitable primary alcohol with a chain length of 1-5 carbon atoms at pressures ranging from 1-10 bar and temperatures ranging from 25° C. to 100° C. or by oxidation with 2,3-dichloro-5,6-dicyano-1,4-benzoquinone (DDQ).

Synthesis of Trisubstituted Pyrazolo[3,4-b]pyridines

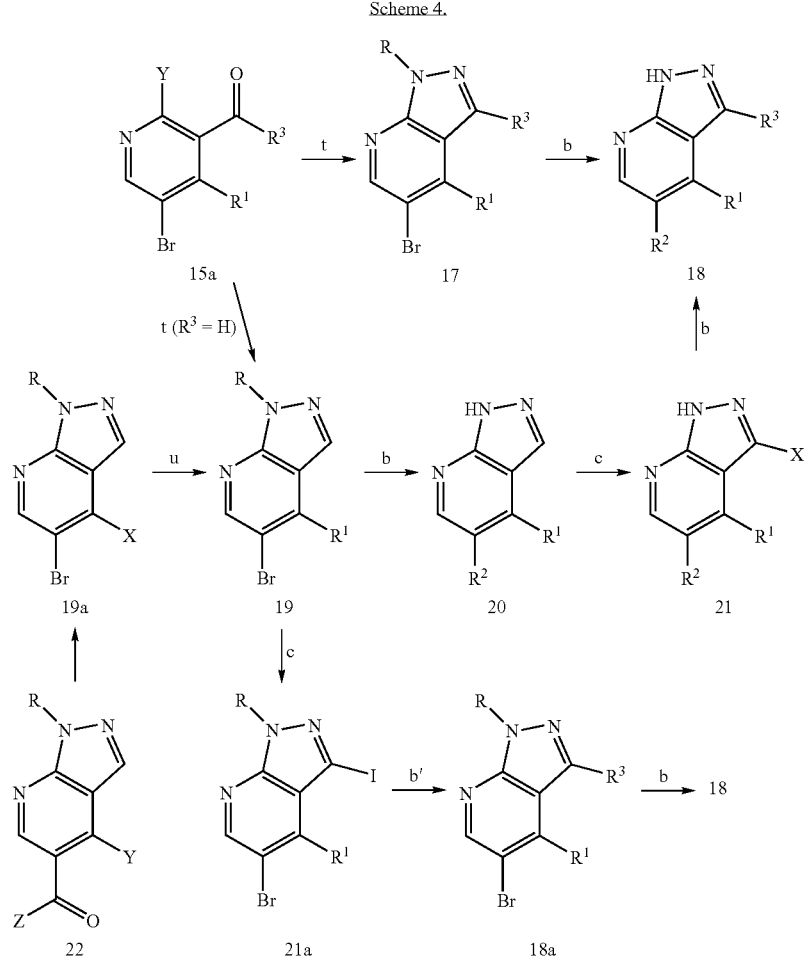

Syntheses of Disubstituted Pyrazolo[3,4-b]pyridines amine substitutent and, in a similar way to the one outlined for the 2-aminonicotinic acid analogs outlined above, sequential olefination of the ketone, subsequent cyclization and, as needed, deprotection of the nitrogen in 1-position of intermediate 5.

Such transformations lead, in the case of ammonia or suitable ammonium salts, directly to the intermediate 5. In those cases in which a primary amine is employed the removal of the protecting group Pg to liberate the intermediate 5 can be achieved by suitable methods well known in the chemical literature (cf. T. W. Greene, P. G. M. Wuts, *Protective Groups in Organic Synthesis*, 3rd ed., John Wiley & Sons, 1999) and depending on the actual substituent $R^3$. In an embodiment $R^3$ is 4-methoxybenzyl and removal of this group can be achieved either by hydrogenolysis using a suitable transition metal catalyst, for example, but not limited to palladium on carbon, in the presence of hydrogen or a suitable hydrogen source such as, but not limited to cyclohexene or cyclohexadiene in a suitable solvent, for example, but not limited to a In another embodiment of this invention, a ketone of general formula 15 is converted (step t in Scheme 4) into a 3,4,5-trisubstituted 1H-pyrazolo[3,4-b]pyridine 17 by condensation with hydrazine or suitable hydrazine salts, such as, for example, the hydrochloride or sulfate, in a suitable solvent such as, but not limited to toluene, xylenes, ethanol, butanol, pentanol, or mixtures thereof either in the presence of an acid such as, but not limited to acetic acid, formic acid, hydrochloric acid or sulfuric acid or without at temperatures ranging from −40° C. to 150° C.

Introduction of an aromatic, olefinic or alkyne substituent at the 5-position of bromide 17 to afford compounds of the general formula 18 can be achieved via standard halogen cross-coupling methodologies (step f in Scheme 2, cf. F. Diederich, P. J. Stang (eds.), *Metal-catalyzed Cross-coupling Reactions*, Wiley-VCH, 1998; J. Tsuji, *Palladium Reagents and Catalysts*, John Wiley & Sons, 1995). Couplings of the bromide 17 with suitable reagents such as, but not limited to, boronic acids and boronates, organoboranes, organostannanes, organozinc compounds, organo-magnesium compounds, olefins or terminal alkynes, either purchased or obtained via protocols well known in the chemical literature and familiar to someone skilled in the art, are carried out in the presence of a suitable transition metal catalyst, for example, but not limited to suitable palladium compounds, either in the presence of ligands such as, but not limited to, phosphines, diphosphines or arsines or without and, as necessary, organic or inorganic bases, such as tertiary or secondary amines, alkaline carbonates, bicarbonates or phosphates and, as needed, other additives that are known in the chemical literature to assist or accelerate such transformations, such as lithium chloride, copper halides or silver salts. These cross coupling reactions are carried out in suitable solvents such as, but not limited to, THF, dioxane, dimethoxyethane, diglyme, dichloromethane, dichloroethane, acetonitrile, DMF, N-methylpyrrolidone or, water, or mixtures of these at temperatures ranging from 25° C. to 200° C. using either no heating, conventional heating or microwave irradiation.

This methodology may be extended to the incorporation of non-carbon based nucleophiles such as, but not limited to alcohols, thiols, primary or secondary amines, that may or may not contain groups which are known in the chemical literature to be suitable protecting groups (examples of such groups can be found in T. W. Greene, P. G. M. Wuts, *Protective Groups in Organic Synthesis,* 3rd ed., John Wiley & Sons, 1999) of alcohols, thiols or amines by methods well known in the chemical literature such as, by way of example, those mentioned in S. V. Ley, A. W. Thomas, *Angew. Chem.* (2003) 115, 5558; J. P. Wolfe, S. Wagaw, J.-F. Marcoux, S. L. Buchwald, *Acc. Chem. Res.* (1998) 31, 805 and J. F. Hartwig, *Acc. Chem. Res.* (1998) 31, 852. As will be apparent to someone skilled in the art, the compounds obtained by such methods can be further elaborated by methods known in the chemical literature to other compounds claimed under this invention.

In some cases it may be advantageous to achieve cross-couplings to carbon or non-carbon atoms such as all those mentioned above, by first converting the bromide 17 into an organometallic derivative such as, by means of example and not limitation, a boronic acid or ester, trifluoroborate salt, organomagnesium, organozinc or organotin compound. Such compounds are accessible by means of substituting the bromide moiety with an appropriate metal or metalloid in which case any functional group present in derivative 17, most notably the ring nitrogen in position I of the pyrazolo[3,4-b]pyridine, may need to be protected by a suitable protecting group PG (examples of such groups can be found in T. W. Greene, P. G. M. Wuts, *Protective Groups in Organic Synthesis,* 3rd ed., John Wiley & Sons, 1999) as needed. Introduction of such metals or metalloids can be achieved in a number of ways known to someone with skill in the art, such as for example via reductive metallation using metals such alkaline or alkaline earth metals or activated forms of such metals such as, for example, sodium, magnesium or lithium naphthalide or via a metal-halogen exchange reactions using suitable organolithium or organomagnesium compounds such as, but not limited to, n-butyllithium, tert-butyllithium or iso-propylmagnesium chloride or bromide and, as needed, subsequent transmetalation reactions of the organometallic intermediate with a suitable soluble and reactive metal compound such as, by means of example and not limitation, magnesium chloride, magnesium bromide, tri-n-butyltin chloride, trimethyltin chloride, trimethyl borate, triethyl borate, tri-iso-propyl borate, zinc triflate or zinc chloride. Introduction of a boronic acid pinacol ester can also most conveniently be achieved by reacting the bromo derivative 17 directly with bis(pinacolato) diboron in the presence of dichloro[1,1'-bis(diphenylphosphino)ferrocene]palladium(II) and suitable bases such as potassium or sodium acetate in solvents such as DMSO, DMF, DMA or N-methylpyrrolidone at temperatures ranging from 80-160° C. either using conventional heating or microwave irradiation (literature precedent for similar transformations can be found in T. Ishiyama, M. Murata, N. Miyaura, *J. Org. Chem.* (1995) 60, 7508. Methods for conversion of the boronic acid pinacol ester obtained by this method into other boronic acid derivatives such as boronic acids, boronates, or trifluoroborate salts are known in the literature and familiar to the skilled artisan.

Cross-couplings of the metallated derivatives with suitable reagents such as, but not limited to, aromatic, heteroaromatic, or olefinic chlorides, bromides, iodides, triflates or acyl halides either purchased or obtained via protocols well known in the chemical literature and familiar to someone skilled in the art, are carried out in the presence of a suitable transition metal catalyst, for example, but not limited to suitable palladium compounds, either in the presence of ligands such as, but not limited to, phosphines, diphosphines, or arsines, or without and, as necessary, organic or inorganic bases, such as tertiary or secondary amines, alkaline carbonates, bicarbonates, or phosphates and, as needed, other additives that are known in the chemical literature to assist or accelerate such transformations, such as lithium chloride, copper halides or silver salts. These cross coupling reactions are carried out in suitable solvents such as, but not limited to, THF, dioxane, dimethoxyethane, diglyme, dichloromethane, dichloroethane, acetonitrile, DMF, N-methylpyrrolidone, or mixtures of these at temperatures ranging from 25° C. to 200° C. using either no heating, conventional heating or microwave irradiation.

More reactive organic nucleophiles, that are organometallic compounds containing alkaline or alkaline earth metals, such as, for example, organolithium, organomagnesium or organozinc compounds, can also be coupled to a range of other electrophilic coupling partners such as, by means of example and not limitation, activated olefins (Michael-acceptors), aldehydes, nitriles, aromatic nitro compounds (see, for example, I. Sapountzis, P. Knochel, *J. Am. Chem. Soc.* (2002) 124, 9390, carboxylic acid derivatives, organic disulfides or organic halides. Such couplings can be achieved using either no catalyst or a suitable transition metal catalyst, such as, by means of example and not limitation, a suitable copper, cobalt or iron compound in suitable solvents such as, but not limited to, ether, THF, dioxane, dimethoxyethane, or diglyme, or mixtures of these at temperatures ranging from −100° C. to 100° C. either in the presence of other additives that are known in the chemical literature to assist or accelerate such transformations, such as, for example, lithium halides, amines or diamines or their derivatives or without.

In another embodiment of this invention 17 may be converted into the corresponding acid 18 ($R^2$=COOH), either by converting it to a nitrile using cuprous cyanide (cf. G. P. Ellis, T. M. Romney-Alexander, *Chem. Rev.* (1987) 87, 779 or using zinc(II)-cyanide in the presence of a suitable palladium catalyst (cf. M. Alternan, M. Hallberg, *J. Org. Chem.* (2000) 65, 7984) and subsequent hydrolysis of the nitrile under acid catalysis or basic conditions in water or a mixture of water and organic solvent(s) such as methanol, ethanol, or acetone by methods that are well known to someone skilled in the art, or by metallation in 5-position by either direct insertion of magnesium under standard Grignard-reaction conditions, transmetallation with iso-propylmagnesium chloride or lithium-bromine exchange with n- or tert-butyllithium and subsequent reaction with dry carbon dioxide, either using 17 directly bearing a suitable protecting group, for example a 2-trimethylsilylethoxymethyl group, on the nitrogen atom in 1-position, again by methods that are well known in the chemical literature.

Formation of amides 18 ($R^2$=C(O)NR'R") can be achieved using standard methods for amide-formation, either by prior activation of the acid in situ or via a direct condensation, methods and reagents for which are described in the chemical literature and known to the skilled artisan. Amide formation may be, for example, but not limited to, achieved by a direct method using suitable coupling reagents such as, but not limited to DCC, PyBOP, HBTU or HATU either in the presence of DMAP or a polymer bound form of DMAP or without.

Alternatively the bromo derivative 17 may be directly converted into amides 18 ($R^2$=C(O)NR'R") by a procedure analogous or identical to one published by J. Wannberg and M. Larhed (*J. Org. Chem.* (2003) 68, 5750, reacting it with an amine in the presence of a metal carbonyl, for example, but not limited to molybdenum hexacarbonyl, a strong organic base, for example, but not limited to 1,8-diazabicyclo[5.4.0] undec-7-ene and a suitable palladium catalyst, for example, but not limited to trans-di(μ-acetato)bis[ortho-(di-orthotolylphosphino)benzyl]-dipalladium(II) (Herrmann's catalyst) in an aprotic solvent such as, but not limited to THF, acetonitrile, DMF or N-methylpyrrolidone, for example, but not limited to DMF or THF at temperatures ranging from 80° C. to 180° C. either using conventional heating or microwave irradiation.

In cases where the nitrogen atom in position 1 of the pyrazolo[3,4-b]pyridine 18 is protected by a protecting group, liberation to the unprotected product can be achieved by a suitable method, known in the chemical literature and to someone skilled in the art (cf. T. W. Greene, P. G. M. Wuts, *Protective Groups in Organic Synthesis,* 3rd ed., John Wiley & Sons, 1999). The protecting group may, for example, be a 2-trimethylsilylethoxymethyl group and deprotection is accomplished by acid such as, but not limited to trifluoroacetic acid, perchloric acid, or hydrochloric acid.

The skilled artisan will recognize that it may be advantageous to introduce an $R^3$ substituent later in the synthesis. Aldehydes 15 ($R^3$=H) may be cyclized under identical conditions as outlined above to afford bromide 19. The bromide may be used as a functional handle to access compounds 20 with a large variety of $R^2$ substituents as outlined above. Final compounds are accessible through iodination and functionalization of the 3-position analogous to methods described within to afford pyrazolo[3,4-b]pyridines 18 (via 21). Alternatively it may be useful to functionalize bromide 19 to afford 4-substituted-5-bromo-3-iodo-pyrazolo[3,4-b]pyridines 21a. Selective functionalization in the more reactive 3-position gives access to bromides 18a spanning a wide range of $R^3$ modifications which can be modified further to give 18.

An alternative synthesis of intermediates 19 has been described by Misra et al. (Bioorg. Med. Chem. Lett, Vol. 13(14), 2003, p. 2405). Suitably protected 4-Hydroxy-1H-pyrazolo[3,4-b]pyridine-5-carboxylic acid (22, Y=OH, Z=OH) can be decarboxylated at temperatures above 200° C. Bromination of the resulting 4-Hydroxy-1H-pyrazolo[3, 4-b]pyridine using elemental bromine in ethanol affords 19a (X=OH). Chlorination using phosphorus oxychloride affords 5-bromo-4-chloro-1H-pyrazolo[3,4-b]pyridine 19b (X=Cl).

A variety of $R^1$ groups can be accessed at any stage of the synthesis from common precursors containing leaving groups in the 4-position of pyrazolo[3,4-b]pyridines, such as, but not limited to fluoro, chloro, bromo, methoxy, and methylsulfonyl substituents. Nucleophilic aromatic substitution may be affected under acidic or basic conditions in suitable solvents such as, but not limited to, THF, dioxane, dimethoxyethane, diglyme, dichloromethane, dichloroethane, acetonitrile, DMF, N-methylpyrrolidone, ethanol, or water, or mixtures of these at temperatures ranging from 25° C. to 200° C. using either no heating, conventional heating or microwave irradiation. Commercially available or synthesized building blocks such as amines, alkoxides, alcohols, thiols, carbon based nucleophiles such as malonates may be used to access a wide range of pyrrolo[2,3-b]pyridines 5. The skilled artisan will recognize that depending on the nature of the $R^1$ substituent it may be advantageous to introduce substituents at different stages utilizing intermediates 1 through 5.

Alternatively $R^1$ may be iodine substituent which can be utilized as a functional handle. Interconversion of a 4-chloro-pyrazolo[3,4-b]pyridine (18, $R^1$=Cl) to a 4-iodo-pyrazolo[3, 4-b]pyridine 18, $R^1$=I) may be achieved at any suitable stage of the synthesis. For example treatment of 5-bromo-4-chloro-pyrazolo[3,4-b]pyridine 19b with hydroiodic acid or sodium iodide in the presence of acid (such as sulfuric acid) may furnish 5-bromo-4-iodo-pyrazolo[3,4-b]pyridine 19c ($R^1$=I).

Someone skilled in the art will recognize that 4-iodopyrazolo[3,4-b]pyridines 18 ($R^1$=I) allow the introduction of aromatic, olefin, alkyne, or an aliphatic substituents at the 4-position of pyrazolo[3,4-b]pyridines which can be achieved via standard halogen cross-coupling methodologies (cf. F. Diederich, P. J. Stang (eds.)—*Metal-catalyzed Cross-coupling Reactions*, Wiley-VCH, 1998; J. Tsuji—*Palladium Reagents and Catalysts*, John Wiley & Sons, 1995). Couplings of the iodide 19 ($R^1$=I) with suitable reagents such as, but not limited to, boronic acids and boronates, organoboranes, trifluoroborate salts (e.g. G. A. Molander, G.-S. Yun, M. Ribagorda, B. Biolatto—*J. Org. Chem.* (2003) 68, 5534; G. A. Molander, B. Biolatto—*J. Org. Chem.* (2003) 68, 4302), organostannanes, organozinc compounds, organomagnesium compounds, olefins or terminal alkynes, either purchased or obtained via protocols well known in the chemical literature and familiar to someone skilled in the art, are carried out in the presence of a suitable transition metal catalyst, for example, but not limited to, suitable palladium compounds, either in the presence of ligands such as, but not limited to, phosphines, diphosphines or arsines or without and, as necessary, organic or inorganic bases, such as tertiary or secondary amines, alkaline carbonates, bicarbonates or phosphates and, as needed, other additives that are known in the chemical literature to assist or accelerate such transformations, such as lithium chloride, copper halides or silver salts. These cross coupling reactions are carried out in suitable solvents such as, but not limited to, THF, dioxane, dimethoxyethane, diglyme, dichloromethane, dichloroethane, acetonitrile, DMF, N-methylpyrrolidone, ethanol, or water, or mixtures of these at temperatures ranging from 25° C. to 200° C. using either no heating, conventional heating or microwave irradiation.

This methodology may be extended to the incorporation of non-carbon based nucleophiles such as, but not limited to alcohols, thiols, primary or secondary amines, heterocyclic rings containing hydrogen attached to a nitrogen atom, that may or may not contain groups which are known in the chemical literature to be suitable protecting groups (examples of such groups can be found in T. W. Greene, P. G. M. Wuts—*Protective Groups in Organic Synthesis,* 3rd ed., John Wiley & Sons, 1999) of alcohols, thiols or amines by methods well known in the chemical literature such as, by way of example, those mentioned in S. V. Ley, A. W. Thomas—*Angew. Chem.* (2003) 115, 5558; J. P. Wolfe, S. Wagaw, J.-F. Marcoux, S. L. Buchwald—*Acc. Chem. Res.* (1998) 31, 805 and J. F. Hartwig—*Acc. Chem. Res.* (1998) 31, 852. As will be apparent to someone with skill in the art, the compounds obtained by such methods can be further elaborated by methods well known in the chemical literature to other compounds claimed under this invention.

In some cases it may be advantageous to achieve cross-couplings to carbon or non-carbon atoms such as all those mentioned above, by first converting 19 ($R^1$=I) into an organometallic derivative ($R^1$=[M]) such as, by means of example and not limitation, a boronic acid or ester, trifluoroborate salt, organomagnesium, organozinc or an organotin compound. Such compounds are accessible by means of substituting the iodide moiety with an appropriate metal or metalloid in which case any functional group present in derivative 18, most notably the ring nitrogen in position 1 of the pyrazolo[3,4-b]pyridine, may be protected by a suitable protecting group (examples of such groups can be found in T. W. Greene, P. G. M. Wuts—*Protective Groups in Organic Synthesis,* 3rd ed., John Wiley & Sons, 1999). Introduction of such metals or metalloids can be achieved in a number of ways, such as for example via reductive metallation using metals such alkaline or alkaline earth metals or activated forms of such metals such as, for example, lithium, magnesium or lithium naphthalide or via a metal-halogen exchange reactions using suitable organolithium or organomagnesium compounds such as, but not limited to, n-butyllithium, tert-butyllithium or iso-propylmagnesium chloride or bromide and, as needed, subsequent transmetalation reactions of the organometallic intermediate with a suitable soluble and reactive metal compound such as, by means of example and not limitation, magnesium chloride, magnesium bromide, tri-n-butyltin chloride, trimethyltin chloride, trimethyl borate, triethyl borate, tri-iso-propyl borate, zinc triflate or zinc chloride. Introduction of a boronic acid pinacol ester can also most conveniently be achieved by reacting the halide derivative 18 ($R^1$=X) directly with bis(pinacolato)diboron in the presence of dichloro[1,1'-bis(diphenylphosphino)ferrocene]palladium(II) and suitable bases such as potassium or sodium acetate in solvents such as DMSO, DMF, DMA or NMP at temperatures ranging from 80-160° C. either using conventional heating or microwave irradiation (literature precedent for similar transformations can be found in T. Ishiyama, M. Murata, N. Miyaura—*J. Org. Chem.* (1995) 60, 7508. Methods for conversion of the boronic acid pinacol ester obtained by this method into other boronic acid derivatives such as boronic acids, boronates, or trifluoroborate salts are known in the literature and familiar to the skilled artisan.

The skilled artisan will recognize that depending on the nature of the $R^1$ substituent it may be advantageous to introduce substituents at different stages utilizing 4-iodo-pyrazolo[3,4-b]pyridines 17 through 22.

Synthesis of 2-substituted Pyrrolo[2,3-b]pyridines

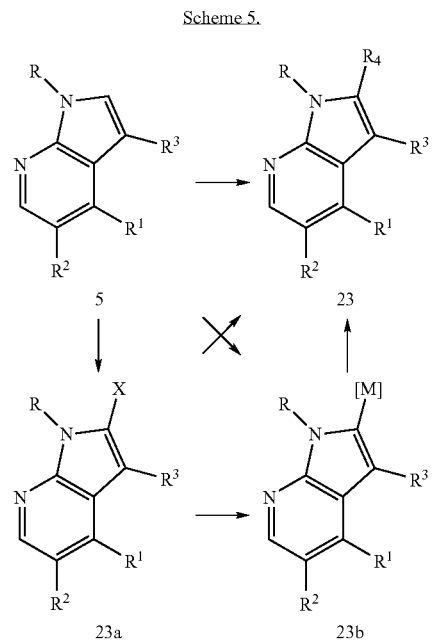

Scheme 5.

2-Substituted pyrrolo[2,3-b]pyridines 23 are accessible from pyrrolo[2,3-b]pyridines 5 through a number of transformations well established in the literature (cf. Song et al., Chem. Soc. Rev. Deprotonation in the 2-position of pyrrolo[2,3-b]pyridines can be achieved using strong base such as lithium diisopropylamide or alkyl lithium reagents followed by quenching of the lithium species with electrophiles such as organic halides, electrophilic halogenating agents (such as elemental bromine, iodine, NIS, NBS, NCS), aldehydes, activated olefins (Michael-acceptors), nitriles, aromatic nitro compounds (see, for example, I. Sapountzis, P. Knochel, *J. Am. Chem. Soc.* (2002) 124, 9390, carboxylic acid derivatives, or organic disulfides.

Depending on the nature and acidity of substituents $R^1$—$R^3$ it may be useful to use a protecting group for the 1-nitrogen of pyrrolo[2,3-b]pyridines 5 which can act as a directing group for the deprotonation of the 2-position proton such as, but not limited to toluenesulfonyl (Ts), tertbutoxycarbonyl (Boc), and trimethylsilylethoxymethyl (SEM).

Another alternative to functionalize the 2-position of pyrrolo[2,3-b]pyridines 5 is direct C—H activation. Nakao et al. (*J. Am. Chem. Soc.* (2006) SIR128(25), 8146) reported the use of nickel complexes in the presence of a phosphine ligand to synthesize 2-alkenyl pyrrolo[2,3-b]pyridines. Friedel-Crafts benzylations with alkyl cations has been reported by Rueping et al. (*Adv. Synth. Catal.* (2006) 348(9), 1033) to synthesize 2-benzyl-pyrrolo[2,3-b]pyridines. Generation of 2-vinyl-pyrrolo[2,3-b]pyridines has been achieved by Grimster et al. (*Angew. Chem. Int. Ed.* (2005) 117(20), 3185) using palladium acetate in the presence of peroxides.

Someone skilled in the art will recognize that it may be advantageous to use 2-halo-pyrrolo[2,3-b]pyridines 23a to synthesize a variety of 2-substituted pyrrolo[2,3-b]pyridines 23, ideally via 2-iodo-pyrrolo[2,3-b]pyridines which can be synthesized as described above. Introduction of an alkyl, olefinic or alkyne substituent at the 2-position of 23a to afford compounds of the general formula 23 can be achieved via standard halogen cross-coupling methodologies (step f in Scheme 2, cf. F. Diederich, P. J. Stang (eds.), *Metal-catalyzed Cross-coupling Reactions*, Wiley-VCH, 1998; J. Tsuji, *Palladium Reagents and Catalysts*, John Wiley & Sons, 1995). Couplings of the iodide 23a (X=I) with suitable reagents such as, but not limited to, boronic acids and boronates, organoboranes, organo-stannanes, organozinc compounds, organomagnesium compounds, olefins or terminal alkynes, either purchased or obtained via protocols well known in the chemical literature and familiar to someone skilled in the art, are carried out in the presence of a suitable transition metal catalyst, for example, but not limited to suitable palladium compounds, either in the presence of ligands such as, but not limited to, phosphines, diphosphines or arsines or without and, as necessary, organic or inorganic bases, such as tertiary or secondary amines, alkaline carbonates, bicarbonates or phosphates and, as needed, other additives that are known in the chemical literature to assist or accelerate such transformations, such as lithium chloride, copper halides or silver salts. These cross coupling reactions are carried out in suitable solvents such as, but not limited to, THF, dioxane, dimethoxyethane, diglyme, dichloromethane, dichloroethane, acetonitrile, DMF, N-methylpyrrolidone or, water, or mixtures of these at temperatures ranging from 25° C. to 200° C. using either no heating, conventional heating or microwave irradiation.

This methodology may be extended to the incorporation of non-carbon based nucleophiles such as, but not limited to alcohols, thiols, primary or secondary amines, heterocyclic rings containing hydrogen attached to a nitrogen atom, that may or may not contain groups which are known in the chemical literature to be suitable protecting groups (examples of such groups can be found in T. W. Greene, P. G. M. Wuts—*Protective Groups in Organic Synthesis,* 3rd ed., John Wiley & Sons, 1999) of alcohols, thiols or amines by methods well known in the chemical literature such as, by way of example, those mentioned in S. V. Ley, A. W. Thomas—*Angew. Chem.* (2003) 115, 5558; J. P. Wolfe, S. Wagaw, J.-F. Marcoux, S. L. Buchwald—*Acc. Chem. Res.* (1998) 31, 805 and J. F. Hartwig—*Acc. Chem. Res.* (1998) 31, 852. As will be apparent to someone with skill in the art, the compounds obtained by such methods can be further elaborated by methods well known in the chemical literature to other compounds claimed under this invention.

In some cases it may be advantageous to achieve cross-couplings to carbon or non-carbon atoms such as all those mentioned above, by first converting the halide 23a into an organometallic derivative 23b such as, by means of example and not limitation, a boronic acid or ester, trifluoroborate salt, organomagnesium, organozinc or organotin compound. Such compounds are accessible by means of substituting the bromide moiety with an appropriate metal or metalloid in which case any functional group present in derivative 23a, most notably the ring nitrogen in position 1 of the pyrazolo[3,4-b] pyridine, may need to be protected by a suitable protecting group PG (examples of such groups can be found in T. W. Greene, P. G. M. Wuts, *Protective Groups in Organic Synthesis,* 3rd ed., John Wiley & Sons, 1999) as needed. Introduction of such metals or metalloids can be achieved in a number of ways known to someone with skill in the art, such as for example via reductive metallation using metals such alkaline or alkaline earth metals or activated forms of such metals such as, for example, sodium, magnesium or lithium naphthalide or via a metal-halogen exchange reactions using suitable organolithium or organomagnesium compounds such as, but not limited to, n-butyllithium, tert-butyllithium or iso-propylmagnesium chloride or bromide and, as needed, subsequent transmetalation reactions of the organometallic intermediate with a suitable soluble and reactive metal compound such as, by means of example and not limitation, magnesium chloride, magnesium bromide, tri-n-butyltin chloride, trimethyltin chloride, trimethyl borate, triethyl borate, tri-iso-propyl borate, zinc triflate or zinc chloride. Introduction of a boronic acid pinacol ester can also most conveniently be achieved by reacting the halide derivative 23a directly with bis(pinacolato)diboron in the presence of dichloro[1,1'-bis(diphenylphosphino)ferrocene]palladium(II) and suitable bases such as potassium or sodium acetate in solvents such as DMSO, DMF, DMA or N-methylpyrrolidone at temperatures ranging from 80-160° C. either using conventional heating or microwave irradiation (literature precedent for similar transformations can be found in T. Ishiyama, M. Murata, N. Miyaura, *J. Org. Chem.* (1995) 60, 7508.). Methods for conversion of the boronic acid pinacol ester obtained by this method into other boronic acid derivatives such as boronic acids, boronates, or trifluoroborate salts are known in the literature and familiar to the skilled artisan.

Cross-couplings of the metallated derivatives with suitable reagents such as, but not limited to, aromatic, heteroaromatic, or olefinic chlorides, bromides, iodides, triflates or acyl halides either purchased or obtained via protocols well known in the chemical literature and familiar to someone skilled in the art, are carried out in the presence of a suitable transition metal catalyst, for example, but not limited to suitable palladium compounds, either in the presence of ligands such as, but not limited to, phosphines, diphosphines, or arsines, or without and, as necessary, organic or inorganic bases, such as tertiary or secondary amines, alkaline carbonates, bicarbonates, or phosphates and, as needed, other additives that are known in the chemical literature to assist or accelerate such transformations, such as lithium chloride, copper halides or silver salts. These cross coupling reactions are carried out in suitable solvents such as, but not limited to, THF, dioxane, dimethoxyethane, diglyme, dichloromethane, dichloroethane, acetonitrile, DMF, N-methylpyrrolidone, or mixtures of these at temperatures ranging from 25° C. to 200° C. using either no heating, conventional heating or microwave irradiation.

More reactive organic nucleophiles, that are organometallic compounds containing alkaline or alkaline earth metals, such as, for example, organolithium, organomagnesium or organozinc compounds, can also be coupled to a range of other electrophilic coupling partners such as, by means of example and not limitation, activated olefins (Michael-acceptors), aldehydes, nitriles, aromatic nitro compounds (see, for example, I. Sapountzis, P. Knochel, *J. Am. Chem. Soc.* (2002) 124, 9390, carboxylic acid derivatives, organic disulfides or organic halides. Such couplings can be achieved using either no catalyst or a suitable transition metal catalyst, such as, by means of example and not limitation, a suitable copper, cobalt or iron compound in suitable solvents such as, but not limited to, ether, THF, dioxane, dimethoxyethane, or diglyme, or mixtures of these at temperatures ranging from −100° C. to 100° C. either in the presence of other additives that are known in the chemical literature to assist or accelerate such transformations, such as, for example, lithium halides, amines or diamines or their derivatives or without.

In another embodiment of this invention 23a may be converted into the corresponding acid 23 ($R^4$=COOH), either by converting it to a nitrile using cuprous cyanide (cf. G. P. Ellis, T. M. Romney-Alexander, *Chem. Rev.* (1987) 87, 779or using zinc(II)-cyanide in the presence of a suitable palladium catalyst (cf. M. Alternan, M. Hallberg, *J. Org. Chem.* (2000) 65, 7984) and subsequent hydrolysis of the nitrile under acid catalysis or basic conditions in water or a mixture of water and organic solvent(s) such as methanol, ethanol, or acetone by methods that are well known to someone skilled in the art, or by metallation in 2-position by either direct insertion of magnesium under standard Grignard-reaction conditions, transmetallation with iso-propylmagnesium chloride or lithium-bromine exchange with n- or tert-butyllithium and subsequent reaction with dry carbon dioxide, either using 23a directly bearing a suitable protecting group, for example a 2-trimethylsilylethoxymethyl group, on the nitrogen atom in 1-position, again by methods that are well known in the chemical literature.

Formation of amides 23 ($R^4$=C(O)NR'R") can be achieved using standard methods for amide-formation, either by prior activation of the acid in situ or via a direct condensation, methods and reagents for which are described in the chemical literature and known to the skilled artisan. Amide formation may be, for example, but not limited to, achieved by a direct method using suitable coupling reagents such as, but not limited to DCC, PyBOP, HBTU or HATU either in the presence of DMAP or a polymer bound form of DMAP or without.

Alternatively the derivative 23a may be directly converted into amides 23 ($R^2$=C(O)NR'R") by a procedure analogous or identical to one published by J. Wannberg and M. Larhed (*J. Org. Chem.* (2003) 68, 5750, reacting it with an amine in the presence of a metal carbonyl, for example, but not limited to molybdenum hexacarbonyl, a strong organic base, for example, but not limited to 1,8-diazabicyclo[5.4.0]undec-7-ene and a suitable palladium catalyst, for example, but not limited to trans-di(μ-acetato)bis[ortho-(di-ortho-tolylphosphino)benzyl]-dipalladium(II) (Herrmann's catalyst) in an aprotic solvent such as, but not limited to THF, acetonitrile, DMF or N-methylpyrrolidone, for example, but not limited to DMF or THF at temperatures ranging from 80° C. to 180° C. either using conventional heating or microwave irradiation.

Protecting Groups

The term "protecting group" refers to chemical moieties that block some or all reactive moieties of a compound and prevent such moieties from participating in chemical reactions until the protective group is removed, for example, those moieties listed and described in Greene T. W. and Wuts P. G. M., *Protective Groups in Organic Synthesis* (3rd ed. 1999). It may be advantageous, where different protecting groups are employed, that each (different) protective group be removable by a different means. Protective groups that are cleaved under totally disparate reaction conditions allow differential removal of such protecting groups. For example, protective groups can be removed by acid, base, and hydrogenolysis. Groups such as trityl, dimethoxytrityl, acetal and tert-butyldimethylsilyl are acid labile and may be used to protect carboxy and hydroxy reactive moieties in the presence of amino groups protected with Cbz groups, which are removable by hydrogenolysis, and Fmoc groups, which are base labile. Carboxylic acid and hydroxy reactive moieties may be blocked with base labile groups such as, without limitation, methyl, ethyl, and acetyl in the presence of amines blocked with acid labile groups such as tert-butyl carbamate or with carbamates that are both acid and base stable but hydrolytically removable.

Carboxylic acid and hydroxy reactive moieties may also be blocked with hydrolytically removable protective groups such as the benzyl group, while amine groups capable of hydrogen bonding with acids may be blocked with base labile groups such as Fmoc. Carboxylic acid reactive moieties may be blocked with oxidatively-removable protective groups such as 2,4-dimethoxybenzyl, while co-existing amino groups may be blocked with fluoride labile silyl carbamates.

Allyl blocking groups are useful in the presence of acid- and base-protecting groups since the former are stable and can be subsequently removed by metal or pi-acid catalysts. For example, an allyl-blocked carboxylic acid can be deprotected with a palladium(0)-catalyzed reaction in the presence of acid labile t-butyl carbamate or base-labile acetate amine protecting groups. Yet another form of protecting group is a resin to which a compound or intermediate may be attached. As long as the residue is attached to the resin, that functional group is blocked and cannot react. Once released from the resin, the functional group is available to react.

Typical blocking/protecting groups include, but are not limited to the following moieties:

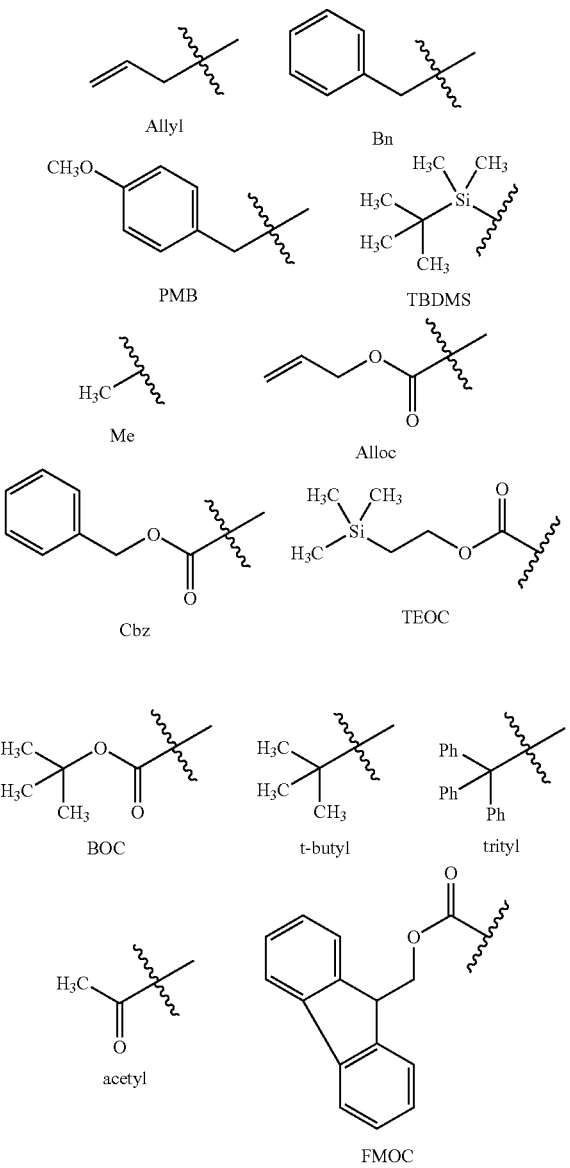

Salts

In some embodiments, the compounds described herein also exist as their pharmaceutically acceptable salts, which in other embodiments are useful for treating disorders. For example, the disclosure provides for methods of treating diseases, by administering pharmaceutically acceptable salts of the compounds described herein. In some embodiments, the pharmaceutically acceptable salts are administered as pharmaceutical compositions.

Thus, in some embodiments, the compounds described herein are prepared as pharmaceutically acceptable salts formed when an acidic proton present in the parent compound either is replaced by a metal ion, for example an alkali metal ion, an alkaline earth ion, or an aluminum ion; or coordinates with an organic base. In other embodiments, base addition salts are also prepared by reacting the free acid form of the compounds described herein with a pharmaceutically acceptable inorganic or organic base, including, but not limited to organic bases such as ethanolamine, diethanolamine, triethanolamine, tromethamine, N-methylglucamine, and the like and inorganic bases such as aluminum hydroxide, calcium hydroxide, potassium hydroxide, sodium carbonate, sodium hydroxide, and the like. In addition, in further embodiments, the salt forms of the disclosed compounds are prepared using salts of the starting materials or intermediates.

Further, in some embodiments, the compounds described herein are prepared as pharmaceutically acceptable salts formed by reacting the free base form of the compound with a pharmaceutically acceptable inorganic or organic acid, including, but not limited to, inorganic acids such as hydrochloric acid, hydroboric acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, and muconic acid.

Solvates

In other embodiments, the compounds described herein also exist in various solvated forms, which in further embodiments are useful for treating disorders. For example, the disclosure provides for methods of treating diseases, by administering solvates of the compounds described herein. In some embodiments, the solvates are administered as pharmaceutical compositions. In other embodiments, the solvates are pharmaceutically acceptable solvates.

Solvates contain either stoichiometric or non-stoichiometric amounts of a solvent, and in further embodiments are formed during the process of crystallization with pharmaceutically acceptable solvents such as water, ethanol, and the like. Hydrates are formed when the solvent is water, or alcoholates are formed when the solvent is alcohol. In some embodiments, solvates of the compounds described herein are conveniently prepared or formed during the processes described herein. By way of example only, in some embodiments, hydrates of the compounds described herein are conveniently prepared by recrystallization from an aqueous/organic solvent mixture, using organic solvents including, but not limited to, dioxane, tetrahydrofuran or methanol. In addition, in other embodiments, the compounds provided herein exist in unsolvated as well as solvated forms. In general, the solvated forms are considered equivalent to the unsolvated forms for the purposes of the compounds and methods provided herein.

Polymorphs

In some embodiments, the compounds described herein also exist in various polymorphic states, all of which are herein contemplated, and in other embodiments, are useful for treating disorders. For example, the disclosure provides for methods of treating diseases, by administering polymorphs of the compounds described herein. In some embodiments, the various polymorphs are administered as pharmaceutical compositions.

Thus, the compounds described herein include all their crystalline forms, known as polymorphs. Polymorphs include the different crystal packing arrangements of the same elemental composition of the compound. In some embodiments, polymorphs have different X-ray diffraction patterns, infrared spectra, melting points, density, hardness, crystal shape, optical and electrical properties, stability, solvates and solubility. In other embodiments, various factors such as the recrystallization solvent, rate of crystallization, and storage temperature cause a single crystal form to dominate.

Prodrugs

In some embodiments, the compounds described herein also exist in prodrug form, which in other embodiments, are useful for treating disorders. For example, the disclosure provides for methods of treating diseases, by administering prodrugs of the compounds described herein. In some embodiments, the prodrugs are administered as pharmaceutical compositions.

Prodrugs are generally drug precursors that, following administration to a subject and subsequent absorption, are converted to an active, or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug the active drug is generated. Prodrugs are often useful because, in some embodiments, they are easier to administer than the parent drug. In further embodiments, they are bioavailable by oral administration whereas the parent is not. In some embodiments, the prodrug has improved solubility in pharmaceutical compositions over the parent drug. An example, without limitation, of a prodrug would be the compound as described herein which is administered as an ester (the "prodrug") to facilitate transmittal across a cell membrane where water solubility is detrimental to mobility but which then is metabolically hydrolyzed to the carboxylic acid, the active entity, once inside the cell where water-solubility is beneficial. In some embodiments, the prodrug is a short peptide (polyamino acid) bonded to an acid group where the peptide is metabolized to reveal the active moiety.

In other embodiments, prodrugs are designed as reversible drug derivatives, for use as modifiers to enhance drug transport to site-specific tissues. The design of prodrugs to date has been to increase the effective water solubility of the therapeutic compound for targeting to regions where water is the principal solvent. See, e.g., Fedorak et al., *Am. J. Physiol.*, 269:G210-218 (1995); McLoed et al., *Gastroenterol*, 106:405-413 (1994); Hochhaus et al., *Biomed. Chrom.*, 6:283-286 (1992); J. Larsen and H. Bundgaard, *Int. J. Pharmaceutics*, 37, 87 (1987); J. Larsen et al., *Int. J. Pharmaceutics*, 47, 103

(1988); Sinkula et al., *J. Pharm. Sci.,* 64:181-210 (1975); T. Higuchi and V. Stella, *Pro-drugs as Novel Delivery Systems,* Vol. 14 of the A.C.S. Symposium Series; and Edward B. Roche, *Bioreversible Carriers in Drug Design,* American Pharmaceutical Association and Pergamon Press, 1987, all incorporated herein in their entirety.

Pharmaceutically acceptable prodrugs of the compounds described herein include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters. Various forms of prodrugs are known. See for example *Design of Prodrugs,* Bundgaard, A. Ed., Elseview, 1985 and *Method in Enzymology,* Widder, K. et al., Ed.; Academic, 1985, vol. 42, p. 309-396; Bundgaard, H. "Design and Application of Prodrugs" in *A Textbook of Drug Design and Development,* Krosgaard-Larsen and H. Bundgaard, Ed., 1991, Chapter 5, p. 113-191; and Bundgaard, H., *Advanced Drug Delivery Review,* 1992, 8, 1-38, each of which is incorporated herein by reference. The prodrugs described herein include, but are not limited to, the following groups and combinations of these groups; amine derived prodrugs:

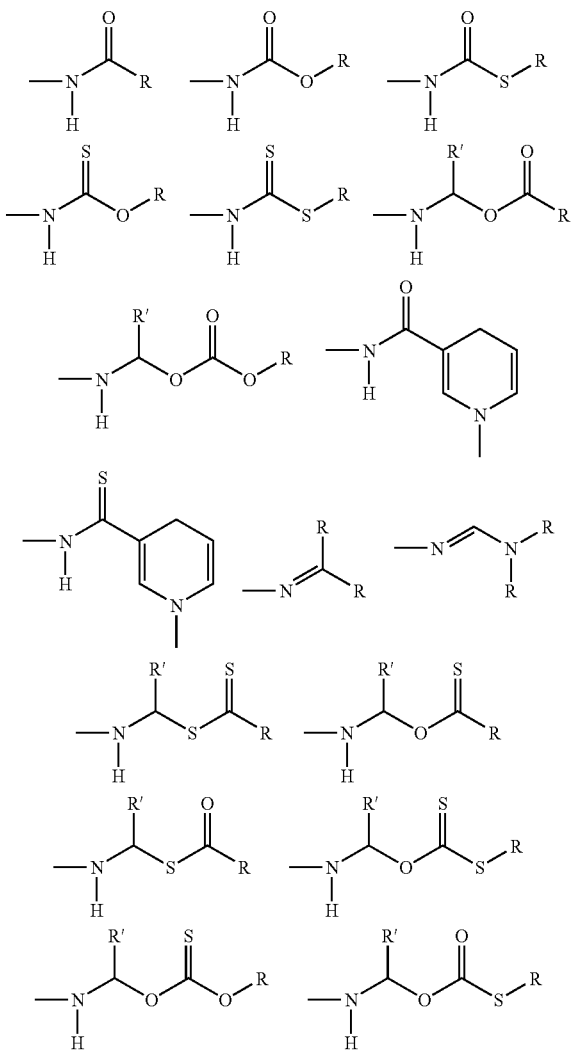

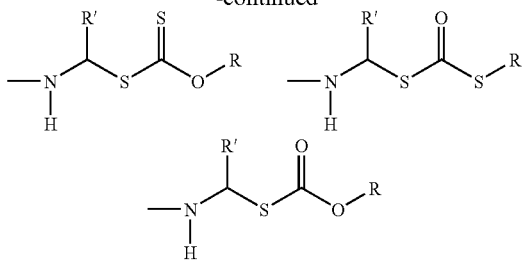

Hydroxy prodrugs include, but are not limited to acyloxyalkyl esters, alkoxycarbonyloxyalkyl esters, alkyl esters, aryl esters and disulfide containing esters.

In some embodiments, prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of the present disclosure. The amino acid residues include but are not limited to the 20 naturally occurring amino acids commonly designated by three letter symbols and also includes 4-hydroxyproline, hydroxylysine, demosine, isodemosine, 3-methylhistidine, norvaline, beta-alanine, gamma-aminobutyric acid, cirtulline, homocysteine, homoserine, ornithine and methionine sulfone. Additional types of prodrugs are also encompassed.

Prodrug derivatives of compounds described herein can be prepared by methods described herein (e.g., for further details see Saulnier et al., (1994), Bioorganic and Medicinal Chemistry Letters, Vol. 4, p. 1985). By way of example only, in some embodiments, appropriate prodrugs are prepared by reacting a non-derivatized compound described herein with a suitable carbamylating agent, such as, but not limited to, 1,1-acyloxyalkylcarbanochloridate, para-nitrophenyl carbonate, or the like. Prodrug forms of the herein described compounds, wherein the prodrug is metabolized in vivo to produce a derivative as set forth herein are included within the scope of the claims. Indeed, in some embodiments, some of the herein-described compounds are a prodrug for another derivative or active compound.

In some embodiments, compounds described herein having free amino, amido, hydroxy or carboxylic groups are converted into prodrugs. For instance, in some embodiments, free carboxyl groups are derivatized as amides or alkyl esters. In other embodiments, free hydroxy groups are derivatized using groups including but not limited to hemisuccinates, phosphate esters, dimethylaminoacetates, and phosphoryloxymethyloxycarbonyls, as outlined in *Advanced Drug Delivery Reviews* 1996, 19, 115. Carbamate prodrugs of hydroxy and amino groups are also included, as are carbonate prodrugs, sulfonate esters and sulfate esters of hydroxy groups.

Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. In some embodiments, free amines are derivatized as amides, sulfonamides or phosphonamides. In some embodiments, all of these prodrug moieties incorporate groups including but not limited to ether, amine and carboxylic acid functionalities. In other embodiments, phosphate ester functionalities are used as prodrug moieties.

In some other embodiments, sites on the aromatic ring portions of the compounds described herein are susceptible to various metabolic reactions, therefore incorporation of appropriate substituents on the aromatic ring structures, reduces, minimizes or eliminates this metabolic pathway.

Further Forms of the Compounds

Isomers

The compounds described herein may exist as geometric isomers. The compounds described herein may possess one or more double bonds. The compounds presented herein include all cis, trans, syn, anti, entgegen (E), and zusammen (Z) isomers as well as the corresponding mixtures thereof. In some situations, compounds may exist as tautomers. The compounds described herein include all possible tautomers within the formulas described herein.

The compounds described herein may possess one or more chiral centers and each center may exist in the R or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion may also be useful for the applications described herein.

In some embodiments, the compounds described herein can be prepared as their individual stereoisomers by reacting a racemic mixture of the compound with an optically active resolving agent to form a pair of diastereoisomeric compounds or complexes, separating the diastereomers and recovering the optically pure enantiomers. While resolution of enantiomers can be carried out using covalent diastereomeric derivatives of the compounds described herein, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The single enantiomer of high optical purity (ee>90%) is then recovered, along with the resolving agent, by any practical means that would not result in racemnization. A more detailed description of the techniques applicable to the resolution of stereoisomers of compounds from their racemic mixture can be found in Jean Jacques, Andre Collet, Samuel H. Wilen, "Enantiomers, Racemates and Resolutions," John Wiley And Sons, Inc., 1981, herein incorporated by reference in its entirety.

Labeled Compounds

It should be understood that the compounds described herein include their isotopically-labeled equivalents, including their use for treating disorders. For example, the disclosure provides for methods of treating diseases, by administering isotopically-labeled the compounds disclosed herein. The isotopically-labeled compounds described herein can be administered as pharmaceutical compositions. Thus, the compounds described herein also include their isotopically-labeled isomers, which are identical to those recited herein, but for the fact that one or more atoms are replaced by an atom having an atomic mass or mass number different from the atomic mass or mass number usually found in nature. Examples of isotopes that can be incorporated into compounds of the present disclosure include isotopes of hydrogen, carbon, nitrogen, oxygen, phosphorous, sulfur, fluorine and chloride, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, pharmaceutically acceptable salts, esters, prodrugs, solvate, hydrates or derivatives thereof which contain the aforementioned isotopes and/or other isotopes of other atoms are within the scope of the disclosure. Certain isotopically-labeled compounds, for example those into which radioactive isotopes such as $^3H$ and $^{14}C$ are incorporated, are useful in drug and/or substrate tissue distribution assays. Tritiated, i.e., $^3H$ and carbon-14, i.e., $^{14}C$, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds, pharmaceutically acceptable salts, esters, prodrugs, solvates, hydrates or derivatives thereof can generally be prepared by carrying out procedures described herein, by substituting a readily available isotopically labeled reagent for a non-isotopically labeled reagent.

The compounds described herein may be labeled by other means, including, but not limited to, the use of chromophores or fluorescent moieties, bioluminescent labels, or chemiluminescent labels.

The present disclosure is not to be limited in scope by the embodiments disclosed herein, which are intended as illustrations of single aspects of the present disclosure. Indeed, various modifications of the aspects described herein are also contemplated. Such modifications are intended to fall within the scope of the present disclosure. Moreover, in some other embodiments, any one or more features of any embodiment is combined with any one or more other features of any other embodiment disclosed herein, without departing from the scope described herein. For example, the heterocyclic kinase modulators described herein are equally applicable to the methods of treatment and methods of inhibiting kinases described herein.

The examples and preparations provided below further illustrate and exemplify the compounds of the present disclosure and methods of preparing such compounds. It is to be understood that the scope of the present disclosure is not limited in any way by the scope of the following examples and preparations.

Methods of Inhibiting Kinases

In another aspect, the present invention provides methods of modulating protein kinase activity using the kinase modulators of the present invention. The term "modulating kinase activity," as used herein, means that the activity of the protein kinase is increased or decreased when contacted with a kinase modulator of the present invention relative to the activity in the absence of the kinase modulator. Therefore, the present disclosure provides a method of modulating protein kinase activity by contacting the protein kinase with a kinase modulator of the present disclosure. In some embodiments, the compound as described herein is contacted with the protein kinase.

In some embodiments, the kinase modulators described herein inhibit kinase activity. The term "inhibit," as used herein in reference to kinase activity, means that the kinase activity is decreased when contacted with a kinase modulator relative to the activity in the absence of the kinase modulator. Therefore, the present invention further provides a method of inhibiting protein kinase activity by contacting the protein kinase with a kinase modulator as described herein.

In certain embodiments, the protein kinase is a protein tyrosine kinase. A protein tyrosine kinase, as used herein, refers to an enzyme that catalyzes the phosphorylation of tyrosine residues in proteins with a phosphate donors (e.g., a nucleotide phosphate donor such as ATP). Protein tyrosine kinases include, for example, Abelson tyrosine kinases ("Abl") (e.g., c-Abl and v-Abl), Ron receptor tyrosine kinases ("RON"), Met receptor tyrosine kinases ("MET"), Fms-like tyrosine kinases ("FLT") (e.g., FLT3), src-family tyrosine kinases (e.g., lyn, CSK), and p21-activated kinase-4 ("PAK"), FLT3, aurora kinases, B-lymphoid tyrosine kinases ("Blk"), cyclin-dependent kinases ("CDK") (e.g., CDK1 and CDK5), src-family related protein tyrosine kinases (e.g., Fyn kinase), glycogen synthase kinases ("GSK") (e.g., GSK3α and GSK3β), lymphocyte protein tyrosine kinases ("Lck"), ribosomal S6 kinases (e.g., Rsk1, Rsk2, and Rsk3), sperm tyrosine kinases (e.g., Yes), and subtypes and homologs thereof exhibiting tyrosine kinase activity. In certain embodiments, the protein tyrosine kinase is Abl, RON, MET, PAK, or FLT3. In other embodiments, the protein tyrosine kinase is a FLT3 or Abl family member.

In another embodiment, the kinase is a mutant kinase, such as a mutant Bcr-Abl kinase, FLT3 kinase or aurora kinases. Useful mutant Bcr-Abl kinases include those having at least one of the following clinically isolated mutations: M244V, L248V, G250E, G250A, Q252H, Q252R, Y253F, Y253H, E255K, E255V, D276G, F311L, T315I, T315N, T315A, F317V, F317L, M343T, M351T, E355G, F359A, F359V, V3791, F382L, L387M, H396P, H396R, S417Y, E459K and F486S. In some embodiments, the mutant Abl kinase has a T315I mutation. The numbering system denoting the position of the amino acid mutation above is the well known wild-type ABL numbering according to ABL exon Ia. See Deininger M. et al., *Blood*, 105(7):2640 (2005). The numbering system is reproduced in FIG. 1 (SEQ ID NO: 11). In some embodiments, the mutant Bcr-Abl kinase includes at least one of the mutations listed above and has at least 80%, 85%, 90%, 95%, 96%, 97%, 98%, 99%, or 100% sequence identity to the sequence of FIG. 1. In some embodiments, the mutant Bcr-Abl kinase includes at least one of the mutations listed above, has a sequence identity to FIG. 1 as discussed above, and includes at least 50, 100, 150, 200, 250, 300, 350, 400, 450, 500, 550, 600, 650, 700, 750, 800, 850, 900, 950, 1000, 1050, or 1100 amino acids.

In some embodiments, the kinase is selected from Abelson tyrosine kinase, Ron receptor tyrosine kinase, Met receptor tyrosine kinase, Fms-like tyrosine kinase-3, Aurora kinases, p21-activated kinase-4, and 3-phosphoinositide-dependent kinase-1. In some embodiments, the compound described herein is contacted with the kinase.

In some embodiments, the kinase is homologous to a known kinase (also referred to herein as a "homologous kinase"). Compounds and compositions useful for inhibiting the biological activity of homologous kinases may be initially screened, for example, in binding assays. Homologous enzymes comprise an amino acid sequence of the same length that is at least 50%, at least 60%, at least 70%, at least 80%, or at least 90% identical to the amino acid sequence of full length known kinase, or 70%, 80%, or 90% homology to the known kinase active domains. Homology may be determined using, for example, a PSI BLAST search, such as, but not limited to that described in Altschul et al., *Nuc. Acids Rec.*, 25:3389-3402 (1997). In certain embodiments, at least 50%, or at least 70% of the sequence is aligned in this analysis. Other tools for performing the alignment include, for example, DbClustal and ESPript, which may be used to generate the PostScript version of the alignment. See Thompson et al., *Nucleic Acids Research*, 28:2919-26 (2000); Gouet, et al., *Bioinformatics*, 15:305-08 (1999). Homologs may, for example, have a BLAST E-value of $1\times10^{-6}$ over at least 100 amino acids (Altschul et al., *Nucleic Acids Res.*, 25:3389-402 (1997) with FLT3, Abl, or another known kinase, or any functional domain of FLT3, Abl, or another known kinase.

Homology may also be determined by comparing the active site binding pocket of the enzyme with the active site binding pockets of a known kinase. For example, in homologous enzymes, at least 50%, 60%, 70%, 80%, or 90% of the amino acids of the molecule or homolog have amino acid structural coordinates of a domain comparable in size to the kinase domain that have a root mean square deviation of the alpha carbon atoms of up to about 1.5 Å, about 1.25 Å, about 1 Å, about 0.75 Å, about 0.5 Å, and or about 0.25 Å.

The compounds and compositions of the present invention are useful for inhibiting kinase activity and also for inhibiting other enzymes that bind ATP. They are thus useful for the treatment of diseases and disorders that may be alleviated by inhibiting such ATP-binding enzyme activity. Methods of determining such ATP-binding enzymes include those known to those of skill in the art, those discussed herein relating to selecting homologous enzymes, and by the use of the database PROSITE, where enzymes containing signatures, sequence patterns, motifs, or profiles of protein families or domains may be identified.

The compounds of the present invention, and their derivatives, may also be used as kinase-binding agents. As binding agents, such compounds and derivatives may be bound to a stable resin as a tethered substrate for affinity chromatography applications. The compounds of this invention, and their derivatives, may also be modified (e.g., radiolabelled or affinity labeled, etc.) in order to utilize them in the investigation of enzyme or polypeptide characterization, structure, and/or function.

In another embodiment, the kinase modulator described herein is a kinase inhibitor. In some embodiments, the kinase inhibitor has an $IC_{50}$ or inhibition constant ($K_i$) of less than 1 micromolar. In another embodiment, the kinase inhibitor has an $IC_{50}$ or inhibition constant ($K_i$) of less than 500 micromolar. In another embodiment, the kinase inhibitor has an $IC_{50}$ or $K_i$ of less than 10 micromolar. In another embodiment, the kinase inhibitor has an $IC_{50}$ or $K_i$ of less than 500 nanomolar. In another embodiment, the kinase inhibitor has an $IC_{50}$ or $K_i$ of less than 10 nanomolar. In another embodiment, the kinase inhibitor has an $IC_{50}$ or $K_i$ of less than 1 nanomolar.

Methods of Treatment

In another aspect, the present invention provides methods of treating a disease mediated by kinase activity (kinase-mediated disease or disorder) in a subject (e.g., mammals, such as humans) in need of such treatment. By "kinase-mediated" or "kinase-associated" diseases is meant diseases in which the disease or symptom can be alleviated by inhibiting kinase activity (e.g., where the kinase is involved in signaling, mediation, modulation, or regulation of the disease process). By "diseases" is meant diseases, or disease symptoms. The method includes administering to the subject an effective amount of the kinase modulator described herein.

Examples of kinase associated diseases include cancer (e.g., leukemia, tumors, and metastases), allergy, asthma, obesity, inflammation (e.g., inflammatory diseases such as inflammatory airways disease), hematological disorders, obstructive airways disease, asthma, autoimmune diseases, metabolic diseases, infection (e.g., bacterial, viral, yeast, fungal), CNS diseases, brain tumors, degenerative neural diseases, cardiovascular diseases, and diseases associated with angiogenesis, neovascularization, and vasculogenesis. In an exemplary embodiment, the compounds are useful for treating cancer, including leukemia, and other diseases or disorders involving abnormal cell proliferation, such as myeloproliferative disorders. In some embodiments, the compounds disclosed herein are administered to the subject.

More specific examples of cancers treated with the compounds of the present invention include breast cancer, lung cancer, melanoma, colorectal cancer, bladder cancer, ovarian cancer, prostate cancer, renal cancer, squamous cell cancer, glioblastoma, pancreatic cancer, Kaposi's sarcoma, multiple myeloma, and leukemia (e.g., myeloid, chronic myeloid, acute lymphoblastic, chronic lymphoblastic, Hodgkins, and other leukemias and hematological cancers).

In some embodiments, the cancer is a solid tumor. Solid tumors can be classified by the type of cells forming the solid tumor, such as sarcomas, carcinomas, and lymphomas. Solid tumors can also be classified by organ site. Examples of solid tumors classified by organ site include head and neck tumors, lung tumors, skin tumors, esophagus tumors, gastric tumors, pancreas tumors, colorectal tumors, prostate tumors, sarcoma tumors, melanoma tumors, breast tumors, cervix tumors, endometrial tumors, ovarian tumors, liver tumors, biliary gall bladder tumors, small bowel tumors, and anus tumors.

In some embodiments, the compositions and methods described herein are used to treat hematologic cancers. Hematologic cancers include leukemia, lymphoma, myeloma, myelodysplastic syndrome, and myeloproliferative disorders. Leukemia includes acute leukemia, acute myelogenous leukemia (AML), acute lymphocytic leukemia (ALL), acute nonlymphocytic leukemia (ANLL), chronic myelogenous leukemia (CML), and chronic lymphocytic leukemia (CLL). Lymphoma includes Hodgkin lymphoma, non-Hodgkin lymphoma, cutaneous t-cell lymphoma (CTCL) (both granulocytic and monocytic), and mantle cell lymphoma (MCL). Myeloma includes multiple myeloma, extramedullary plasmacytoma, solitary myeloma, and indolent myeloma. Myelodysplastic syndrome includes clonal anemia, clonal sideroblastic anemia, clonal pancytopenia, and oligoblastic myelogenous leukemia. Myeloproliferative disorders include polycythemia vera, primary thrombocythemia, and idiopathic myelofibrosis.

In some embodiments, the compositions and methods described herein are used to treat cancers of epithelial origin. Generally, cancers having an epithelial origin include squamous cell carcinoma, adenocarcinoma, and transitional cell carcinoma. Specifically, non-limiting examples of premalignant or precancerous cancers/tumors having epithelial origin include actinic keratoses, arsenic keratoses, xeroderma pigmentosum, Bowen's disease, leukoplakias, metaplasias, dysplasias and papillomas of mucous membranes, e.g. of the mouth, tongue, pharynx and larynx, precancerous changes of the bronchial mucous membrane such as metaplasias and dysplasias (especially frequent in heavy smokers and people who work with asbestos and/or uranium), dysplasias and leukoplakias of the cervix uteri, vulval dystrophy, precancerous changes of the bladder, e.g. metaplasias and dysplasias, papillomas of the bladder as well as polyps of the intestinal tract. Non-limiting examples of semi-malignant or malignant cancers/tumors of the epithelial origin are breast cancer, skin cancer (e.g., basal cell carcinomas), bladder cancer (e.g., superficial bladder carcinomas), colon cancer, gastro-intestinal (GI) cancer, prostate cancer, uterine cancer, cervical cancer, ovarian cancer, esophageal cancer, stomach cancer, laryngeal cancer and lung cancer.

More specific examples of cancers of epithelial origin include adenocarcinoma, basal cell carcinoma, choriocarcinoma, cystadenocarcinoma, embryonal carcinoma, epithelial carcinoma, hepatocellular carcinoma, hepatoma, large cell carcinoma, medullary thyroid carcinoma, papillary carcinoma, papillary adenocarcinomas, sebaceous gland carcinoma, small cell lung carcinoma, squamous cell carcinoma, and sweat gland carcinoma.

In some embodiments, the compositions and methods described herein are used to treat cancers of the central nervous system. Cancers of the central nervous system include hemangioblastoma, medulloblastoma, meningioma, and neuroblastoma.

In some embodiments, the compositions and methods described herein are used to treat genital cancers. Gynecological cancers include cervical cancer, endometrial cancer, ovarian cancer, uterine cancer, vaginal cancer, uveal melanoma, and vulvar cancer. Male genital cancer includes prostate cancer, testicular cancer, seminoma, and penile cancer.

In some embodiments, the compositions and methods described herein are used to treat oral cancers. Oral cancers include cancers of the oral cavity, and cancers of the oropharynx.

In some embodiments, the compositions and methods described herein are used to treat skin cancers. Skin cancers include basal cell carcinoma, squamous cell carcinoma, Kaposi's sarcoma, merkel cell cancer, actinic keratosis, melanoma, cutaneous melanoma, and other non-epithelial skin cancers.

In some embodiments, the compositions and methods described herein are used to treat genitourinary cancers. Genitourinary cancers include bladder cancer, renal cell cancer, adrenocortical carcinoma, prostate cancer, testicular cancer, penile cancer, renal pelvis cancer, and urethral cancer.

In some embodiments, the compositions and methods described herein are used to treat endocrine cancers. Endocrine cancers include thyroid cancer, adrenocortical cancer, neuroblastoma, pheochromocytoma, pinealoma, and parathyroid cancer.

In some embodiments, the compositions and methods described herein are used to treat kidney cancers. Kidney cancers include kidney cancer, renal cell carcinoma (RCC), Wilm's tumor, clear cell carcinoma, papillary renal cell carcinoma, and pelvic renal cancer.

In some embodiments, the compositions and methods described herein are used to treat thoracic cancers. Thoracic cancers include non-small cell lung cancer (NSCLC), small cell lung cancer (SCLC), mesothelioma, EGFR-inhibitor-resistant NSCLC, esophageal cancer, bronchial cancer, mesothelioma, and other cancers of the respiratory organs.

In some embodiments, the compositions and methods described herein are used to treat gastrointestinal tract cancers. Gastrointestinal tract cancers include gastrointestinal stromal tumors (GIST), esophageal cancer, gastric cancer, hepatocellular carcinoma (HCC), gallbladder cancer, pancreatic cancer, colorectal cancer, anal cancer, anorectal cancer, liver cancer, intrahepatic bile duct cancer, extrahepatic bile duct cancer, small intestine cancer, and other biliary or digestive organ cancers.

In some embodiments, the compositions and methods described herein are used to treat brain cancers. Brain cancers can be classified by the type of cells where the cancer originates. Brain cancers that originate in the glial cells (gliomas or glioblastomas) include astrocytoma, anaplastic astrocytoma, glioblastoma multiforme, brain stem gliomas, ependymomas, blastoglioma, optic nerve gliomas, ependymoma, and oligodendrogliomas. Brain cancers that originate in the schwann cells (schwannomas) include acoustic neuroma. Brain cancers that originate in cells other than the glial cells include medulloblastomas, meningiomas, schwannomas, craniopharyngiomas, germ cell tumors, chordoma, craniopharyngioma, and pineal region tumors.

In some embodiments, the compositions and methods described herein are used to treat sarcomas. Sarcomas include leiomyosarcoma, angiosarcoma, chondrosarcoma, endotheliosarcoma, fibrosarcoma, Kaposi's sarcoma, liposarcoma, lymphangiosarcoma, lymphangioendotheliosarcoma, myxosarcoma, neurofibrosarcoma, osteogenic sarcoma, rhabdomyosarcoma, hepatoma, chandro sarcoma, fibrosarcoma, myxofibrosacroma, desmoid tumors, synovial sarcomas, malignant peripheral nerve sheet tumors (MPNST), gastrointestinal stromal tumors (GIST), and Ewing's tumors. Sarcomas can be classified as soft tissue sarcomas, osteosarcomas, and chondrosarcomas. Soft tissue sarcomas include fibrosarcoma, myxofibrosarcoma, desmoid tumors, liposarcoma, synovial sarcoma, rhabdomyosarcoma, leiomyosarcoma, malignant peripheral nerve sheet tumors (MPNST), gastrointestinal stromal tumors (GIST), angiosarcoma, Kaposi's sarcoma, and Ewing's tumors. Osteosarcomas include Ewing's tumors. Chondrosarcomas include central chondrosarcoma, peripheral chondrosarcoma, de-differentiated chondrosarcoma, clear cell chondrosarcoma, mesenchymal chondrosarcoma, and juxtacortical chondrosarcoma.

In some embodiments, the compositions and methods described herein are used to treat pancreatic cancers. Pancreatic cancer includes adenocarcinoma of the pancreas, and cystadenocarcinoma.

In some embodiments, the compositions and methods described herein are used to treat head and neck cancer. Head and neck cancer include laryngeal cancer, oropharyngeal cancer, parathyroid cancer, thyroid cancer, oral cancer, nasopharyngeal cancer, nasal cavity and paranasal sinus cancers, esophageal cancer, and hypopharyngeal cancer.

Other specific examples of diseases or disorders for which treatment by the compounds or compositions of the invention are useful for treatment or prevention include, but are not limited to transplant rejection (e.g., kidney, liver, heart, lung, islet cells, pancreas, bone marrow, cornea, small bowel, skin allografts or xenografts and other transplants), graft vs. host disease, osteoarthritis, rheumatoid arthritis, multiple sclerosis, diabetes, diabetic retinopathy, inflammatory bowel disease (e.g., Crohn's disease, ulcerative colitis, and other bowel diseases), renal disease, cachexia, septic shock, lupus, myasthenia gravis, psoriasis, dermatitis, eczema, seborrhea, Alzheimer's disease, Parkinson's disease, stem cell protection during chemotherapy, ex vivo selection or ex vivo purging for autologous or allogeneic bone marrow transplantation, ocular disease, retinopathies (e.g., macular degeneration, diabetic retinopathy, and other retinopathies), corneal disease, glaucoma, infections (e.g., bacterial, viral, or fungal), heart disease, including, but not limited to, restenosis.

Pharmaceutical Compositions and Administration

In some embodiments, administration of the compounds and compositions described herein are effected by any method that enables delivery of the compounds to the site of action. These methods include oral routes, intraduodenal routes, parenteral injection (including intravenous, subcutaneous, intraperitoneal, intramuscular, intravascular or infusion), topical, intrapulmonary, rectal administration, by implant, by a vascular stent impregnated with the compound, and other suitable methods commonly known in the art. For example, in other embodiments, compounds described herein are administered locally to the area in need of treatment. In some other embodiments, this is achieved by, for example, but not limited to, local infusion during surgery, topical application, e.g., cream, ointment, injection, catheter, or implant, said implant made, e.g., out of a porous, non-porous, or gelatinous material, including membranes, such as sialastic membranes, or fibers. In some embodiments, the administration is by direct injection at the site (or former site) of a tumor or neoplastic or pre-neoplastic tissue. Those of ordinary skill in the art are familiar with formulation and administration techniques that can be employed with the compounds and methods of the present disclosure, e.g., as discussed in Goodman and Gilman, The Pharmacological Basis of Therapeutics, current ed.; Pergamon; and Remington's, Pharmaceutical Sciences (current edition), Mack Publishing Co., Easton, Pa.

In some embodiments, the formulations include those suitable for oral, parenteral (including subcutaneous, intradermal, intramuscular, intravenous, intraarticular, intramedullary, intracardiac, intrathecal, intraspinal, intracapsular, subcapsular, intraorbital, intratracheal, subcuticular, intraarticular, subarachnoid, and intrasternal), intraperitoneal, transmucosal, transdermal, rectal and topical (including dermal, buccal, sublingual, intranasal, intraocular, and vaginal) administration although in other embodiments the most suitable route depends upon for example the condition and disorder of the recipient. In yet other embodiments, the formulations are conveniently presented in unit dosage form and may be prepared by any of the methods well known in the art of pharmacy. All methods include the step of bringing into association the compound of the subject disclosure or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

In another aspect, the present disclosure provides a pharmaceutical composition including a receptor tyrosine kinase modulator in admixture with a pharmaceutically acceptable excipient. One of skill in the art will recognize that the pharmaceutical compositions include the pharmaceutically acceptable salts of the tyrosine kinase modulators described above.

In some embodiments, in therapeutic and/or diagnostic applications, the compounds of the disclosure are formulated for a variety of modes of administration, including systemic and topical or localized administration. In further embodiments, techniques and formulations generally are found in Remington: The Science and Practice of Pharmacy ($20^{th}$ ed.) Lippincott, Williams & Wilkins (2000).

According to another aspect, the disclosure provides pharmaceutical compositions including compounds of the formulas described herein, and a pharmaceutically acceptable carrier, adjuvant, or vehicle. The amount of compound in the compositions of the disclosure is such that is effective to detectably inhibit a protein kinase in a biological sample or in a patient.

Pharmaceutically acceptable salts are generally known, and may include, by way of example but not limitation, acetate, benzenesulfonate, besylate, benzoate, bicarbonate, bitartrate, bromide, calcium edetate, camsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington: The Science and Practice of Pharmacy ($20^{th}$ ed.) Lippincott, Williams & Wilkins (2000). In some embodiments, pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

In some embodiments, depending on the specific conditions being treated, such agents are formulated into liquid or solid dosage forms and administered systemically or locally. In further embodiments, the agents are delivered, for example, in a timed- or sustained-low release forms is known to those skilled in the art. In further embodiments, techniques for formulation and administration are found in Remington: The Science and Practice of Pharmacy ($20^{th}$ ed.) Lippincott, Williams & Wilkins (2000). In other embodiments, suitable routes include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intrasternal, intra-synovial, intra-hepatic, intralesional, intracranial, intraperitoneal, intranasal, or intraocular injections or other modes of delivery.

In other embodiments, for injection, the agents of the disclosure are formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the disclosure into dosages suitable for systemic administration is within the scope of the disclosure. With proper choice of carrier and suitable manufacturing practice, in other embodiments, the compositions of the present disclosure, in particular, those formulated as solutions, are administered parenterally, such as by intravenous injection. In yet other embodiments, the compounds are formulated readily using pharmaceutically acceptable carriers well known in the art into dosages suitable for oral administration. Such carriers enable the compounds of the disclosure to be formulated as tablets, pills, capsules, liquids, gels, syrups, slurries, suspensions and the like, for oral ingestion by a patient to be treated.

In other embodiments, for nasal or inhalation delivery, the agents of the disclosure are also formulated by methods known to those of skill in the art, and include, for example, but not limited to, examples of solubilizing, diluting, or dispersing substances such as, saline, preservatives, such as benzyl alcohol, absorption promoters, and fluorocarbons.

Pharmaceutical compositions suitable for use in the present disclosure include compositions wherein active ingredients are contained in an effective amount to achieve its intended purpose. Determination of the effective amounts is well within the capability of those skilled in the art, especially in light of the detailed disclosure provided herein.

In addition to the active ingredients, in other embodiments, these pharmaceutical compositions contain suitable pharmaceutically acceptable carriers comprising excipients and auxiliaries which facilitate processing of the active compounds into preparations which are used pharmaceutically. In some embodiments, the preparations formulated for oral administration are in the form of tablets, dragees, capsules, or solutions.

In other embodiments, pharmaceutical preparations for oral use are obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, in some other embodiments, disintegrating agents are added, such as the cross-linked polyvinylpyrrolidone, agar, or alginic acid or a salt thereof such as sodium alginate.

Dragee cores are provided with suitable coatings. For this purpose, concentrated sugar solutions may be used, which in some embodiments optionally contain gum arabic, talc, polyvinylpyrrolidone, carbopol gel, polyethylene glycol (PEG), and/or titanium dioxide, lacquer solutions, and suitable organic solvents or solvent mixtures. In further embodiments, dye-stuffs or pigments are added to the tablets or dragee coatings for identification or to characterize different combinations of active compound doses.

In yet other embodiments, pharmaceutical preparations that are used orally include push-fit capsules made of gelatin, as well as soft, sealed capsules made of gelatin, and a plasticizer, such as glycerol or sorbitol. In some other embodiments, push-fit capsules contain the active ingredients in admixture with filler such as lactose, binders such as starches, and/or lubricants such as talc or magnesium stearate and, optionally, stabilizers. In other embodiments, with soft capsules, the active compounds are dissolved or suspended in suitable liquids, such as fatty oils, liquid paraffin, or liquid polyethylene glycols (PEGs). In addition, stabilizers may be added.

In some embodiments, pharmaceutical preparations are formulated as a depot preparation. In other embodiments, such long acting formulations are administered by implantation (for example subcutaneously or intramuscularly) or by intramuscular injection. Thus, for example in further embodiments, the compounds are formulated with suitable polymeric or hydrophobic materials (for example as an emulsion in an acceptable oil) or ion exchange resins, or as sparingly soluble derivatives, for example, as a sparingly soluble salt.

In some other embodiments, for buccal or sublingual administration, the compositions take the form of tablets, lozenges, pastilles, or gels formulated in conventional manner. In further embodiments, such compositions comprise the active ingredient in a flavored basis such as sucrose and acacia or tragacanth.

In yet other embodiments, pharmaceutical preparations are formulated in rectal compositions such as suppositories or retention enemas, e.g., containing conventional suppository bases such as cocoa butter, polyethylene glycol, or other glycerides.

In some other embodiments, pharmaceutical preparations are administered topically, that is by non-systemic administration. This includes the application of the compound of the present disclosure externally to the epidermis or the buccal cavity and the instillation of such the compound into the ear, eye and nose, such that the compound does not significantly enter the blood stream. In contrast, systemic administration refers to oral, intravenous, intraperitoneal and intramuscular administration.

Pharmaceutical preparations suitable for topical administration include liquid or semi-liquid preparations suitable for penetration through the skin to the site of inflammation such as gels, liniments, lotions, creams, ointments or pastes, suspensions, powders, solutions, spray, aerosol, oil, and drops suitable for administration to the eye, ear or nose. Alternatively, a formulation may comprise a patch or a dressing such as a bandage or adhesive plaster impregnated with active ingredients and optionally one or more excipients or diluents. The amount of active ingredient present in the topical formulation may vary widely. The active ingredient may comprise, for topical administration, from about 0.001% to about 10% w/w, for instance from about 1% to about 2% by weight of the formulation. It may however comprise as much as about 10% w/w but in other embodiments will comprise less than about 5% w/w, in yet other embodiments from about 0.1% to about 1% w/w of the formulation.

Formulations suitable for topical administration in the mouth include losenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations suitable for topical administration to the eye also include eye drops wherein the active ingredient is dissolved or suspended in a suitable carrier, especially an aqueous solvent for the active ingredient.

Pharmaceutical preparations for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

Depending upon the particular condition, or disease state, to be treated or prevented, additional therapeutic agents, which are normally administered to treat or prevent that condition, in other embodiments are administered together with the inhibitors of this disclosure.

The present disclosure is not to be limited in scope by the exemplified embodiments, which are intended as illustrations of single aspects of the disclosure. Indeed, various modifications of the disclosure in addition to those described herein will become apparent to those having skill in the art from the foregoing description. Such modifications are intended to fall within the scope of the disclosure. Moreover, any one or more features of any embodiment of the disclosure may be combined with any one or more other features of any other embodiment of the disclosure, without departing from the scope of the disclosure. References cited throughout this application are examples of the level of skill in the art and are hereby incorporated by reference herein in their entirety for all purposes, whether previously specifically incorporated or not.

Dosing

In some embodiments, continuously or discontinuously dosages are administered, for example once, twice or more per cycle or course of treatment, which in other embodiments are repeated for example every 7, 14, 21 or 28 days.

In other embodiments, the compounds of the present disclosure are continuously or discontinuously administered to a subject systemically, for example, intravenously, orally, subcutaneously, intramuscular, intradermal, or parenterally. In other embodiments, the compounds of the present disclosure are continuously or discontinuously administered to a subject locally. Non-limiting examples of local delivery systems include the use of intraluminal medical devices that include intravascular drug delivery catheters, wires, pharmacological stents and endoluminal paving.

In other embodiments the compounds of the present disclosure are further continuously or discontinuously administered to a subject in combination with a targeting agent to achieve high local concentration of the compound at the target site. In some embodiments, the compounds of the present disclosure are formulated for fast-release or slow-release with the objective of maintaining the drugs or agents in contact with target tissues for a period ranging from hours to weeks.

In other embodiments the optimum method and order of continuously or discontinuously dosing or administration and the dosage amounts and regime are readily determined using conventional methods and in view of the information set out herein.

In various embodiments, the compounds disclosed herein are administered continuously or discontinuously.

In one embodiment, the compound is administered once or twice daily for 28 days with patients then being evaluated for continuation of treatment. In another embodiment, the compound is administered once or twice daily dosing on a 14 days on, 7 days off therapy schedule, cycling every 21 days. In various embodiments, the therapy can last up to 12 months. In some embodiments, the therapy lasts for at least two months, at least three months, at least four months, at least five months, at least six months, at least seven months, at least eight months, at least nine months, or at least eleven months.

In addition to the aforementioned examples and embodiments of dosages, cycles, and schedules of cycles, numerous permutations of the aforementioned dosages, cycles, and schedules of cycles for the co-administration of a compound with a second chemotherapeutic compound, radiotherapy, or surgery are contemplated herein and in some embodiments are administered according to the patient, type of cancer, and/or appropriate treatment schedule as determined by qualified medical professionals.

The compounds according to the disclosure are effective over a wide dosage range. For example, in the treatment of adult humans, dosages from about 0.01 to about 10,000 mg, from about 0.5 to about 1000 mg, from about 1 to about 500 mg per day, and from about 5 to about 100 mg per day are examples of dosages that in some embodiments are used. In some embodiments, the compound is administered in an amount of about 20 mg/day to about 5 g/day, or about 80 mg/day to about 1 g/day. In some embodiments, the compound is administered in an amount of about 5 to about 500 mg/day. In some embodiments, the compound is administered in an amount of about 5 to about 250 mg/day. In some embodiments, the compound is administered in an amount of about 20 to about 200 mg/day. In some embodiments, the compound is administered in an amount of about 20 to about 150 mg/day. In various embodiments, the compound is administered in an amount of about 20 mg/day, about 30 mg/day, about 40 mg/day, about 50 mg/day, about 60 mg/day, about 70 mg/day, about 80 mg/day, about 90 mg/day, about 100 mg/day, about 110 mg/day, about 120 mg/day, about 130 mg/day, about 140 mg/day, about 150 mg/day, about 160 mg/day, about 170 mg/day, about 180 mg/day, about 190 mg/day or about 200 mg/day or more.

In some embodiments, the compound is administered in a dosage of about 1 mg/kg/day to about 120 mg/kg/day, for example about 10 to about 100 mg/kg/day, particularly in a dosage of about 60 mg/kg/day. In some embodiments, the compound is administered in a dosage of about 2 to about 10 mg/kg. In some embodiments the compound is administered in a dosage of about 5 mg/kg. In some embodiments the compound is administered in an amount of about 10 mg/kg. In some embodiments the compound is administered in an amount of about 20 mg/kg. In some embodiments the compound is administered in an amount of about 30 mg/kg. In some embodiments the compound is administered in an amount of about 40 mg/kg. In some embodiments the compound is administered in an amount of about 50 mg/kg. In some embodiments the compound is administered in an amount of about 60 mg/kg.

In some embodiments, the compound is administered in an amount of about 20 mg/day to about 5 g/day, or about 80 mg/day to about 1 g/day. In some embodiments, the compound is administered in an amount of about 5 to about 500 mg/day. In some embodiments, the compound is administered in an amount of about 5 to about 250 mg/day. In some embodiments, the compound is administered in an amount of about 20 to about 200 mg/day. In some embodiments, the compound is administered in an amount of about 20 to about 150 mg/day. In various embodiments, the compound is administered in an amount of about 20 mg/day, about 30 mg/day, about 40 mg/day, about 50 mg/day, about 60 mg/day, about 70 mg/day, about 80 mg/day, about 90 mg/day, about 100 mg/day, about 110 mg/day, about 120 mg/day, about 130 mg/day, about 140 mg/day, about 150 mg/day, about 160 mg/day, about 170 mg/day, about 180 mg/day, about 190 mg/day or about 200 mg/day or more.

Alternatively, the dosage may be determined on a mg/m$^2$ basis.

In various embodiments, the compounds administered once a day, twice a day, three times a day, or four times a day. In specific embodiments, the compounds are administered twice a day.

The exact dosage will depend upon the route of administration, the form in which the compound is administered, the subject to be treated, the body weight of the subject to be treated, and the preference and experience of the attending physician.

Combination Therapy

In another aspect, the disclosure provides combination therapies for treating or inhibiting the onset of a cell proliferative disorder or a disorder related to a tyrosine kinase in a subject. In one embodiment, are combination therapies for treating or inhibiting the onset of a cell proliferative disorder or a disorder related to the RON receptor tyrosine kinase in a subject. In another embodiment are combination therapies for treating or inhibiting the onset of a cell proliferative disorder or a disorder related to an Abl tyrosine kinase in a subject. In one embodiment, are combination therapies for treating or inhibiting the onset of a cell proliferative disorder or a disorder related to the MET receptor tyrosine kinase in a subject. The combination therapy comprises continuously or discontinuously dosing or administering to the subject a therapeutically or prophylactically effective amount of a compound of the formulas described herein, and one or more other anti-cell proliferation therapy including chemotherapy, radiation therapy, gene therapy and immunotherapy.

In another aspect, the compounds of the disclosure are continuously or discontinuously administered in combination with chemotherapy. As used herein, chemotherapy refers to a therapy involving a chemotherapeutic agent. In some embodiments, a variety of chemotherapeutic agents are used in the combined treatment methods disclosed herein. Chemotherapeutic agents contemplated as exemplary, include, but are not limited to: platinum compounds (e.g., cisplatin, carboplatin, oxaliplatin); taxane compounds (e.g., paclitaxcel, docetaxol); campotothecin compounds (irinotecan, topotecan); vinca alkaloids (e.g., vincristine, vinblastine, vinorelbine); anti-tumor nucleoside derivatives (e.g., 5-fluorouracil, leucovorin, gemcitabine, capecitabine) alkylating agents (e.g., cyclophosphamide, carmustine, lomustine, thiotepa); epipodophyllotoxins/podophyllotoxins (e.g. etoposide, teniposide); aromatase inhibitors (e.g., anastrozole, letrozole, exemestane); anti-estrogen compounds (e.g., tamoxifen, fulvestrant), antifolates (e.g., premetrexed disodium); hypomethylating agents (e.g., azacitidine); biologics (e.g., gemtuzamab, cetuximab, rituximab, pertuzumab, trastuzumab, bevacizumab); antibiotics/anthracylines (e.g. idarubicin, actinomycin D, bleomycin, daunorubicin, doxorubicin, mitomycin C, dactinomycin, caminomycin, daunomycin); anti-metabolites (e.g., clofarabine, aminopterin, cytosine arabinoside, methotrexate); tubulin-binding agents (e.g. combretastatin, colchicine, nocodazole); topoisomerase inhibitors (e.g., camptothecin); differentiating agents (e.g., retinoids, vitamin D and retinoic acid); retinoic acid metabolism blocking agents (RAMBA) (e.g., accutane); kinase inhibitors (e.g., flavopiridol, imatinib mesylate, gefitinib, erlotinib, sunitinib, lapatinib, sorafinib, temisirolimus, dasatinib); farnesyltransferase inhibitors (e.g., tipifarnib); histone deacetylase inhibitors; inhibitors of the ubiquitin-proteasome pathway (e.g., bortezomib, Yondelis).

Further useful agents include verapamil, a calcium antagonist found to be useful in combination with antineoplastic agents to establish chemosensitivity in tumor cells resistant to accepted chemotherapeutic agents and to potentiate the efficacy of such compounds in drug-sensitive malignancies. See Simpson W G, The calcium channel blocker verapamil and cancer chemotherapy. Cell Calcium. December 1985; 6(6): 449-67. Additionally, yet to emerge chemotherapeutic agents are contemplated as being useful in combination with the compound of the present disclosure.

In further embodiments, specific, non-limiting examples of combination therapies include use of the compounds of the present disclosure with agents found in the following pharmacotherapeutic classifications as indicated below. These lists should not be construed to be closed, but should instead serve as illustrative examples common to the relevant therapeutic area at present. Moreover, in other embodiments, combination regimens include a variety of routes of administration and should include oral, intravenous, intraocular, subcutaneous, dermal, and inhaled topical.

In some embodiments, therapeutic agents include chemotherapeutic agents, but are not limited to, anticancer agents, alkylating agents, cytotoxic agents, antimetabolic agents, hormonal agents, plant-derived agents, and biologic agents.

Examples of anti-tumor substances, for example those selected from, mitotic inhibitors, for example vinblastine; alkylating agents, for example cis-platin, carboplatin and cyclophosphamide; anti-metabolites, for example 5-fluorouracil, cytosine arabinside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example, interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of treatment.

Alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfhydryl, carboxyl, and imidazole groups. Under physiological conditions, these drugs ionize and produce positively charged ion that attach to susceptible nucleic acids and proteins, leading to cell cycle arrest and/or cell death. In some embodiments, combination therapy including a compound as described herein and an alkylating agent has therapeutic synergistic effects on cancer and reduces side effects associated with these chemotherapeutic agents.

Cytotoxic agents are a group of drugs that produced in a manner similar to antibiotics as a modification of natural products. Examples of cytotoxic agents include, but are not limited to, anthracyclines (e.g. doxorubicin, daunorubicin, epirubicin, idarubicin and anthracenedione), mitomycin C, bleomycin, dactinomycin, plicatomycin. These cytotoxic agents interfere with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death. In some embodiments, combination therapy including a compound as described herein and a cytotoxic agent has therapeutic synergistic effects on cancer and reduces side effects associated with these chemotherapeutic agents.

Antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. In other embodiments, combination therapy including a compound as described herein and an antimetabolic agent has therapeutic synergistic effects on cancer and reduces side effects associated with these chemotherapeutic agents.

Hormonal agents are a group of drug that regulate the growth and development of their target organs. Most of the hormonal agents are sex steroids and their derivatives and analogs thereof, such as estrogens, androgens, and progestins. These hormonal agents may serve as antagonists of receptors for the sex steroids to down regulate receptor expression and transcription of vital genes. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone. In other embodiments, combination therapy including a compound as described herein and a hormonal agent has therapeutic synergistic effects on cancer and reduces side effects associated with these chemotherapeutic agents.

Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase II, leading to DNA strand scission. In other embodiments, combination therapy including a compound as described herein and a plant-derived agent having therapeutic synergistic effects on cancer and reducing side effects associated with these chemotherapeutic agents.

Biologic agents are a group of biomolecules that elicit cancer/tumor regression when used alone or in combination with chemotherapy and/or radiotherapy. Examples of biologic agents include, but are not limited to, immuno-modulating proteins such as cytokines, monoclonal antibodies against tumor antigens, tumor suppressor genes, and cancer vaccines. In another embodiment is a combination therapy a compound as described herein and a biologic agent having therapeutic synergistic effects on cancer, enhance the patient's immune responses to tumorigenic signals, and reduce potential side effects associated with this chemotherapeutic agent.

For the treatment of oncologic diseases, proliferative disorders, and cancers, compounds according to the present disclosure may be administered with an agent selected from the group comprising: aromatase inhibitors, antiestrogen, anti-androgen, corticosteroids, gonadorelin agonists, topoisomerase 1 and 2 inhibitors, microtubule active agents, alkylating agents, nitrosoureas, antineoplastic antimetabolites, platinum containing compounds, lipid or protein kinase targeting agents, IMiDs, protein or lipid phosphatase targeting agents, anti-angiogenic agents, Akt inhibitors, IGF-I inhibitors, FGF3 modulators, mTOR inhibitors, Smac mimetics, HDAC inhibitors, agents that induce cell differentiation, bradykinin 1 receptor antagonists, angiotensin II antagonists, cyclooxygenase inhibitors, heparanase inhibitors, lymphokine inhibitors, cytokine inhibitors, IKK inhibitors, P38MAPK inhibitors, HSP90 inhibitors, multlikinase inhibitors, bisphosphanates, rapamycin derivatives, anti-apoptotic pathway inhibitors, apoptotic pathway agonists, PPAR agonists, inhibitors of Ras isoforms, telomerase inhibitors, protease inhibitors, metalloproteinase inhibitors, aminopeptidase inhibitors, dacarbazine (DTIC), actinomycins $C_2$, $C_3$, D, and $F_1$, cyclophosphamide, melphalan, estramustine, maytansinol, rifamycin, streptovaricin, doxorubicin, daunorubicin, epirubicin, idarubicin, detorubicin, caminomycin, idarubicin, epirubicin, esorubicin, mitoxantrone, bleomycins A, $A_2$, and B, camptothecin, Irinotecang, Topotecan®, 9-aminocamptothecin, 10,11-methylenedioxycamptothecin, 9-nitrocamptothecin, bortezomib, temozolomide, TAS103, NP10052, combretastatin, combretastatin A-2, combretastatin A-4, calicheamicins, neocarcinostatins, epothilones A B, C, and semi-synthetic variants, Herceptin®, Rituxan®, CD40 antibodies, asparaginase, interleukins, interferons, leuprolide, and pegaspargase, 5-fluorouracil, fluorodeoxyuridine, ptorafuir, 5'-deoxyfluorouridine, UFT, MITC, S-1 capecitabine, diethylstilbestrol, tamoxifen, toremefine, tolmudex, thymitaq, flutamide, fluoxymesterone, bicalutamide, finasteride, estradiol, trioxifene, dexamethasone, leuproelin acetate, estramustine, droloxifene, medroxyprogesterone, megesterol acetate, aminoglutethimide, testolactone, testosterone, diethylstilbestrol, hydroxyprogesterone, mitomycins A, B and C, porfiromycin, cisplatin, carboplatin, oxaliplatin, tetraplatin, platinum-DACH, ormaplatin, thalidomide, lenalidomide, CI-973, telomestatin, CHIR258, Rad 001, SAHA, Tubacin, 17-AAG, sorafenib, JM-216, podophyllotoxin, epipodophyllotoxin, etoposide, teniposide, Tarceva®, Iressa®, Imatinib®, Miltefosine®, Perifosine®, aminopterin, methotrexate, methopterin, dichloro-methotrexate, 6-mercaptopurine, thioguanine, azattuoprine, allopurinol, cladribine, fludarabine, pentostatin, 2-chloroadenosine, deoxycytidine, cytosine arabinoside, cytarabine, azacitidine, 5-azacytosine, gencitabine, 5-azacytosine-arabinoside, vincristine, vinblastine, vinorelbine, leurosine, leurosidine and vindesine, paclitaxel, taxotere and docetaxel.

Cytokines possess profound immunomodulatory activity. Some cytokines such as interleukin-2 (IL-2, aldesleukin) and interferon have demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. In some embodiments, examples of interleukins that are used in conjunction with a compound as described herein include, but are not limited to, interleukin 2 (IL-2), and interleukin 4 (IL-4), interleukin 12 (IL-12).

Interferons include more than 23 related subtypes with overlapping activities, all of the IFN subtypes within the scope of the present disclosure. IFN has demonstrated activity against many solid and hematologic malignancies, the later appearing to be particularly sensitive.

In further embodiments, other cytokines that are used in conjunction with a tyrosine kinase modulator include those cytokines that exert profound effects on hematopoiesis and immune functions. Examples of such cytokines include, but are not limited to erythropoietin, granulocyte-CSF (filgrastin), and granulocyte, macrophage-CSF (sargramostim). In further embodiments, these cytokines are used in conjunction with a compound as described herein to reduce chemotherapy-induced myelopoietic toxicity.

In yet other embodiments, other immuno-modulating agents other than cytokines are used in conjunction with a tyrosine kinase modulator as described herein to inhibit abnormal cell growth. Examples of such immuno-modulating agents include, but are not limited to *bacillus* Calmette-Guerin, levamisole, and ocreotide, a long-acting octapeptide that mimics the effects of the naturally occurring hormone somatostatin.

Monoclonal antibodies against tumor antigens are antibodies elicited against antigens expressed by tumors, preferably tumor-specific antigens. For example, monoclonal antibody HERCEPTIN® (Trastrizumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein. In some embodiments are combination therapy including a compound as described herein and HERCEPTIN® having therapeutic synergistic effects on tumors, especially on metastatic cancers.

Another example of monoclonal antibodies against tumor antigens is RITUXAN® (Rituximab) that is raised against CD20 on lymphoma cells and selectively deplete normal and malignant $CD20^+$ pre-B and mature B cells. RITUXAN® is used as single agent for the treatment of patients with relapsed or refractory low-grade or follicular, $CD20^+$, B cell non-Hodgkin's lymphoma. In another embodiment is a combination therapy including a compound as described herein and RITUXAN® having therapeutic synergistic effects not only on lymphoma, but also on other forms or types of malignant tumors.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth-cancer. Examples of the tumor suppressor genes include, but are not limited to, DPC-4, NF-1, NF-2, RB, p53, WT1, BRCA1 and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. The tumor suppressor gene can be transferred into the tumor cells where it exerts its tumor suppressing functions. In another embodiment is a combination therapy including a compound described herein and a tumor suppressor having therapeutic synergistic effects on patients suffering from various forms of cancer.

Cancer vaccines are a group of agents that induce the body's specific immune response to tumors. Most of cancer vaccines under research and development and clinical trials are tumor-associated antigens (TAAs). TAA are structures (i.e. proteins, enzymes or carbohydrates) which are present on tumor cells and relatively absent or diminished on normal cells. By virtue of being fairly unique to the tumor cell, TAAs provide targets for the immune system to recognize and cause their destruction. Example of TAAs include, but are not limited to gangliosides (GM2), prostate specific antigen (PSA), alpha-fetoprotein (AFP), carcinoembryonic antigen (CEA) (produced by colon cancers and other adenocarcinomas, e.g. breast, lung, gastric, and pancreas cancer s), melanoma associated antigens (MART-1, gp 100, MAGE 1,3 tyrosinase), papillomavirus E6 and E7 fragments, whole cells or portions/lysates of antologous tumor cells and allogeneic tumor cells.

In some embodiments, an additional component is used in the combination to augment the immune response to TAAs. Examples of adjuvants include, but are not limited to, *bacillus* Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan, a chemotherapeutic agent which is believe to reduce tumor-induced suppression when given in low doses.

In another aspect, the disclosure provides compounds which are continuously or discontinuously administered in combination with radiation therapy. As used herein, "radiation therapy" refers to a therapy comprising exposing the subject in need thereof to radiation. Such therapy is known to those skilled in the art. In other embodiments, the appropriate scheme of radiation therapy is similar to those already employed in clinical therapies wherein the radiation therapy is used alone or in combination with other chemotherapeutics.

In another aspect, the disclosure provides compounds which are continuously or discontinuously administered in combination with a gene therapy. As used herein, "gene therapy" refers to a therapy targeting on particular genes involved in tumor development. Possible gene therapy strategies include the restoration of defective cancer-inhibitory genes, cell transduction or transfection with antisense DNA corresponding to genes coding for growth factors and their receptors, RNA-based strategies such as ribozymes, RNA decoys, antisense messenger RNAs and small interfering RNA (siRNA) molecules and the so-called 'suicide genes'.

In other aspect, the disclosure provides compounds which are continuously or discontinuously administered in combination with an immunotherapy. As used herein, "immunotherapy" refers to a therapy targeting particular protein involved in tumor development via antibodies specific to such protein. For example, monoclonal antibodies against vascular endothelial growth factor have been used in treating cancers.

In other embodiments, where a second pharmaceutical is used in addition to a compound of the disclosure, the two pharmaceuticals are continuously or discontinuously administered simultaneously (e.g. in separate or unitary compositions) sequentially in either order, at approximately the same time, or on separate dosing schedules. In further embodiments, the two compounds are continuously or discontinuously administered within a period and in an amount and manner that is sufficient to ensure that an advantageous or synergistic effect is achieved. It will be appreciated that in some embodiments, the method and order of administration and the respective dosage amounts and regimes for each component of the combination will depend on the particular chemotherapeutic agent being administered in conjunction with the compound of the present disclosure, their route of administration, the particular tumor being treated and the particular host being treated.

In certain embodiments, the tyrosine kinase modulating compounds described herein are taken alone or in combination with other compounds. In one embodiment, two or more tyrosine kinase modulating compounds are administered to a subject in need thereof.

In yet another embodiment, one or more tyrosine kinase modulating compounds are administered with one or more therapeutic agents for the treatment or prevention of various diseases, including, for example, cancer, diabetes, neurodegenerative diseases, cardiovascular disease, blood clotting, inflammation, flushing, obesity, ageing, stress, etc. In various embodiments, combination therapies comprising a tyrosine kinase modulating compound refer to (1) pharmaceutical compositions that comprise one or more tyrosine kinase modulating compounds in combination with one or more therapeutic agents (e.g., one or more therapeutic agents described herein); and (2) co-administration of one or more tyrosine kinase modulating compounds with one or more therapeutic agents wherein the tyrosine kinase modulating compound and therapeutic agent have not been formulated in the same compositions (but in some embodiments, are present within the same kit or package, such as a blister pack or other multi-chamber package; connected, separately sealed containers (e.g., foil pouches) that in further embodiments are separated by the user; or a kit where the tyrosine kinase modulating compound(s) and other therapeutic agent(s) are in separate vessels). In further embodiments, when using separate formulations, the tyrosine kinase modulating compound is administered at the same, intermittent, staggered, prior to, subsequent to, or combinations thereof, with the administration of another therapeutic agent.

In certain embodiments, the compounds described herein, their pharmaceutically acceptable salts, prodrug, solvates, polymorphs, tautomers or isomers are administered in combination with another cancer therapy or therapies. In other embodiments, these additional cancer therapies are for example, surgery, and the methods described herein and combinations of any or all of these methods. In further embodiments, combination treatments occur sequentially or concurrently and the combination therapies are neoadjuvant therapies or adjuvant therapies.

In some embodiments, the compounds described herein are administered with an additional therapeutic agent. In these embodiments, the compounds described herein are in a fixed combination with the additional therapeutic agent or a non-fixed combination with the additional therapeutic agent.

By way of example only, if one of the side effects experienced by a patient upon receiving one of the compounds described herein is hypertension, then in some embodiments, it is appropriate to administer an anti-hypertensive agent in combination with the compound. Or, by way of example only, the therapeutic effectiveness of one of the compounds described herein is enhanced by administration of another therapeutic agent, the overall therapeutic benefit to the patient is enhanced. Or, by way of example only, in other embodiments, the benefit experienced by a patient is increased by administering one of the compounds described herein with another therapeutic agent (which also includes a therapeutic regimen) that also has therapeutic benefit. In any case, in some embodiments, regardless of the disease, disorder or condition being treated, the overall benefit experienced by the patient is simply additive of the two therapeutic agents or in further embodiments, the patient experiences a synergistic benefit.

In some embodiments, the appropriate doses of chemotherapeutic agents is generally similar to or less than those already employed in clinical therapies wherein the chemotherapeutics are administered alone or in combination with other chemotherapeutics.

By way of example only, platinum compounds are advantageously administered in a dosage of about 1 to about 500 mg per square meter ($mg/m^2$) of body surface area, for example about 50 to about 400 $mg/m^2$, particularly for cisplatin in a dosage of about 75 $mg/m^2$ and for carboplatin in about 300 $mg/m^2$ per course of treatment. Cisplatin is not absorbed orally and must therefore be delivered via injection intravenously, subcutaneously, intratumorally or intraperitoneally.

By way of example only, taxane compounds are advantageously continuously or discontinuously administered in a dosage of about 50 to about 400 mg per square meter ($mg/m^2$) of body surface area, for example about 75 to about 250 $mg/m^2$, particularly for paclitaxel in a dosage of about 175 to about 250 $mg/m^2$ and for docetaxel in about 75 to about 150 $mg/m^2$ per course of treatment.

By way of example only, camptothecin compounds are advantageously continuously or discontinuously administered in a dosage of about 0.1 to about 400 mg per square meter ($mg/m^2$) of body surface area, for example about 1 to about 300 $mg/m^2$, particularly for irinotecan in a dosage of about 100 to about 350 mg/m$^2$ and for topotecan in about 1 to about 2 mg/m$^2$ per course of treatment.

By way of example only, in some embodiments, vinca alkaloids are advantageously continuously or discontinuously administered in a dosage of about 2 to about 30 mg per square meter (mg/m$^2$) of body surface area, particularly for vinblastine in a dosage of about 3 to about 12 mg/m$^2$, for vincristine in a dosage of about 1 to about 2 mg/m$^2$, and for vinorelbine in dosage of about 10 to about 30 mg/m$^2$ per course of treatment.

By way of example only, in further embodiments, antitumor nucleoside derivatives are advantageously continuously or discontinuously administered in a dosage of about 200 to about 2500 mg per square meter (mg/m$^2$) of body surface area, for example about 700 to about 1500 mg/m$^2$. 5-fluorouracil (5-FU) is commonly used via intravenous administration with doses ranging from about 200 to about 500 mg/m$^2$ (in some embodiments from about 3 to about 15 mg/kg/day). Gemcitabine is advantageously continuously or discontinuously administered in a dosage of about 800 to about 1200 mg/m$^2$ and capecitabine is advantageously continuously or discontinuously administered in about 1000 to about 2500 mg/m$^2$ per course of treatment.

By way of example only, in other embodiments, alkylating agents are advantageously continuously or discontinuously administered in a dosage of about 100 to about 500 mg per square meter (mg/m$^2$) of body surface area, for example about 120 to about 200 mg/m$^2$, in other embodiments for cyclophosphamide in a dosage of about 100 to about 500 mg/m$^2$, for chlorambucil in a dosage of about 0.1 to about 0.2 mg/kg of body weight, for carmustine in a dosage of about 150 to about 200 mg/m$^2$, and for lomustine in a dosage of about 100 to about 150 mg/m$^2$ per course of treatment.

By way of example only, in yet other embodiments podophyllotoxin derivatives are advantageously continuously or discontinuously administered in a dosage of about 30 to about 300 mg per square meter (mg/m2) of body surface area, for example about 50 to about 250 mg/m$^2$, particularly for etoposide in a dosage of about 35 to about 100 mg/m$^2$ and for teniposide in about 50 to about 250 mg/m$^2$ per course of treatment.

By way of example only, in other embodiments, anthracycline derivatives are advantageously continuously or discontinuously administered in a dosage of about 10 to about 75 mg per square meter (mg/m$^2$) of body surface area, for example about 15 to about 60 mg/m$^2$, particularly for doxorubicin in a dosage of about 40 to about 75 mg/m$^2$, for daunorubicin in a dosage of about 25 to about 45 mg/m$^2$, and for idarubicin in a dosage of about 10 to about 15 mg/m$^2$ per course of treatment.

By way of example only, in further embodiments, antiestrogen compounds are advantageously continuously or discontinuously administered in a dosage of about 1 to about 100 mg daily depending on the particular agent and the condition being treated. Tamoxifen is advantageously administered orally in a dosage of about 5 to about 50 mg, about 10 to about 20 mg twice a day, continuing the therapy for sufficient time to achieve and maintain a therapeutic effect. Toremifene is advantageously continuously or discontinuously administered orally in a dosage of about 60 mg once a day, continuing the therapy for sufficient time to achieve and maintain a therapeutic effect. Anastrozole is advantageously continuously or discontinuously administered orally in a dosage of about 1 mg once a day. Droloxifene is advantageously continuously or discontinuously administered orally in a dosage of about 20-100 mg once a day. Raloxifene is advantageously continuously or discontinuously administered orally in a dosage of about 60 mg once a day. Exemestane is advantageously continuously or discontinuously administered orally in a dosage of about 25 mg once a day.

By way of example only, in further embodiments, biologics are advantageously continuously or discontinuously administered in a dosage of about 1 to about 5 mg per square meter (mg/m$^2$) of body surface area, or as known in the art, if different. For example, trastuzumab is advantageously administered in a dosage of 1 to about 5 mg/m$^2$, in other embodiments, from about 2 to about 4 mg/m$^2$ per course of treatment.

In other embodiments, when a compound is administered with an additional treatment such as radiotherapy, the radiotherapy is administered at 1 day, 2 days, 3 days, 4 days, 5 days, 6 days, 7 days, 14 days, 21 days, or 28 days after administration of at least one cycle of a compound. In some embodiments, the radiotherapy is administered at 1 day, 2 days, 3 days, 4 days, 5 days, 6 days, 7 days, 14 days, 21 days, or 28 days before administration of at least one cycle of a compound. In additional embodiments, the radiotherapy is administered in any variation of timing with any variation of the aforementioned cycles for a compound. In other embodiments, additional schedules for co-administration of radiotherapy with cycles of a compound are further determined by appropriate testing, clinical trials, or in some embodiments are determined by qualified medical professionals.

When a compound is administered with an additional treatment such as surgery, the compound is administered 1, 2, 3, 4, 5, 6, 7, 14, 21, or 28 days prior to surgery. In additional embodiments, at least one cycle of the compound is administered 1, 2, 3, 4, 5, 6, 7, 14, 21, or 28 days after surgery. In yet further embodiments, additional variations of administering compound cycles in anticipation of surgery, or after the occurrence of surgery, are further determined by appropriate testing and/or clinical trials, or in some embodiments are determined by assessment of qualified medical professionals.

Other therapies include, but are not limited to administration of other therapeutic agents, radiation therapy or both. In the instances where the compounds described herein are administered with other therapeutic agents, the compounds described herein need not be administered in the same pharmaceutical composition as other therapeutic agents, and may, because of different physical and chemical characteristics, be administered by a different route. For example, in some embodiments, the compounds/compositions are administered orally to generate and maintain good blood levels thereof, while the other therapeutic agent is administered intravenously. The determination of the mode of administration and the advisability of administration, where possible, in the same pharmaceutical composition, is within the knowledge of the skilled clinician with the teachings described herein. In some embodiments, the initial administration is made according to established protocols, and then, based upon the observed effects, the dosage, modes of administration and times of administration in other embodiments, is modified by the skilled clinician. The particular choice of compound (and where appropriate, other therapeutic agent and/or radiation) will depend upon the diagnosis of the attending physicians and their judgment of the condition of the patient and the appropriate treatment protocol.

In other embodiments, the compounds and compositions described herein (and where appropriate chemotherapeutic agent and/or radiation) is administered concurrently (e.g., simultaneously, essentially simultaneously or within the same treatment protocol) or sequentially, depending upon the nature of the disease, the condition of the patient, and the actual choice of chemotherapeutic agent and/or radiation to be administered in conjunction (i.e., within a single treatment protocol) with the compound/composition.

In combinational applications and uses, the compound/composition and the chemotherapeutic agent and/or radiation need not be administered simultaneously or essentially simultaneously, and the initial order of administration of the compound/composition, and in other embodiments, the chemotherapeutic agent and/or radiation, is not important. Thus, in some embodiments, the compounds/compositions of the present disclosure are administered first followed by the administration of the chemotherapeutic agent and/or radiation; or the chemotherapeutic agent and/or radiation is administered first followed by the administration of the compounds/compositions described herein. In further embodiments, this alternate administration is repeated during a single treatment protocol. With the teachings described herein, the determination of the order of administration, and the number of repetitions of administration of each therapeutic agent during a treatment protocol, would be within the knowledge of the skilled physician after evaluation of the disease being treated and the condition of the patient. For example, in some embodiments, the chemotherapeutic agent and/or radiation is administered first, especially if it is a cytotoxic agent, and then the treatment continued with the administration of the compounds/compositions of the present disclosure followed, where determined advantageous, by the administration of the chemotherapeutic agent and/or radiation, and so on until the treatment protocol is complete. Thus, in other embodiments and in accordance with experience and knowledge, the practicing physician modifies each protocol for the administration of the compound/composition for treatment according to the individual patient's needs, as the treatment proceeds. The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. In further embodiments, relief of disease-related symptoms such as pain, and improvement in overall condition is used to help judge effectiveness of treatment.

In some embodiments, a composition described herein is administered before the administration of one or more chemotherapeutic agents. As non-limiting examples of this embodiment, the chemotherapeutic agent is administered hours (e.g. one, five, ten, etc.) or days (e.g., one, two, three, etc.) after administration of the composition described herein. In some embodiments, the subsequent administration is shortly after (e.g., within an hour) administration of the compound described herein.

Anti-emetic agents are a group of drugs effective for treatment of nausea and emesis (vomiting). Cancer therapies frequently cause urges to vomit and/or nausea. Many anti-emetic drugs target the 5-$HT_3$ serotonin receptor which is involved in transmitting signals for emesis sensations. These 5-$HT_3$ antagonists include, but are not limited to, dolasetron (Anzemet®), granisetron (Kytril®), ondensetron (Zofran®), palonosetron and tropisetron. Other anti-emetic agents include, but are not limited to, the dopamine receptor antagonists such as chlorpromazine, domperidone, droperidol, haloperidol, metoclopramide, promethazine, and prochlorperazine; antihistamines such as cyclizine, diphenhydramine, dimenhydrinate, meclizine, promethazine, and hydroxyzine; lorazepram, scopolamine, dexamethasone, Emetrol®, propofol, and trimethobenzamide. Administration of these anti-emetic agents in addition to the above described combination treatment will manage the potential nausea and emesis side effects caused by the combination treatment.

Immuno-restorative agents are a group of drugs that counter the immuno-suppressive effects of many cancer therapies. The therapies often cause myelosuppression, a substantial decrease in the production of leukocytes (white blood cells). The decreases subject the patient to a higher risk of infections. Neutropenia is a condition where the concentration of neutrophils, the major leukocyte, is severely depressed. Immuno-restorative agents are synthetic analogs of the hormone, granulocyte colony stimulating factor (G-CSF), and act by stimulating neutrophil production in the bone marrow. These include, but are not limited to, filgrastim (Neupogen®), PEG-filgrastim (Neulasta®) and lenograstim. Administration of these immuno-restorative agents in addition to the above described combination treatment will manage the potential myelosupression effects caused by the combination treatment.

Antibiotic agents are a group of drugs that have anti-bacterial, anti-fungal, and anti-parasite properties. Antibiotics inhibit growth or causes death of the infectious microorganisms by various mechanisms such as inhibiting cell wall production, preventing DNA replication, or deterring cell proliferation. Potentially lethal infections occur from the myelosupression side effects due to cancer therapies. The infections can lead to sepsis where fever, widespread inflammation, and organ dysfunction arise. Antibiotics manage and abolish infection and sepsis and include, but are not limited to, amikacin, gentamicin, kanamycin, neomycin, netilmicin, streptomycin, tobramycin, loracarbef, ertapenem, cilastatin, meropenem, cefadroxil, cefazolin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, teicoplanin, vancomycin, azithromycin, clarithromycin, dirithromycin, erthromycin, roxithromycin, troleandomycin, aztreonam, amoxicillin, ampicillin, azlocillin, carbenicillin, cloxacillin, dicloxacillin, flucloxacillin, mezlocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, ofloxacin, trovafloxacin, benzolamide, bumetanide, chlorthalidone, clopamide, dichlorphenamide, ethoxzolamide, indapamide, mafenide, mefruside, metolazone, probenecid, sulfanilamides, sulfamethoxazole, sulfasalazine, sumatriptan, xipamide, democlocycline, doxycycline, minocycline, oxytetracycline, tetracycline, chloramphenical, clindamycin, ethambutol, fosfomycin, fusidic acid, furazolidone, isoniazid, linezolid, metronidazole, mupirocin, nitro furantoin, platesimycin, pyrazinamide, dalfopristin, rifampin, spectinomycin, and telithromycin. Administration of these antibiotic agents in addition to the above described combination treatment will manage the potential infection and sepsis side effects caused by the combination treatment.

Anemia treatment agents are compounds directed toward treatment of low red blood cell and platelet production. In addition to myelosuppression, many cancer therapies also cause anemias, deficiencies in concentrations and production of red blood cells and related factors. Anemia treatment agents are recombinant analogs of the glycoprotein, erythropoietin, and function to stimulate erythropoiesis, the formation of red blood cells. Anemia treatment agents include, but are not limited to, recombinant erythropoietin (EPOGEN®, Dynopro®) and Darbepoetin alfa (Aranesp®). Administration of these anemia treatment agents in addition to the above described combination treatment will manage the potential anemia side effects caused by the combination treatment.

In some embodiments, pain and inflammation side effects arising from the described herein combination treatment are treated with compounds selected from the group comprising: corticosteroids, non-steroidal anti-inflammnatories, muscle relaxants and combinations thereof with other agents, anesthetics and combinations thereof with other agents, expectorants and combinations thereof with other agents, antidepressants, anticonvulsants and combinations thereof, antihypertensives, opioids, topical cannabinoids, and other agents, such as capsaicin.

In some embodiments, for the treatment of pain and inflammation side effects, compounds according to the present disclosure are administered with an agent selected from the group comprising: betamethasone dipropionate (augmented and nonaugmented), betamethasone valerate, clobetasol propionate, prednisone, methyl prednisolone, diflorasone diacetate, halobetasol propionate, amcinonide, dexamethasone, dexosimethasone, fluocinolone acetononide, fluocinonide, halcinonide, clocortolone pivalate, dexosimetasone, flurandrenolide, salicylates, ibuprofen, ketoprofen, etodolac, diclofenac, meclofenamate sodium, naproxen, piroxicam, celecoxib, cyclobenzaprine, baclofen, cyclobenzaprine/lidocaine, baclofen/cyclobenzaprine, cyclobenzaprine/lidocaine/ketoprofen, lidocaine, lidocaine/deoxy-D-glucose, prilocaine, EMLA Cream (Eutectic Mixture of Local Anesthetics (lidocaine 2.5% and prilocaine 2.5%), guaifenesin, guaifenesin/ketoprofen/cyclobenzaprine, amitryptyline, doxepin, desipramine, imipramine, amoxapine, clomipramine, nortriptyline, protriptyline, duloxetine, mirtazapine, nisoxetine, maprotiline, reboxetine, fluoxetine, fluvoxamine, carbamazepine, felbamate, lamotrigine, topiramate, tiagabine, oxcarbazepine, carbamezipine, zonisamide, mexiletine, gabapentin/clonidine, gabapentin/carbamazepine, carbamazepine/cyclobenzaprine, antihypertensives including clonidine, codeine, loperamide, tramadol, morphine, fentanyl, oxycodone, hydrocodone, levorphanol, butorphanol, menthol, oil of wintergreen, camphor, eucalyptus oil, turpentine oil; CB1/CB2 ligands, acetaminophen, infliximab) nitric oxide synthase inhibitors, particularly inhibitors of inducible nitric oxide synthase; and other agents, such as capsaicin. Administration of these pain and inflammation analgesic agents in addition to the above described combination treatment will manage the potential pain and inflammation side effects caused by the combination treatment.

Kits/Articles of Manufacture

For use in the therapeutic applications described herein, kits and articles of manufacture are also described herein. In some embodiments, kits comprise a carrier, package, or container that is compartmentalized to receive one or more containers such as vials, tubes, and the like, each of the container(s) comprising one of the separate elements to be used in a method described herein. Suitable containers include, for example, bottles, vials, syringes, and test tubes. In other embodiments, the containers are formed from a variety of materials such as glass or plastic.

The articles of manufacture provided herein contain packaging materials. Packaging materials for use in packaging pharmaceutical products include, but are not limited to, blister packs, bottles, tubes, inhalers, pumps, bags, vials, containers, syringes, bottles, and any packaging material suitable for a selected formulation and intended mode of administration and treatment.

For example, in one embodiment, the container(s) comprise one or more compounds described herein, optionally in a composition or in combination with another agent as disclosed herein. The container(s) optionally have a sterile access port (for example, in another embodiment, the container is an intravenous solution bag or a vial having a stopper pierceable by a hypodermic injection needle). Such kits optionally comprising a compound with an identifying description or label or instructions relating to its use in the methods described herein.

In another embodiment is a kit comprised of one or more additional containers, each with one or more of various materials (such as reagents, optionally in concentrated form, and/or devices) desirable from a commercial and user standpoint for use of a compound described herein. Non-limiting examples of such materials include, but not limited to, buffers, diluents, filters, needles, syringes; carrier, package, container, vial and/or tube labels listing contents and/or instructions for use, and package inserts with instructions for use. In a further embodiment, a set of instructions is included.

In yet another embodiment, a label is on or associated with the container. In a further embodiment a label is on a container when letters, numbers or other characters forming the label are attached, molded or etched into the container itself. In one embodiment, a label is associated with a container when it is present within a receptacle or carrier that also holds the container, e.g., as a package insert. In another embodiment, a label is used to indicate that the contents are to be used for a specific therapeutic application. In yet another embodiment, the label also indicates directions for use of the contents, such as in the methods described herein.

In certain embodiments, the pharmaceutical compositions are presented in a pack or dispenser device which contains one or more unit dosage forms containing a compound provided herein. In a further embodiment, the pack for example contains metal or plastic foil, such as a blister pack. In yet a further embodiment, the pack or dispenser device optionally is accompanied by instructions for administration. In another embodiment, the pack or dispenser is accompanied with a notice associated with the container in form prescribed by a governmental agency regulating the manufacture, use, or sale of pharmaceuticals, which notice is reflective of approval by the agency of the form of the drug for human or veterinary administration. Such notice, for example, in one embodiment, the labeling approved by the U.S. Food and Drug Administration for prescription drugs, or the approved product insert. Compositions containing a compound provided herein formulated in a compatible pharmaceutical carrier are also contemplated, placed in an appropriate container, and labeled for treatment of an indicated condition.

Assays

The compounds of the present invention may be easily assayed to determine their ability to modulate protein kinases, bind protein kinases, and/or prevent cell growth or proliferation. Some examples of useful assays are presented below.

Kinase Inhibition and Binding Assays

Inhibition of various kinases is measured by methods known to those of ordinary skill in the art, such as the various methods presented herein, and those discussed in the Upstate KinaseProfiler Assay Protocols June 2003 publication.

For example, where in vitro assays are performed, the kinase is typically diluted to the appropriate concentration to form a kinase solution. A kinase substrate and phosphate donor, such as ATP, is added to the kinase solution. The kinase is allowed to transfer a phosphate to the kinase substrate to form a phosphorylated substrate. The formation of a phosphorylated substrate may be detected directly by any appropriate means, such as radioactivity (e.g., $[\gamma\text{-}^{32}P\text{-}ATP]$), or the use of detectable secondary antibodies (e.g., ELISA). Alternatively, the formation of a phosphorylated substrate may be detected using any appropriate technique, such as the detection of ATP concentration (e.g., Kinase-Glo® assay system (Promega)). Kinase inhibitors are identified by detecting the formation of a phosphorylated substrate in the presence and absence of a test compound (see Examples section below).

The ability of the compound to inhibit a kinase in a cell may also be assayed using methods well known in the art. For example, cells containing a kinase may be contacted with an activating agent (such as a growth factor) that activates the kinase. The amount of intracellular phosphorylated substrate formed in the absence and the presence of the test compound may be determined by lysing the cells and detecting the presence phosphorylated substrate by any appropriate method (e.g., ELISA). Where the amount of phosphorylated substrate produced in the presence of the test compound is decreased relative to the amount produced in the absence of the test compound, kinase inhibition is indicated. More detailed cellular kinase assays are discussed in the Examples section below.

To measure the binding of a compound to a kinase, any method known to those of ordinary skill in the art may be used. For example, a test kit manufactured by Discoverx (Fremont, Calif.), ED-Staurosporine NSIP™ Enzyme Binding Assay Kit (see U.S. Pat. No. 5,643,734) may be used. Kinase activity may also be assayed as in U.S. Pat. No. 6,589,950, issued Jul. 8, 2003.

Suitable kinase inhibitors may be selected from the compounds of the invention through protein crystallographic screening, as disclosed in, for example Antonysamy, et al., PCT Publication No. WO03087816A 1, which is incorporate herein by reference in its entirety for all purposes.

The compounds of the present invention may be computationally screened to assay and visualize their ability to bind to and/or inhibit various kinases. The structure may be computationally screened with a plurality of compounds of the present invention to determine their ability to bind to a kinase at various sites. Such compounds can be used as targets or leads in medicinal chemistry efforts to identify, for example, inhibitors of potential therapeutic importance (Travis, *Science*, 262:1374 (1993). The three dimensional structures of such compounds may be superimposed on a three dimensional representation of kinases or an active site or binding pocket thereof to assess whether the compound fits spatially into the representation and hence the protein. In this screening, the quality of fit of such entities or compounds to the binding pocket may be judged either by shape complementarity or by estimated interaction energy (Meng et al., *J. Comp. Chem.*, 13:505-24 (1992)).

The screening of compounds of the present invention that bind to and/or modulate kinases (e.g., inhibit or activate kinases) according to this invention generally involves consideration of two factors. First, the compound must be capable of physically and structurally associating, either covalently or non-covalently with kinases. For example, covalent interactions may be important for designing irreversible or suicide inhibitors of a protein. Non-covalent molecular interactions important in the association of kinases with the compound include hydrogen bonding, ionic interactions, van der Waals, and hydrophobic interactions. Second, the compound must be able to assume a conformation and orientation in relation to the binding pocket, that allows it to associate with kinases. Although certain portions of the compound will not directly participate in this association with kinases, those portions may still influence the overall conformation of the molecule and may have a significant impact on potency. Conformational requirements include the overall three-dimensional structure and orientation of the chemical group or compound in relation to all or a portion of the binding pocket, or the spacing between functional groups of a compound comprising several chemical groups that directly interact with kinases.

Docking programs described herein, such as, for example, DOCK, or GOLD, are used to identify compounds that bind to the active site and/or binding pocket. Compounds may be screened against more than one binding pocket of the protein structure, or more than one set of coordinates for the same protein, taking into account different molecular dynamic conformations of the protein. Consensus scoring may then be used to identify the compounds that are the best fit for the protein (Charifson P. S. et al., *J. Med. Chem.*, 42:5100-9 (1999)). Data obtained from more than one protein molecule structure may also be scored according to the methods described in Klingler et al., U.S. Utility Application, filed May 3, 2002, entitled "Computer Systems and Methods for Virtual Screening of Compounds." Compounds having the best fit are then obtained from the producer of the chemical library, or synthesized, and used in binding assays and bioassays.

Computer modeling techniques may be used to assess the potential modulating or binding effect of a chemical compound on kinases. If computer modeling indicates a strong interaction, the molecule may then be synthesized and tested for its ability to bind to kinases and affect (by inhibiting or activating) its activity.

Modulating or other binding compounds of kinases may be computationally evaluated by means of a series of steps in which chemical groups or fragments are screened and selected for their ability to associate with the individual binding pockets or other areas of kinases. This process may begin by visual inspection of, for example, the active site on the computer screen based on the kinases coordinates. Selected fragments or chemical groups may then be positioned in a variety of orientations, or docked, within an individual binding pocket of kinases (Blaney J. M. and Dixon J. S., *Perspectives in Drug Discovery and Design, 1*:301 (1993)). Manual docking may be accomplished using software such as Insight II (Accelrys, San Diego, Calif.) MOE (Chemical Computing Group, Inc., Montreal, Quebec, Canada); and SYBYL (Tripos, Inc., St. Louis, Mo., 1992), followed by energy minimization and/or molecular dynamics with standard molecular mechanics force fields, such as CHARMM (Brooks et al., *J. Comp. Chem.*, 4:187-217 (1983)), AMBER (Weiner et al., *J. Am. Chem. Soc.*, 106:765-84 (1984)) and $C^2$ MMFF (Merck Molecular Force Field; Accelrys, San Diego, Calif.). More automated docking may be accomplished by using programs such as DOCK (Kuntz et al., *J. Mol. Biol.*, 161:269-88 (1982); DOCK is available from University of California, San Francisco, Calif.); AUTODOCK (Goodsell & Olsen, *Proteins: Structure, Function, and Genetics*, 8:195-202 (1990); AUTODOCK is available from Scripps Research Institute, La Jolla, Calif.); GOLD (Cambridge Crystallographic Data Centre (CCDC); Jones et al., *J. Mol. Biol.*, 245:43-53 (1995)); and FLEXX (Tripos, St. Louis, Mo.; Rarey M. et al., *J. Mol. Biol.*, 261:470-89 (1996). Other appropriate programs are described in, for example, Halperin et al.

During selection of compounds by the above methods, the efficiency with which that compound may bind to kinases may be tested and optimized by computational evaluation. For example, a compound that has been designed or selected to function as a kinases inhibitor may occupy a volume not overlapping the volume occupied by the active site residues when the native substrate is bound, however, those of ordinary skill in the art will recognize that there is some flexibility, allowing for rearrangement of the main chains and the side chains. In addition, one of ordinary skill may design compounds that could exploit protein rearrangement upon binding, such as, for example, resulting in an induced fit. An effective kinase inhibitor may demonstrate a relatively small difference in energy between its bound and free states (i.e., it must have a small deformation energy of binding and/or low conformational strain upon binding). Thus, the most efficient kinase inhibitors should, for example, be designed with a deformation energy of binding of not greater than 10 kcal/mol, not greater than 7 kcal/mol, not greater than 5 kcal/mol, or not greater than 2 kcal/mol. Kinase inhibitors may interact with the protein in more than one conformation that is similar in overall binding energy. In those cases, the deformation energy of binding is taken to be the difference between the energy of the free compound and the average energy of the conformations observed when the inhibitor binds to the enzyme.

Specific computer software is available in the art to evaluate compound deformation energy and electrostatic interaction. Examples of programs designed for such uses include: Gaussian 94, revision C (Frisch, Gaussian, Inc., Pittsburgh, Pa. ©1995); AMBER, version 7. (Kollman, University of California at San Francisco, ©2002); QUANTA/CHARMM (Accelrys, Inc., San Diego, Calif., ©1995); Insight II/Discover (Accelrys, Inc., San Diego, Calif., ©1995); Delphi (Accelrys, Inc., San Diego, Calif., (1995); and AMSOL (University of Minnesota) (Quantum Chemistry Program Exchange, Indiana University). These programs may be implemented, for instance, using a computer workstation, as are well known in the art, for example, a LINUX, SGI or Sun workstation. Other hardware systems and software packages will be known to those skilled in the art.

Those of ordinary skill in the art may express kinase protein using methods known in the art, and the methods disclosed herein. The native and mutated kinase polypeptides described herein may be chemically synthesized in whole or part using techniques that are well known in the art (see, e.g., Creighton, *Proteins: Structures and Molecular Principles* (1983).

Gene expression systems may be used for the synthesis of native and mutated polypeptides. Expression vectors containing the native or mutated polypeptide coding sequence and appropriate transcriptional/translational control signals, that are known to those skilled in the art may be constructed. These methods include in vitro recombinant DNA techniques, synthetic techniques and in vivo recombination/genetic recombination. See, e.g., the techniques described in Sambrook et al., *Molecular Cloning: A Laboratory Manual* (2001), and Ausubel et al., *Current Protocols in Molecular Biology* (1989).

Host-expression vector systems may be used to express kinase. These include, but are not limited to, microorganisms such as bacteria transformed with recombinant bacteriophage DNA, plasmid DNA or cosmid DNA expression vectors containing the coding sequence; yeast transformed with recombinant yeast expression vectors containing the coding sequence; insect cell systems infected with recombinant virus expression vectors (e.g., baculovirus) containing the coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the coding sequence; or animal cell systems. The protein may also be expressed in human gene therapy systems, including, for example, expressing the protein to augment the amount of the protein in an individual, or to express an engineered therapeutic protein. The expression elements of these systems vary in their strength and specificities.

Specifically designed vectors allow the shuttling of DNA between hosts such as bacteria-yeast or bacteria-animal cells. An appropriately constructed expression vector may contain: an origin of replication for autonomous replication in host cells, one or more selectable markers, a limited number of useful restriction enzyme sites, a potential for high copy number, and active promoters. A promoter is defined as a DNA sequence that directs RNA polymerase to bind to DNA and initiate RNA synthesis. A strong promoter is one that causes mRNAs to be initiated at high frequency.

The expression vector may also comprise various elements that affect transcription and translation, including, for example, constitutive and inducible promoters. These elements are often host and/or vector dependent. For example, when cloning in bacterial systems, inducible promoters such as the T7 promoter, pL of bacteriophage λ, plac, ptrp, ptac (ptrp-lac hybrid promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll a/b binding protein) or from plant viruses (e.g., the 35S RNA promoter of CaMV; the coat protein promoter of TMV) may be used; when cloning in mammalian cell systems, mammalian promoters (e.g., metallothionein promoter) or mammalian viral promoters, (e.g., adenovirus late promoter; vaccinia virus 7.5K promoter; SV40 promoter; bovine papilloma virus promoter; and Epstein-Barr virus promoter) may be used.

Various methods may be used to introduce the vector into host cells, for example, transformation, transfection, infection, protoplast fusion, and electroporation. The expression vector-containing cells are clonally propagated and individually analyzed to determine whether they produce the appropriate polypeptides. Various selection methods, including, for example, antibiotic resistance, may be used to identify host cells that have been transformed. Identification of polypeptide expressing host cell clones may be done by several means, including but not limited to immunological reactivity with anti-kinase antibodies, and the presence of host cell-associated activity.

Expression of cDNA may also be performed using in vitro produced synthetic mRNA. Synthetic rRNA can be efficiently translated in various cell-free systems, including but not limited to wheat germ extracts and reticulocyte extracts, as well as efficiently translated in cell-based systems, including, but not limited, to microinjection into frog oocytes.

To determine the cDNA sequence(s) that yields optimal levels of activity and/or protein, modified cDNA molecules are constructed. A non-limiting example of a modified cDNA is where the codon usage in the cDNA has been optimized for the host cell in which the cDNA will be expressed. Host cells are transformed with the cDNA molecules and the levels of kinase RNA and/or protein are measured.

Levels of kinase protein in host cells are quantitated by a variety of methods such as immunoaffinity and/or ligand affinity techniques, kinase-specific affinity beads or specific antibodies are used to isolate $^{35}$S-methionine labeled or unlabeled protein. Labeled or unlabeled protein is analyzed by SDS-PAGE. Unlabeled protein is detected by Western blotting, ELISA or RIA employing specific antibodies.

Following expression of kinase in a recombinant host cell, polypeptides may be recovered to provide the protein in active form. Several purification procedures are available and suitable for use. Recombinant kinase may be purified from cell lysates or from conditioned culture media, by various combinations of, or individual application of, fractionation, or chromatography steps that are known in the art.

In addition, recombinant kinase can be separated from other cellular proteins by use of an immuno-affinity column made with monoclonal or polyclonal antibodies specific for full length nascent protein or polypeptide fragments thereof. Other affinity based purification techniques known in the art may also be used.

Alternatively, the polypeptides may be recovered from a host cell in an unfolded, inactive form, e.g., from inclusion bodies of bacteria. Proteins recovered in this form may be solubilized using a denaturant, e.g., guanidinium hydrochloride, and then refolded into an active form using methods known to those skilled in the art, such as dialysis.

Cell Growth Assays

A variety of cell growth assays are known in the art and are useful in identifying compounds capable of inhibiting (e.g., reducing) cell growth and/or proliferation.

For example, a variety of cells are known to require specific kinases for growth and/or proliferation. The ability of such a cell to grow in the presence of a test compound may be assessed and compared to the growth in the absence of the test compound thereby identifying the anti-proliferative properties of the test compound. One common method of this type is to measure the degree of incorporation of label, such as tritiated thymidine, into the DNA of dividing cells. Alternatively, inhibition of cell proliferation may be assayed by determining the total metabolic activity of cells with a surrogate marker that correlates with cell number. Cells may be treated with a metabolic indicator in the presence and absence of the test compound. Viable cells metabolize the metabolic indicator thereby forming a detectable metabolic product. Where detectable metabolic product levels are decreased in the presence of the test compound relative to the absence of the test compound, inhibition of cell growth and/or proliferation is indicated. Exemplary metabolic indicators include, for example tetrazolium salts and AlamorBlue® (see Examples section below).

Pharmaceutical Compositions and Administration

In another aspect, the present invention provides a pharmaceutical composition including a kinase modulator as described herein in admixture with a pharmaceutically acceptable excipient. One of skill in the art will recognize that the pharmaceutical compositions include the pharmaceutically acceptable salts of the kinase modulators described herein.

In therapeutic and/or diagnostic applications, the compounds of the invention can be formulated for a variety of modes of administration, including systemic and topical or localized administration. Techniques and formulations generally may be found in Remington, *The Science and Practice of Pharmacy*, (20$^{th}$ ed. 2000).

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. Another dosage range is 10 to 30 mg per day. The exact dosage will depend upon the route of administration, the form in which the compound is administered, the subject to be treated, the body weight of the subject to be treated, and the preference and experience of the attending physician.

Pharmaceutically acceptable salts are generally well known to those of ordinary skill in the art, and may include, by way of example but not limitation, acetate, benzenesulfonate, besylate, benzoate, bicarbonate, bitartrate, bromide, calcium edetate, carnsylate, carbonate, citrate, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, mucate, napsylate, nitrate, pamoate (embonate), pantothenate, phosphate/diphosphate, polygalacturonate, salicylate, stearate, subacetate, succinate, sulfate, tannate, tartrate, or teoclate. Other pharmaceutically acceptable salts may be found in, for example, Remington, *The Science and Practice of Pharmacy* (20$^{th}$ ed. 2000). Other pharmaceutically acceptable salts include, for example, acetate, benzoate, bromide, carbonate, citrate, gluconate, hydrobromide, hydrochloride, maleate, mesylate, napsylate, pamoate (embonate), phosphate, salicylate, succinate, sulfate, or tartrate.

Depending on the specific conditions being treated, such agents may be formulated into liquid or solid dosage forms and administered systemically or locally. The agents may be delivered, for example, in a timed- or sustained-low release form as is known to those skilled in the art. Techniques for formulation and administration may be found in Remington, *The Science and Practice of Pharmacy* (20$^{th}$ ed. 2000). Suitable routes may include oral, buccal, by inhalation spray, sublingual, rectal, transdermal, vaginal, transmucosal, nasal or intestinal administration; parenteral delivery, including intramuscular, subcutaneous, intramedullary injections, as well as intrathecal, direct intraventricular, intravenous, intra-articular, intra-sternal, intra-synovial, intra-hepatic, intralesional, intracranial, intraperitoneal, intranasal, or intraocular injections or other modes of delivery.

For injection, the agents of the invention may be formulated and diluted in aqueous solutions, such as in physiologically compatible buffers such as Hank's solution, Ringer's solution, or physiological saline buffer. For such transmucosal administration, penetrants appropriate to the barrier to be permeated are used in the formulation. Such penetrants are generally known in the art.

Use of pharmaceutically acceptable inert carriers to formulate the compounds herein disclosed for the practice of the invention into dosages suitable for systemic administration is within the scope of the invention. With proper choice of carrier and suitable manufacturing practice, the compositions of the present invention, in particular, those formulated as solutions, may be administered parenterally, such as by intravenous injection. The compounds can be formulated readily using pharmaceutically acceptable carriers well known in the art into dosages suitable for oral administration. Such carriers enable the compounds of the invention to be formulated as tablets, pills, capsules, liquids, gels, syrups, slurries, suspensions and the like, for oral ingestion by a subject (e.g., patient) to be treated.

For nasal or inhalation delivery, the agents of the invention may also be formulated by methods known to those of skill in the art, and may include, for example, but not limited to, examples of solubilizing, diluting, or dispersing substances such as, saline, preservatives, such as benzyl alcohol, absorption promoters, and fluorocarbons.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients, these pharmaceutical compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions.

Pharmaceutical preparations for oral use can be obtained by combining the active compounds with solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations, for example, maize starch, wheat starch, rice starch, potato starch, gelatin, gum tragacanth, methyl cellulose, hydroxypropylmethyl-cellulose, sodium carboxymethyl-cellulose (CMC), and/or polyvinylpyrrolidone (PVP: povidone). If desired, disintegrating agents may be added, such as the cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinylpyrrolidone, carbopol gel, polyethylene glycol (PEG), and/or titanium dioxide, lacquer solutions, and suitable organic solvents or solvent mixtures. Dye-stuffs or pigments may be added to the tablets or dragee coatings for identification or to characterize different combinations of active compound doses.

Pharmaceutical preparations that can be used orally include push-fit capsules made of gelatin, as well as soft, sealed capsules made of gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols (PEGs). In addition, stabilizers may be added.

Depending upon the particular condition, or disease state, to be treated or prevented, additional therapeutic agents, which are normally administered to treat or prevent that condition, may be administered together with the inhibitors of this invention. For example, chemotherapeutic agents or other anti-proliferative agents may be combined with the inhibitors of this invention to treat proliferative diseases and cancer. Examples of known chemotherapeutic agents include, but are not limited to, adriamycin, dexamethasone, vincristine, cyclophosphamide, fluorouracil, topotecan, taxol, interferons, and platinum derivatives.

Other examples of agents the inhibitors of this invention may also be combined with include, without limitation, anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophosphamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents for treating diabetes such as insulin, insulin analogues, alpha glucosidase inhibitors, biguanides, and insulin sensitizers; and agents for treating immunodeficiency disorders such as gamma globulin.

These additional agents may be administered separately, as part of a multiple dosage regimen, from the inhibitor-containing composition. Alternatively, these agents may be part of a single dosage form, mixed together with the inhibitor in a single composition.

The present invention is not to be limited in scope by the exemplified embodiments, which are intended as illustrations of single aspects of the invention. Indeed, various modifications of the invention in addition to those described herein will become apparent to those having skill in the art from the foregoing description. Such modifications are intended to fall within the scope of the invention. Moreover, any one or more features of any embodiment of the invention may be combined with any one or more other features of any other embodiment of the invention, without departing from the scope of the invention. References cited throughout this application are examples of the level of skill in the art and are hereby incorporated by reference herein in their entirety for all purposes, whether previously specifically incorporated or not.

EXAMPLES

Example 1

Chemical Synthesis

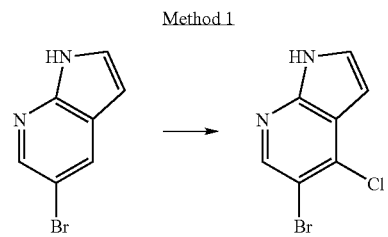

Synthesis of
5-Bromo-4-chloro-1H-pyrrolo[2,3-b]pyridine

5-Bromo-1H-pyrrolo[2,3-b]pyridine (20 g, 0.1 mol) was suspended in 300 mL of NMP. A solution of 3-Chloroperbenzoic acid (40 g, 0.16 mol) in 100 mL NMP was added dropwise over 30 min. The solution was stirred at 23° C. for 1 h after which 600 mL of ether were added. The grey precipitate was filtered off and washed with ether to yield 18 g of 5-Bromo-7-hydroxy-1H-pyrrolo[2,3-b]pyridin-7-ium 3-chlorobenzoate. The filtrate was stirred with 250 mL saturated sodium bicarbonate solution and 250 mL water to give 5-Bromo-1H-pyrrolo[2,3-b]pyridine 7-oxide (4.3 g, 20.2 mmol). The filtered 5-Bromo-7-hydroxy-1H-pyrrolo[2,3-b]pyridin-7-ium 3-chlorobenzoate was suspended in 200 mL of water and 200 mL of saturated sodium bicarbonate solution and was vigorously stirred for 1 h. The grey solids were filtered and washed with water to give a second crop of 5-Bromo-1H-pyrrolo[2,3-b]pyridine 7-oxide (11.15 g, 52.3 mmol, 71% combined yield). $^1$H NMR (500 MHz, DMSO-d6) δ 12.68 (s, 1H), 8.39 (d, J=1.5 Hz, 1H), 7.9 (d, J=1.5 Hz, 1H), 7.5 (d, J=3.5 Hz, 1H), 6.54 (d, J=3.5 Hz, 1H). MS: m/z 212.9 (M+H$^+$).

5-Bromo-1H-pyrrolo[2,3-b]pyridine 7-oxide (19.18 g, 90 mmol) were suspended in 200 mL NMP and cooled to −20° C. Phosphorus oxychloride (41 mL, 450 mmol) was added dropwise over 30 min. The mixture was allowed to warm to 23° C. over 1 h after which it was cooled on an ice bath and quenched with water (800 mL). The solids were filtered and recrystallized from ethyl acetate and hexanes to give 5-Bromo-4-chloro-1H-pyrrolo[2,3-b]pyridine (10 g, 48%). ¹H NMR (500 MHz, DMSO-d6) δ 12.25 (bs, 1H), 8.4 (s, 1H), 7.65 (m, 1H), 6.52 (m, 1H). MS: m/z 230.8/232.8 (M+H⁺).

Other compounds synthesized using Method 1:

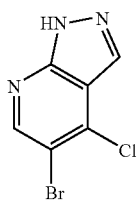

5-Bromo-4-chloro-1H-pyrazolo[3,4-b]pyridine
5-bromo-1H-pyrazolo[3,4-b]pyridine was used as the staring material
MS [MH⁺] m/z: 234.0/236.0

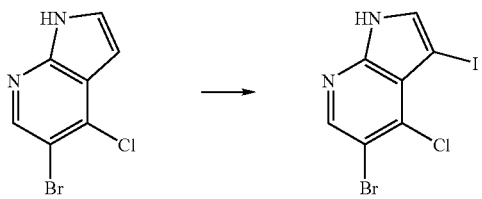

Method 2

Synthesis of
5-Bromo-4-chloro-3-iodo-1H-pyrrolo[2,3-b]pyridine

5-Bromo-4-chloro-1H-pyrrolo[2,3-b]pyridine (5.19 g, 22.4 mmol) and N-iodosuccinimide (5.55 g, 24.6 mmol) were suspended in 100 mL acetone. The mixture was stirred at 23° C. for 2 h and diluted with 150 mL water and 20 mL of saturated sodium thiosulfate solution. The precipitate was filtered and residual water was removed by dissolving the solids in dry benzene and followed by evaporation (2×100 mL) to yield 5-Bromo-4-chloro-3-iodo-1H-pyrrolo[2,3-b] pyridine (7.68 g, 21.5 mmol, 96%). ¹H NMR (500 MHz, DMSO-d6) δ 12.65 (bs, 1H), 8.45 (s, 1H), 7.87 (d, J=3 Hz, 1H). MS: m/z 356.8/358.8 (M+H⁺).

Other compounds synthesized using Method 2:

5-Bromo-3-iodo-4-methylsulfanyl-1H-pyrrolo[2,3-b]pyridine
¹H-NMR [500 MHz, d₆-DMSO] δ: 12.52 (s, 1H), 8.44 (s, 1H), (7.85 (d, 1H) 2.44 (s, 3H); MS [MH⁺] m/z: 369, 371

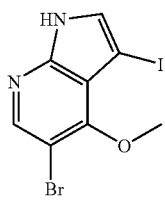

5-Bromo-3-iodo-4-methoxy-1H-pyrrolo[2,3-b]pyridine
¹H NMR (500 MHz, DMSO-d6) δ 12.36 (bs, 1H), 8.33 (s, 1H), 7.69 (d, J = 2.5 Hz, 1H), 3.94 (s, 3H). MS: m/z 352.9/354.9 (M + H⁺).

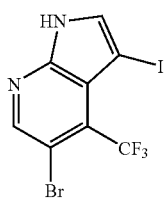

5-Bromo-3-iodo-4-trifluoromethyl-1H-pyrrolo[2,3-b]pyridine
¹H NMR (500 MHz, DMSO-d6) δ 12.98 (bs, 1H), 8.57 (s, 1H), 8.10 (d, J = 2 Hz, 1H). MS: m/z 390.9/392.9 (M + H⁺).

5-Bromo-4-chloro-3-iodo-1H-pyrazolo[3,4-b]pyridine
MS: m/z 358.0/360.0 (M + H⁺).

Method 3

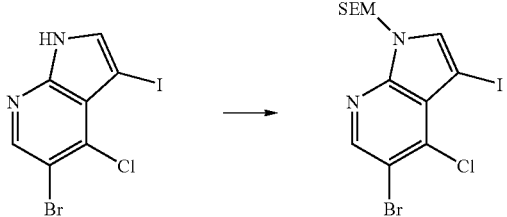

Synthesis of 5-Bromo-4-chloro-3-iodo-1-(2-trimethylsilanyl-ethoxymethyl)-1H-pyrrolo[2,3-b]pyridine 5-Bromo-4-chloro-3-iodo-1H-pyrrolo[2,3-b]pyridine (7.68 g, 21.5 mmol) was dissolved in 100 mL dry DMF and cooled to 0° C. Sodium hydride (60% suspension in mineral oil, 1.03 g, 25.8 mmol) was added cautiously over 5 min. The mixture was cooled to −42° C. and 2-trimethylsilanyl-ethoxymethylchloride (5 mL, 28 mmol) was added slowly over 10 min. The mixture was stirred at −42° C. for 2 h and quenched with 200 mL saturated ammonium chloride solution and 200 mL water. The aqueous mixture was extracted with dichloromethane and the organic phase was washed with water, dried and concentrated to afford 5-Bromo-4-chloro-3-iodo-1-(2-trimethylsilanyl-ethoxymethyl)-1H-pyrrolo[2,3-b]pyridine (10.1 g, 20.7 mmol, 96% yield). $^1$H NMR (500 MHz, DMSO-d6) δ 8.53 (s, 1H), 8.07 (s, 1H), 5.57 (s, 2H), 3.49 (t, J=8 Hz, 2H), 0.79 (t, J=8 Hz, 2H), −0.11 (s, 9H). MS: m/z 486.7/488.7 (M+H$^+$).

Other compounds synthesized using Method 3:

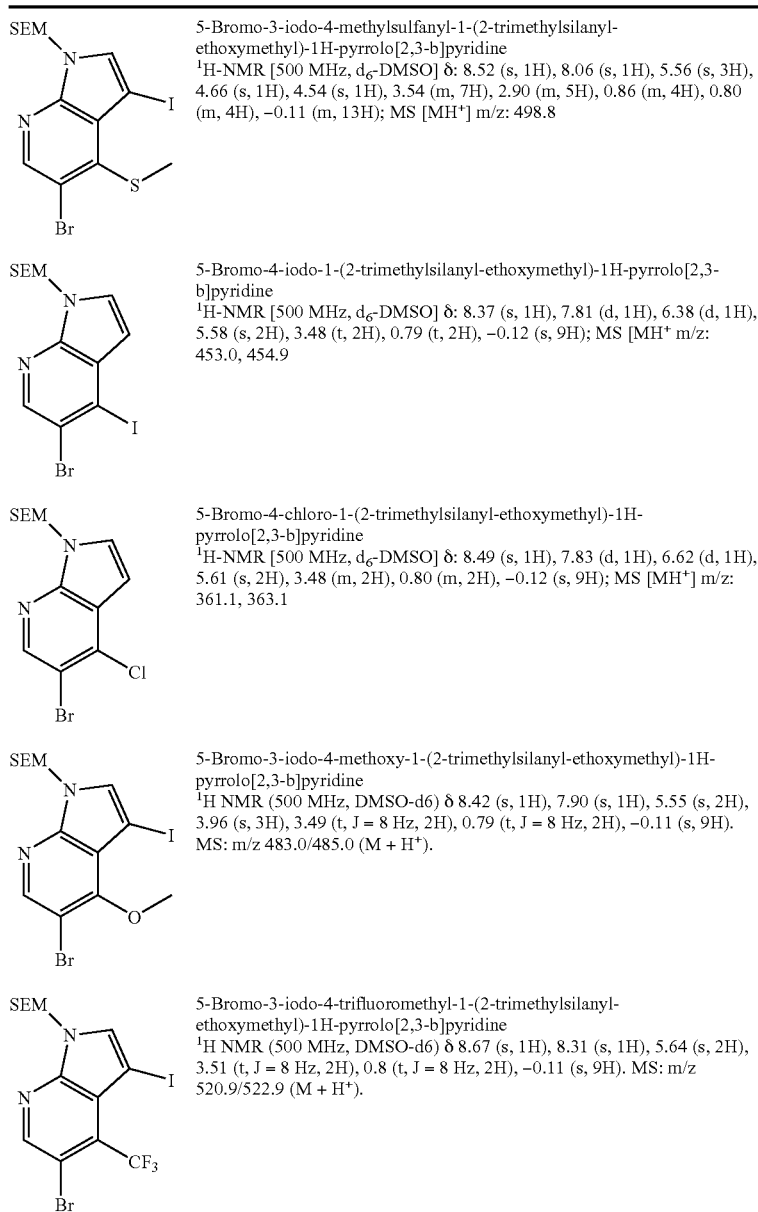

5-Bromo-3-iodo-4-methylsulfanyl-1-(2-trimethylsilanyl-ethoxymethyl)-1H-pyrrolo[2,3-b]pyridine
$^1$H-NMR [500 MHz, d$_6$-DMSO] δ: 8.52 (s, 1H), 8.06 (s, 1H), 5.56 (s, 3H), 4.66 (s, 1H), 4.54 (s, 1H), 3.54 (m, 7H), 2.90 (m, 5H), 0.86 (m, 4H), 0.80 (m, 4H), −0.11 (m, 13H); MS [MH$^+$] m/z: 498.8

5-Bromo-4-iodo-1-(2-trimethylsilanyl-ethoxymethyl)-1H-pyrrolo[2,3-b]pyridine
$^1$H-NMR [500 MHz, d$_6$-DMSO] δ: 8.37 (s, 1H), 7.81 (d, 1H), 6.38 (d, 1H), 5.58 (s, 2H), 3.48 (t, 2H), 0.79 (t, 2H), −0.12 (s, 9H); MS [MH$^+$ m/z: 453.0, 454.9

5-Bromo-4-chloro-1-(2-trimethylsilanyl-ethoxymethyl)-1H-pyrrolo[2,3-b]pyridine
$^1$H-NMR [500 MHz, d$_6$-DMSO] δ: 8.49 (s, 1H), 7.83 (d, 1H), 6.62 (d, 1H), 5.61 (s, 2H), 3.48 (m, 2H), 0.80 (m, 2H), −0.12 (s, 9H); MS [MH$^+$] m/z: 361.1, 363.1

5-Bromo-3-iodo-4-methoxy-1-(2-trimethylsilanyl-ethoxymethyl)-1H-pyrrolo[2,3-b]pyridine
$^1$H NMR (500 MHz, DMSO-d6) δ 8.42 (s, 1H), 7.90 (s, 1H), 5.55 (s, 2H), 3.96 (s, 3H), 3.49 (t, J = 8 Hz, 2H), 0.79 (t, J = 8 Hz, 2H), −0.11 (s, 9H). MS: m/z 483.0/485.0 (M + H$^+$).

5-Bromo-3-iodo-4-trifluoromethyl-1-(2-trimethylsilanyl-ethoxymethyl)-1H-pyrrolo[2,3-b]pyridine
$^1$H NMR (500 MHz, DMSO-d6) δ 8.67 (s, 1H), 8.31 (s, 1H), 5.64 (s, 2H), 3.51 (t, J = 8 Hz, 2H), 0.8 (t, J = 8 Hz, 2H), −0.11 (s, 9H). MS: m/z 520.9/522.9 (M + H$^+$).

-continued

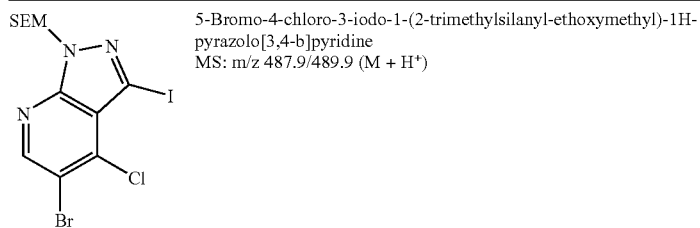

5-Bromo-4-chloro-3-iodo-1-(2-trimethylsilanyl-ethoxymethyl)-1H-pyrazolo[3,4-b]pyridine
MS: m/z 487.9/489.9 (M + H$^+$)

Other compounds synthesized using Method 2 and Method 3:

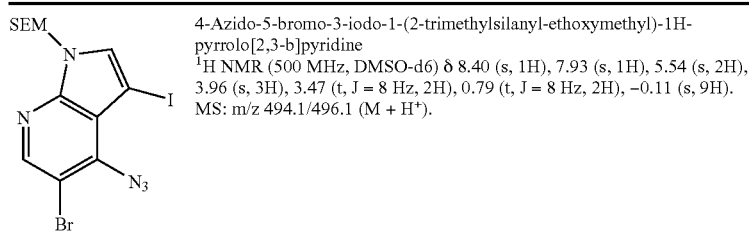

4-Azido-5-bromo-3-iodo-1-(2-trimethylsilanyl-ethoxymethyl)-1H-pyrrolo[2,3-b]pyridine
$^1$H NMR (500 MHz, DMSO-d6) δ 8.40 (s, 1H), 7.93 (s, 1H), 5.54 (s, 2H), 3.96 (s, 3H), 3.47 (t, J = 8 Hz, 2H), 0.79 (t, J = 8 Hz, 2H), −0.11 (s, 9H).
MS: m/z 494.1/496.1 (M + H$^+$).

Method 4

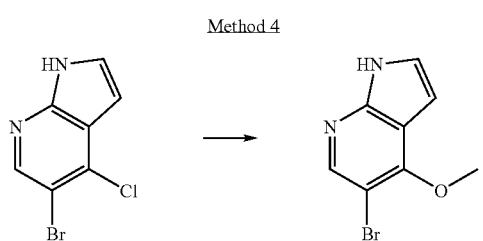

Synthesis of 5-Bromo-4-methoxy-1H-pyrrolo[2,3-b]pyridine

5-Bromo-4-chloro-1H-pyrrolo[2,3-b]pyridine (500 mg, 2.16 mmol) was combined with sodium methoxide (583 mg, 10.8 mmol) and suspended in anhydrous methanol (10 mL). The reaction was heated in the microwave to 175° C. for 4 h. The reaction mixture was concentrated and purified by flash silica gel chromatography using a gradient of (ethyl acetate/methanol 9:1) in hexanes to afford 5-Bromo-4-methoxy-1H-pyrrolo[2,3-b]pyridine (130 mg, 0.57 mmol, 27%) as a light yellow powder. $^1$H NMR (500 MHz, DMSO-d6) δ 11.84 (bs, 1H), 8.14 (s, 1H), 7.40 (m, 1H), 6.80 (m, 1H), 4.30 (s, 3H). MS: m/z 226.9/228.9 (M+H).

Method 5

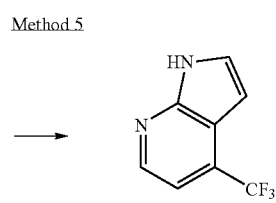

Synthesis of 4-Trifluoromethyl-1H-pyrrolo[2,3-b]pyridine

4-Iodo-1H-pyrrolo[2,3-b]pyridine (3.15 g, 12.9 mmol) was suspended in dimethylformamide (36 mL) and cooled to 0° C. Sodium hydride (570 mg, 14.2 mmol) was added in small portions and the mixture was stirred at 23° C. for 1 h. Toluenesulfonyl chloride (2.7 g, 14.2 mmol) was added and the mixture was stirred at 23° C. for 2 h. The reaction was quenched with saturated ammonium chloride solution (50 mL) and diluted with water (150 mL). The precipitate was collected and washed with water. The solids were dissolved in dichloromethane; the solution was dried over magnesium sulfate and concentrated to give 5.24 g of a brown solid.

Cuprous iodide (4.8 g, 25.1 mmol) and potassium fluoride (1.46 g, 25.1 mmol) were combined in a Schlenk tube and dried under high vacuum until the solids turned pale green. The solid from above (5 g, 12.5 mmol) was added followed by NMP (25 mL), DMF (25 mL), and trimethylsilyltrifluoromethane (3.7 mL, 25 mmol). The suspension was heated to 60° C. and stirred under nitrogen for 5 h. The reaction mixture was poured into ammonium hydroxide (7M in water) and the mixture was extracted with ether. The organic layer was washed with ammonium hydroxide (7M in water, 3 times), hydrochloric acid (1N), and saturated sodium bicarbonate solution. The organic layer was dried over magnesium sulfate and concentrated. The brown oil was purified by flash silica gel chromatography using a gradient of dichloromethane in hexanes to afford a clear oil.

The oil was dissolved in methanol (500 mL) and potassium hydroxide solution (50% w/w in water, 20 mL) was added. The mixture was stirred for 12 h and the reaction was quenched with acetic acid. The mixture was concentrated, suspended in water and filtered to afford 4-Trifluoromethyl-1H-pyrrolo[2,3-b]pyridine (1.58 g, 8.5 mmol). $^1$H NMR (500 MHz, DMSO-d6) δ 12.27 (bs, 1H), 8.42 (d, J=5 Hz, 1H), 7.76 (d, J=3.5 Hz, 1H), 7.40 (d, J=5 Hz, 1H), 6.56 (m, 1H). MS: m/z 187.2 (M+H$^+$).

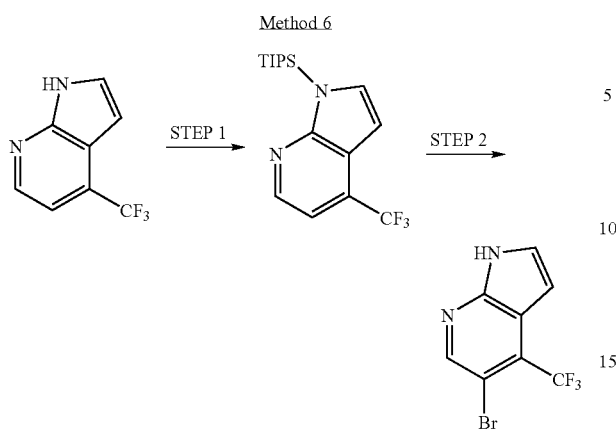

Synthesis of 5-Bromo-4-trifluoromethyl-1H-pyrrolo[2,3-b]pyridine

STEP 1: Synthesis of 4-Trifluoromethyl-1-triisopropylsilanyl-1H-pyrrolo[2,3-b]pyridine 4-Trifluoromethyl-1H-pyrrolo[2,3-b]pyridine (1.5 g, 8 mmol) was suspended in tetrahydrofuran (20 mL) and cooled to 0° C. Sodium hydride (390 mg, 9.7 mmol) was added in small portions and the mixture was stirred at 0° C. for 1 h. Triisopropylsilyl chloride (2.6 mL, 12 mmol) was added and the mixture was stirred at 23° C. for 12 h. The reaction was quenched with saturated ammonium chloride solution (10 mL) and diluted with water (5 mL). The mixture was applied to a Varian chemelut cartridge and eluted with ethyl acetate. Purification by flash silica gel chromatography using a gradient of dichloromethane in hexanes afforded 4-Trifluoromethyl-1-triisopropylsilanyl-1H-pyrrolo[2,3-b]pyridine (2.5 g, 7.3 mmol, 90% yield). $^1$H NMR (500 MHz, DMSO-d6) δ 8.44 (d, J=5 Hz, 1H), 7.76 (d, J=4 Hz, 1H), 7.44 (d, J=5.5 Hz, 1H), 6.74 (m, 1H), 1.88 (septet, J=7.5 Hz, 3H), 1.05 (d, J=7.5 Hz, 18H). MS: m/z 343.2 (M+H$^+$).

STEP 2: Synthesis of 5-Bromo-4-trifluoromethyl-1H-pyrrolo[2,3-b]pyridine

4-Trifluoromethyl-1-triisopropylsilanyl-1H-pyrrolo[2,3-b]pyridine (1.54 g, 4.5 mmol) was dissolved in tetrahydrofuran (50 mL) and cooled to −78° C. Sec-butyllithium (1.4 M in cyclohexane, 10 mL, 14 mmol) was added dropwise and the mixture was stirred at −78° C. for 1 h. A solution of carbontetrabromide (4.5 g, 13.5 mmol) in tetrahydrofuran (20 mL) was added quickly at −78° C. and the mixture was stirred for 15 min. The reaction was quenched with saturated ammonium chloride solution. The mixture was warmed to ambient temperature and the layers were separated. The organic layer was dried with magnesium and concentrated. Purification by flash silica gel chromatography using a gradient of (ethyl acetate and methanol 9:1) in hexanes afforded 5-Bromo-4-trifluoromethyl-1H-pyrrolo[2,3-b]pyridine (170 mg, 0.64 mmol, 9% yield). $^1$H NMR (500 MHz, DMSO-d6) δ 12.49 (bs, 1H), 8.54 (s, 1H), 7.82 (m, 1H), 6.61 (m, 1H). MS: m/z 264.9/266.9 (M+H$^+$).

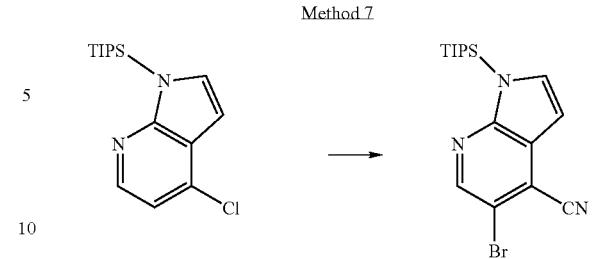

Synthesis of 5-Bromo-1-triisopropylsilanyl-1H-pyrrolo[2,3-b]pyridine-4-carbonitrile 4-Chloro-1-triisopropylsilanyl-1H-pyrrolo[2,3-b]pyridine (2.84 g, 9.2 mmol), zinc cyanide (650 mg, 5.5 mmol), and zinc dust (120 mg, 1.8 mmol) were suspended in dimethylacetamide (40 mL). The mixture was degassed thoroughly, bis (tri-t-butylphosphine)palladium (511 mg, 0.46 mmol) was added, and the mixture was stirred at 80° C. for 3d. The mixture was poured into water (80 mL) and filtered. The solids were washed with ethyl acetate and the filtrates were combined. The organic layer was separated, washed with water and brine, dried over magnesium sulfate, and concentrated. The oily residue was triturated with hexanes, the solution was decanted and the solvent was evaporated to give 1-triisopropylsilanyl-1H-pyrrolo[2,3-b]pyridine-4-carbonitrile (676 mg, 2.25 mmol, 25% yield).

2,2,6,6-Tetramethylpiperidine (380 μL, 2.25 mol) was dissolved in tetrahydrofuran (3 mL) and cooled to 0° C. N-Butyllithium (2.5 M in hexanes, 1.06 mL, 2.66 mmol) was added dropwise and the mixture was stirred at 0° C. for 10 min, then cooled to −78° C. A solution of 1-triisopropylsilanyl-1H-pyrrolo[2,3-b]pyridine-4-carbonitrile (613 mg, 2.04 mmol) in tetrahydrofuran (2 mL) was added at −78° C. and the mixture was stirred at −78° C. for 1 h. A solution of carbontetrabromide (2 g, 6.1 mmol) in tetrahydrofuran (5 mL) was added quickly at −78° C. and the mixture was stirred for 15 min. The reaction was quenched with saturated ammonium chloride solution. The mixture was warmed to ambient temperature and applied to a Varian chemelut cartridge and eluted with ethyl acetate. The crude product was purified by flash silica gel chromatography using a gradient of dichloromethane in hexanes to afford 5-Bromo-1-triisopropylsilanyl-1H-pyrrolo[2,3-b]pyridine-4-carbonitrile (160 mg, 0.42 mmol, 21% yield). $^1$H NMR (500 MHz, DMSO-d6) δ 8.57 (s, 1H), 7.88 (d, J=3.5 Hz, 1H), 6.83 (d, J=3.5 Hz, 1H), 1.85 (septet, J=7.5 Hz, 3H), 1.04 (d, J=7.5 Hz, 18H). MS: m/z 378.0/380.0 (M+H$^+$).

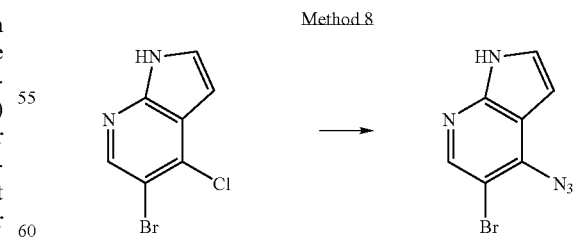

Synthesis of 4-Azido-5-bromo-1H-pyrrolo[2,3-b]pyridine

5-Bromo-4-chloro-1H-pyrrolo[2,3-b]pyridine (1.5 g, 6.5 mmol), sodium azide (2.11 g, 32 mmol), and ammonium chloride (1.73 g, 32 mmol) were suspended in anhydrous dimethylformamide (10 mL). The reaction was heated to 110° C. for 19 h. The reaction mixture was diluted with water and the solids were collected. The solids were dissolved in a mixture of acetone and ethylacetate, the solution was filtered and concentrated to afford 4-Azido-5-bromo-1H-pyrrolo[2,3-b]pyridine (670 mg, 2.8 mmol, 43%). MS: m/z 238.0/240.0 (M+H$^+$).

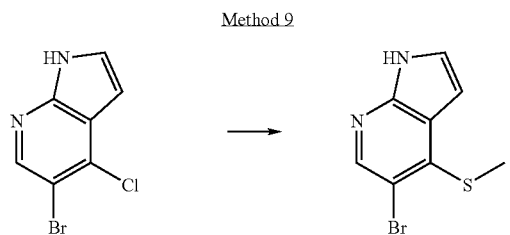

Method 9

Synthesis of
5-Bromo-4-methylsulfanyl-1H-pyrrolo[2,3-b]pyridine

5-Bromo-4-chloro-1H-pyrrolo[2,3-b]pyridine (500 mg, 2.16 mmol) was combined with sodium thiomethoxide (151 mg, 2.16 mmol) and dissolved in N,N-dimethylformaldehyde (5 mL). The solution was at 80° C. for 15 hours when additional sodium thiomethoxide (75 mg, 1.08 mmol) was added. The solution was stirred for at 80° C. for 2 hours. Water (50 mL) was added to the reaction mixture, and the precipitate was collected by vacuum filtration to afford 5-Bromo-4-methylsulfanyl-1H-pyrrolo[2,3-b]pyridine (524 mg, 2.16 mmol, >99% yield) as a white solid. $^1$H-NMR [500 MHz, d$_6$-DMSO] δ: 11.99 (s, 1H), 8.22 (s, 1H), 7.54 (d, 1H), 6.69 (d, 1H), 2.74 (s, 3H); MS [MH$^+$] m/z: 243.0, 244.9

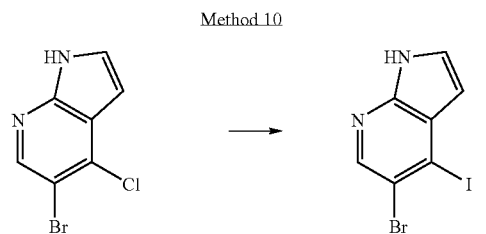

Method 10

Synthesis of
5-Bromo-4-iodo-1H-pyrrolo[2,3-b]pyridine

5-Bromo-4-chloro-1H-pyrrolo[2,3-b]pyridine (4.00 g, 17.3 mmol) was combined with sodium iodide (13.0 g, 86.4 mmol) and suspended in anhydrous acetonitrile (160 mL). Acetyl chloride (3.69 mL, 51.8 mmol) was added, and the reaction was stirred under reflux for 12 hours. Aqueous saturated sodium bicarbonate solution (75 mL) was added. Solids were collected by filtration, rinsing with water (2×50 mL) to afford 6.48 g of the light whitish-yellow crude intermediate 1-(5-Bromo-4-iodo-pyrrolo[2,3-b]pyridin-1-yl)-ethanone. The intermediate was resuspended in methanol (200 mL) and aqueous sodium hydroxide (200 mL, 1 N). The mixture was stirred for 1 h at 23° C. Solids were collected by filtration and rinsed with water (100 mL) to afford 5-Bromo-4-iodo-1H-pyrrolo[2,3-b]pyridine (4.20 g, 13.0 mmol, 75%) as a yellow-white powder. $^1$H-NMR [500 MHz, d$_6$-DMSO] δ: 12.20 (s, 1H), 8.29 (s, 1H), 7.62 (t, 1H), 6.28 (m, 1H); MS [MH$^+$] m/z: 322.9, 324.9

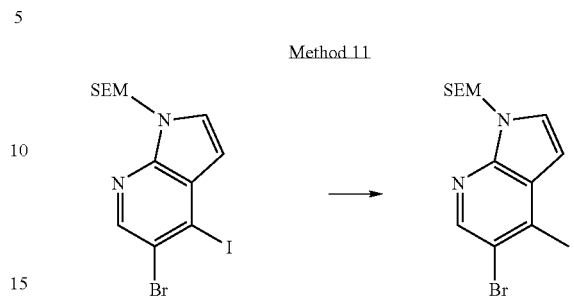

Method 11

Synthesis of 5-Bromo-4-methyl-1-(2-trimethylsilanyl-ethoxymethyl)-1H-pyrrolo[2,3-b]pyridine 5-Bromo-4-iodo-1-(2-trimethylsilanyl-ethoxymethyl)-1H-pyrrolo[2,3-b]pyridine (1.00 g, 2.21 mmol) and bis(tri-t-butylphosphine)palladium(0) (56 mg, 0.110 mmol) were combined and dissolved in anhydrous tetrahydrofuran (20 mL) in an oven-dried round-bottom flask. Dimethylzinc (552 µL, 1.11 mmol, 2.0 M solution in tetrahydrofuran). The solution was allowed to stir at 23° C. for 1 hour. To the mixture was added water (50 mL) followed by ethyl acetate (50 mL). Layers were mixed well, and the organic layer was stirred over sodium sulfate, filtered and concentrated in vacuo. The crude product was purified by flash silica gel chromatography using a gradient of ethyl acetate in hexanes to afford 5-Bromo-4-methyl-1-(2-trimethylsilanyl-ethoxymethyl)-1H-pyrrolo[2,3-b]pyridine (307 mg, 0.899 mmol, 41%) as a brown oil. $^1$H-NMR [500 MHz, d$_6$-DMSO]: 8.43 (s, 1H), 7.71 (d, 1H), 6.79 (d, 1H), 5.69 (s, 1H), 3.61 (t, 2H), 2.66 (s, 3H), 0.93 (t, 2H), 0.0 (s, 9H); MS [MH$^+$] m/z: 341.1, 343.0

Other compounds synthesized using Method 11:

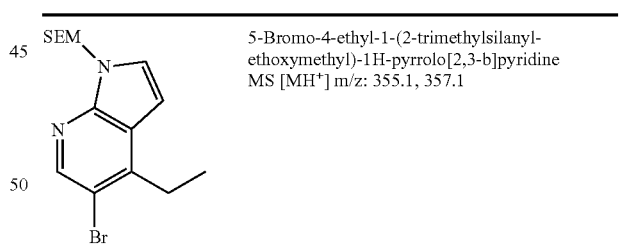

5-Bromo-4-ethyl-1-(2-trimethylsilanyl-ethoxymethyl)-1H-pyrrolo[2,3-b]pyridine
MS [MH$^+$] m/z: 355.1, 357.1

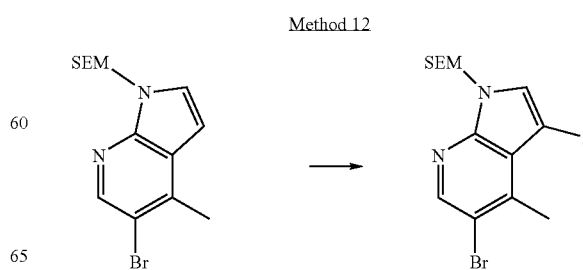

Method 12

Synthesis of 5-Bromo-3-iodo-4-methyl-1-(2-trimethylsilanyl-ethoxymethyl)-1H-pyrrolo[2,3-b]pyridine 5-Bromo-4-methyl-1-(2-trimethylsilanyl-ethoxymethyl)-1H-pyrrolo[2,3-b]pyridine (150 mg, 0.439 mmol) was dissolved in anhydrous 1,2 dichloroethane (6 mL), and N-iodosuccinimide (198 mg, 0.879 mmol) was added. The solution was stirred at 23° C. for 15 hours when ethyl acetate was added. A solution of water (25 mL) and aqueous saturated sodium bicarbonate (25 mL) was added. Layers were mixed well. The organic layer was stirred over sodium sulfate, filtered and concentrated in vacuo. The crude oil was purified by flash silica gel chromatography by using a gradient of ethyl acetate in hexanes to afford 5-Bromo-3-iodo-4-methyl-1-(2-trimethylsilanyl-ethoxymethyl)-1H-pyrrolo[2,3-b]pyridine (80 mg, 0.171 mmol, 39%) as a white soft solid. 8.39 (s, 1H), 7.93 (s, 1H), 5.54 (s, 2H), 3.47 (t, 2H), 2.85 (s, 3H), 0.79 (s, 2H), −0.11 (s, 8H); MS [MH$^+$] m/z: 466.9, 468.9

Other compounds synthesized using Method 12:

Method 13

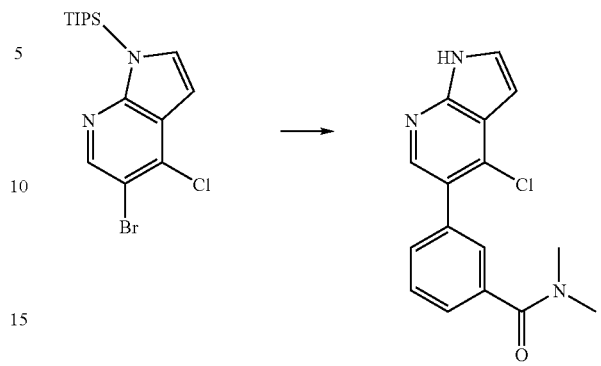

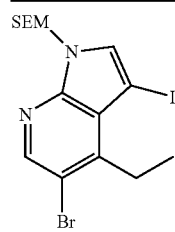

5-Bromo-4-ethyl-3-iodo-1-(2-trimethylsilanyl-ethoxymethyl)-1H-pyrrolo[2,3-b]pyridine
MS [MH$^+$] m/z: 480.9, 483.0

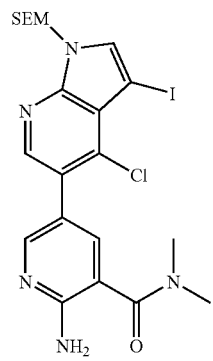

2-Amino-5-[4-chloro-3-iodo-1-(2-trimethylsilanyl-ethoxymethyl)-1H-pyrrolo[2,3-b]pyridin-5-yl]-N,N-dimethyl-nicotinamide
The reaction was conducted at 50° C.
$^1$H-NMR [500 MHz, d$_6$-DMSO] δ: 8.28 (s, 1H), 8.07 (d, 1H), 8.05 (s, 1H), 7.52 (d, 1H), 6.22 (s, 2H), 5.61 (s, 2H), 3.53 (m, 3H), 2.97 (s, 6H), 0.83 (m, 3H), −0.08 (m, 11H); MS [MH$^+$] m/z: 572.2

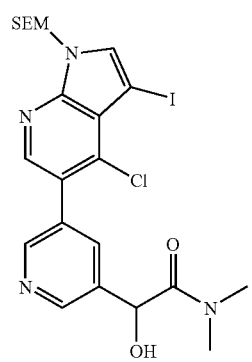

Synthesis of {5-[4-chloro-3-iodo-1-(2-trimethylsilanyl-ethoxymethyl)-1H-pyrrolo [2,3-b]pyridin-5-yl]pyridin-3-yl}-2-hydroxy-N,N-dimethyl-acetamide
$^1$H NMR (500 MHz, DMSO-d6) δ 0.05 (s, 9H), 0.91 (t, 2H), 2.94 (d, 6H), 3.61 (t, 2H), 5.61 (s, 1H), 5.71 (s, 2H), 5.92 (s, 1H), 7.95 (s, 1H), 8.04 (s, 1H), 8.18 (s, 1H), 8.40 (s, 1H), 8.61 (s, 1H), 8.68 (s, 1H), 8.70 (s, 1H). MS: m/z 587.2 (M + H$^+$).

Synthesis of 3-(4-Chloro-1H-pyrrolo[2,3-b]pyridin-5-yl)-N,N-dimethyl-benzamide A mixture of 5-Bromo-4-chloro-1-triisopropylsilanyl-1H-pyrrolo[2,3-b]pyridine (76 mg, 0.2 mmol, prepared using the method of L'Heureux et al., Tet. Lett., 45 (2004) p. 2317-2319), [3-(N,N-dimethylaminocarbonyl)phenyl]boronic acid (38 mg, 0.2 mmol) and 1,1'-bis(diphenylphosphino)ferrocenepalladium(II)-dichloride dichlormethane adduct (8 mg, 0.01 mmol) in acetonitrile (11 mL) and aqueous solution of sodium carbonate (2M, 0.2 mL) was irradiated in a Personal Chemistry Optimizer at 120° C. for 15 min. Sodium sulfate was added to the crude reaction mixture and the solids were filtered over Celite. The solids were rinsed with ethyl acetate and the combined filtrate was concentrated. Purification by flash silica gel chromatography using a gradient of ethyl acetate and hexanes afforded 71 mg of a white solid. MS: m/z 457 [MH+]

The solid was dissolved in 1 mL of dichloromethane and 1 mL of a 1M solution of tetrabutylammonium fluoride in tetrahydrofuran was added. The solution was stirred at room temperature for 2 h when it was directly loaded onto silica gel and purified by flash silica gel chromatography using a gradient of ethyl acetate and hexanes to afford 35 mg of a white solid. $^1$H-NMR (500 MHz, d$_6$-DMSO).: 12.12 (s, 1H), 8.22 (s, 1H), 7.65 (t, J=3 Hz, 1H), 7.56 (m, 2H), 7.5 (m, 1H), 7.45 (m, 1H), 6.56 (dd, J$_1$=3 Hz, J$_2$=2 Hz, 1H), 2.99 (s, 3H), 2.97 (s, 3H). MS: m/z 300 [M+H+]

Method 14

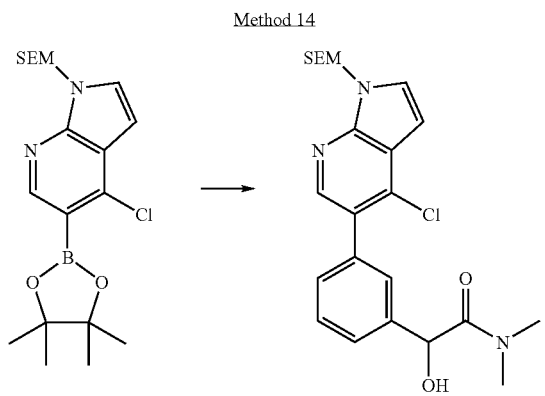

Synthesis of 2-{5-[4-chloro-1-(2-trimethylsilanyl-ethoxymethyl)-1H-pyrrolo[2,3-b]pyridin-5-yl]pyridin-3-yl}-2-hydroxy-N,N-dimethyl-acetamide A mixture of 4-chloro-5-(4,4,5,5-tetramethyl-[1,3,2]dioxaborolan-2-yl)-1-(2-trimethylsilanyl-ethoxymethyl)-1H-pyrrolo[2,3-b]pyridine (1.3 g, 3.3 mmol), 2-(5-bromo-pyridin-3-yl)-2-hydroxy-N,N-dimethyl-acetamide (0.8 g, 3.3 mmol) and dichloro[1,1'-bis(diphenylphosphino)ferrocene]palladium(II) dichloromethane adduct (133 mg, 0.2 mmol) in THF/Acetonitrile/saturated NaHCO$_3$ (20 ml/20 ml/20 ml) was stirred at 70° C. overnight. The mixture was allowed to cool down to room temperature and then extracted with ethyl acetate (2×). The combined organic layers were extracted with brine, dried with Na$_2$SO$_4$, decanted, and concentrated to dryness. Silica chromatography of the crude using a gradient of ethyl acetate and hexane afforded 2-{5-[4-chloro-1-(2-trimethylsilanyl-ethoxymethyl)-1H-pyrrolo[2,3-b]pyridine-5-yl]pyridine-3-yl}-2-hydroxy-N,N-dimethyl-acetamide (1.3 g, 85% yield). $^1$H NMR (500 MHz, DMSO-d6) δ 0.05 (s, 9H), 0.92 (t, 2H), 2.95 (d, 6H), 3.62 (t, 2H), 5.68 (s, 1H), 6.77 (s, 1H), 7.96, (s, 1H), 7.98 (s, 1H), 8.41 (s, 1H), 8.71 (s, 1H), 8.72 (s, 1H). MS: m/z 461.3 (M+H+).

Method 15

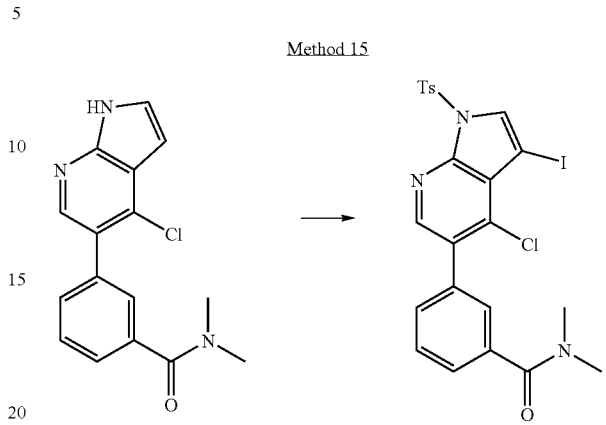

Synthesis of 3-[4-Chloro-3-iodo-1-(toluene-4-sulfonyl)-1H-pyrrolo[2,3-b]pyridin-5-yl]-N,N-dimethyl-benzamide 3-(4-Chloro-1H-pyrrolo[2,3-b]pyridin-5-yl)-N,N-dimethyl-benzamide (148 mg, 0.5 mmol) was dissolved in 3.5 mL acetone, and N-iodosuccinimide (133 mg, 0.6 mmol) was added. The suspension was stirred for 1 h at 23° C., diluted with water and sodium thiosulfate solution, filtered, and washed with water. The yellow powder was dissolved in 5 mL dry DMF and sodium hydride (30 mg, 0.75 mmol) was added. After the gas evolution subsided (10 min), toluenesulfonyl chloride (141 mg, 0.75 mmol) was added. The mixture was stirred at 60° C. for 12 h and quenched with saturated ammonium chloride solution. The suspension was filtered and washed with water to afford 3-[4-Chloro-3-iodo-1-(toluene-4-sulfonyl)-1H-pyrrolo[2,3-b]pyridin-5-yl]-N,N-dimethyl-benzamide as a light brown solid (310 mg, 0.49 mmol, quantitative). $^1$H NMR (500 MHz, DMSO-d6) δ 8.38 (s, 1H), 8.28 (s, 1H), 8.05 (m, 2H), 7.44-7.56 (m, 6H), 2.97 (bs, 3H), 2.93 (bs, 3H), 2.36 (s, 3H). MS: m/z 580.2 (M+H).

Method 16

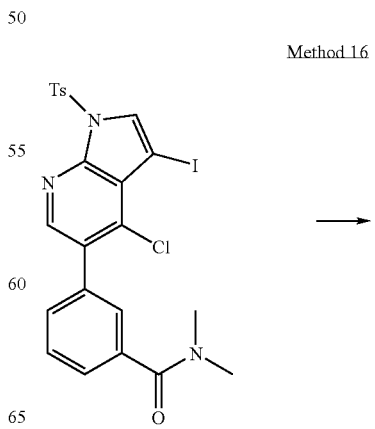

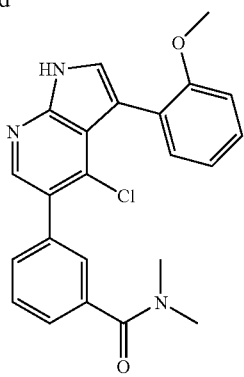

Synthesis of 3-[4-Chloro-3-(2-methoxy-phenyl)-1H-pyrrolo[2,3-b]pyridin-5-yl]-N,N-dimethyl-benzamide Into a 5 mL Personal Chemistry microwave reaction vial were added 3-[4-Chloro-3-iodo-1-(toluene-4-sulfonyl)-1H-pyrrolo[2,3-b]pyridin-5-yl]-N,N-dimethyl-benzamide (60 mg, 0.1 mmol), 2-methoxyphenylboronic acid (17 mg, 0.11 mmol), 1,1'-bis(diphenylphosphino)ferrocenepalladium(II)-dichloride dichloromethane adduct (4 mg, 0.005 mmol), acetonitrile (1 mL) and aqueous $Na_2CO_3$ solution (2M, 103 μL). The vial was purged with nitrogen, sealed, and irradiated in a Personal Chemistry Optimizer at 120° C. for 15 min. Sodium sulfate was added to the reaction mixture and the slurry was filtered over Celite and concentrated. The crude product was purified by flash silica gel chromatography using a gradient of ethyl acetate in hexanes to afford the toluene-sulfonyl protected title compound as an off-white powder (39 mg, m/z 561.2 (M+H$^+$)). Deprotection was accomplished by dissolving the powder in a mixture of 3 mL THF, 1 mL water and 2 mL isopropanol. Aqueous lithium hydroxide (4N, 200 μL) was added and the mixture was stirred at 23° C. for 5 h. Acetic acid (200 μL) was added to quench the reaction, the mixture was concentrated and purified by flash silica gel chromatography using a gradient of ethyl acetate in hexanes to afford 3-[4-Chloro-3-(2-methoxy-phenyl)-1H-pyrrolo[2,3-b]pyridin-5-yl]-N,N-dimethyl-benzamide as a white solid (18 mg, 0.045 mmol, 45%). $^1$H NMR (500 MHz, DMSO-d6) δ 12.17 (d, J=2 Hz, 1H), 8.19 (s, 1H), 7.53 (m, 3H), 7.42 (m, 2H), 7.32 (m, 1H), 7.28 (dd, J=7 Hz, J$_2$=2 Hz, 1H), 7.01 (d, J=8 Hz, 1H), 6.94 (t, J=7 Hz, 1H), 3.68 (s, 3H), 2.97 (bs, 3H), 2.94 (bs, 3H). MS: m/z 406.1 (M+H$^+$).

Other compounds synthesized using Method 13-Method 16:

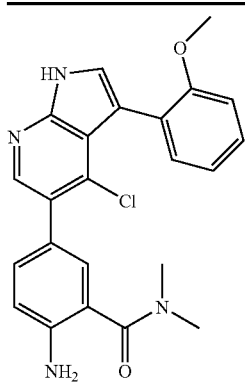

2-Amino-5-[4-chloro-3-(2-methoxy-phenyl)-1H-pyrrolo[2,3-b]pyridin-5-yl]-N,N-dimethyl-benzamide
$^1$H NMR (500 MHz, DMSO-d6) δ 12.07 (bs, 1H), 8.49 (s, 1H), 8.11 (s, 1H), 7.46 (d, J = 2.5 Hz, 1H), 7.31 (m, 1H), 7.25 (dd, J$_1$ = 7.5 Hz, J$_2$ = 2 Hz, 1H), 7.16 (dd, J$_2$ = 8.5 Hz, J$_2$ = 2.5 Hz, 1H), 7.05 (d, J = 2 Hz, 1H), 7.0 (d, J = 7.5 Hz, 1H), 6.94 (td, J$_1$ = 7.5 Hz, J$_2$ = 1 Hz, 1H), 6.77 (d, J = 8 Hz, 1H), 5.34 (s, 2H), 3.67 (s, 3H), 2.94 (s, 6H). MS: m/z 421.1 (M + H$^+$).

Method 17

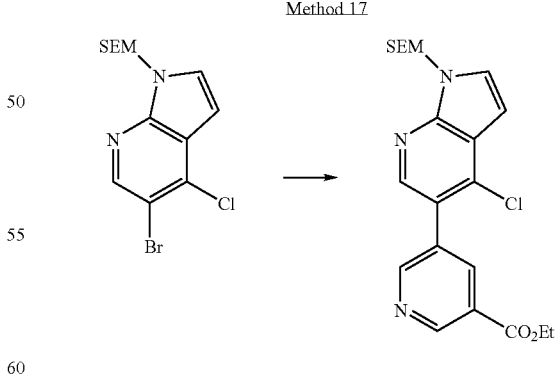

Synthesis of 5-[4-Chloro-1-(2-trimethylsilanyl-ethoxymethyl)-1H-pyrrolo[2,3-b]pyridin-5-yl]-nicotinic acid ethyl ester 1.59 g (4.40 mmol) of 5-bromo-4-chloro-1-(2-trimethylsilanyl-ethoxymethyl)-1H-pyrrolo[2,3-b]pyridine, 1.482 g (5.35 mmol) of 3-(ethoxycarbonyl)pyridine-5-boronic acid pinacol ester and 181 mg (0.22 mmol) of (1,1'-bis(diphenylphosphino)ferrocenepalladium(II)-dichloride dichloromethane adduct were dissolved in a mixture of 7 mL of acetonitrile, 7 mL of toluene and 8 mL of a saturated aqueous solution of sodium bicarbonate. The resulting mixture was heated to 110° C. in a closed vial for 15 h. The resulting mixture was distributed between dichloromethane and water. The aqueous phase was separated and extracted three times with dichloromethane and the once with ethyl acetate. The ethyl acetate phase was washed with brine and combined with the other organic phases, dried over sodium sulfate and evaporated. The resulting crude was purified by flash chromatography on silica gel using a gradient of ethyl acetate in hexanes to afford 1.0703 g (2.48 mmol, 56%) of 5-[4-chloro-1-(2-trimethylsilanyl-ethoxymethyl)-1H-pyrrolo[2,3-b]pyridin-5-yl]-nicotinic acid ethyl ester as a pale yellow oil. $^1$H-NMR [500 MHz, $d_6$-DMSO] δ: 9.15 (d, 1H), 8.97 (d, 1H), 8.41 (m, 1H), 8.40 (m, 1H), 7.89 (d, 1H), 5.69 (s, 2H), 4.38 (q, 2H), 3.55 (t, 2H), 1.35 (t, 3H), 0.84 (t, 2H), −0.08 (s, 9H); MS [MH$^+$] m/z: 432+434.

Other compounds synthesized using Method 17:

Synthesis of 5-[4-Chloro-1-(2-trimethylsilanyl-ethoxymethyl)-1H-pyrrolo[2,3-b]pyridin-5-yl]-nicotinic acid 1.070 g (2.48 mmol) of 5-[4-chloro-1-(2-trimethylsilanyl-ethoxymethyl)-1H-pyrrolo[2,3-b]pyridin-5-yl]-nicotinic acid ethyl ester was dissolved in 10 mL of ethanol. 2 mL of 50% w/v solution of potassium hydroxide in water and 10 mL of water were added and the resulting solution was left standing at ambient temperature for 16 h. Subsequently the pH was adjusted to approximately 4 by addition of concentrated aqueous hydrochloric acid and the mixture diluted with 100 mL of water. The resulting precipitate was filtered off and dried by suction to afford 1.1153 g (2.76 mmol, quant.) of 5-[4-chloro-1-(2-trimethylsilanyl-ethoxymethyl)-1H-pyrrolo[2,3-b]pyridin-5-yl]-nicotinic acid. $^1$H-NMR [500 MHz, $d_6$-DMSO] δ: 9.13 (d, 1H), 8.94 (d, 1H), 8.393 (m, 1H), 8.388 (m, 1H), 7.89 (d, 1H), 6.70 (d, 1H), 5.69 (s, 2H), 3.55 (t, 2H), 0.84 (t, 2H), 0.08 (s, 9H); MS [MH$^+$] m/z: 404; [M−H$^-$] m/z: 402.

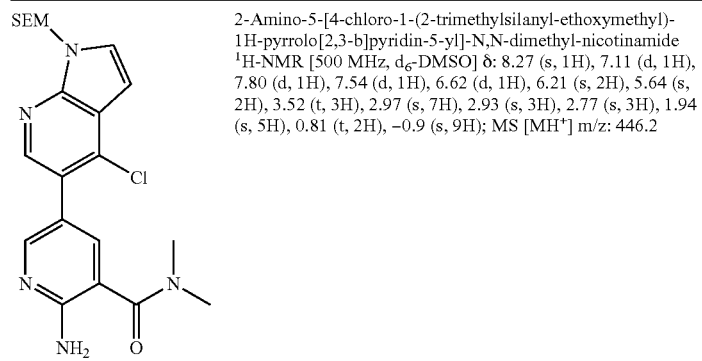

2-Amino-5-[4-chloro-1-(2-trimethylsilanyl-ethoxymethyl)-1H-pyrrolo[2,3-b]pyridin-5-yl]-N,N-dimethyl-nicotinamide
$^1$H-NMR [500 MHz, $d_6$-DMSO] δ: 8.27 (s, 1H), 7.11 (d, 1H), 7.80 (d, 1H), 7.54 (d, 1H), 6.62 (d, 1H), 6.21 (s, 2H), 5.64 (s, 2H), 3.52 (t, 3H), 2.97 (s, 7H), 2.93 (s, 3H), 2.77 (s, 3H), 1.94 (s, 5H), 0.81 (t, 2H), −0.9 (s, 9H); MS [MH$^+$] m/z: 446.2

Method 18

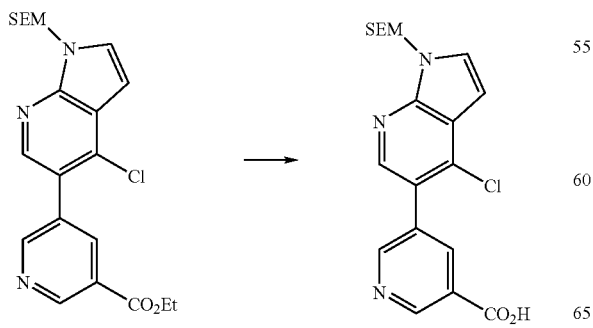

Other compounds synthesized using Method 18:

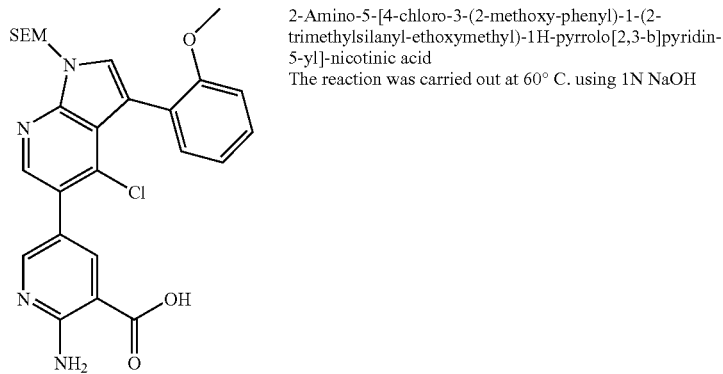

2-Amino-5-[4-chloro-3-(2-methoxy-phenyl)-1-(2-trimethylsilanyl-ethoxymethyl)-1H-pyrrolo[2,3-b]pyridin-5-yl]-nicotinic acid
The reaction was carried out at 60° C. using 1N NaOH

Method 19

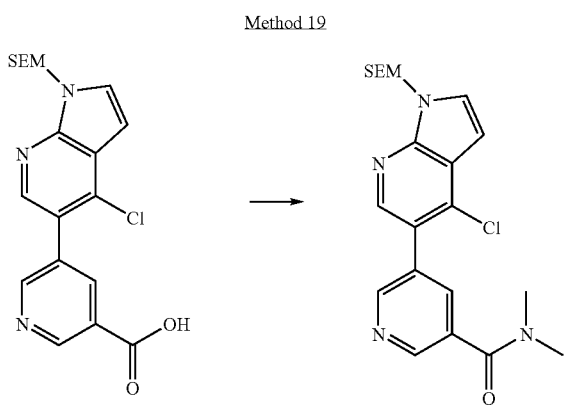

Synthesis of 5-[4-Chloro-1-(2-trimethylsilanyl-ethoxymethyl)-1H-pyrrolo[2,3-b]pyridin-5-yl]-N,N-dimethyl-nicotinamide The material was dissolved in 75 mL of 20% v/v of acetonitrile in dichloromethane. 1.10 g (2.89 mmol) of N,N,N',N'-tetramethyl-O-(7-azabenzotriazol-1-yl)uronium hexafluorophosphate and 3 mL (6 mmol) of a 2 M solution of dimethyl amine in anhydrous THF were added and the mixture allowed to stir for 1 h at ambient temperature. 1 mL of glacial acetic acid was added and the mixture stirred for an additional 30 minutes. The mixture was distributed between dichloromethane and a saturated aqueous solution of sodium bicarbonate. The aqueous phase was separated and extracted three times with dichloromethane. The combined organic phases were dried over sodium sulfate and evaporated to afford 1.211 g (2.81 mmol, 113% over two steps) of 5-[4-chloro-1-(2-trimethylsilanyl-ethoxymethyl)-1H-pyrrolo[2,3-b]pyridin-5-yl]-N,N-dimethyl-nicotinamide as a colorless oil. 1H-NMR [500 MHz, $d_6$-DMSO] δ: 8.78 (d, 1H), 8.69 (d, 1H), 8.38 (s, 1H), 8.03 (t, 1H), 7.88 (d, 1H), 6.70 (d, 1H), 5.68 (s, 2H), 3.55 (t, 2H), 3.03 (s, 3H), 3.01 (s, 3H), 0.84 (t, 2H), −0.07 (s, 9H); MS [MH$^+$] m/z: 431.

Other compounds synthesized using method 19:

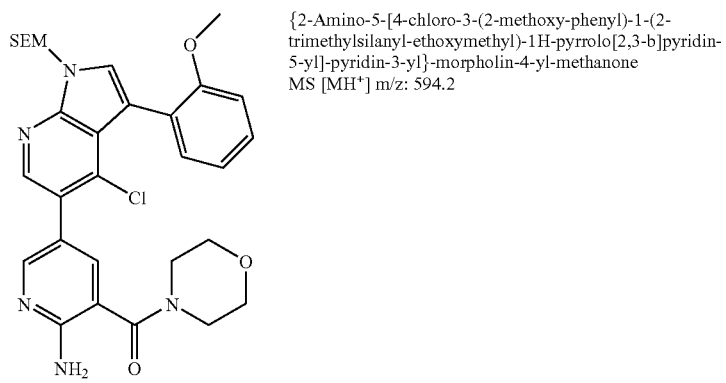

{2-Amino-5-[4-chloro-3-(2-methoxy-phenyl)-1-(2-trimethylsilanyl-ethoxymethyl)-1H-pyrrolo[2,3-b]pyridin-5-yl]-pyridin-3-yl}-morpholin-4-yl-methanone
MS [MH$^+$] m/z: 594.2

-continued

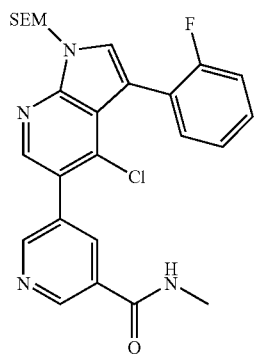

5-[4-chloro-3-(2-fluoro-phenyl)-1-(2-trimethylsilanyl-ethoxymethyl)-1H-pyrrolo[2,3-b]pyridin-5-yl]-N-methyl-nicotinamide
$^1$H-NMR [500 MHz, d$_6$-DMSO] δ: 9.03 (d, 1H), 8.81 (d, 1H), 8.72 (q, br., 1H), 8.42 (s, 1H), 8.29 (t, 1H), 7.97 (s, 1H), 7.49-7.42 (m, 2H), 7.31-7.25 (m, 2H), 5.740 (s, 2H), 3.62 (t, 2H), 2.69 (s, 3H), 0.87 (t, 2H), −0.06 (s, 9H); MS [MH$^+$] m/z: 511.

Method 20

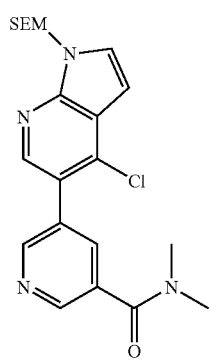  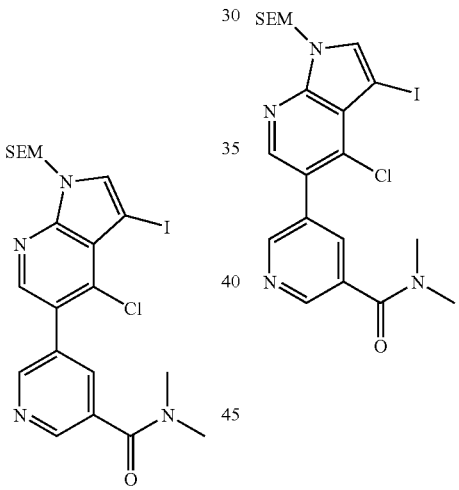

Synthesis of 5-[4-Chloro-3-iodo-1-(2-trimethylsilanyl-ethoxymethyl)-1H-pyrrolo[2,3-b]pyridin-5-yl]-N,N-dimethyl-nicotinamide 1.117 g (2.59 mmol) of 5-[4-chloro-1-(2-trimethylsilanyl-ethoxymethyl)-1H-pyrrolo[2,3-b]pyridin-5-yl]-N,N-dimethyl-nicotinamide was dissolved in 19 ml of anhydrous 1,2-dichloroethane. 1.506 g (6.69 mmol) of N-iodosuccinimide was added and the mixture irradiated in a microwave reactor to 140° C. for 30 minutes. Saturated aqueous solution of sodium thiosulfate was added and the resulting mixture stirred at ambient temperature, then diluted with water and dichloromethane. The aqueous phase was separated and extracted three times with dichloromethane. The combined organic phases were dried over sodium sulfate and evaporated. The resulting crude was purified by flash chromatography on silica gel using a gradient of 10% v/v methanol in ethyl acetate and hexanes to afford 904.7 mg (62%, 1.625 mmol) of (5-[4-chloro-3-iodo-1-(2-trimethylsilanyl-ethoxymethyl)-1H-pyrrolo[2,3-b]pyridin-5-yl]-N,N-dimethyl-nicotinamide as a brown oil. $^1$H-NMR [500 MHz, d$_6$-DMSO] d 8.75 (m, 1H), 8.69 (m, 1H), 8.39 (m, 1H), 8.12 (s, 1H), 8.02 (m, 1H), 5.64 (s, 2H), 3.54 (t, 2H), 3.02 (s, 3H), 3.00 (s, 3H), 0.84 (t, 2H), 0.09 (s, 9H); MS [MH$^+$] m/z: 557.

Method 21

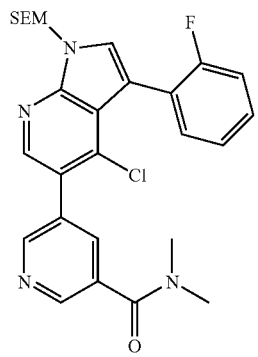

Synthesis of 5-[4-Chloro-3-(2-fluoro-phenyl)-1-(2-trimethylsilanyl-ethoxymethyl)-1H-pyrrolo[2,3-b]pyridin-5-yl]-N,N-dimethyl-nicotinamide 78 mg (0.14 mmol) of (5-[4-chloro-3-iodo-1-(2-trimethylsilanyl-ethoxymethyl)-1H-pyrrolo[2,3-b]pyridin-5-yl]-N,N-dimethyl-nicotinamide, 21 mg (0.15 mmol) of 2-fluoro-phenylboronic acid and 6 mg (7 μmol) of (1,1′-bis(diphenylphosphino)ferrocenepalladium(II)-dichloride dichloromethane adduct were dissolved in a mixture of 2.6 mL of acetonitrile, 2.6 mL of toluene and 1.5 mL of a saturated aqueous solution of sodium bicarbonate. The resulting mixture was heated to 110° C. in a closed vial for 22 h. The resulting mixture was diluted with ethyl acetate, dried over sodium sulfate and evaporated. The resulting crude was purified by flash chromatography on silica gel using a gradient of 10% v/v methanol in ethyl acetate and hexanes to afford 56.6 mg (0.10 mmol) of 5-[4-chloro-3-(2-fluoro-phenyl)-1-(2-trimethylsilanyl-ethoxymethyl)-1H-pyrrolo[2,3-b]pyridin-5-yl]-N,N-dimethyl-nicotinamide. $^1$H-NMR [500 MHz, $d_6$-DMSO] δ: 8.73 (d, 1H), 8.67 (d, 1H), 8.41 (s, 1H), 7.99 (t, 1H), 7.97 (s, 1H), 7.49-7.41 (m, 2H), 7.30-7.25 (m, 2H), 5.74 (s, 2H), 3.62 (t, 2H), 3.01 (s, 3H), 2.97 (s, 3H), 0.86 (t, 2H), −0.06 (s, 9H); MS [MH$^+$] m/z: 525.

Method 22

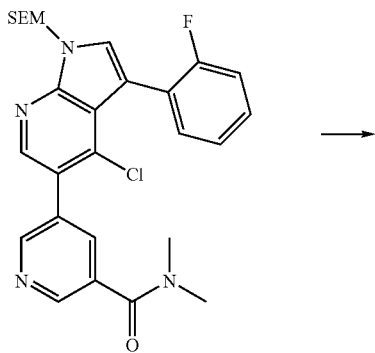

→

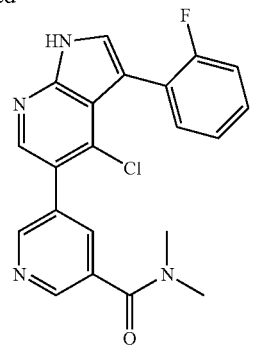

Synthesis of 5-[4-Chloro-3-(2-fluoro-phenyl)-1H-pyrrolo[2,3-b]pyridin-5-yl]-N,N-dimethyl-nicotinamide 5-[4-chloro-3-(2-fluoro-phenyl)-1-(2-trimethylsilanyl-ethoxymethyl)-1H-pyrrolo[2,3-b]pyridin-5-yl]-N,N-dimethyl-nicotinamide was taken up in dichloromethane and 500 µL of trifluoroacetic acid added. The mixture was left at ambient temperature for 10 h and then evaporated. The residue was re-dissolved in 3 mL of dichloromethane and 100 µL of 1,2-ethylenediamine. After 6 h at ambient temperature the mixture was evaporated to dryness. The resulting crude was dissolved in dimethylsulfoxide and purified by mass-triggered reverse phase HPLC to afford 18.2 mg (46 µmol, 33%) of 5-[4-chloro-3-(2-fluoro-phenyl)-1H-pyrrolo[2,3-b]pyridin-5-yl]-N,N-dimethyl-nicotinamide as an off-white solid. $^1$H-NMR [500 MHz, $d_6$-DMSO] δ: 12.50 (s, br., 1H), 8.73 (d, 1H), 8.65 (d, 1H), 8.32 (s, 1H), 7.97 (t, 1H), 7.76 (s, 1H), 7.47 (ddd, 1H), 7.41 (, 1H), 7.28-7.21 (m, 2H), 3.01 (s, 3H), 2.97 (s, 3H); MS [MH$^+$] m/z: 395.

Other compound synthesized according to Method 17-Method 22:

| Structure | MS [MH$^+$] m/z | $^1$H-NMR [500 MHz $d_6$-DMSO] δ |
|---|---|---|
| 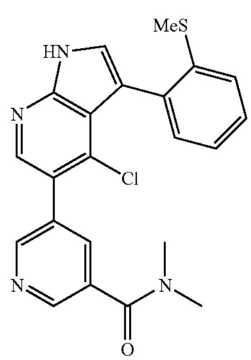 | 423 | 5-[4-Chloro-3-(2-methylsulfanyl-phenyl)-1H-pyrrolo[2,3-b]pyridin-5-yl]-N,N-dimethyl-nicotinamide 8.71 (d, 1H), 8.63 (d, 1H), 8.29 (s, 1H), 7.94 (t, 1H), 7.62 (s, 1H), 7.38 (ddd, 1H), 7.29-7.25 (m, 2H), 7.17 (ddd, 1H), 3.01 (s, 3H), 2.96 (s, 3H), 2.34 (s, 3H) |

| Structure | MS [MH+] m/z | ¹H-NMR [500 MHz d₆-DMSO] δ |
|---|---|---|
| | 413 | 5-[4-Chloro-3-(2,3-difluoro-phenyl)-1H-pyrrolo[2,3-b]pyridin-5-yl]-N,N-dimethyl-nicotinamide<br>8.73 (d, 1H), 8.65 (d, 1H), 8.34 (s, 1H), 7.98 (t, 1H), 7.82 (s, 1H), 7.47-7.40 (m, 2H), 7.30 (m, 1H), 7.25 (m, 1H), 3.01 (s, 3H), 2.97 (s, 3H) |
| 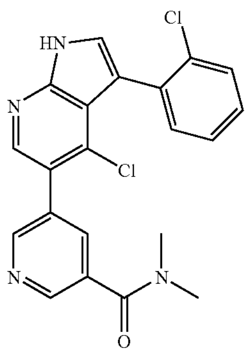 | 411 | 5-[4-Chloro-3-(2-chloro-phenyl)-1H-pyrrolo[2,3-b]pyridin-5-yl]-N,N-dimethyl-nicotinamide<br>12.38 (s, br., 1H), 8.66 (d, 1H), 8.58 (d, 1H), 8.25 (s, 1H), 7.89 (t, 1H), 7.64 (s, 1H), 7.46 (dd(d), 1H), 7.42 (dd(d), 1H), 7.34 (ddd, 1H), 7.31 (ddd, 1H), 2.94 (s, 3H), 2.89 (s, 3H) |
| 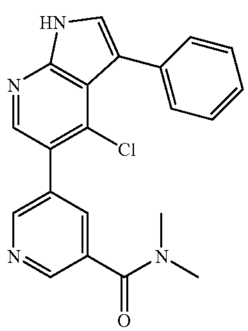 | 377 | 5-(4-Chloro-3-phenyl-1H-pyrrolo[2,3-b]pyridin-5-yl)-N,N-dimethyl-nicotinamide<br>8.75 (d, 1H), 8.65 (d. 1H), 8.32 (s, 1H), 8.00 (t, 1H), 7.73 (s, 1H), 7.52 (d(m), 2H), 7.40 (t(m), 2H), 7.31 (tt, 1H), 3.02 (s, 3H), 2.98 (s, 3H) |
| | 413 | 5-[4-Chloro-3-(2,4-difluoro-phenyl)-1H-pyrrolo[2,3-b]pyridin-5-yl]-N,N-dimethyl-nicotinamide<br>8.73 (d, 1H0, 8.65 (d, 1H), 8.33 (s, 1H), 7.97 (t, 1H), 7.77 (s, 1H), 7.52 (ddd, 1H), 7.31 (dt, 1H), 7.14 (dt, 1H), 3.01 (s, 3H), 2.97 (s, 3H). |

-continued

| Structure | MS [MH+] m/z | ¹H-NMR [500 MHz d₆-DMSO] δ |
|---|---|---|
| 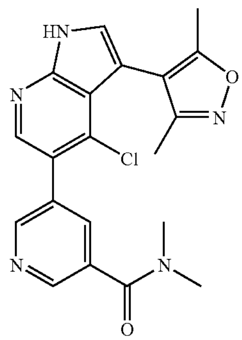 | 396 | 5-[4-Chloro-3-(3,5-dimethyl-isoxazol-4-yl)-1H-pyrrolo[2,3-b]pyridin-5-yl]-N,N-dimethyl-nicotinamide<br>8.75 (d, 1H), 8.66 (d, 1H), 8.32 (s, 1H), 8.00 (t, 1H), 7.73 (s, 1H), 3.02 (s, 3H), 2.98 (s, 3H), 2.28 (s, 3H), 2.09 (s, 3H). |
| 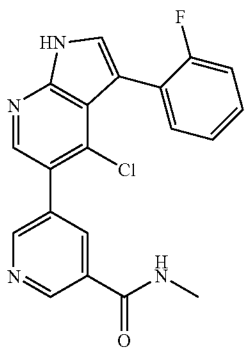 | 381 | 5-[4-chloro-3-(2-fluoro-phenyl)-1H-pyrrolo[2,3-b]pyridin-5-yl]-N-methyl-nicotinamide<br>¹H-NMR [500 MHz, d₆-DMSO]δ: 12.52 (s, br., 1H), 9.01 (d, 1H), 8.81 (d, 1H), 8.72 (q, br., 1H), 8.34 (s, 1H), 8.29 (t, 1H), 7.77 (s, 1H), 7.48 (ddd, 1H), 7.44 (m, 1H), 7.28-7.23 (m, 2H), 2.82 (s, 3H); |
| | 438.0 | 2-{5-[4-Chloro-3-(2-methoxy-pyridin-3-yl)-1H-pyrrolo[2,3-b]pyridin-5-yl]-pyridin-3-yl}-2-hydroxy-N,N-dimethyl-acetamide<br>2.82 (s, 3H), 2.96 (s, 3H), 3.80 (s, 3H), 5.57 (s, 1H), 5.82 (s, 1H), 7.03 (t, 1H), 7.68 (s, 1H), 7.69 (d, 1H), 7.85 (s, 1H), 8.16 (d, 1H), 8.24 (s, 1H), 8.59 (m, 2H) |
| | 438.0 | 2-{5-[4-Chloro-3-(3-methoxy-pyridin-4-yl)-1H-pyrrolo[2,3-b]pyridin-5-yl]-pyridin-3-yl}-2-hydroxy-N,N-dimethyl-acetamide<br>2.82 (s, 3H), 2.98 (s, 3H), 3.82 (s, 3H), 5.68 (s, 1H), 7.34 (d, 1H), 7.38 (s, 1H), 7.86 (s, 1H), 7.24 (d, 1H), 8.26 (s, 1H), 8.38 (s, 1H), 8.59 (s, 1H), 8.61 (s, 1H) |

-continued

| Structure | MS [MH+] m/z | ¹H-NMR [500 MHz d₆-DMSO] δ |
|---|---|---|
| 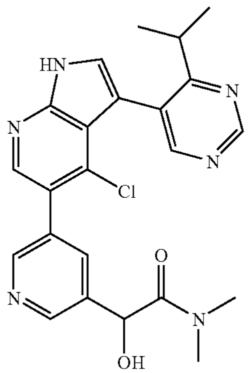 | 451.0 | 2-{5-[4-Chloro-3-(4-isopropyl-pyrimidin-5-yl)-1H-pyrrolo[2,3-b]pyridin-5-yl]-pyridin-3-yl}-2-hydroxy-N,N-dimethyl-acetamide 1.07 (d, 3H), 1.17 (d, 3H), 2.85 (s, 3H), 2.95 (s, 3H), 3.09 (m, 1H), 5.57 (s, 1H), 7.84 (s, 1H), 7.85 (m, 1H), 8.31 (s, 1H), 8.60 (m, 2H), 8.63 (s, 1H), 9.12 (s, 1H) |
| 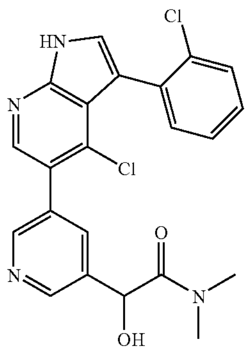 | 441.0 | 2-{5-[4-Chloro-3-(2-chloro-phenyl)-1H-pyrrolo[2,3-b]pyridin-5-yl]-pyridin-3-yl}-2-hydroxy-N,N-dimethyl-acetamide 2.84 (s, 3H), 2.95 (s, 3H), 5.57 (s, 1H), 5.83 (s, 1H), 7.35-7.42 (m, 2H), 7.47-7.49 (d, 1H), 7.52-7.54 (d, 1H), 7.70 (s, 1H), 7.86 (s, 1H), 8.27 (s, 1H), 8.59 (m, 2H) |
| 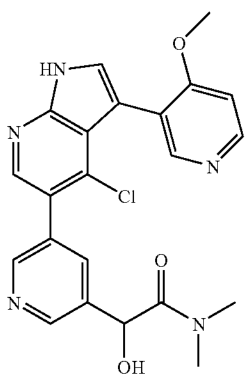 | 438.0 | 2-{5-[4-Chloro-3-(4-methoxy-pyridin-3-yl)-1H-pyrrolo[2,3-b]pyridin-5-yl]-pyridin-3-yl}-2-hydroxy-N,N-dimethyl-acetamide ¹H NMR (500 MHz, DMSO-d6) δ 2.90 (s, 3H), 2.93 (s, 3H), 3.80 (s, 3H), 5.60 (s, 1H), 7.18, (d, 1H), 7.69 (s, 1H), 7.86 (m, 1H), 8.25 (s, 1H), 8.34 (s, 1H), 8.46 (d, 1H), 8.59 (d, 1H), 8.61 (d, 1H). |

Method 23

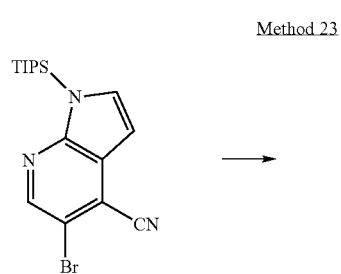

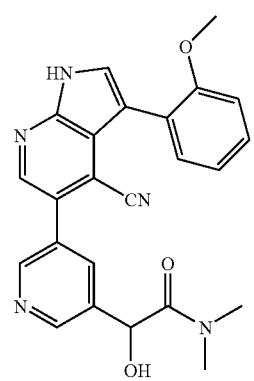

-continued

Synthesis of 2-{5-[4-Cyano-3-(2-methoxy-phenyl)-1H-pyrrolo[2,3-b]pyridin-5-yl]-pyridin-3-yl}-2-hydroxy-N,N-dimethyl-acetamide A mixture of 2-(5-Bromo-pyridin-3-yl)-2-hydroxy-N,N-dimethyl-acetamide (160 mg, 0.62 mmol), bis(pinacol)diborane (173 mg, 0.68 mmol), potassium acetate (182 mg, 1.85 mmol), and 1,1'-bis(diphenylphosphino)ferrocenepalladium(II)-dichloride dichlormethane adduct (10 mg, 0.012 mmol) in dimethylacetamide (1 mL) was irradiated in a Personal Chemistry Optimizer at 120° C. for 30 min. 5-Bromo-1-triisopropylsilanyl-1H-pyrrolo[2,3-b]pyridine-4-carbonitrile (159 mg, 0.42 mmol), sodium carbonate solution (2M in water, 1 mL, 2 mmol), dimethylacetamide (2 mL) and additional 1,1'-bis(diphenylphosphino)ferrocenepalladium(II)-dichloride dichlormethane adduct (10 mg, 0.012 mmol) was added and the mixture was irradiated for an additional 30 min at 120° C. Sodium sulfate was added to the crude reaction mixture and the solids were filtered over Celite. The solids were rinsed with ethyl acetate and acetonitrile and the combined filtrate was concentrated. The resulting residue was purified by flash silica gel chromatography using a gradient of ethyl acetate in hexanes to afford 2-[5-(4-Cyano-1H-pyrrolo[2,3-b]pyridin-5-yl)-pyridin-3-yl]-2-hydroxy-N,N-dimethyl-acetamide (35 mg). The material was dissolved in acetone (5 mL), and N-iodosuccinimide (27 mg, 0.12 mmol) was added. The mixture was stirred at 23° C. for 3d. The reaction was quenched with sodium thiosulfate solution (1N, 1 mL) and water (1 mL). The mixture was concentrated suspended in ethyl acetate and loaded onto silica. Purification by flash silica gel chromatography using a gradient of (dichloromethane, methanol, and conc. ammonium hydroxide 80:20:1) in dichloromethane afforded 2-[5-(3-Iodo-4-cyano-1H-pyrrolo[2,3-b]pyridin-5-yl)-pyridin-3-yl]-2-hydroxy-N,N-dimethyl-acetamide (46 mg, MS: m/z 447.9 (M+H$^+$)). The material was dissolved in dimethylformamide (1.5 mL), and cooled to 0° C. Sodium hydride (60% suspension in mineral oil, 40 mg, 1 mmol) was added. The mixture was cooled to −42° C. and 2-trimethylsilanyl-ethoxymethyl-chloride (180 μL) was added slowly over 10 min. The mixture was stirred at −42° C. for 2 h and quenched with 2 mL saturated ammonium chloride solution and 2 mL water. The aqueous mixture was applied to a Varian chemelut cartridge and eluted with ethyl acetate. The crude product was purified by flash silica gel chromatography using a gradient of (ethyl acetate and methanol 9:1) in hexanes to afford 2-{5-[4-Cyano-3-iodo-1-(2-trimethylsilanyl-ethoxymethyl)-1H-pyrrolo[2,3-b]pyridin-5-yl]-pyridin-3-yl}-N,N-dimethyl-2-(2-trimethylsilanyl-ethoxymethoxy)-acetamide (49 mg). The material was loaded into a 5 mL Personal Chemistry microwave reaction vial and 2-methoxyphenylboronic acid (16 mg, 0.10 mmol), 1,1'-bis(diphenylphosphino)ferrocenepalladium(II)-dichloride dichloromethane adduct (3 mg, 0.003 mmol), acetonitrile (1 mL) and aqueous Na$_2$CO$_3$ solution (2M, 71 μL) were added. The vial was purged with nitrogen, sealed, and irradiated in a Personal Chemistry Optimizer at 120° C. for 30 min. Sodium sulfate was added to the reaction mixture and the slurry was filtered over Celite and concentrated. The crude product was dissolved in trifluoroacetic acid and shaken at 23° C. for 1 h. The mixture was concentrated and dissolved in dimethylsulfoxide and ethylenediamine. Purification by mass triggered reverse phase HPLC afforded 2-{5-[4-Cyano-3-(2-methoxy-phenyl)-1H-pyrrolo[2,3-b]pyridin-5-yl]-pyridin-3-yl}-2-hydroxy-N,N-dimethyl-acetamide as a white solid (2.3 mg, 0.005 mmol). $^1$H NMR (500 MHz, MeOH-d4) δ 8.75 (d, J=2 Hz, 1H), 8.72 (d, J=2 Hz, 1H), 8.46 (s, 1H), 8.06 (t, J=2 Hz, 1H), 7.68 (s, 1H), 7.37 (m, 2H), 7.05 (d, J=8 Hz, 1H), 7.03 (t, J=8 Hz, 1H), 5.67 (s, 1H), 3.8 (s, 3H), 2.99 (s, 6H). MS: m/z 428.4 (M+H$^+$).

Method 24

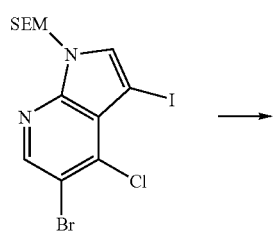

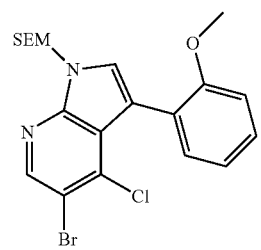

Synthesis of 5-Bromo-4-chloro-3-(2-methoxy-phenyl)-1-(2-trimethylsilanyl-ethoxymethyl)-1H-pyrrolo[2,3-b]pyridine 5-Bromo-4-chloro-3-iodo-1-(2-trimethylsilanyl-ethoxymethyl)-1H-pyrrolo[2,3-b]pyridine (916 mg, 2 mmol), 2-methoxyphenyl boronic acid (321 mg, 2.2 mmol), dichlorobis(triphenylphosphine)palladium(II) (74 mg, 0.1 mmol), and 2 mL of 2M Na$_2$CO$_3$ (aq) were dissolved in 10 mL of acetonitrile and 10 mL of THF under an atmosphere of nitrogen. The mixture was heated at 60° C. with rapid stirring under N$_2$ for 2 h. Sodium sulfate was added to the reaction mixture and the slurry was filtered over Celite and concentrated. The crude product was purified by flash silica gel chromatography using a gradient of ethyl acetate in hexanes to afford the title compound (452 mg, 1.02 mmol, 51% yield). $^1$H NMR (500 MHz, DMSO-d6) δ 8.50 (s, 1H), 7.74 (s, 1H), 7.37 (m, 1H), 7.23 (dd, J=7.5 Hz, J$_2$=1.5 Hz, 1H), 7.05 (dd, J=8 Hz, J$_2$=1 Hz, 1H), 6.98 (td, J=7.5 Hz, J$_2$=1 Hz, 1H), 5.63 (s, 2H), 3.67 (s, 3H), 3.56 (t, J=8 Hz, 2H), 0.82 (t, J=8 Hz, 2H), −0.09 (s, 9H). MS: m/z 467.1/469.1 (M+H$^+$).

Other compounds synthesized using Method 24:

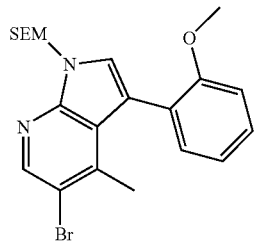

5-Bromo-3-(2-methoxy-phenyl)-4-methyl-1-(2-trimethylsilanyl-ethoxymethyl)-1H-pyrrolo[2,3-b]pyridine
$^1$H-NMR [500 MHz, d$_6$-DMSO] δ: 8.45 (1H), 7.67 (s, 1H), 7.35 (td, 1H), 7.25 (dd, 1H), 7.01 (d, 1H), 6.96 (t, 1H), 5.62 (s, 2H), 3.66 (s, 3H), 3.56 (t, 2H), 2.05 (s, 3H), 0.82 (t, 2H), −0.11 (s, 8H); MS [MH$^+$] m/z: 447.1, 449.1

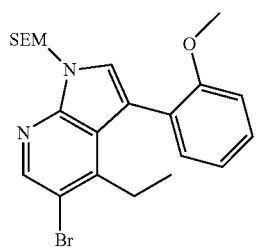

5-Bromo-4-ethyl-3-(2-methoxy-phenyl)-1-(2-trimethylsilanyl-ethoxymethyl)-1H-pyrrolo[2,3-b]pyridine
MS [MH$^+$] m/z: 461.1, 463.1

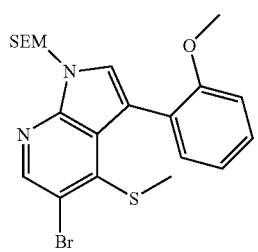

5-Bromo-3-(2-methoxy-phenyl)-4-methylsulfanyl-1-(2-trimethylsilanyl-ethoxymethyl)-1H-pyrrolo[2,3-b]pyridine
$^1$H-NMR [500 MHz, d$_6$-DMSO] δ: 8.45 (s, 1H), 7.67 (s, 1H), 7.5 (td, 1H), 7.25 (dd, 1H), 7.01 (d, 1H), 6.96 (t, 1H), 5.62 (s, 2H), 3.66 (s, 3H), 3.56 (t, 2H), 2.05 (s, 3H), 0.82 (t, 2H), −0.10 (s, 9H); MS [MH$^+$] m/z: 479.1, 481.1

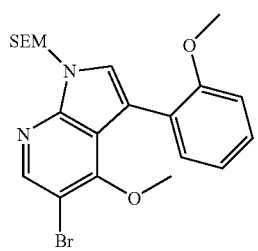

5-Bromo-3-(2-methoxy-phenyl)-4-methoxy-1-(2-trimethylsilanyl-ethoxymethyl)-1H-pyrrolo[2,3-b]pyridine
$^1$H NMR (500 MHz, CDCl$_3$) δ 8.37 (s, 1H), 7.47 (m, 1H), 7.42 (s, 1H), 7.32 (m, 1H), 7.74 (s, 1H), 7.00 (m, 2H), 5.66 (s, 2H), 3.80 (s, 3H), 3.61 (t, J = 8 Hz, 2H), 0.93 (t, J = 8 Hz, 2H), −0.05 (s, 9H). MS: m/z 463.1/465.1 (M + H$^+$).

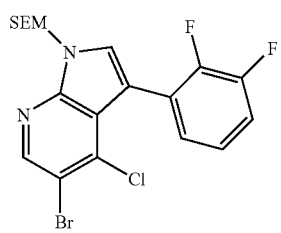

5-Bromo-4-chloro-3-(2,3-difluoro-phenyl)-1-(2-trimethylsilanyl-ethoxymethyl)-1H-pyrrolo[2,3-b]pyridine
$^1$H-NMR [500 MHz, d$_6$-DMSO] δ: 8.56 (s, 1H), 8.01 (s, 1H), 7.49 (m, 1H), 7.27 (m, 2H), 5.68 (s, 2H), 3.58 (m, 2H), 0.82 (t, 2H), −0.11 (s, 9H); MS MS [MH$^+$] m/z: 473.2, 475.2

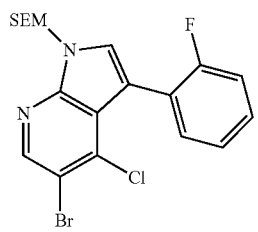

5-Bromo-4-chloro-3-(2-fluoro-phenyl)-1-(2-trimethylsilanyl-ethoxymethyl)-1H-pyrrolo[2,3-b]pyridine
$^1$H-NMR [500 MHz, d$_6$-DMSO] δ: 8.56 (s, 1H), 7.93 (s, 1H), 7.44 (m, 2H), 7.29 (m, 2H), 5.57 (s, 2H), 3.57 (s, 3H), 0.82 (t, 3H), −0.010 (s, 11H); MS MS [MH$^+$] m/z: 455.1, 457.2

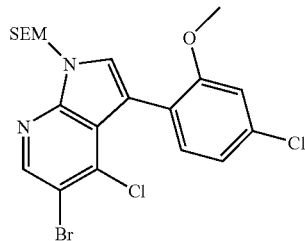

5-Bromo-4-chloro-3-(4-chloro-2-methoxy-phenyl)-1-(2-trimethylsilanyl-ethoxymethyl)-1H-pyrrolo[2,3-b]pyridine
$^1$H-NMR [500 MHz, d$_6$-DMSO] δ: 8.50 (s, 1H), 7.76 (s, 1H), 7.25 (d, 1H), 7.13 (d, 1H), 7.05 (dd, 1H), 5.63 (s, 2H), 3.70 (s, 3H), 3.56 (t, 2H), 0.82 (t, 2H), −0.10 (s, 10H); MS MS [MH$^+$] m/z: 501.0, 503.0, 505.0

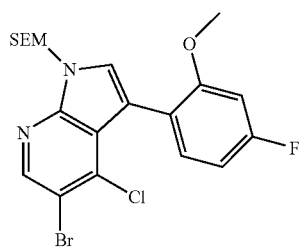

5-Bromo-4-chloro-3-(4-fluoro-2-methoxy-phenyl)-1-(2-trimethylsilanyl-ethoxymethyl)-1H-pyrrolo[2,3-b]pyridine
$^1$H-NMR [500 MHz, d$_6$-DMSO] δ: 8.49 (s, 1H), 7.74 (s, 1H), 7.25 (s, 1H), 6.96 (dd, 1H), 6.80 (td, 1H), 5.63 (s, 2H), 3.69 (s, 4H), 3.56 (t, 2H), 0.82 (t, 2H), −0.10 (s, 9H); MS MS [MH$^+$] m/z: 485.1, 487.0

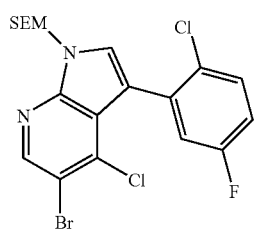

5-Bromo-4-chloro-3-(2-chloro-5-fluoro-phenyl)-1-(2-trimethylsilanyl-ethoxymethyl)-1H-pyrrolo[2,3-b]pyridine
$^1$H-NMR [500 MHz, d$_6$-DMSO] δ: 8.56 (s, 1H), 7.94 (s, 1H), 7.61 (dd, 1H), 7.36 (m, 2H), 5.67 (m, 3H), 3.55 (t, 2H), 3.49 (t, 1H), 0.81 (t, 3H), −0.11 (s, 10H); MS [MH$^+$] m/z: 489.0, 491.0, 493.0

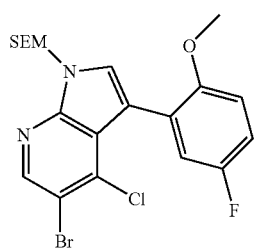

5-Bromo-4-chloro-3-(5-fluoro-2-methoxy-phenyl)-1-(2-trimethylsilanyl-ethoxymethyl)-1H-pyrrolo[2,3-b]pyridine
$^1$H-NMR [500 MHz, d$_6$-DMSO] δ: 8.51 (s, 1H), 7.81 (s, 1H), 7.12 (m, 4H), 5.63 (s, 2H), 3.68 (s, 1H), 3.66 (s, 3H), 3.56 (t, 2H), 0.83 (t, 2H), −0.09 (s, 9H); MS [MH$^+$] m/z: 485.2, 487.2

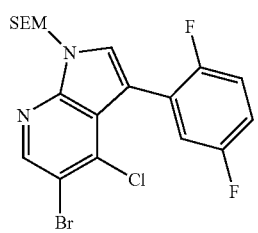

5-Bromo-4-chloro-3-(2,5-difluoro-phenyl)-1-(2-trimethylsilanyl-ethoxymethyl)-1H-pyrrolo[2,3-b]pyridine
$^1$H-NMR [500 MHz, d$_6$-DMSO] δ: 8.57 (s, 1H), 8.00 (s, 1H), 7.33 (m, 3H), 5.67 (s, 2H), 3.56 (m, 2H), 0.82 (m, 2H), −0.10, 9H); MS [MH$^+$] m/z: 473.1, 475.1

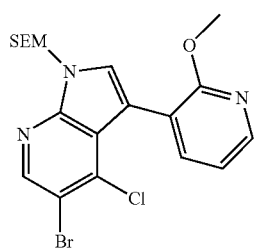

5-Bromo-4-chloro-3-(2-methoxy-pyridin-3-yl)-1-(2-trimethylsilanyl-ethoxymethyl)-1H-pyrrolo[2,3-b]pyridine
$^1$H-NMR [500 MHz, d$_6$-DMSO] δ: 8.53 (s, 1H), 8.20 (dd, 1H), 7.85 (s, 1H), 7.66 (dd, 1H), 7.06 (m, 1H), 5.75 (s, 1H), 5.64 (s, 2H), 3.80 (s, 1H), 3.79 (s, 3H), 3.57 (t, 3H), 0.83 (t, 2H), −0.09 (s, 9H); MS [MH$^+$] m/z: 468.0, 470.0

-continued

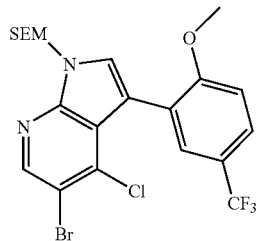

5-Bromo-4-chloro-3-(2-methoxy-5-trifluoromethyl-phenyl)-1-(2-trimethylsilanyl-ethoxymethyl)-1H-pyrrolo[2,3-b]pyridine
$^1$H-NMR [500 MHz, d$_6$-DMSO] δ: 8.52 (s, 1H), 7.88 (s, 1H), 7.76 (s, 1H), 7.56 (d, 1H), 7.25 (d, 1H), 5.64 (s, 2H), 3.77 (s, 3H), 3.56 (m, 2H), 3.31 (s, 2H), 0.82 (t, 2H), −010 (s, 9H); MS [MH$^+$] m/z: 489.0, 491.0

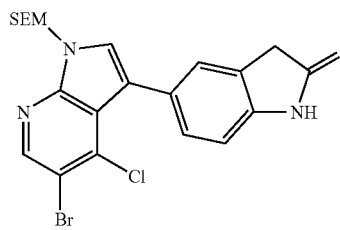

5-[5-Bromo-4-chloro-1-(2-trimethylsilanyl-ethoxymethyl)-1H-pyrrolo[2,3-b]pyridin-3-yl]-1,3-dihydro-indol-2-one
[MH$^+$] m/z: 492.0, 494.1

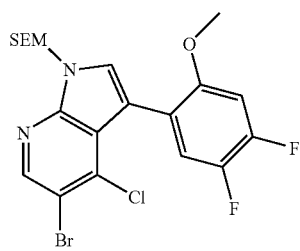

5-Bromo-4-chloro-3-(4,5-difluoro-2-methoxy-phenyl)-1-(2-trimethylsilanyl-ethoxymethyl)-1H-pyrrolo[2,3-b]pyridine
[MH$^+$] m/z: 503.0, 505.0

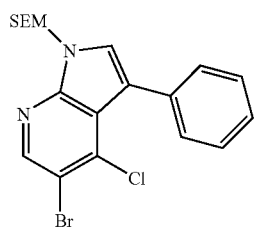

5-bromo-4-chloro-3-phenyl-1-(2-trimethylsilanyl-ethoxymethyl)-1H-pyrrolo 2,3,b]-pyridine
$^1$H NMR (500 MHz, DMSO-d6) δ 0.01 (s, 9H), 0.92 (m, 2H), 3.66 (m, 2H), 5.76 (s, 2H), 7.52 (m, 1H), 7.55 (m, 3H), 7.91 (s, 1H), 8.64 (s, 1H). MS: m/z 437.1 (M + H$^+$).

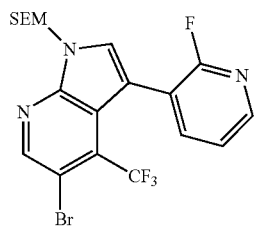

5-bromo-4-chloro-3-(2-fluoro-pyridin-3-yl)-1-(2-trimethyl-silanyl-ethoxymethyl)-1H-pyrrolo[2,3-b]pyridine
$^1$H NMR (500 MHz, DMSO-d6) δ 0.02 (s, 9H), 0.93 (t, 2H), 3.66 (t, 2H), 5.77 (s, 2H), 7.75 (m, 2H), 8.11 (m, 1H), 8.37 (m, 1H), 8.67 (s, 1H). MS: m/z 457.1 (M + H$^+$)

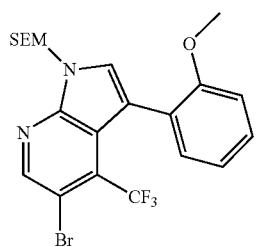

5-Bromo-3-(2-methoxy-phenyl)-4-trifluoromethyl-1-(2-trimethylsilanyl-ethoxymethyl)-1H-pyrrolo[2,3-b]pyridine
MS: m/z 501.0 (M + H$^+$)

-continued

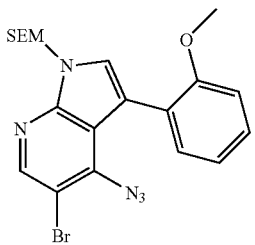

4-Azido-5-bromo-3-(2-methoxy-phenyl)-1-(2-trimethylsilanyl-ethoxymethyl)-1H-pyrrolo[2,3-b]pyridine
$^1$H NMR (500 MHz, DMSO-d6) δ 8.39 (s, 1H), 7.68 (s, 1H), 7.37 (m, 1H), 7.28 (dd, J$_1$ = 7.5 Hz, J$_2$ = 2 Hz, 1H), 7.10 (d, J = 7.5 Hz, 1H), 7.00 (td, J$_1$ = 7.5 Hz, J$_2$ = 1 Hz, 1H), 5.62 (s, 2H), 3.74 (s, 3H), 3.56 (t, J = 8 Hz, 2H), 0.82 (t, J = 8 Hz, 2H), −0.10 (s, 9H). MS: m/z 474.0/476.0 (M + H$^+$).

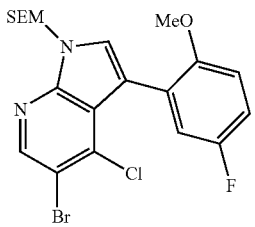

5-Bromo-4-chloro-3-(5-fluoro-2-methoxy-phenyl)-1-(2-trimethylsilanyl-ethoxymethyl)-1H-pyrrolo[2,3-b]pyridine
$^1$H-NMR [500 MHz, d$_6$-DMSO] δ: 8.53 (s, 1H), 7.83 (s, 1H), 7.22 (ddd, 1H), 7.12 (dd, 1H), 7.06 (dd, 1H), 5.66 (s, 2H), 3.68 (s, 3H), 3.58 (t, 2H), 0.84 (t, 2H), −0.7 (s, 9H); MS [MH$^+$] m/z: 484.8 + 486.8.

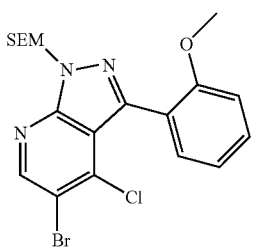

5-Bromo-4-chloro-3-(2-methoxy-phenyl)-1-(2-trimethylsilanyl-ethoxymethyl)-1H-pyrazolo[3,4-b]pyridine
MS: m/z 468.0/470.0 (M + H$^+$).

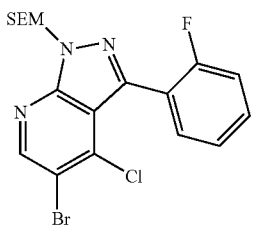

5-Bromo-4-chloro-3-(2-fluoro-phenyl)-1-(2-trimethylsilanyl-ethoxymethyl)-1H-pyrazolo[3,4-b]pyridine
$^1$H NMR (500 MHz, DMSO-d6) δ 0.01 (s, 9H), 0.92 (m, 2H), 3.66 (m, 2H), 5.85 (s, 2H), 7.52 (m, 1H), 7.55 (m, 1H), 7.68 (m, 1H), 7.96 (dt, 1H), 8.84 (d, 1H). MS: m/z 456.0/458.0 (M + H$^+$).

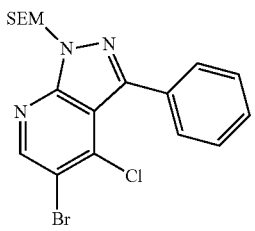

5-Bromo-4-chloro-3-phenyl-1-(2-trimethylsilanyl-ethoxymethyl)-1H-pyrazolo[3,4-b]pyridine
$^1$H NMR (500 MHz, DMSO-d6) δ 0.01 (s, 9H), 0.92 (m, 2H), 3.66 (m, 2H), 5.83 (s, 2H), 7.60 (m, 3H), 8.14 (m, 2H), 9.16 (s, 1H). MS: m/z 438.0/440.0 (M + H$^+$).

Method 25

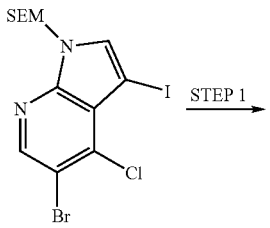

STEP 1 →

-continued

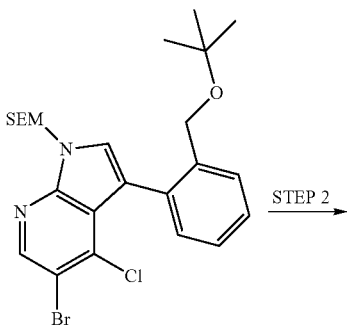

STEP 2 →

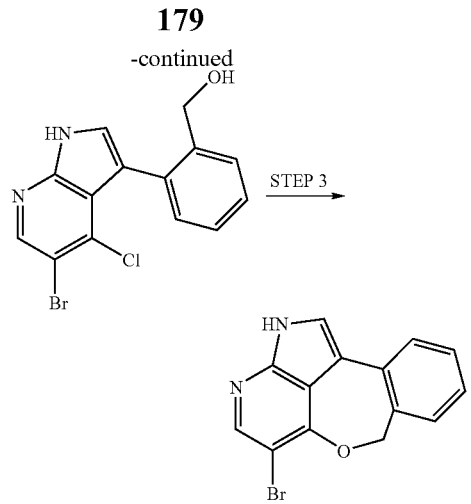

STEP 3

STEP 1: Synthesis of 5-Bromo-3-(2-tert-butoxymethyl-phenyl)-4-chloro-1-(2-trimethylsilanylethoxymethyl)-1H-pyrrolo[2,3-b]pyridine 5-Bromo-4-chloro-3-iodo-1-(2-trimethylsilanylethoxymethyl)-1H-pyrrolo[2,3-b]pyridine (500 mg, 1.02 mmol), 2-(tert-Butoxymethyl)phenylboronic acid (224 mg, 1.05 mmol), dichlorobis(triphenylphosphine)palladium(II) (42 mg, 0.05 mmol), and 1 mL of sodium carbonate solution (2M, 2 mmol) were dissolved in 5 mL of acetonitrile and 5 mL of THF under an atmosphere of nitrogen. The mixture was heated at 60° C. with rapid stirring under $N_2$ for 2 h. Sodium sulfate was added to the reaction mixture and the slurry was filtered over Celite and concentrated. The crude product was purified by flash silica gel chromatography using a gradient of ethyl acetate in hexanes to afford the title compound (66 mg, 0.12 mmol, 12% yield).

STEP 2: Synthesis of 5-Bromo-3-(2-tert-butoxymethyl-phenyl)-4-chloro-1-(2-trimethylsilanylethoxymethyl)-1H-pyrrolo[2,3-b]pyridine 5-Bromo-3-(2-tert-butoxymethyl-phenyl)-4-chloro-1-(2-trimethylsilanyl-ethoxymethyl)-1H-pyrrolo[2,3-b]pyridine (66 mg, 0.12 mmol) was dissolved in dichloromethane (1 mL) and trifluoroacetic acid (1 mL) and stirred at 23° C. for 15 h. The solvent was evaporated and the resulting oil was dissolved in methanol (1 mL) and ethylenediamine (0.2 mL) and stirred at 23° C. for 1 h. The mixture was concentrated to afford [2-(5-Bromo-4-chloro-1H-pyrrolo[2,3-b]pyridin-3-yl)-phenyl]-methanol which was used in the next step without further purification.

STEP 3: Synthesis of 5-Bromo-2H,7H-6-oxa-2,3-diaza-dibenzo[cd,h]azulene

[2-(5-Bromo-4-chloro-1H-pyrrolo[2,3-b]pyridin-3-yl)-phenyl]-methanol (66 mg, 0.2 mmol) was dissolved in 5 mL DMF and NaH was added until the gas evolution stops. The mixture was stirred at 80° C. for 14 h. The reaction was concentrated and quenched with saturated ammonium chloride solution (2 mL) and water (2 mL). The mixture was applied to a Varian chemelut cartridge and eluted with ethyl acetate. The crude product was purified by flash silica gel chromatography using a gradient of ethyl acetate in hexanes followed by mass triggered reverse phase HPLC to afford the title compound (1.3 mg, 0.004 mmol, 2.2% yield over 2 steps). $^1$H NMR (500 MHz, MeCN-d3) δ 8.23 (s, 1H), 7.75 (m, 2H), 7.43 (m, 2H), 7.25 (t, J=7 Hz, 1H), 5.30 (s, 2H). MS: m/z 301.0/303.0 (M+H$^+$).

Method 26

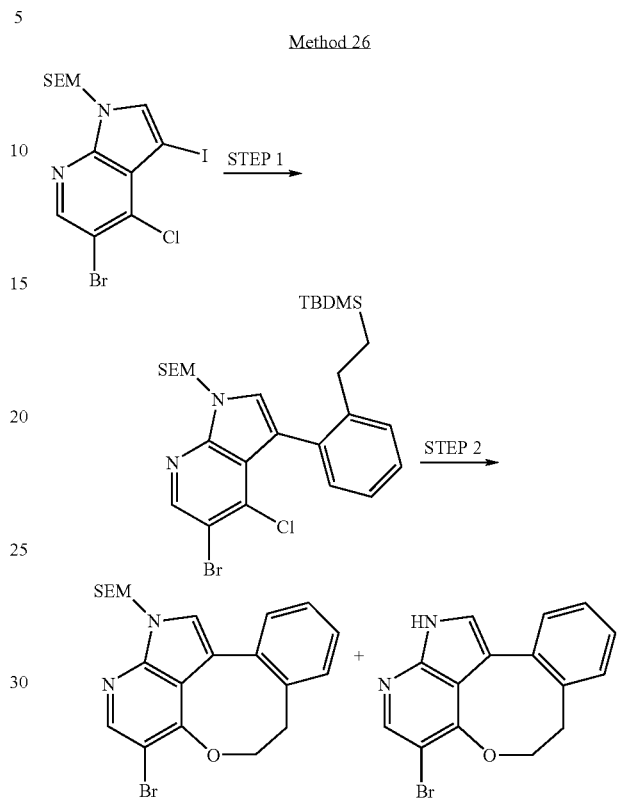

Synthesis of 5-Bromo-2-(2-trimethylsilanylethoxymethyl)-7,8-dihydro-2H-6-oxa-2,3-diazabenzocycloocta[cd]indene STEP 1: Synthesis of 2-{2-[5-Bromo-4-chloro-1-(2-trimethylsilanyl-ethoxymethyl)-1H-pyrrolo[2,3-b]pyridin-3-yl]-phenyl}-ethanol 5-Bromo-4-chloro-3-iodo-1-(2-trimethylsilanylethoxymethyl)-1H-pyrrolo[2,3-b]pyridine (500 mg, 1.02 mmol), [2-(2-(tert-Butyldimethylsilyloxy)ethyl)phenyl]boronic acid (287 mg, 1.02 mmol), dichlorobis(triphenylphosphine)palladium(II) (42 mg, 0.05 mmol), and 1.03 mL of sodium carbonate solution (2M, 2.05 mmol) were dissolved in acetonitrile (2 mL) and THF (2 mL) under an atmosphere of nitrogen. The mixture was heated at 60° C. with rapid stirring under $N_2$ for 12 h. Sodium sulfate was added to the reaction mixture and the slurry was filtered over Celite and concentrated. The crude product was purified by flash silica gel chromatography using a gradient of ethyl acetate in hexanes to afford 5-Bromo-3-{2-[2-(tert-butyl-dimethyl-silanyl)-ethyl]-phenyl}-4-chloro-1-(2-trimethylsilanylethoxymethyl)-1H-pyrrolo[2,3-b]pyridine as a colorless oil (250 mg, 0.42 mmol, 41%). The material was dissolved in acetonitrile (5 mL), dioxane (5 mL), and hydrochloric acid (0.1 N, 5 nm). After 12 h the mixture was quenched with saturated sodium bicarbonate solution (5 mL) and the organic solvent was removed on a rotary evaporator. The aqueous mixture was applied to a Varian chemelut cartridge and eluted with ethyl acetate. The crude product was purified by flash silica gel chromatography using a gradient of (ethyl acetate/methanol 9:1) in hexanes to afford 2-{2-[5-Bromo-4-chloro-1-(2-trimethylsilanyl-ethoxymethyl)-1H-pyrrolo[2,3-b]pyridin-3-yl]-phenyl}-ethanol as a colorless oil (197 mg, 0.41 mmol, 97%). $^1$H NMR (500 MHz, DMSO-d6) δ 8.53 (d, J=1.5 Hz, 1H), 7.78 (d, J=1.5 Hz, 1H), 7.32 (m, 2H), 7.22 (m, 2H), 5.67 (m, 2H), 4.46 (m, 1H), 3.57 (m, 2H), 3.38 (m, 2H), 2.67 (, 1H), 2.54 (m, 1H), 0.83 (m, 2H), −0.10 (s, 9H). MS: m/z 481.0/483.1 (M+H$^+$).

STEP 2: Synthesis of 5-Bromo-2-(2-trimethylsilanyl-ethoxymethyl)-7,8-dihydro-2H-6-oxa-2,3-diaza-benzocycloocta[cd]indene 2-{2-[5-Bromo-4-chloro-1-(2-trimethylsilanyl-ethoxymethyl)-1H-pyrrolo[2,3-b]pyridin-3-yl]-phenyl}-ethanol was dissolved in DMF (20 mL) and sodium hydride (100 mg) was added until the gas evolution stops. The mixture was stirred at 80° C. for 12 h. The reaction was quenched with saturated ammonium chloride solution (5 mL) and concentrated. The solid was suspended in water (20 mL) and was applied to a Varian chemelut cartridge and eluted with ethyl acetate. The crude product was purified by flash silica gel chromatography using a gradient of ethyl acetate in hexanes followed by mass triggered reverse phase HPLC to afford 5-Bromo-7,8-dihydro-2H-6-oxa-2,3-diaza-benzocycloocta[cd]indene (28.6 mg, 0.09 mmol, 23% yield). $^1$H NMR (500 MHz, MeCN-d3) δ 12.18 (s, 1H), 8.33 (s, 1H), 7.62 (d, J=2.5 Hz, 1H), 7.47 (m, 1H), 7.38 (m, 1H), 7.29 (m, 2H), 4.30 (t, J=6 Hz, 2H), 2.91 (t, J=6 Hz, 2H). MS: m/z 315.0/317.0 (M+H$^+$) and 5-Bromo-2-(2-trimethylsilanyl-ethoxymethyl)-7,8-dihydro-2H-6-oxa-2,3-diaza-benzocycloocta[cd] indene (45 mg, 0.01 mmol, 26% yield).

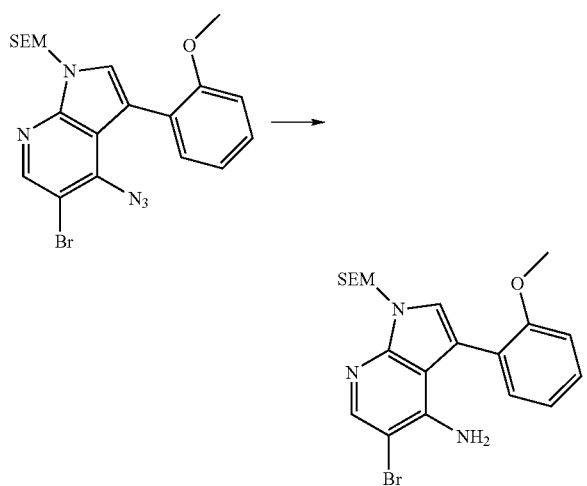

Method 27

Synthesis of 5-Bromo-3-(2-methoxy-phenyl)-1-(2-trimethylsilanyl-ethoxymethyl)-1H-pyrrolo[2,3-b]pyridin-4-ylamine 4-Azido-5-bromo-3-(2-methoxy-phenyl)-1-(2-trimethylsilanyl-ethoxymethyl)-1H-pyrrolo[2,3-b]pyridine (115 mg, 0.24 mmol), triphenylphosphine (64 mg, 0.24 mmol), and water (44 μL, 2.4 mmol) were dissolved in tetrahydrofuran (1 mL). The reaction was stirred at 23° C. for 1 h. Water (100 μL, 5.5 mmol) was added and the mixture was stirred an additional 14 h. The reaction mixture was directly loaded onto silica gel and purified using flash silica gel chromatography using a gradient of (ethyl acetate and methanol 9:1) in hexanes to afford 5-Bromo-3-(2-methoxy-phenyl)-1-(2-trimethylsilanyl-ethoxymethyl)-1H-pyrrolo[2,3-b]pyridin-4-ylamine (MS: m/z 448.1/450.1 (M+H$^+$).

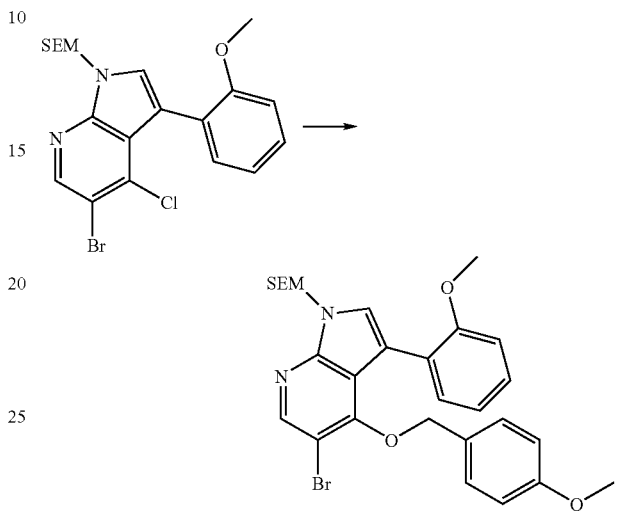

Method 28

Synthesis of 5-Bromo-4-(4-methoxy-benzyloxy)-3-(2-methoxy-phenyl)-1-(2-trimethylsilanyl-ethoxymethyl)-1H-pyrrolo[2,3-b]pyridine 5-Bromo-4-chloro-3-(2-methoxy-phenyl)-1-(2-trimethylsilanyl-ethoxymethyl)-1H-pyrrolo[2,3-b]pyridine (245 mg, 0.52 mmol) and methoxybenzyl alcohol (723 mg, 5.2 mmol) were dissolved in dimethylformamide (0.25 mL). Sodium hydride (167 mg, 4.2 mmol) was added and the mixture was irradiated in a Personal Chemistry Optimizer at 120° C. for 5 min. The reaction was quenched with water, applied to a Varian chemelut cartridge and eluted with ethyl acetate. The crude product was purified by flash silica gel chromatography using a gradient of (ethyl acetate and methanol 9:1) in hexanes to afford 5-Bromo-4-(4-methoxy-benzyloxy)-3-(2-methoxy-phenyl)-1-(2-trimethylsilanyl-ethoxymethyl)-1H-pyrrolo[2,3-b]pyridine (220 mg, 0.38 mmol, 74% yield). $^1$H NMR (500 MHz, DMSO-d$_6$) δ 8.39 (s, 1H), 7.66 (s, 1H), 7.40 (m, 1H), 7.35 (dd, J=7 Hz, J$_2$=2 Hz, 1H), 7.08 (d, J=8 Hz, 1H), 7.01 (td, J$_1$=7 Hz, J$_2$=1 Hz, 1H), 6.77 (m, 4H), 5.63 (s, 2H), 4.37 (s, 2H), 3.71 (s, 3H), 3.64 (s, 3H), 3.58 (t, J=8 Hz, 1H), 0.83 (t, J=8 Hz, 1H), −0.08 (s, 9H). MS: m/z 569.4/571.3 (M+H$^+$).

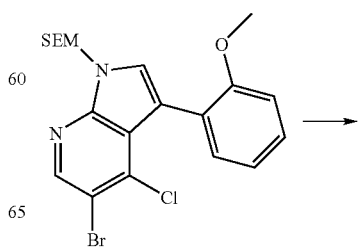

Method 29

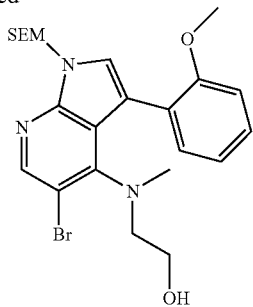

Synthesis of 2-{[5-Bromo-3-(2-methoxy-phenyl)-1-(2-trimethylsilanyl-ethoxymethyl)-1H-pyrrolo[2,3-b]pyridin-4-yl]-methyl-amino}-ethanol 5-Bromo-4-chloro-3-(2-methoxy-phenyl)-1-(2-trimethylsilanyl-ethoxymethyl)-1H-pyrrolo[2,3-b]pyridine (94 mg, 0.201 mmol) was combined 2-(methylamino)ethanol (161 μL, 2.01 mmol) in a sealed tube and heated for 15 hours at 145° C. The crude product was purified by flash silica gel chromatography using a gradient of ethyl acetate in hexanes to afford 2-{[5-Bromo-3-(2-methoxy-phenyl)-1-(2-trimethylsilanyl-ethoxymethyl)-1H-pyrrolo[2,3-b]pyridin-4-yl]-methyl-amino}-ethanol (67 mg, 0.132 mmol, 66% yield) as a clear oil.

Other compounds synthesized using Method 29:

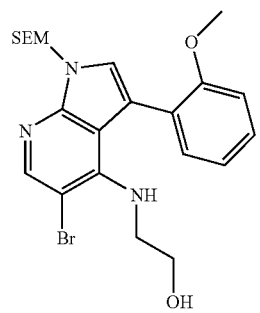

5-Bromo-3-(2-methoxy-phenyl)-4-methylsulfanyl-1H-pyrrolo[2,3b]pyridine
$^1$H-NMR [500 MHz, d$_6$-DMSO] δ: 12.12 (s, 1H), 8.36 (s, 1H), 7.47 (s, 1H), 7.32 (m, 1H), 7.26 (m, 1H), 7.99 (d, 1H) 6.94 (t, 1H), 3.65 (s, 3H) 2.03 (s, 4H); MS [MH$^+$] m/z: 349, 351.

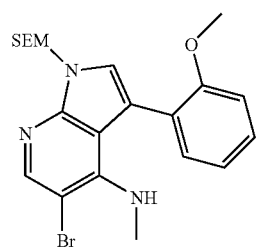

[5-Bromo-3-(2-methoxy-phenyl)-1-(2-trimethylsilanyl-ethoxymethyl)-1H-pyrrolo[2,3-b]pyridin-4-yl]-methyl-amine

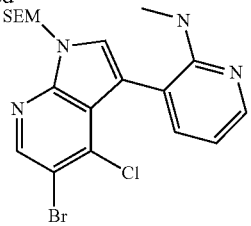

Synthesis of {3-[5-bromo-4-chloro-1-(2-trimethylsilanyl-ethoxymethyl)-1H-pyrrolo[2,3-b]pyridine-3-yl]-pyridin-2-yl}-methyl-amine A mixture of 5-bromo-4-chloro-3-(2-fluoro-pyridin-3-yl)-1-(2-trimethylsilanyl-ethoxymethyl)-1H-pyrrolo[2,3-b]pyridine (0.5 g, 1.2 mmol), methylamine (1.1 ml, 13.0 mmol, 40% in H$_2$O) in 1-butanol (5 nm i) was flushed with nitrogen and allowed to stirred at 120° C. overnight. The reaction was allowed to cool to room temperature and water (5 ml) was added. The mixture was extracted with ethyl acetate (x2). The combined organic layers were extracted with brine, dried with Na$_2$SO$_4$, decanted, and concentrated to dryness. Silica chromatography of the crude using a gradient of ethyl acetate and hexane afforded {3-[5-bromo-4-chloro-1-(2-trimethylsilanyl-ethoxymethyl)-1H-pyrrolo[2,3-b]pyridine-3-yl]-pyridin-2-yl}-methyl-amine (0.3 g, 60% yield). $^1$H NMR (500 MHz, DMSO-d6) δ 0.05 (s, 9H), 0.92 (t, 2H), 2.81 (d, 3H), 3.64 (t, 2H), 5.38 (m, 1H), 5.64 (m, 2H), 6.63 (m, 1H), 7.30 (d, 1H), 7.85 (s, 1H), 8.11 (m, 1H), 8.57 (s, 1H). MS: m/z 467.2 (M+H$^+$).

Method 30

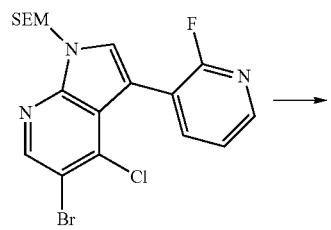

Method 31

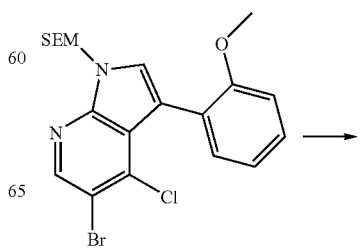

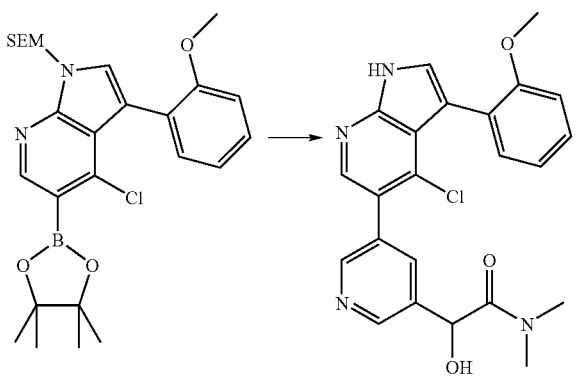

Synthesis of 2-{5-[4-Chloro-3-(2-methoxy-phenyl)-1H-pyrrolo[2,3-b]pyridin-5-yl]-pyridin-3-yl}-2-hydroxy-N,N-dimethyl-acetamide 5-Bromo-4-chloro-3-(2-methoxy-phenyl)-1-(2-trimethylsilanyl-ethoxymethyl)-1H-pyrrolo[2,3-b]pyridine (350 mg, 0.77 mmol), bis(pinacolato)diboron (215 mg, 0.85 mmol), 1,1'-bis(diphenylphosphino)ferrocenepalladium(II)-dichloride dichloromethane adduct (28 mg, 0.035 mmol), and anhydrous potassium acetate (230 mg, 2.3 mmol) were suspended in anhydrous DMA under an under an atmosphere of nitrogen. The mixture was heated at 120° C. under $N_2$ for 2 h. Diethyl ether was added to the reaction mixture and the slurry was filtered over Celite and concentrated. The crude product was purified by flash silica gel chromatography using a gradient of ethyl acetate in hexanes to afford 4-Chloro-3-(2-methoxy-phenyl)-5-(4,4,5,5-tetramethyl-[1,3,2]-dioxaborolan-2-yl)-1-(2-trimethylsilanyl-ethoxymethyl)-1H-pyrrolo[2,3-b]pyridine (38 mg, 0.075 mmol, 9% yield).

Into a 5 mL Personal Chemistry microwave reaction vial were added 4-Chloro-3-(2-methoxy-phenyl)-5-(4,4,5,5-tetramethyl-[1,3,2]dioxaborolan-2-yl)-1-(2-trimethylsilanyl-ethoxymethyl)-1H-pyrrolo[2,3-b]pyridine (38 mg, 0.075 mmol), 2-(5-Bromo-pyridin-3-yl)-2-hydroxy-N,N-dimethyl-acetamide (29 mg, 0.12 mmol; preparation described below), 1,1'-bis(diphenylphosphino)ferrocenepalladium(II)-dichloride dichloromethane adduct (3 mg, 0.004 mmol), acetonitrile (1 mL) and saturated aqueous $Na_2CO_3$ (75 μL). The vial was purged with nitrogen, sealed, and irradiated in a Personal Chemistry Optimizer at 120° C. for 30 min. Sodium sulfate was added to the reaction mixture and the slurry was filtered over Celite and concentrated. The crude product was dissolved in 1 mL TFA and stirred at 23° C. for 15 min. The solvent was evaporated and the resulting oil was dissolved in 1 mL DMSO and 50 μL ethylenediamine and purified by mass triggered reverse phase HPLC to afford the title compound (9.5 mg, 0.015 mmol, 25% yield). $^1$H NMR (500 MHz, DMSO-d6) δ 12.24 (s, 1H), 8.58 (m, 2H), 8.20 (s, 1H), 7.83 (t, J=2 Hz, 1H), 7.33 (td, J=8 Hz, $J_2$=1.5 Hz, 1H), 7.27 (dd, J=7 Hz, $J_2$=1.5 Hz, 1H), 7.05 (d, J=8 Hz, 1H), 6.95 (td, J=8 Hz, $J_2$=1 Hz, 1H), 5.81 (d, J=6.5 Hz, 1H), 5.56 (d, J=6.5 Hz, 1H), 3.68 (s, 3H), 2.95 (s, 3H), 2.84 (s, 3H). MS: m/z 437.0 (M+H$^+$).

Other compounds synthesized using Method 31:

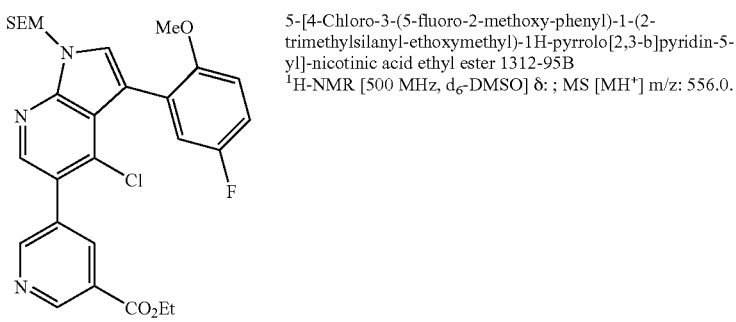

5-[4-Chloro-3-(5-fluoro-2-methoxy-phenyl)-1-(2-trimethylsilanyl-ethoxymethyl)-1H-pyrrolo[2,3-b]pyridin-5-yl]-nicotinic acid ethyl ester 1312-95B
$^1$H-NMR [500 MHz, $d_6$-DMSO] δ: ; MS [MH$^+$] m/z: 556.0.

Method 32

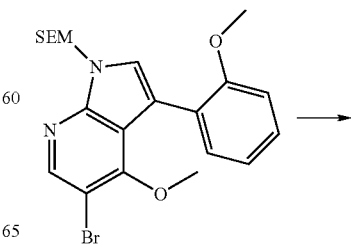

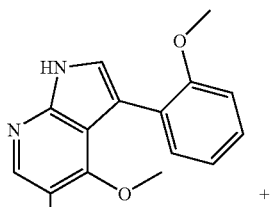

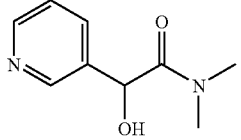

Synthesis of 2-Hydroxy-2-{5-[4-methoxy-3-(2-methoxy-phenyl)-1H-pyrrolo[2,3-b]pyridin-5-yl]-pyridin-3-yl}-N,N-dimethyl-acetamide and 2-{5-[4-Methoxy-3-(2-methoxy-phenyl)-1H-pyrrolo[2,3-b]pyridin-5-yl]-pyridin-3-yl}-N,N-dimethyl-2-oxo-acetamide A mixture of 5-Bromo-3-(2-methoxy-phenyl)-4-methoxy-1-(2-trimethylsilanyl-ethoxymethyl)-1H-pyrrolo[2,3-b]pyridine (95 mg, 0.2 mmol), N,N-dimethyl-2-oxo-2-[5-(4,4,5,5-tetramethyl-[1,3,2]dioxaborolan-2-yl)-pyridin-3-yl]-acetamide (49 mg, 0.16 mmol) and 1,1'-bis(diphenylphosphino)ferrocenepalladium(II)-dichloride dichlormethane adduct (10 mg, 0.012 mmol) in acetonitrile (2 mL) and aqueous solution of sodium carbonate (2M, 0.2 mL) was irradiated in a Personal Chemistry Optimizer at 120° C. for 30 min. Sodium sulfate was added to the crude reaction mixture and the solids were filtered over Celite. The solids were rinsed with ethyl acetate and the combined filtrate was concentrated. Purification by flash silica gel chromatography using a gradient of ethyl acetate and hexanes afforded 80 mg of a white solid. MS: m/z 561 [MH+]

The solid was dissolved in dichloromethane (2 mL) and trifluoroacetic acid (2 mL) and stirred overnight. The mixture was concentrated and dissolved in methanol (5 mL) and ethylenediamine (0.1 mL). Palladium hydroxide on carbon (20%, 20 mg) was added, the mixture was thoroughly degassed and placed under an atmosphere of hydrogen. The mixture was stirred vigorously for 24 h, the vessel was purged with nitrogen and filtered over Celite. Mass triggered reverse phase HPLC to afforded 2-Hydroxy-2-{5-[4-methoxy-3-(2-methoxy-phenyl)-1H-pyrrolo[2,3-b]pyridin-5-yl]-pyridin-3-yl}-N,N-dimethyl-acetamide (12.1 mg): $^1$H NMR (500 MHz, DMSO-d6) δ 11.99 (d, J=2 Hz, 1H), 8.63 (d, J=2.5 Hz, 1H), 8.52 (d, J=2 Hz, 1H), 8.18 (s, 1H), 7.87 (t, J=2 Hz, 1H), 7.47 (d, J=2.5 Hz, 1H), 7.36 (dd, J=7.5 Hz, J$_2$=1.5 Hz, 1H), 7.30 (td, J=7 Hz, J$_2$=1.5 Hz, 1H), 7.06 (d, J=7.5 Hz, 1H), 6.97 (td, J=8 Hz, J$_2$=1 Hz, 1H), 5.78 (bs, 1H), 5.55 (s, 1H), 3.72 (s, 3H), 3.11 (s, 3H), 2.94 (s, 3H), 2.84 (s, 3H). MS: m/z 433.2 (M+H+)) and 2-{5-[4-Methoxy-3-(2-methoxy-phenyl)-1H-pyrrolo[2,3-b]pyridin-5-yl]-pyridin-3-yl}-N,N-dimethyl-2-oxo-acetamide (4.1 mg): $^1$H NMR (500 MHz, MeCN-d3) δ 10.06 (bs, 1H), 9.01 (d, J=1.5 Hz, 1H), 9.00 (d, J=2 Hz, 1H), 8.37 (t, J=2 Hz, 1H), 8.28 (s, 1H), 7.43 (m, 2H), 7.34 (m, 1H), 7.07 (m, 1H), 7.02 (m, 1H), 3.77 (s, 3H), 3.17 (s, 3H), 3.04 (s, 3H), 2.94 (s, 3H). MS: m/z 431.2 (M+H+)).

Other compounds synthesized using Method 32:

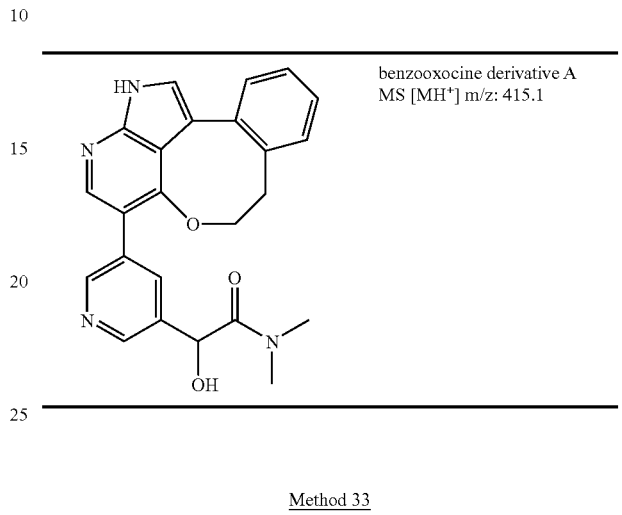

benzooxocine derivative A
MS [MH+] m/z: 415.1

Method 33

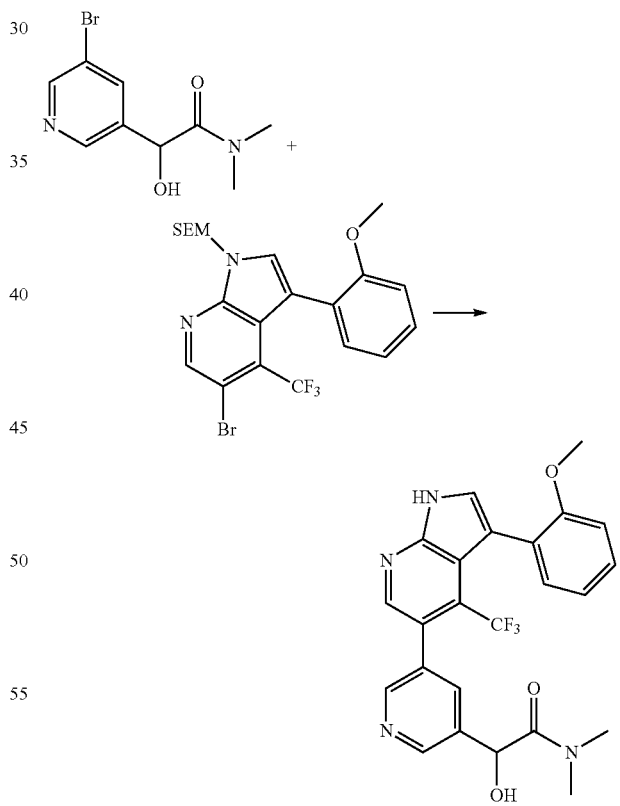

Synthesis of 2-Hydroxy-2-{5-[3-(2-methoxy-phenyl)-4-trifluoromethyl-1H-pyrrolo[2,3-b]pyridin-5-yl]-pyridin-3-yl}-N,N-dimethyl-acetamide A mixture of 2-(5-Bromo-pyridin-3-yl)-2-hydroxy-N,N-dimethyl-acetamide (40 mg, 0.15 mmol), bis(pinacol)diborane (47 mg, 0.18 mmol), potassium acetate (45 mg, 0.46 mmol), and 1,1'-bis(diphenylphosphino)ferrocenepalladium (II)-dichloride dichlormethane adduct (6 mg, 0.007 mmol) in dimethylacetamide (1 mL) was irradiated in a Personal Chemistry Optimizer at 120° C. for 30 min. 5-Bromo-3-(2-methoxy-phenyl)-4-trifluoromethyl-1-(2-trimethylsilanyl-ethoxymethyl)-1H-pyrrolo[2,3-b]pyridine (39 mg, 0.077 mmol), sodium carbonate solution (2M in water, 0.39 mL, 0.77 mmol), and additional 1,1'-bis(diphenylphosphino)ferrocenepalladium(II)-dichloride dichlormethane adduct (3 mg, 0.03 mmol) was added and the mixture was irradiated for an additional 30 min at 120° C. Sodium sulfate was added to the crude reaction mixture and the solids were filtered over Celite. The solids were rinsed with ethyl acetate and the combined filtrate was concentrated. The solids were resuspended in ethyl acetate, filtered through a plug of silica and the eluent was concentrated. The resulting oil was dissolved in trifluoroacetic acid (2 mL) and shaken for 5 min. The solution was concentrated and the mixture was redissolved in dimethyl sulfoxide and ethylenediamine. Purification by mass triggered reverse phase HPLC afforded 2-Hydroxy-2-{5-[3-(2-methoxy-phenyl)-4-trifluoromethyl-1H-pyrrolo[2,3-b]pyridin-5-yl]-pyridin-3-yl}-N,N-dimethyl-acetamide (2.5 mg, 0.005 mmol, 7% yield). $^1$H NMR (500 MHz, MeOH-d4) δ 12.55 (bs, 1H), 8.60 (s, 1H), 8.51 (s, 1H), 8.24 (s, 1H), 7.72 (s, 1H), 7.71 (m, 1H), 7.31 (m, 1H), 7.24 (dd, J=7 Hz, $J_2$=2 Hz, 1H), 6.99 (d, J=7.5 Hz, 1H), 6.95 (td, J=7.5 Hz, $J_2$=1 Hz, 1H), 5.8 (bs, 1H), 5.56 (s, 1H), 3.65 (s, 3H), 2.90 (m, 3H), 2.84 (s, 3H). MS: m/z 471.0 (M+H$^+$).

Other compounds synthesized using Method 33:

Method 34

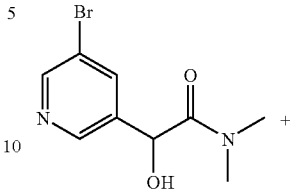

+

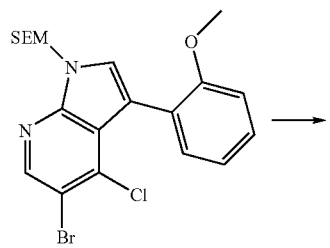

→

| | |
|---|---|
| 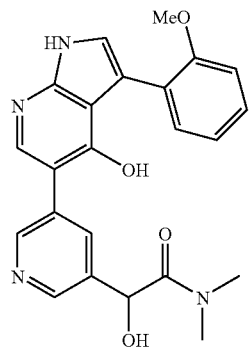 | 2-Hydroxy-2-{5-[4-hydroxy-3-(2-methoxy-phenyl)-1H-pyrrolo[2,3-b]pyridin-5-yl]-pyridin-3-yl}-N,N-dimethyl-acetamide<br>5-Bromo-4-(4-methoxy-benzyloxy)-3-(2-methoxy-phenyl)-1-(2-trimethylsilanyl-ethoxymethyl)-1H-pyrrolo[2,3-b]pyridine was used.<br>$^1$H NMR (500 MHz, DMSO-d$_6$) δ 11.47 (d, J = 2.5 Hz, 1H), 8.54 (d, J = 2 Hz, 1H), 8.50 (d, J = Hz, 1H), 7.76 (t, J = 2 Hz, 1H), 7.74 (s, 1H), 7.36 (ddd, $J_1$ = 8 Hz, $J_2$ = 7 Hz, $J_3$ = 2 Hz, 1H), 7.29 (dd, $J_1$ = 7.5 Hz, $J_2$ = 1.5 Hz, 1H), 7.11 (dd, $J_1$ = 8.5 Hz, $J_2$ = 1 Hz, 1H), 7.09 (d, J = 2.5 Hz, 1H), 7.01 (td, $J_1$ = 7.5 Hz, $J_2$ = 1 Hz, 1H), 5.73 (d, J = 7 Hz, 1H), 5.52 (d, J = 7.5 Hz, 1H), 4.88 (s, 2H), 3.73 (s, 3H), 2.95 (s, 3H), 2.84 (s, 3H). MS: m/z 419.0 (M + H$^+$). |
| 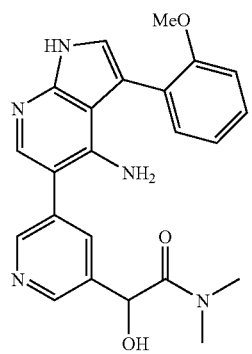 | 2-{5-[4-Amino-3-(2-methoxy-phenyl)-1H-pyrrolo[2,3-b]pyridin-5-yl]-pyridin-3-yl}-2-hydroxy-N,N-dimethyl-acetamide<br>4-Azido-5-bromo-3-(2-methoxy-phenyl)-1-(2-trimethylsilanyl-ethoxymethyl)-1H-pyrrolo[2,3-b]pyridine was used.<br>$^1$H NMR (500 MHz, DMSO-d$_6$) δ 11.47 (d, J = 2.5 Hz, 1H), 8.54 (d, J = 2 Hz, 1H), 8.50 (d, J = Hz, 1H), 7.76 (t, J = 2 Hz, 1H), 7.74 (s, 1H), 7.36 (ddd, $J_1$ = 8 Hz, $J_2$ = 7 Hz, $J_3$ = 2 Hz, 1H), 7.29 (dd, $J_1$ = 7.5 Hz, $J_2$ = 1.5 Hz, 1H), 7.11 (dd, $J_1$ = 8.5 Hz, $J_2$ = 1 Hz, 1H), 7.09 (d, J = 2.5 Hz, 1H), 7.01 (td, $J_1$ = 7.5 Hz, $J_2$ = 1 Hz, 1H), 5.73 (d, J = 7 Hz, 1H), 5.52 (d, J = 7.5 Hz, 1H), 4.88 (s, 2H), 3.73 (s, 3H), 2.95 (s, 3H), 2.84 (s, 3H). MS: m/z 418.0 (M + H$^+$). |

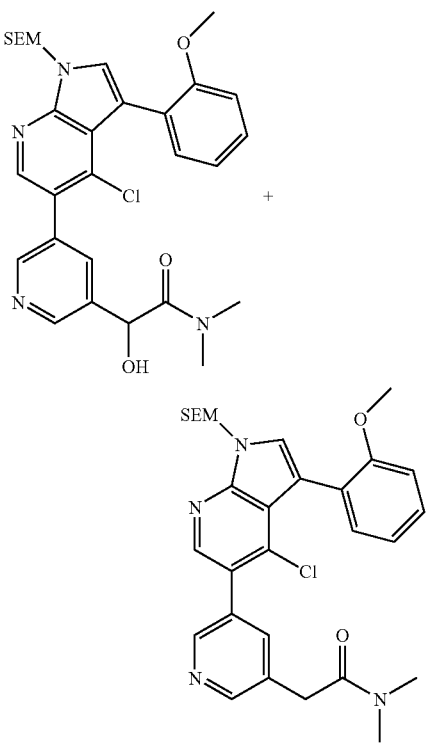

Synthesis of 2-{5-[4-Chloro-3-(2-methoxy-phenyl)-1-(2-trimethylsilanyl-ethoxymethyl)-1H-pyrrolo[2,3-b]pyridin-5-yl]-pyridin-3-yl}-2-hydroxy-N,N-dimethyl-acetamide and 2-{5-[4-Chloro-3-(2-methoxy-phenyl)-1-(2-trimethylsilanyl-ethoxymethyl)-1H-pyrrolo[2,3-b]pyridin-5-yl]-pyridin-3-yl}-N,N-dimethyl-acetamide A mixture of 2-(5-Bromo-pyridin-3-yl)-2-hydroxy-N,N-dimethyl-acetamide (400 mg, 1.54 mmol), bis(pinacol)diborane (431 mg, 1.7 mmol), potassium acetate (454 mg, 4.6 mmol), and 1,1'-bis(diphenylphosphino)ferrocenepalladium(II)-dichloride dichlormethane adduct (25 mg, 0.03 mmol) in dimethylacetamide (2 mL) was stirred under nitrogen at 120° C. for 12 h. 5-Bromo-3-(2-methoxy-phenyl)-4-chloro-1-(2-trimethylsilanyl-ethoxymethyl)-1H-pyrrolo[2,3-b]pyridine (491 mg, 1.05 mmol), sodium carbonate solution (2M in water, 2.3 mL, 4.6 mmol), dimethylacetamide (2 mL) and additional 1,1'-bis(diphenylphosphino)ferrocenepalladium(II)-dichloride dichlormethane adduct (30 mg, 0.035 mmol) was added and the mixture was stirred for an additional 2 h at 120° C. Sodium sulfate was added to the crude reaction mixture and the solids were filtered over Celite. The solids were rinsed with ethyl acetate and acetonitrile and the combined filtrate was concentrated. The resulting oil was purified by flash silica gel chromatography using a gradient of ethyl acetate in hexanes to afford 2-{5-[4-Chloro-3-(2-methoxy-phenyl)-1-(2-trimethylsilanyl-ethoxymethyl)-1H-pyrrolo[2,3-b]pyridin-5-yl]-pyridin-3-yl}-2-hydroxy-N,N-dimethyl-acetamide (202 mg, 0.35 mmol, 34% yield; and 2-{5-[4-Chloro-3-(2-methoxy-phenyl)-1-(2-trimethylsilanyl-ethoxymethyl)-1H-pyrrolo[2,3-b]pyridin-5-yl]-pyridin-3-yl}-N,N-dimethyl-acetamide.

Method 35

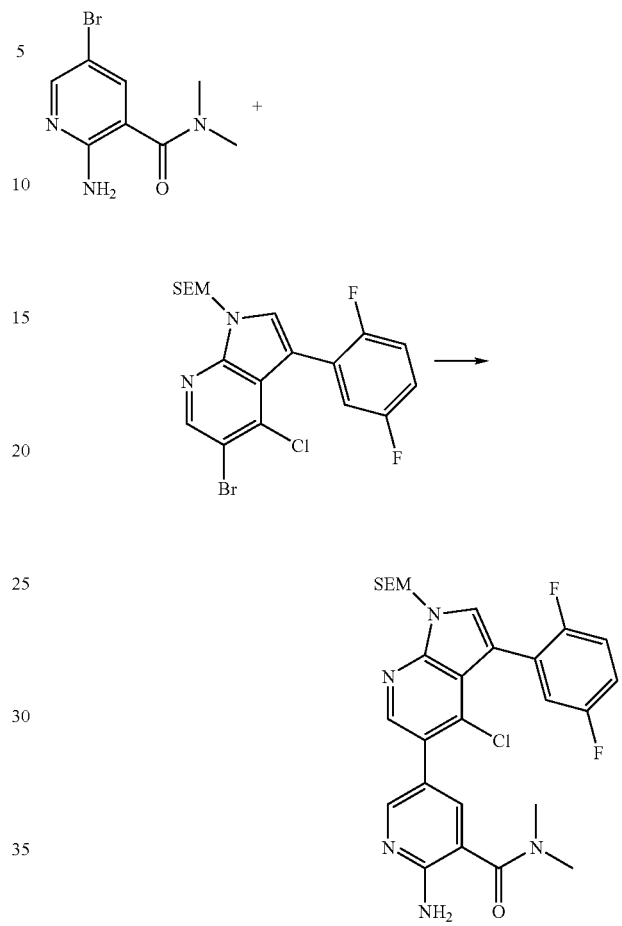

Synthesis of 2-Amino-5-[4-chloro-3-(2,5-difluoro-phenyl)-1-(2-trimethylsilanyl-ethoxymethyl)-1H-pyrrolo[2,3-b]pyridin-5-yl]-N,N-dimethyl-nicotinamide Into a 5 mL Personal Chemistry microwave reaction vial, 2-Amino-5-bromo-N,N-dimethyl-nicotinamide (1.14 g, 4.67 mmol) was combined with bis(pinacolato)diboron (1.42 g, 5.60 mmol), bis(diphenylphosphino)ferrocenepalladium(II)-dichloride dichlormethane adduct (191 mg, 0.0233 mmol), and potassium acetate (1.37 g, 14.0 mmol). N,N-dimethylacetamide was added (8 mL). The vial was purged with nitrogen, sealed, and irradiated in a Personal Chemistry Optimizer at 120° C. for 20 minutes. Sodium sulfate was added to the reaction mixture and the slurry was filtered over Celite® and concentrated. The crude product was purified by flash silica gel chromatography using a gradient of ethyl acetate in hexanes to afford 2-Amino-5-[4-chloro-3-(2,5-difluoro-phenyl)-1-(2-trimethylsilanyl-ethoxymethyl)-1H-pyrrolo[2,3-b]pyridin-5-yl]-N,N-dimethyl-nicotinamide (556 mg, 0.996 mmol, 32% yield) $^1$H-NMR [500 MHz, d$_6$-DMSO] δ: 8.32 (s, 1H), 8.07 (d, 1H), 7.96 (s, 1H), 7.51 (d, 1H), 7.30 (m, 3H), 6.20 (s, 2H), 5.70 (s, 2H), 3.59 (t, 3H), 2.94 (m, 26H), 2.77 (s, 17H), 2.68 (s, 3H), 1.94 (s, 18H), 1.89 (s, 1H), 1.06 (s, 3H), 0.84 (t, 3H), −0.8 (m, 11H); MS [MH$^+$] m/z: 558.2

Other compounds synthesized using Method 35:

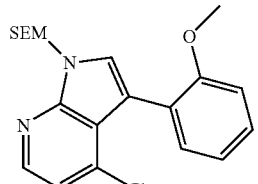

2-Amino-5-[4-chloro-3-(2-methoxy-phenyl)-1-(2-trimethylsilanyl-ethoxymethyl)-1H-pyrrolo[2,3-b]pyridin-5-yl]-nicotinic acid methyl ester
$^1$H-NMR [500 MHz, $d_6$-DMSO] δ: 8.29 (d, 1H), 8.26 (s, 1HO) 8.19 (m, 1H), 8.11 (d, 1H), 8.03 (dd, 1H), 7.69 (s, 1H), 7.34 (m, 3H), 7.25 (dd, 1H), 7.14 (broad s, 1H), 7.02 (d, 1H), 6.96 (t, 1H), 6.60 (m, 1H), 5.67 (s, 1H), 4.09 (broad s, 1H), 3.92 (s, 10H), 8.90 (d, 5H), 3.68 (s, 3H), 3.59 (t, 2H), 3.34 (s, 1H), 2.49 (m, 2H), 1.07 (m, 60H), 0.85 (t, 3H), −0.07 (s, 9H); MS [MH$^+$] m/z: 539.2

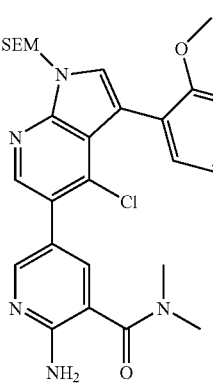

2-Amino-5-[4-chloro-3-(4-fluoro-2-methoxy-phenyl)-1-(2-trimethylsilanyl-ethoxymethyl)-1H-pyrrolo[2,3-b]pyridin-5-yl]-N,N-dimethyl-nicotinamide
$^1$H-NMR [500 MHz, $d_6$-DMSO] δ: 8.25 (s, 1H), 8.05 (d, 1H), 7.70 (s, 1H), 7.47 (d, 1H), 7.26 (m, 1H), 6.94 (dd, 1H), 6.79 (td, 1H), 6.17 (s, 2H), 5.66 (s, 2H), 3.70 (s, 3H), 3.59 (t, 3H), 2.94 (s, 7H), 0.85 (t, 2H), −0.07 (s, 8H); MS [MH$^+$] m/z: 570.2

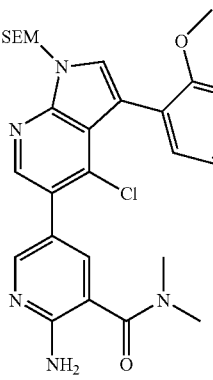

2-Amino-5-[4-chloro-3-(4,5-difluoro-2-methoxy-phenyl)-1-(2-trimethylsilanyl-ethoxymethyl)-1H-pyrrolo[2,3-b]pyridin-5-yl]-N,N-dimethyl-nicotinamide
$^1$H-NMR [500 MHz, $d_6$-DMSO] δ: 826 (s, 1H) 8.06 (d, 1H), 7.76 (s, 1H), 7.48 (d, 1H), 7.35 (m, 1H), 7.19 (m, 1H), 6.18 (s, 2H), 5.66 (s, 2H), 3.69 (s, 3H), 3.59 (t, 2H), 3.16 (d, 1H), 2.94 (s, 6H), 1.95 (s, 1H), 0.86 (t, 2H), −0.07 (s, 8H); MS [MH$^+$] m/z: 588.2

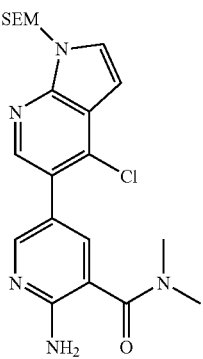

2-Amino-5-[4-chloro-1-(2-trimethylsilanyl-ethoxymethyl)-1H-pyrrolo[2,3-b]pyridin-5-yl]-N,N-dimethyl-nicotinamide
$^1$H-NMR [500 MHz, $d_6$-DMSO] δ: 8.27 (s, 1H), 7.80 (d, 1H), 7.54 (d, 1H), 6.62 (d, 1H), 6.21 (s, 2H), 5.64 (s, 2H), 3.52 (t, 3H), 2.97 (s, 7H), 2.93 (s, 4H), 2.77 (s, 5H), 1.94 (s, 5H), 0.81 (t, 2H), −0.9 (s, 9H); MS [MH$^+$] m/z: 446.3

-continued

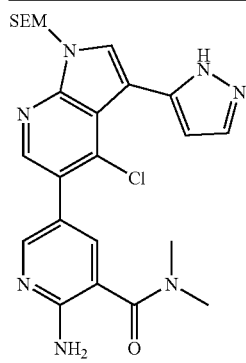

2-Amino-5-[4-chloro-3-(2H-pyrazol-3-yl)-1-(2-trimethylsilanyl-ethoxymethyl)-1H-pyrrolo[2,3-b]pyridin-5-yl]-N,N-dimethyl-nicotinamide
The reaction was carried out using tetrakis(triphenyl-phosphine)palladium(0) as the catalyst MS [MH$^+$] m/z: 512.3

Method 36

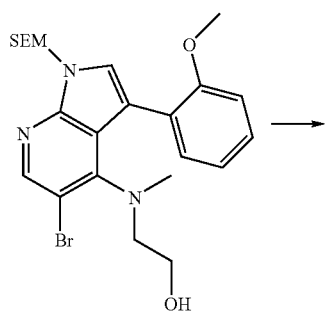

→

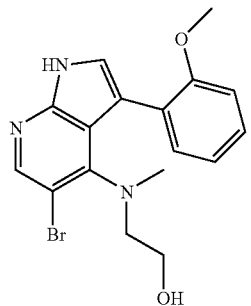

Synthesis of 2-{[5-Bromo-3-(2-methoxy-phenyl)-1H-pyrrolo[2,3-b]pyridin-4-yl]-methyl-amino}-ethanol 2-{[5-Bromo-3-(2-methoxy-phenyl)-1-(2-trimethylsilanyl-ethoxymethyl)-1H-pyrrolo[2,3-b]pyridin-4-yl]-methyl-amino}-ethanol (10 mg, 0.0197 mmol) was dissolved in a solution of trifluoroacetic acid (1 mL) and dichloromethane (1 mL) and stirred at 23° C. for 1.5 hours. The solvent was evaporated and the resulting oil was dissolved in 1 mL DMSO and 100 µL ethylenediamine and purified by mass triggered reverse phase HPLC to afford 2-{[5-Bromo-3-(2-methoxy-phenyl)-1H-pyrrolo[2,3-b]pyridin-4-yl]-methyl-amino}-ethanol (1.1 mg, 0.00266, 13% yield). $^1$H-NMR [500 MHz, d$_6$-DMSO] δ: 8.14 (s, 1H), 7.31 (m, 1H), 7.27 (s, 1H) 7.21 (dd, 1H), 7.02 (d, 1H), 6.96, (td, 1H), 6.67, (s, 5H), 3.14 (t, 2H), 2.75 (s, 4H); MS [MH$^+$] m/z: 376, 378.

Other compounds synthesized using Method 36:

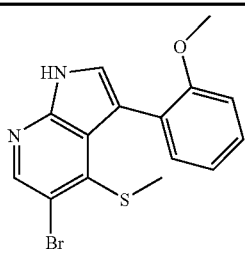

5-Bromo-3-(2-methoxy-phenyl)-4-methylsulfanyl-1H-pyrrolo[2,3b]pyridine
$^1$H-NMR [500 MHz, d$_6$-DMSO] δ: 12.12 (s, 1 H), 8.36 (s, 1 H), 7.47 (s, 1 H), 7.32 (m, 1 H), 7.26 (m, 1 H), 7.99 (d, 1 H) 6.94 (t, 1 H) 3.65 (s, 4 H) 2.03 (s, 4 H); MS [MH$^+$] m/z: 349, 351.

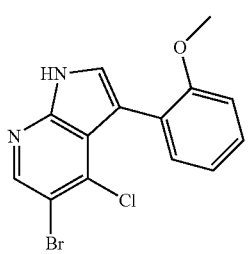

5-Bromo-4-chloro-3-(2-methoxy-phenyl)-1H-pyrrolo[2,3-b]pyridine
$^1$H-NMR [500 MHz, d$_6$-DMSO] δ: 8.40 (s, 1 H), 7.53 (s, 1 H), 7.35 (m, 1 H0, 7.24 (m, 1 H), 7.03 (d, 1 H), 7.00 (m, 1 H), 3.67 (s, 4 H); MS [MH$^+$] m/z: 339

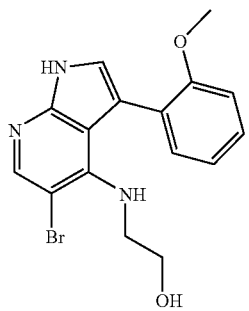

2-[5-Bromo-3-(2-methoxy-phenyl)-1H-pyrrolo[2,3-b]pyridin-4-ylamino]-ethanol
$^1$H-NMR [500 MHz, d$_6$-DMSO] δ: 8.03 (s, 1 H), 7.31 (td, 1 H), 7.23 (dd, 1 H), 7.19 (s, 1 H), 7.05 (d, 1 H), 6.97 (t, 1 H), 4.91 (t, 1 H), 4.59 (broad s, 1 H), 4.71 (s, 4 H), 3.07 (t, 3 H), 2.79 (quart, 3 H); MS [MH$^+$] m/z: 362, 364.

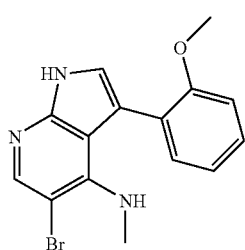

[5-Bromo-3-(2-methoxy-phenyl)-1H-pyrrolo[2,3-b]pyridin-4-yl]-methyl-amine
$^1$H-NMR [500 MHz, d$_6$-DMSO] δ: 11.62 (s, 1 H), 7.33 (td, 1 H), 7.23 (dd, 1 H), 7.13 (s, 1 H), 7.05 (d, 1 H), 6.973 (td, 1 H), 5.01 (quart, 1 H), 3.71 (s, 4 H), 2.43 (d, 4 H); MS [MH$^+$] m/z: 332.

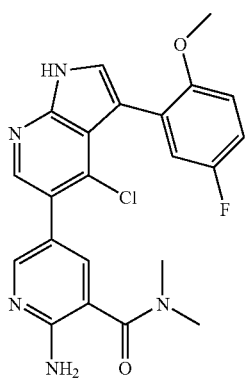

2-Amino-5-[4-chloro-3-(5-fluoro-2-methoxy-phenyl)-1H-pyrrolo[2,3-b]pyridin-5-yl]-N,N-dimethyl-nicotinamide
$^1$H-NMR [500 MHz, d$_6$-DMSO] δ: 8.18 (s, 1 H), 8.06 (d, 1 H), 7.56 (s, 1 H), 7.48 (d, 1 H), 7.13 (m, 2 H), 7.00 (m, 1 H), 6.15 (s, 2 H), 3.67 (s, 3 H), 2.95 (s, 7 H); MS [MH$^+$] m/z: 440.

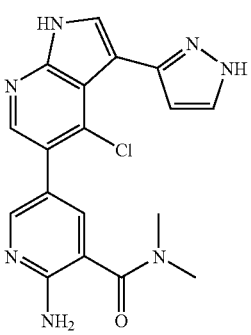

2-Amino-5-[4-chloro-3-(1H-pyrazol-3-yl)-1H-pyrrolo[2,3-b]pyridin-5-yl]-N,N-dimethyl-nicotinamide
$^1$H-NMR [500 MHz, d$_6$-DMSO] δ: 8.20 (s, 1 H), 8.07 (d, 1 H), 7.69 (s, 1 H), 7.57 (s, 1 H), 7.50 (d, 1 H), 6.9 (broad s, 1 H), 6.40 (d, 1 H), 6.14 (s, 2 H), 2.95 (s, 7 H); MS [MH$^+$] m/z: 382

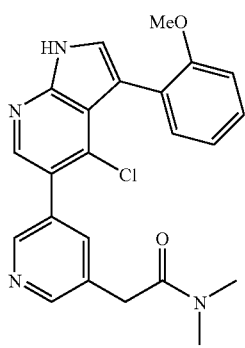

2-{5-[4-Chloro-3-(2-methoxy-phenyl)-1H-pyrrolo[2,3-b]pyridin-5-yl]-pyridin-3-yl}-N,N-dimethyl-acetamide
$^1$H NMR (500 MHz, DMSO-d6) δ 8.51 (d, J = 2 Hz, 1 H), 8.42 (d, J = 2 Hz, 1 H), 8.18 (s, 1 H), 7.72 (t, J = 2 Hz, 1 H), 7.54 (s, 1 H), 7.33 (m, 1 H), 7.27 (dd, J$_1$ = 7 Hz, J$_2$ = 2 Hz, 1 H), 7.02 (dd, J$_1$ = 8 Hz, J$_2$ = 1 Hz, 1 H), 6.97 (td, J$_1$ = 8 Hz, J$_2$ = 1 Hz, 1 H), 3.80 (s, 2 H), 3.69 (s, 3 H), 3.05 (s, 3 H), 2.83 (s, 3 H). MS: m/z 451.2 (M + H$^+$).

-continued

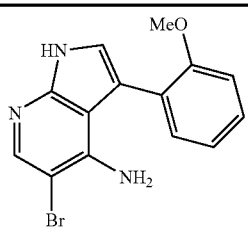

5-Bromo-3-(2-methoxy-phenyl)-1H-pyrrolo[2,3-b]pyridin-4-ylamine
$^{1}$H NMR (500 MHz, DMSO-$d_6$) δ 11.54 (s, 1 H), 7.95 (s, 1 H), 7.37 (m, 1 H), 7.25 (dd, $J_1$ = 7.5 Hz, $J_2$ = 1.5 Hz, 1 H), 7.13 (d, J = 8 Hz, 1 H), 7.08 (s, 1 H), 7.02 (t, J = 7.5 Hz, 1 H), 5.14 (s, 2 H), 3.73 (s, 3 H). MS: m/z 317.9/319.9 (M + H$^+$).

Other compounds synthesized using Method 35+Method 36:

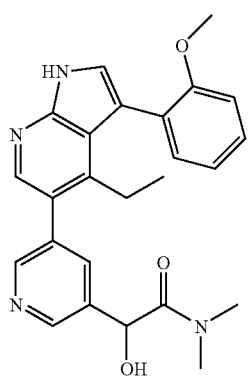

2-{5-[4-Ethyl-3-(2-methoxy-phenyl)-1H-pyrrolo[2,3-b]pyridin-5-yl]-pyridin-3-yl}-2-hydroxy-N,N-dimethyl-acetamide
$^{1}$H-NMR [500 MHz, $d_3$-CD$_3$OD] δ: 8.61 (s, 1 H), 8.50 (s, 1 H), 8.01 (s, 1 H), 7.85 (d, 1 H), 7.38 (t, 1 H), 7.32 (d, 1 H), 7.26 (s, 1 H), 7.05 (d, 2 H), 7.00 (t, 2 H), 5.65 (s, 1 H), 3.73 (s, 4 H), 3.01 (s, 5 H), 2.94 (s, 5 H), 0.628 (t, 4 H); MS [MH$^+$] m/z: 431.

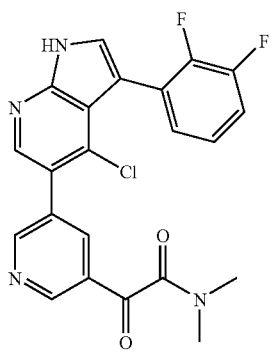

2-{5-[4-Chloro-3-(2,3-difluoro-phenyl)-1H-pyrrolo[2,3-b]pyridin-5-yl]-pyridin-3-yl}-N,N-dimethyl-2-oxo-acetamide
$^{1}$H-NMR [500 MHz, $d_6$-DMSO] δ: 9.04 (d, 1 H), 9.01 (d, 1 H), 8.35 (s, 1 H), 8.33 (t, 1 H), 7.85 (s, 1 H), 7.43 (m, 1 H), 7.30 (m, 1 H), 7.25 (m, 1 H), 3.01 (s, 4 H), 2.94 (s, 4 H); MS [MH$^+$] m/z: 441.

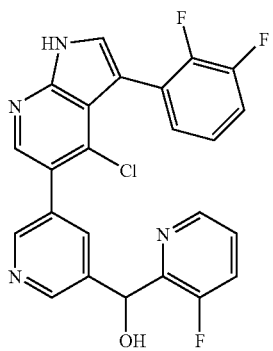

{5-[4-Chloro-3-(2,3-difluoro-phenyl)-1H-pyrrolo[2,3-b]pyridin-5-yl]-pyridin-3-yl}-(3-fluoro-pyridin-2-yl)-methanol
$^{1}$H-NMR [500 MHz, $d_6$-DMSO] δ: 8.61 (d, 1 H), 8.86 (d, 1 H), 8.39 (m, 1 H), 8.26 (s, 1 H), 7.93 (t, 1 H), 7.81 (s, 1 H), 7.69 (m, 1 H), 7.43 (m, 2 H), 7.26 (m, 2 H), 6.35 (broad s, 1 H), 6.14 (s, 1 H); MS [MH$^+$] m/z: 467.

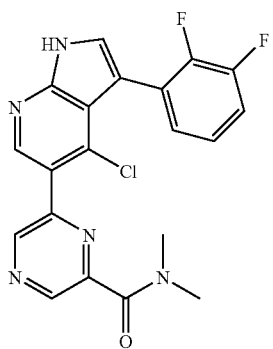

6-[4-Chloro-3-(2,3-difluoro-phenyl)-1H-pyrrolo[2,3-b]pyridin-5-yl]-pyrazine-2-carboxylic acid dimethylamide
$^1$H-NMR [500 MHz, $d_6$-DMSO] δ: 9.02 (s, 1 H), 8.82 (s, 1 H), 8.45 (s, 1 H), 7.84 (s, 1 H) 7.42 (m, 1 H), 7.29 (m, 1 H), 7.25 (m, 1 H), 3.03 (d, 7 H); MS [MH$^+$] m/z: 414

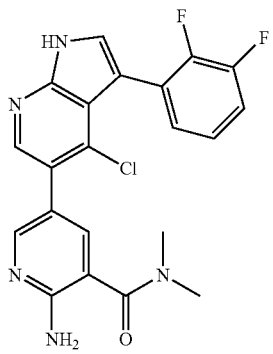

2-Amino-5-[4-chloro-3-(2,3-difluoro-phenyl)-1H-pyrrolo[2,3-b]pyridin-5-yl]-N,N-dimethyl-nicotinamide
$^1$H-NMR [500 MHz, $d_6$-DMSO] δ: 8.24 (s, 1 H), 8.07 (d, 1 H), 7.76 (s, 1 H), 7.49 (d, 1 H), 7.42 (m, 1 H), 7.25 (m, 2 H), 6.16 (s, 2 H), 2.94 (s, 6 H); MS [MH$^+$] m/z: 428.

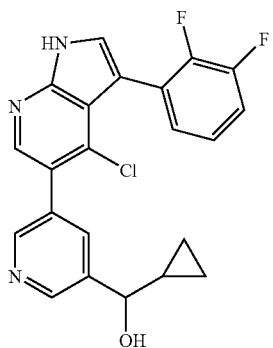

{5-[4-Chloro-3-(2,3-difluoro-phenyl)-1H-pyrrolo[2,3-b]pyridin-5-yl]-pyridin-3-yl}-cyclopropyl-methanol
$^1$H-NMR [500 MHz, $d_6$-DMSO] δ: 8.61 (d, 1 H), 8.54 (d, 1 H), 8.29 (s, 1 H), 7.78 (t, 1 H), 7.82 (s, 1 H), 7.45 (m, 1 H), 7.30 (t, 1 H), 7.24 (m, 1 H), 5.43 (d, 1 H), 4.10 (quart, 1 H), 1.10 (m, 1 H), 0.48 (m, 1 H), 0.41 (m, 3 H); MS [MH$^+$] m/z: 412

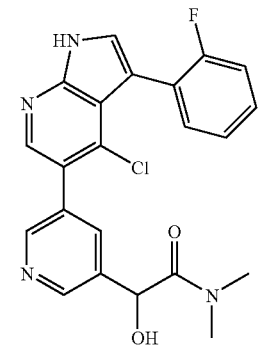

2-{5-[4-Chloro-3-(2-fluoro-phenyl)-1H-pyrrolo[2,3-b]pyridin-5-yl]-pyridin-3-yl}-2-hydroxy-N,N-dimethyl-acetamide
$^1$H-NMR [500 MHz, $d_6$-DMSO] δ: 8.59 (t, 2 H), 8.26 (s, 1 H), 7.86 (t, 1 H), 7.74 (s, 1 H), 7.46 (td, 1 H), 7.40 (m, 1 H), 7.25 (m, 2 H), 5.82 (d, 1 H), 5.56 (d, 1 H), 2.95 (s, 4 H), 2.84 (s, 3 H); MS [MH$^+$] m/z: 425.

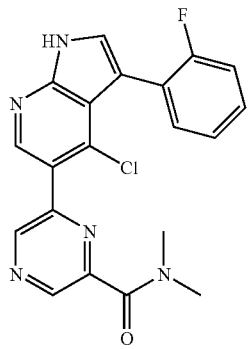

6-[4-Chloro-3-(2-fluoro-phenyl)-1H-pyrrolo[2,3-b]pyridin-5-yl]-pyrazine-2-carboxylic acid dimethylamide
$^1$H-NMR [500 MHz, d$_3$-CD$_3$OD] δ: 9.03 (s, 1 H), 8.84 (s, 1 H), 8.45 (s, 1 H), 7.56 (s, 2 H), 7.46 (td, 1 H), 7.40 (m, 1 H), 7.22 (dd, 1 H), 7.16 (t, 1 H), 3.17 (s, 7 H); MS [MH$^+$] m/z: 396.

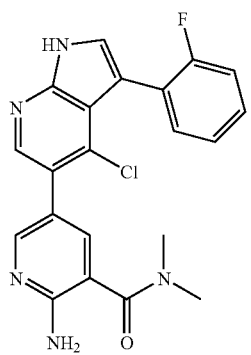

2-Amino-5-[4-chloro-3-(2-fluoro-phenyl)-1H-pyrrolo[2,3-b]pyridin-5-yl]-N,N-dimethyl-nicotinamide
$^1$H-NMR [500 MHz, d$_6$-DMSO] δ: 8.22 (s, 1 H), 8.06 (d, 1 H), 7.68 (s, 1 H), 7.48 (d, 1 H), 7.44 (td, (1 H), 7.39 (m, 1 H), 7.23 (m, 2 H), 7.23 (s, 1 H), 6.16 (s, 2 H), 2.94 (s, 7 H); MS [MH$^+$] m/z: 410.

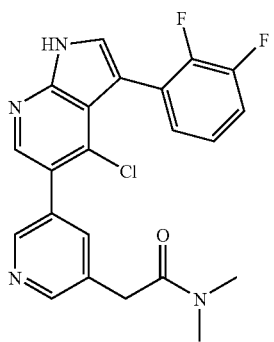

2-{5-[4-Chloro-3-(2,3-difluoro-phenyl)-1H-pyrrolo[2,3-b]pyridin-5-yl]-pyridin-3-yl}-N,N-dimethyl-acetamide
$^1$H-NMR [500 MHz, d$_6$-DMSO] δ: 8.52 (d, 1 H), 8.44 (d, 1 H), 8.27 (s, 1 H), 7.81 (s, 1 H), 7.75 (t, 1 H), 7.43 (m, 1 H), 7.29 (m, 1 H), 7.25 (m, 1 H), 3.81 (s, 3 H), 3.05 (s, 3 H), 2.83 (s, 3 H); MS [MH$^+$] m/z: 427.

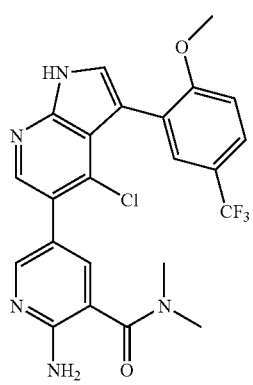

2-Amino-5-[4-chloro-3-(2-methoxy-5-trifluoromethyl-phenyl)-1H-pyrrolo[2,3-b]pyridin-5-yl]-N,N-dimethyl-nicotinamide
$^1$H-NMR [500 MHz, d$_6$-DMSO] δ: 8.19 (s, 1 H), 8.06 (s, 1 H), 7.70 (dd, 1 H), 7.64 (d, 1 H), 7.56 (d, 1 H), 7.21 (d, 1 H), 6.15 (s, 2 H), 3.78 (s, 4 H), 2.94 (s, 9 H); MS [MH$^+$] m/z: 490.

-continued

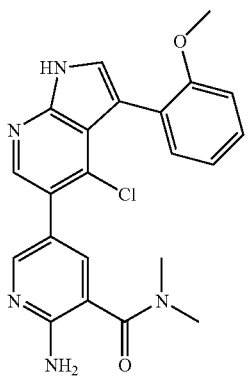

2-Amino-5-[4-chloro-3-(2-methoxy-phenyl)-1H-pyrrolo[2,3-b]pyridin-5-yl]-N,N-dimethyl-nicotinamide
$^1$H-NMR [500 MHz, d$_6$-DMSO] δ: 8.16 (s, 1 H), 8.05 (d, 1 H), 7.49 (s, 1 H), 7.47 (d, 1 H), 7.32 (td, 1 H), 7.25 (dd, 1 H), 7.01 (dd, 1 H), 6.95 (t, 1 H), 6.13 (s, 2 H) 3.68 (s, 4 H), 2.94 (s, 6 H); MS [MH$^+$] m/z: 422

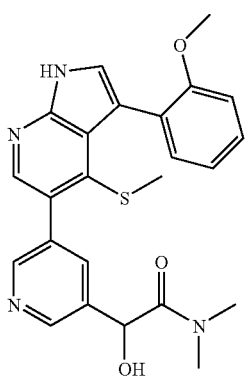

2-Hydroxy-2-{5-[3-(2-methoxy-phenyl)-4-methylsulfanyl-1H-pyrrolo[2,3-b]pyridin-5-yl]-pyridin-3-yl}-N,N-dimethyl-acetamide
$^1$H-NMR [500 MHz, d$_6$-DMSO] δ: 12.05 (s, 1 H), 8.59 (d, 1 H), 8.56 (d, 1 H) 8.12 (s, 1 H), 7.83 (t, 1 H), 7.49 (s, 1 H) 7.30 (m, 2 H), 6.99 (d, 1 H), 6.93 (m, 1 H), 5.76 (d, 1 H), 5.55 (d, 1 H), 3.70 (s, 3 H), 2.92 (s, 4 H), 2.84 (s, 3 H), 1.54 (s, 3 H); MS [MH$^+$] m/z: 449.

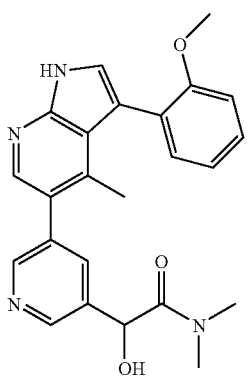

2-Hydroxy-2-{5-[3-(2-methoxy-phenyl)-4-methyl-1H-pyrrolo[2,3-b]pyridin-5-yl]-pyridin-3-yl}-N,N-dimethyl-acetamide
$^1$H-NMR [500 MHz, d$_4$-CD$_3$OD] δ: 8.59 (d, 1 H), 8.51 (d, 1 H) 8.05 (s, 1 H) 7.87 (t, 1 H), 7.36 (td, 1 H), 7.30 (dd, 1 H) 7.27 (s, 1 H) 7.04 (d, 1 H) 6.99 (td, 1 H) 5.62 (s, 1 H), 5.50 (s, 1 H) 3.76 (s, 3 H), 3.02 (s, 3 H), 2.98 (s, 3 H), 2.01 (s, 3 H); MS [MH$^+$] m/z: 417

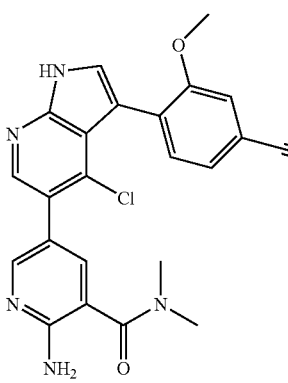

2-Amino-5-[4-chloro-3-(4-cyano-2-methoxy-phenyl)-1H-pyrrolo[2,3-b]pyridin-5-yl]-N,N-dimethyl-nicotinamide
$^1$H NMR (500 MHz, DMSO-d6) δ 12.5 (bs, 1 H), 8.43 (s, 1 H), 8.21 (d, J = 2.5 Hz, 1 H), 7.83 (s, 1 H), 7.63 (d, J = 2.5 Hz, 1 H), 7.35 (d, J = 7.5 Hz, 1 H), 7.13 (d, J = 2 Hz, 1 H), 7.06 (dd, J$_1$ = 7.5 Hz, J$_2$ = 2 Hz, 1 H), 6.30 (bs, 2 H), 3.75 (s, 3 H), 2.96 (s, 6 H). MS: m/z 447.1 (M + H$^+$).

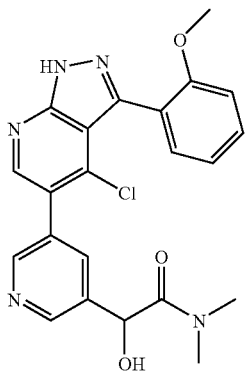

2-{5-[4-Chloro-3-(2-methoxy-phenyl)-1H-pyrazolo[3,4-b]pyridin-5-yl]-pyridin-3-yl}-2-hydroxy-N,N-dimethyl-acetamide
$^1$H NMR (500 MHz, DMSO-d$_6$) δ 2.79 (s, 3 H), 2.90 (s, 3 H), 3.75 (s, 3 H), 5.52 (s, 1 H), 7.02 (dt, 1 H), 7.12 (d, 1 H), 7.39 (m, 1 H), 7.60 (dd, 1 H), 7.83 (t, 1 H), 8.15 (s, 1 H), 8.55 (d, 1 H), 8.58 (d, 1 H). MS: m/z 438.0 (M + H$^+$).

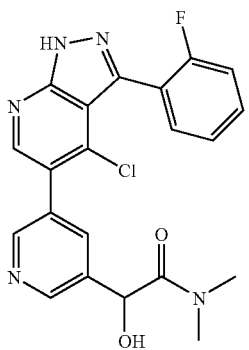

2-{5-[4-Chloro-3-(2-fluoro-phenyl)-1H-pyrazolo[3,4-b]pyridin-5-yl]-pyridin-3-yl}-2-hydroxy-N,N-dimethyl-acetamide
$^1$H NMR (500 MHz, DMSO-d$_6$) δ 2.80 (s, 3 H), 2.91 (s, 3 H), 3.75 (s, 3 H), 5.51 (d, 1 H), 5.78 (d, 1 H), 7.30 (m, 2 H), 7.44 (m, 1 H), 7.84 (t, 1 H), 7.86 (dt, 1 H), 8.24 (d, 1 H), 8.54 (d, 1 H), 8.56 (d, 1 H). MS: m/z 426.0 (M + H$^+$).

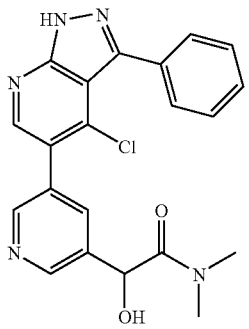

2-[5-(4-Chloro-3-phenyl-1H-pyrazolo[3,4-b]pyridin-5-yl)-pyridin-3-yl]-2-hydroxy-N,N-dimethyl-acetamide
$^1$H NMR (500 MHz, DMSO-d$_6$) δ 2.80 (s, 3 H), 2.91 (s, 3 H), 3.75 (s, 3 H), 5.52 (d, 1 H), 5.78 (d, 1 H), 7.35 (t, 2 H), 7.44 (t, 2 H), 7.88 (t, 1 H), 8.01 (d, 1 H), 8.56 (d, 1 H), 8.60 (s, 1 H), 8.61 (d, 1 H). MS: m/z 408.0 (M + H$^+$).

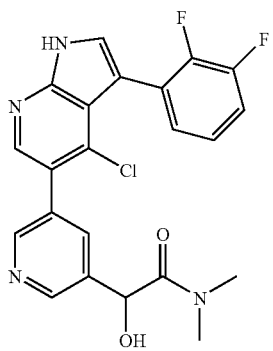

2-{5-[4-Chloro-3-(2,3-difluoro-phenyl)-1H-pyrrolo[2,3-b]pyridin-5-yl]-pyridin-3-yl}-2-hydroxy-N,N-dimethyl-acetamide
$^1$H-NMR [500 MHz, d$_6$-DMSO] δ: 8.59 (m, 2 H), 8.28 (s, 1 H), 7.87 (t, 1 H), 7.82 (s, 1 H), 7.44 (m, 1 H), 7.29 (m, 1 H), 7.25 (m, 1 H), 5.83 (d, 1 H), 5.57 (d, 1 H), 2.95 (s, 3 H), 2.84 (s, 3 H); MS [MH$^+$] m/z: 443.

| | |
|---|---|
| 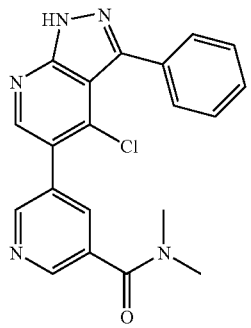 | 5-(4-Chloro-3-phenyl-1H-pyrazolo[3,4-b]pyridin-5-yl)-N,N-dimethyl-nicotinamide.<br>$^1$H NMR (500 MHz, DMSO-$d_6$) δ 2.94 (d, 6 H), 7.37 (m, 1 H), 7.45 (m, 2 H), 8.02 (m, 3 H), 8.62 (d, 1 H), 8.68 (s, 1 H), 8.75 (d, 1 H). MS: m/z 378 (M + H$^+$). |
| 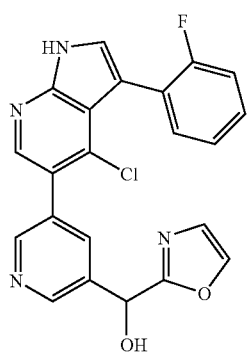 | {5-[4-Chloro-3-(2-fluoro-phenyl)-1H-pyrrolo[2,3-b]pyridin-5-yl]-pyridin-3-yl}-oxazol-2-yl-methanol<br>$^1$H-NMR [500 MHz, $d_6$-DMSO] δ: 5.99 (d, 1 H), 6.69 (d, 1 H), 7.18 (d, 1 H), 7.24 (m, 2 H), 7.41 (m, 1 H), 7.47 (dt, 1 H), 7.75 (s, 1 H), 7.96 (t, 1 H), 8.09 (d, 1 H), 8.26 (s, 1 H), 8.61 (d, 1 H), 8.66 (d, 1 H). MS [MH$^+$] m/z: 421 |
| 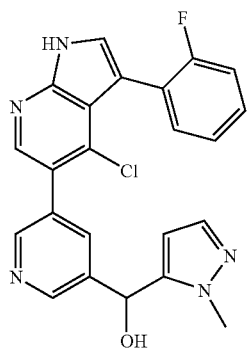 | {5-[4-Chloro-3-(2-fluoro-phenyl)-1H-pyrrolo[2,3-b]pyridin-5-yl]-pyridin-3-yl}-(2-methyl-2H-pyrazol-3-yl)-methanol<br>$^1$H-NMR [500 MHz, $d_6$-DMSO] δ: 3.73 (s, 3 H), 1.16 (d, 1 H), 5.97 (d, 1 H), 6.25 (d, 1 H), 7.17 (m, 7.67 (s, 1 H), 7.83 (t, 1 H), 8.21 (s, 1 H), 8.53 (dd, 1 H), 12.42 (br s, 1 H). MS [MH$^+$] m/z: 434 |

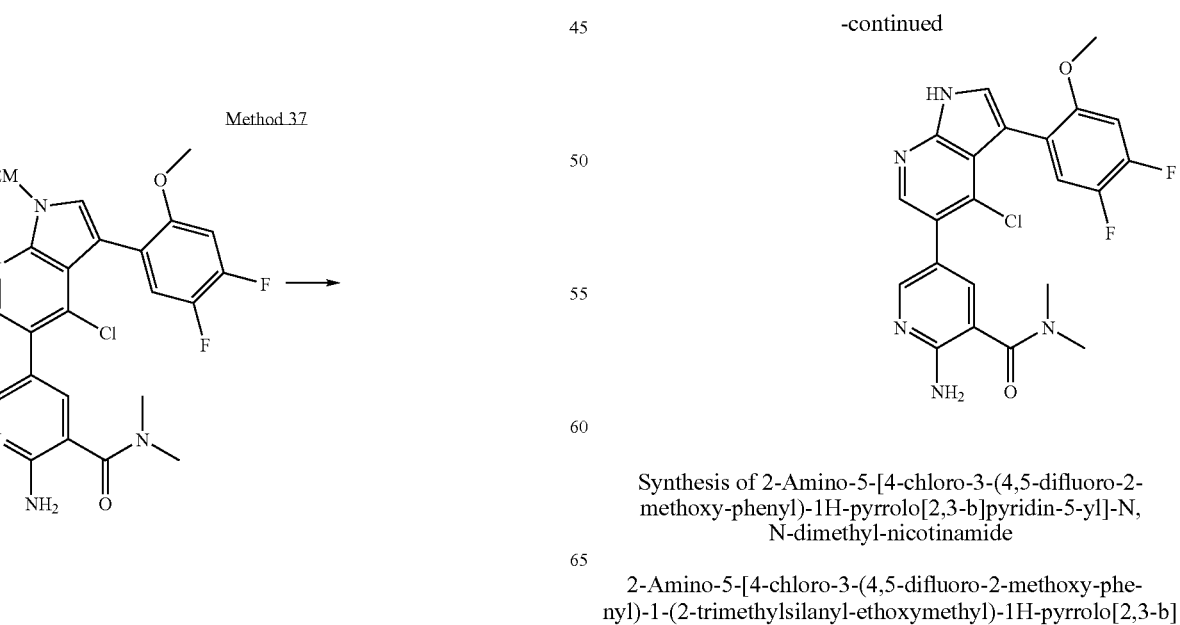

Synthesis of 2-Amino-5-[4-chloro-3-(4,5-difluoro-2-methoxy-phenyl)-1H-pyrrolo[2,3-b]pyridin-5-yl]-N,N-dimethyl-nicotinamide 2-Amino-5-[4-chloro-3-(4,5-difluoro-2-methoxy-phenyl)-1-(2-trimethylsilanyl-ethoxymethyl)-1H-pyrrolo[2,3-b]

pyridin-5-yl]-N,N-dimethyl-nicotinamide (76 mg, 0.136 mmol) was dissolved in trifluoroacetic acid (3 mL) and stirred at 23° C. for 45 minutes. The solution was concentrated under vacuum and taken up in methanol (10 mL). Ethylenediamine (100 μL, 5.39 mmol) was added, and the mixture was stirred at 35° C. for 20 minutes. Methanol was removed under vacuum. The crude was taken up in methanol (0.5 mL) and water (1 mL) was added. The resulting precipitate was collect by filtration to afford 2-Amino-5-[4-chloro-3-(4,5-difluoro-2-methoxy-phenyl)-1H-pyrrolo[2,3-b]pyridin-5-yl]-N,N-dimethyl-nicotinamide (49.6 mg, 0.108 mmol, 80% yield).
$^1$H-NMR [500 MHz, d$_6$-DMSO] δ: 8.18 (s, 1H), 8.05 (d, 1H), 7.56 (s, 1H), 7.47 (d, 1H), 7.35 (m, 1H), 7.15 (m, 1H), 6.15 (s, 2H), 6.68 (s, 2H), 2.95 (s, 6H); MS [MH$^+$] m/z: 458.

Other compounds synthesized using Method 35+Method 37:

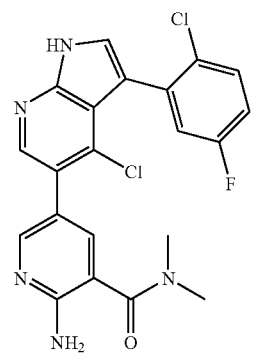

2-Amino-5-[4-chloro-3-(2-chloro-5-fluoro-phenyl)-1H-pyrrolo[2,3-b]pyridin-5-yl]-N,N-dimethyl-nicotinamide
$^1$H-NMR [500 MHz, d$_6$-DMSO] δ: 8.23 (s, 1 H), 8.06 (d, 1 H), 7.69, 1 H), 7.48 (d, 1 H), 7.36 (dd, 1 H), 7.26 (td, 1 H), 6.16 (s, 2 H), 2.94 (s, 6 H); MS [MH$^+$] m/z: 444

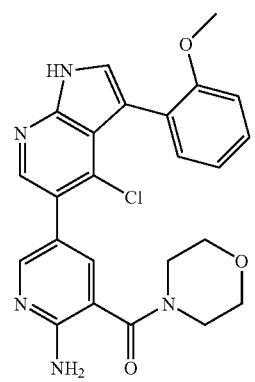

{2-Amino-5-[4-chloro-3-(2-methoxy-phenyl)-1H-pyrrolo[2,3-b]pyridin-5-yl]-pyridin-3-yl}-morpholin-4-yl-methanone
$^1$H-NMR [500 MHz, d$_6$-DMSO] δ: 8.17 (s, 1 H), 8.07 (s, 1 H), 7.48 (d, 2 H), (7.32 (t, 1 H), (7.25 (d, 1 H), 7.01 (d, 1 H), 7.694 (t, 1 H), 6.18 (s, 2 H), 3.68 (s, 3 H), 3.49 (s, 4 H), 3.47 (s, 4 H); MS [MH$^+$] m/z: 464

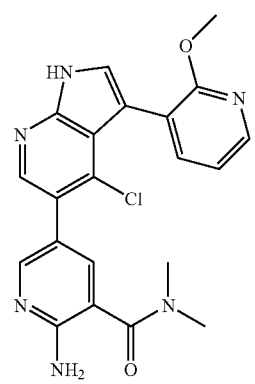

2-Amino-5-[4-chloro-3-(2-methoxy-pyridin-3-yl)-1H-pyrrolo[2,3-b]pyridin-5-yl]-N,N-dimethyl-nicotinamide
$^1$H-NMR [500 MHz, d$_6$-DMSO] δ: 8.19 (s, 1 H), 8.14 (dd, 1 H), 8.06 (d, 1 H), 7.66 (dd, 1 H), 7.61 (s, 1 H), 7.47 (d, 1 H), 7.01 (dd, 1 H), 6.15 (s, 2 H), 3.79 (s, 3 H), 2.94 (s, 6 H); MS [MH$^+$] m/z: 423.1

-continued

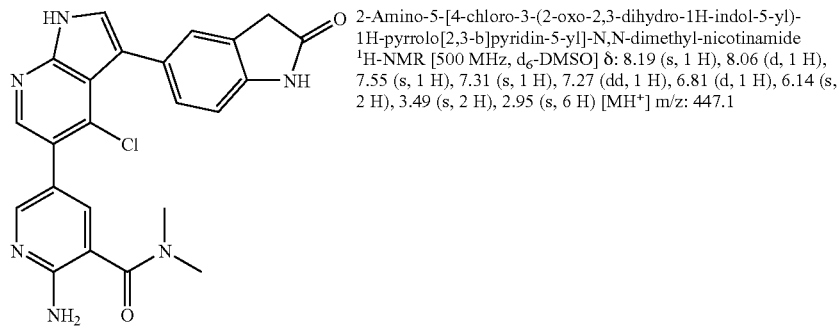

2-Amino-5-[4-chloro-3-(2-oxo-2,3-dihydro-1H-indol-5-yl)-1H-pyrrolo[2,3-b]pyridin-5-yl]-N,N-dimethyl-nicotinamide
$^{1}$H-NMR [500 MHz, d$_6$-DMSO] δ: 8.19 (s, 1 H), 8.06 (d, 1 H), 7.55 (s, 1 H), 7.31 (s, 1 H), 7.27 (dd, 1 H), 6.81 (d, 1 H), 6.14 (s, 2 H), 3.49 (s, 2 H), 2.95 (s, 6 H) [MH$^+$] m/z: 447.1

Method 38

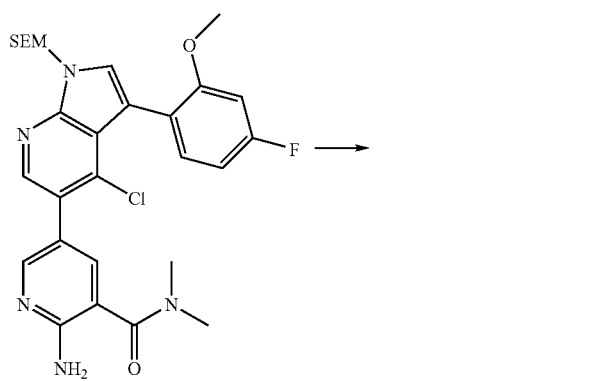

Synthesis of 2-Amino-5-[4-chloro-3-(4-fluoro-2-methoxy-phenyl)-1H-pyrrolo[2,3-b]pyridin-5-yl]-N,N-dimethyl-nicotinamide 2-Amino-5-[4-fluoro-3-(4-chloro-2-methoxy-phenyl)-1-(2-trimethylsilanyl-ethoxymethyl)-1H-pyrrolo[2,3-b]pyridin-5-yl]-N,N-dimethyl-nicotinamide (376 mg, 0.626 mmol) was dissolved in trifluoroacetic acid (10 mL) and stirred at 23° C. for 30 minutes. The solution was concentrated under vacuum. To the residue were added ethylenediamine (300 μL, 4.48 mmol) followed by methanol (5 mL). The solution was stirred at 40° C. for 1 hour. The resulting slurry was allowed to cool to 23° C. and stirred at ambient temperature for 3 hours. The solids were collected by filtration and rinsed with cold methanol (10 mL) followed by water (20 mL). The solids were allowed to dry under high vacuum to afford 2-Amino-5-[4-chloro-3-(4-fluoro-2-methoxy-phenyl)-1H-pyrrolo[2,3-b]pyridin-5-yl]-N,N-dimethyl-nicotinamide (187 mg, 0.410 mmol, 65% yield) as a white powder. $^{1}$H-NMR [500 MHz, d$_6$-DMSO] δ: 8.163 (s, 1H), 8.05 (d, 1H), 7.50 (s, 1H), 7.47 (d, 1H), 7.60 (m, 1H), 6.92 (dd, 1H), 6.76 (dt, 1H), 6.14 (s, 2H), 3.67 (s, 3H), 2.94 (s, 6H); MS [MH$^+$] m/z: 440.

Other compounds synthesized using Method 35+Method 38:

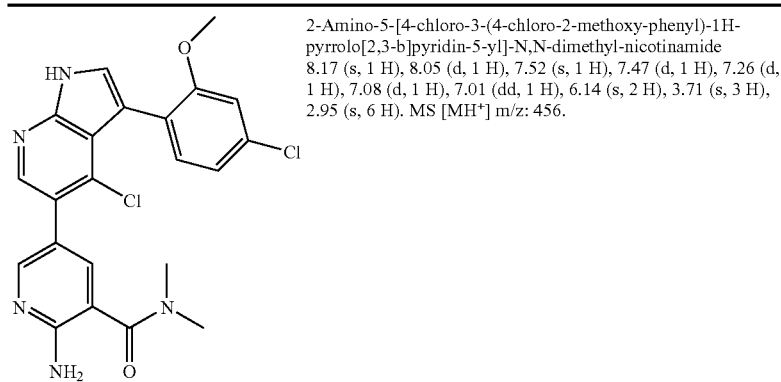

2-Amino-5-[4-chloro-3-(4-chloro-2-methoxy-phenyl)-1H-pyrrolo[2,3-b]pyridin-5-yl]-N,N-dimethyl-nicotinamide
8.17 (s, 1 H), 8.05 (d, 1 H), 7.52 (s, 1 H), 7.47 (d, 1 H), 7.26 (d, 1 H), 7.08 (d, 1 H), 7.01 (dd, 1 H), 6.14 (s, 2 H), 3.71 (s, 3 H), 2.95 (s, 6 H). MS [MH$^+$] m/z: 456.

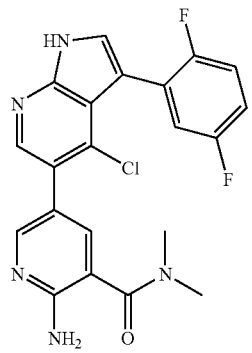

2-Amino-5-[4-chloro-3-(2,5-difluoro-phenyl)-1H-pyrrolo[2,3-b]pyridin-5-yl]-N,N-dimethyl-nicotinamide
$^1$H-NMR [500 MHz, $d_6$-DMSO] δ: 8.23 (s, 1 H), 8.07 (d, 1 H), 7.75 (s, 1 H), 7.49 (d, 1 H), 7.31 (m, 2 H), 7.23 (m, 1 H), 6.16 (s, 2 H), 2.94 (s, 6 H); MS [MH$^+$] m/z: 428.

Method 39

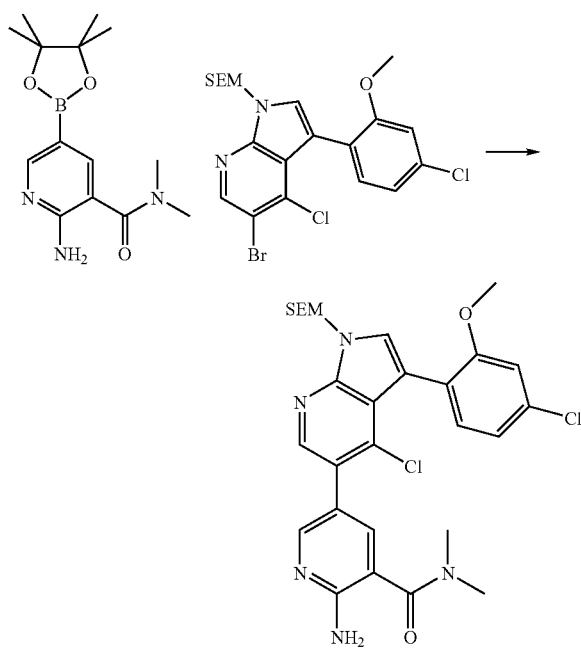

Synthesis of 2-Amino-5-[4-chloro-3-(4-chloro-2-methoxy-phenyl)-1-(2-trimethylsilanyl-ethoxymethyl)-1H-pyrrolo[2,3-b]pyridin-5-yl]-N,N-dimethyl-nicotinamide Into a 20 mL Personal Chemistry microwave reaction vial were added 2-Amino-N,N-dimethyl-5-(4,4,5,5-tetramethyl-[1,3,2]dioxaborolan-2-yl)-nicotinamide (1.55 g, 5.35 mmol), 5-Bromo-4-chloro-3-(4-chloro-2-methoxy-phenyl)-1-(2-trimethylsilanyl-ethoxymethyl)-1H-pyrrolo[2,3-b]pyridine (1.58 g, (3.15 mmol), bis(diphenylphosphino)ferrocenepalladium(II)-dichloride dichloromethane adduct (129 mg, 0.158 mmol), sodium carbonate solution (3.15 mL, 6.30 mmol, 2.0 M solution in water) and N,N-dimethylformamide (15 mL). The vial was purged with nitrogen, sealed, and irradiated in a Personal Chemistry Optimizer at 120° C. for 30 minutes. The mixture was concentrated in vacuo. The crude was taken up in dichloromethane (150 mL) and washed with aqueous saturated sodium carbonate solution (1×150 mL) and brine (1×150 mL). The organ phase was dried over sodium sulfate, filtered and concentrated in vacuo. The residue was purified by flash silica gel chromatography using a gradient of ethyl acetate in hexanes to afford 2-Amino-5-[4-chloro-3-(4-chloro-2-methoxy-phenyl)-1-(2-trimethylsilanyl-ethoxymethyl)-1H-pyrrolo[2,3-b]pyridin-5-yl]-N,N-dimethyl-nicotinamide (1.02 g, 1.74 mmol, 55% yield).
$^1$H-NMR [500 MHz, $d_6$-DMSO] δ: 8.26 (s, 1H), 8.06 (d, 1H), 7.72 (s, 1H), 7.48 (d, 1H), 7.26 (d, 1H), 7.11 (d, 1H), 7.03 (dd, 1H), 6.18 (s, 2H), 5.66 (s, 2H), 3.71 (s, 3H), 3.59 (t, 2H), 2.94 (s, 6H), 0.85 (s, 2H), −0.08 (s, 8H); MS [MH$^+$] m/z: 486

Other compounds synthesized using Method 39:

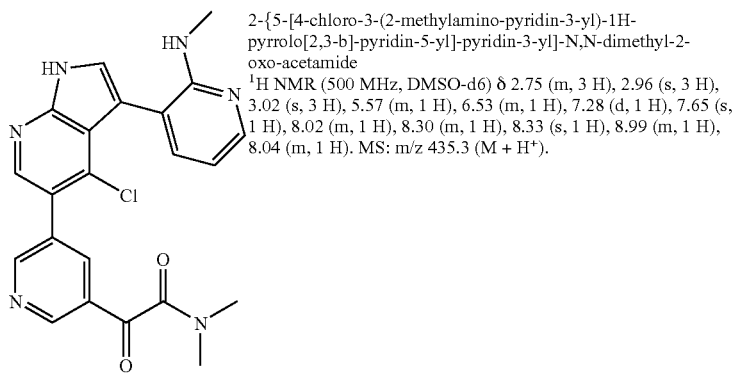

2-{5-[4-chloro-3-(2-methylamino-pyridin-3-yl)-1H-pyrrolo[2,3-b]-pyridin-5-yl]-pyridin-3-yl}-N,N-dimethyl-2-oxo-acetamide
$^1$H NMR (500 MHz, DMSO-d6) δ 2.75 (m, 3 H), 2.96 (s, 3 H), 3.02 (s, 3 H), 5.57 (m, 1 H), 6.53 (m, 1 H), 7.28 (d, 1 H), 7.65 (s, 1 H), 8.02 (m, 1 H), 8.30 (m, 1 H), 8.33 (s, 1 H), 8.99 (m, 1 H), 8.04 (m, 1 H). MS: m/z 435.3 (M + H$^+$).

-continued

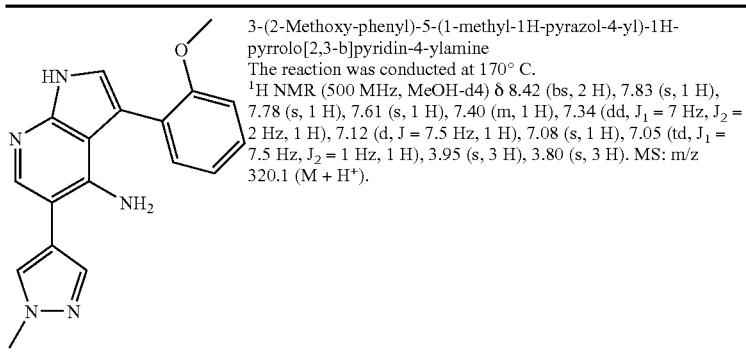

3-(2-Methoxy-phenyl)-5-(1-methyl-1H-pyrazol-4-yl)-1H-pyrrolo[2,3-b]pyridin-4-ylamine
The reaction was conducted at 170° C.
$^1$H NMR (500 MHz, MeOH-d4) δ 8.42 (bs, 2 H), 7.83 (s, 1 H), 7.78 (s, 1 H), 7.61 (s, 1 H), 7.40 (m, 1 H), 7.34 (dd, J$_1$ = 7 Hz, J$_2$ = 2 Hz, 1 H), 7.12 (d, J = 7.5 Hz, 1 H), 7.08 (s, 1 H), 7.05 (td, J$_1$ = 7.5 Hz, J$_2$ = 1 Hz, 1 H), 3.95 (s, 3 H), 3.80 (s, 3 H). MS: m/z 320.1 (M + H$^+$).

Other compounds synthesized using Method 39 followed by Method 18:

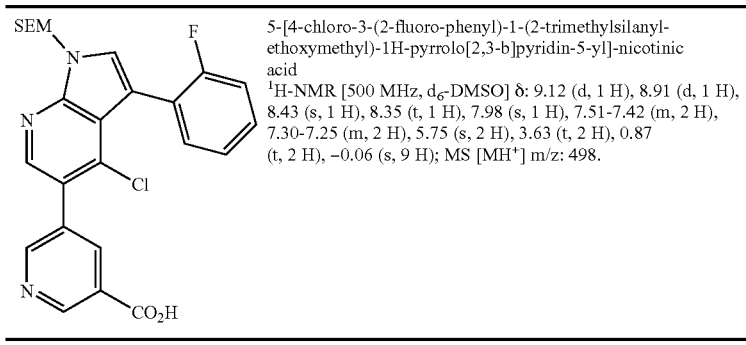

5-[4-chloro-3-(2-fluoro-phenyl)-1-(2-trimethylsilanyl-ethoxymethyl)-1H-pyrrolo[2,3-b]pyridin-5-yl]-nicotinic acid
$^1$H-NMR [500 MHz, d$_6$-DMSO] δ: 9.12 (d, 1 H), 8.91 (d, 1 H), 8.43 (s, 1 H), 8.35 (t, 1 H), 7.98 (s, 1 H), 7.51-7.42 (m, 2 H), 7.30-7.25 (m, 2 H), 5.75 (s, 2 H), 3.63 (t, 2 H), 0.87 (t, 2 H), −0.06 (s, 9 H); MS [MH$^+$] m/z: 498.

Method 40

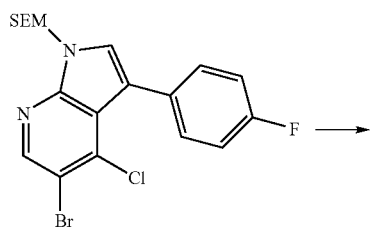

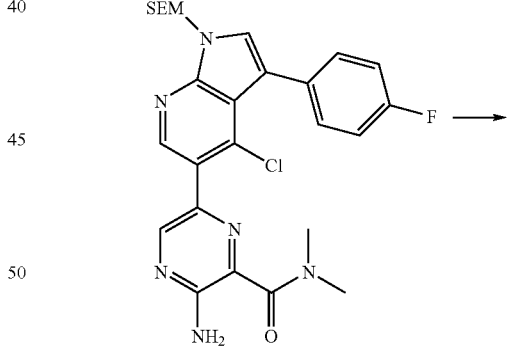

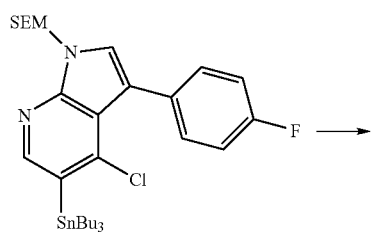

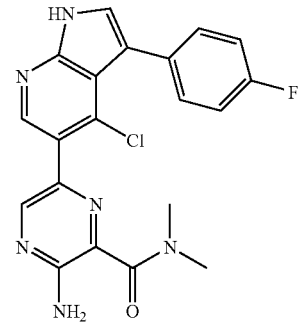

Synthesis of 3-amino-6-[4-chloro-3-(4-fluoro-phenyl)-1H-pyrrolo[2,3-b]pyridin-5-yl]-pyrazine-2-carboxylic acid dimethylamide 1.30 g (2.85 mmol) of 5-bromo-4-chloro-3-(4-fluoro-phenyl)-1-(2-trimethylsilanyl-ethoxymethyl)-1H-pyrrolo[2,3-b] pyridine and 750 mg (17.69 mmol) of anhydrous vacuum dried lithium chloride were dissolved under nitrogen in 50 mL of anhydrous THF. The resulting solution was cooled to −25° C. and 2.0 mL (4 mmol) of a 2 M solution of iso-propyl-magnesium chloride in anhydrous THF was added dropwise. The resulting mixture was allowed to stir at −25 to −5° C. for 2 h. 2.0 mL (7.4 mmol) of tri-n-butyltin chloride was added slowly to the resulting mixture. Upon complete addition the reaction mixture was allowed to stir for 18 h, allowing to warm to ambient temperature. The resulting reaction mixture was distributed between diethyl ether and a saturated aqueous solution of ammonium chloride. The aqueous phase was separated and extracted twice with diethyl ether. The combined organic phases were dried over sodium sulfate and evaporated. The residue was purified by flash chromatography on silica gel using a gradient of ethyl acetate and hexanes to afford 2.298 g (3.45 mmol, 121%) of 4-chloro-3-(4-fluoro-phenyl)-5-tributylstannanyl-1-(2-trimethylsilanyl-ethoxymethyl)-1H-pyrrolo[2,3-b]pyridine as a colorless oil. $^1$H-NMR [500 MHz, $d_6$-DMSO] δ: 8.13 (s, 1H), 7.77 (s, 1H), 7.49-7.45 (m, 2H), 7.27-7.22 (m, 2H), 5.66 (s, 2H), 3.55 (t, 2H), 1.63-1.47* (m, 6H), 1.34-1.08* (m, 12H), 0.89-0.80* (t, 9H), −0.12 (s, 9H) [*: compound contaminated with other tri-n-butyl tin side product(s) in shift ranges indicated, appearing as distinct sets of peaks with equal integration to desired product]; MS [MH$^+$] m/z: 665+667.

120 mg (0.18 mmol) of 4-chloro-3-(4-fluoro-phenyl)-5-tributylstannanyl-1-(2-trimethylsilanyl-ethoxymethyl)-1H-pyrrolo[2,3-b]pyridine, 64 mg (0.22 mmol) of 3.5 mg (9.1 μmol) bis(benzonitrile)palladium(II)-chloride, 3.4 mg (18 μmol) of copper(I)-iodide and 85 mg (0.56 mmol) of cesium fluoride were placed in a vial. The vial was flushed with nitrogen and 2 mL of anhydrous DMF were added, followed by 60 μL of 10% w/v tri-tert-butylphosphine in hexanes. The resulting mixture was heated in a sealed tube to 80° C. for 5.5 h. The resulting mixture was evaporated and the crude product purified by flash chromatography on silica gel using a gradient of 10% v/v of methanol in ethyl acetate and hexanes to afford 59 mg (0.11 mmol, 30%) of 3-amino-6-[4-chloro-3-(4-fluoro-phenyl)-1-(2-trimethylsilanyl-ethoxymethyl)-1H-pyrrolo[2,3-b]pyridin-5-yl]-pyrazine-2-carboxylic acid dimethylamide. $^1$H-NMR [500 MHz, CDCl$_3$] δ: 8.39 (m, 1H), 8.29 (s, 1H), 7.48 (m, 2H), 7.09 (m, 2H), 5.76 (s, 2H), 3.64 (t, 2H), 3.15 (s, 6H), 0.9 (m, 2H), −0.1 (s, 9H).

The material obtained was dissolved in dichloromethane and 650 μL of trifluoroacetic acid were added. The resulting mixture was left at ambient temperature for 24 h and then evaporated. The residue was dissolved in dichloromethane containing 150 μL of 1,2-ethylenediamine. After leaving the mixture at ambient temperature for 24 h the volatiles were removed and the resulting residue was purified by mass-triggered reverse-phase HPLC to afford 1.4 mg (3.4 μmol, 2% over two steps) of 3-amino-6-[4-chloro-3-(4-fluoro-phenyl)-1H-pyrrolo[2,3-b]pyridin-5-yl]-pyrazine-2-carboxylic acid dimethylamide as an ivory solid. $^1$H-NMR [500 MHz, $d_6$-DMSO] δ: 8.34 (s, 1H), 8.32 (s, 1H), 7.68 (s, 1H), 7.53 (dd, 2H), 7.23 (t, 2H), 6.69 (s, br., 2H), 3.02 (s, 6H); MS [MH$^+$] m/z: 411.

Other compound synthesized according to Method 40:

| Structure | MS: MH$^+$ [m/z] | $^1$H-NMR 500 MHz $d_6$-DMSO δ: |
|---|---|---|
| 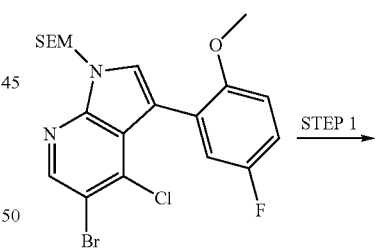 | 423 | 2-{5-[4-Chloro-3-(4-fluoro-phenyl)-1H-pyrrolo[2,3-b]pyridin-5-yl]-pyridin-3-yl}-N,N-dimethyl-2-oxo-acetamide 9.05(d, 1 H), 9.03(d, 1 H), 8.36(t, 1 H), 8.35(s, 1 H), 7.75(s, 1 H), 7.55(dd, 2 H), 7.23(t(m), 2 H), 3.02(s, 3 H), 2.96(s, 3 H). |

Method 41

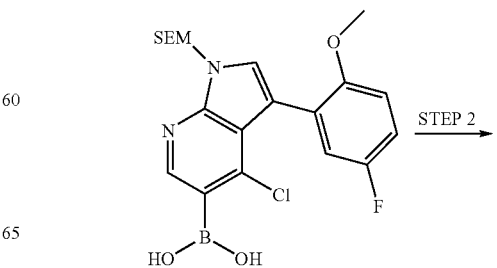

-continued

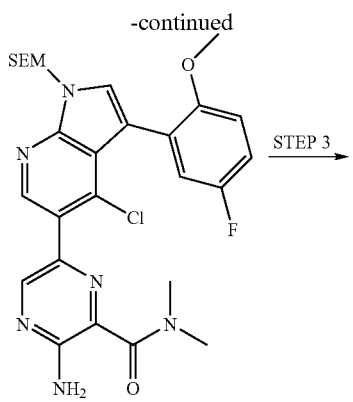

STEP 3

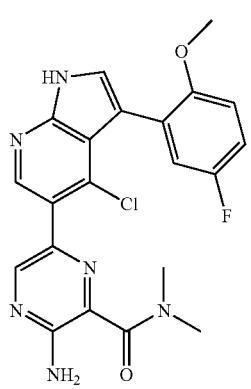

Synthesis of 3-amino-6-[4-chloro-3-(5-fluoro-2-methoxy-phenyl)-1H-pyrrolo[2,3-b]pyridin-5-yl]-pyrazine-2-carboxylic acid dimethylamide STEP 1: Synthesis of 4-Chloro-3-(5-fluoro-2-methoxy-phenyl)-1-(2-trimethylsilanyl-ethoxymethyl)-1H-pyrrolo[2,3-b]pyridine-5-boronic acid 770 mg (1.58 mmol) of 5-bromo-4-chloro-3-(5-fluoro-2-methoxy-phenyl)-1-(2-trimethylsilanyl-ethoxymethyl)-1H-pyrrolo[2,3-b]pyridine and 470 mg (11.09 mmol) of vacuum dried anhydrous lithium chloride were dissolved in 30 mL of anhydrous THF under nitrogen. The mixture was cooled to −25° C. and 1.1 mL (2.2 mmol) of a 2 M solution of iso-propylmagnesium chloride in anhydrous THF was added. The reaction mixture was allowed to stir at −25 to 0° C. for 1.5 h, then cooled to −5° C. and 0.6 mL (2.6 mmol) of tri-iso-propyl borate was added. The resulting mixture was allowed to stir for 16 h, allowing to slowly warm to ambient temperature. The resulting mixture was cooled to −40° C. and 1.1 mL (2.2 mmol) of a 2 M solution of iso-propylmagnesium chloride in anhydrous THF was added. The reaction mixture was stirred for 9 h, allowing to warm to ambient temperature. The resulting reaction mixture was distributed between dichloromethane and a saturated aqueous solution of ammonium chloride. The aqueous phase was separated and extracted twice with dichloromethane. The combined organic phases were dried over sodium sulfate and evaporated. The residue was purified by flash chromatography on silica gel using a gradient of ethyl acetate and hexanes to afford 179 mg (0.37 mmol, 23%) of recovered starting material and 139 mg (0.31 mmol, 25% based on recovered starting material) of 4-chloro-3-(5-fluoro-2-methoxy-phenyl)-1-(2-trimethylsilanyl-ethoxymethyl)-1H-pyrrolo[2,3-b]pyridine-5-boronic acid as a pale beige solid. $^1$H-NMR [500 MHz, d$_6$-DMSO] δ: 8.25 (s, 1H), 7.67 (s, 1H), 7.18 (m, 1H), 7.09-7.00 (m, 2H), 5.65 (s, 2H), 3.67 (s, 3H), 3.56 (t, 2H), 0.85 (t, 2H), 0.06 (s, 9H); MS [MH$^+$] m/z: 451.

STEP 2: Synthesis of 3-amino-6-[4-chloro-3-(5-fluoro-2-methoxy-phenyl)-1-(2-trimethylsilanyl-ethoxymethyl)-1H-pyrrolo[2,3-b]pyridin-5-yl]-pyrazine-2-carboxylic acid dimethylamide 42 mg (93 μmol) of 4-chloro-3-(5-fluoro-2-methoxy-phenyl)-1-(2-trimethylsilanyl-ethoxymethyl)-1H-pyrrolo[2,3-b]pyridine-5-boronic acid, 5 mg (6 μmol) of (1,1'-bis(diphenylphosphino)ferrocene palladium(II)-dichloride dichloromethane adduct and 41 mg (0.14 mmol) of 3-amino-6-iodo-pyrazine-2-carboxylic acid dimethylamide were dissolved in a mixture of 1 mL of acetonitrile and 1 mL of toluene. 2 mL of a saturated aqueous solution of sodium bicarbonate was added and the resulting mixture heated in closed vial to 110° C. for 20 h. The aqueous layer was removed and the organic phase evaporated. The residue was purified by flash chromatography on silica gel using a gradient of 10% v/v of methanol in ethyl acetate and hexanes to afford 25 mg (44 μmol, 47%) of 3-amino-6-[4-chloro-3-(5-fluoro-2-methoxy-phenyl)-1-(2-trimethylsilanyl-ethoxymethyl)-1H-pyrrolo[2,3-b]pyridin-5-yl]-pyrazine-2-carboxylic acid dimethylamide.

STEP 3: Synthesis of 3-amino-6-[4-chloro-3-(5-fluoro-2-methoxy-phenyl)-1H-pyrrolo[2,3-b]pyridin-5-yl]-pyrazine-2-carboxylic acid dimethylamide The material was dissolved in 3 mL of 25% v/v trifluoroacetic acid in dichloromethane and left at ambient temperature for 16 h. The mixture was evaporated and the residue dissolved in dichloromethane and 100 μL of 1,2-ethylenediamine was added. After 1 h at ambient temperature the volatiles were removed and the residue purified by mass-triggered reverse-phase HPLC to afford 3.4 mg (7.7 μmol, 8%) of 3-amino-6-[4-chloro-3-(5-fluoro-2-methoxy-phenyl)-1H-pyrrolo[2,3-b]pyridin-5-yl]-pyrazine-2-carboxylic acid dimethylamide as an ivory solid. $^1$H-NMR [500 MHz, d6-DMSO] δ: 12.22 (s, br., 1H), 8.24 (s, 1H), 8.22 (s, 1H), 7.53 (s, 1H), 7.12-7.05 (m, 2H), 6.95 (dd, 1H), 6.63 (s, br. 2H), 3.61 (s, 3H), 2.96 (s, 3H), 2.95 (s, 3H); MS [MH$^+$] m/z:

Other compound synthesized according to the Method 41:

| Structure | MS: MH+ [m/z] | 1H-NMR 500 MHz d6-DMSO δ: |
|---|---|---|
| (structure) | 479 | {5-[4-Chloro-3-(5-fluoro-2-methoxy-phenyl)-1H-pyrrolo[2,3-b]pyridin-5-yl]-pyridin-3-yl}-(3-fluoro-pyridin-2-yl)-methanol 12.26(s, br., 1 H), 8.55(d, 1 H), 8.49(d, 1 H), 8.34 (dt, 1 H), 8.14(s, 1 H), 7.84(t, 1 H), 7.64(ddd, 1 H), 7.56(s, 1 H), 7.36(m, 1 H), 7.12-7.05(m, 2 H), 6.95(dd, 1 H), 6.29((m), b., 1 H), 6.08(s, br., 1 H), 3.61(s, 3 H). |
| (structure) | 426 | 6-[4-Chloro-3-(5-fluoro-2-methoxy-phenyl)-1H-pyrrolo[2,3-b]pyridin-5-yl]-pyrazine-2-carboxylic acid dimethylamide 8.95(s, 1 H), 8.78(s, 1 H), 8.36(s, 1 H), 7.60(s, 1 H), 7.13-7.08(m, 2 H), 7.96(dd, 1 H), 3.62(s, 3 H), 2.99(s, 3 H), 2.98(s, 3 H). |

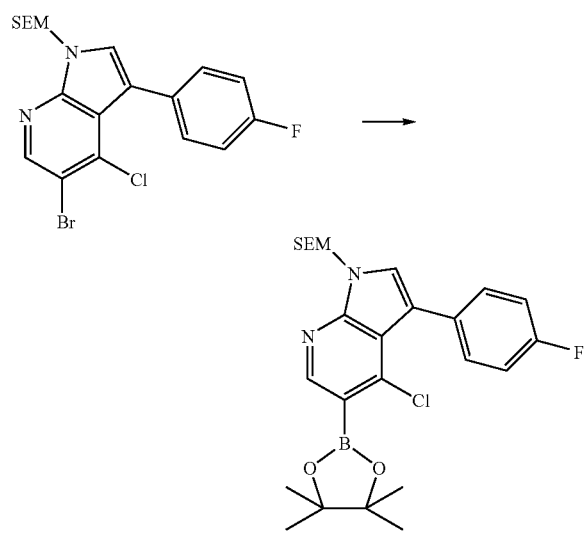

Method 42

Synthesis of 6-[4-chloro-3-(4-fluoro-phenyl)-1H-pyrrolo[2,3-b]pyridin-5-yl]-pyrazine-2-carboxylic acid dimethylamide 580 mg (13.69 mmol) of vacuum dried anhydrous lithium chloride was dissolved in 30 mL of anhydrous THF under nitrogen. The mixture was cooled to 0° C. and 1.5 mL (3.0 mmol) of a 2 M solution of iso-propylmagnesium chloride in anhydrous THF was added. To this mixture was added at 0° C. a solution of 1.064 g (2.33 mmol) of 5-bromo-4-chloro-3-(4-fluoro-phenyl)-1-(2-trimethylsilanyl-ethoxymethyl)-1H-pyrrolo[2,3-b]pyridine in 20 mL of anhydrous THF under nitrogen. The resulting mixture was stirred at 0° C. for 2 h before 1.0 mL (4.3 mmol) of tri-iso-propylborate was added at 0° C. The resulting mixture was allowed to stir at that temperature for 2.5 h. 990 mg (8.38 mmol) of pinacol was added and the mixture stirred for 24 h, allowing to warm to room temperature. The resulting reaction mixture was distributed between diethyl ether and a saturated aqueous solution of ammonium chloride. The organic phase was separated, dried over sodium sulfate and evaporated. The residue was purified by flash chromatography on silica gel using a gradient of ethyl acetate and hexanes to afford 569 mg (1.13 mmol, 48%) of 4-chloro-3-(4-fluoro-phenyl)-5-(4,4,5,5-tetramethyl-[1,3,2]dioxaborolan-2-yl)-1-(2-trimethylsilanyl-ethoxymethyl)-1H-pyrrolo[2,3-b]pyridine as a beige solid. 1H-NMR [500 MHz, d6-DMSO] δ: 8.46 (s, 1H), 7.83 (s, 1H), 7.50 (dd (m), 2H), 7.27 (t (m), 2H), 5.68 (s, 2H), 3.57 (t, 2H), 1.32 (s, 12H), −0.09 (s, 9H); MS [MH+] m/z: 503

Method 43

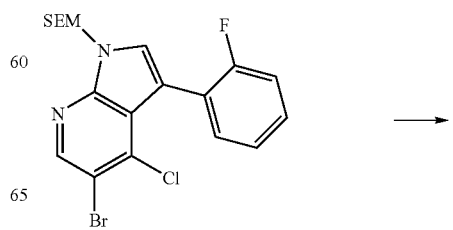

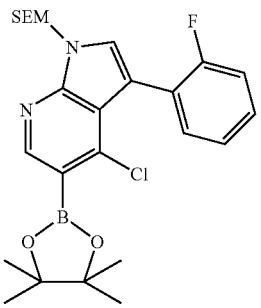

Synthesis of 4-chloro-3-(2-fluoro-phenyl)-5-(4,4,5,5-tetramethyl[1,3,2]-dioxaborolan-2-yl)-1-(2-trimethylsilanyl-ethoxymethyl)-1H-pyrrolo[2,3-b]pyridine Isopropyl magnesium chloride/Li—Cl complex (10.7 ml, 10.9 mmol-14% in THF) was added dropwise to a solution of 5-bromo-4-chloro-3-(2-fluoro-phenyl)-1-(2-trimethylsilanyl-ethoxymethyl)-1H-pyrrolo-[2,3-b]pyridine (2.5 g, 5.4 mmol) under nitrogen in THF at −20° C. The reaction was let to proceed at −20° C. for another 2 hours. Then triisopropyl borate (3.1 ml, 13.6 mmol) in THF was added dropwise and the reaction was continued at −20° C. for another hour. At this time pinacol (1.3 g, 10.9 mmol) was added. The reaction was stirred at room temperature overnight. The solvent was removed under vacuum. Silica chromatography of the crude using a gradient of ethyl acetate and hexane afforded 4-chloro-3-(2-fluoro-phenyl)-5-(4,4,5,5-tetramethyl[1,3,2]-dioxaborolan-2-yl)-1-(2-trimethylsilanyl-ethoxymethyl)-1H-pyrrolo[2,3-b]pyridine (1.0 g, 63% yield). $^1$H NMR (500 MHz, DMSO-d6) δ 0.01 (s, 9H), 0.94 (t, 2H), 1.58 (s, 12H), 3.69 (t, 2H), 5.81 (s, 2H), 7.40 (m, 2H), 7.56 (m, 2H), 7.99 (s, 1H), 8.40 (m, 1H). MS: m/z 503.2 (M+H$^+$).

Other compounds synthesized using Method 43:

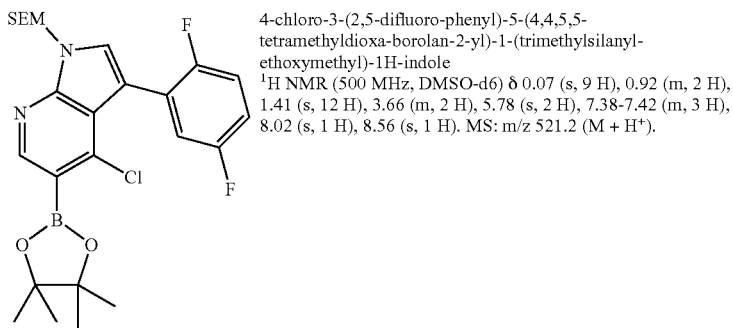

4-chloro-3-(2,5-difluoro-phenyl)-5-(4,4,5,5-tetramethyldioxa-borolan-2-yl)-1-(trimethylsilanyl-ethoxymethyl)-1H-indole
$^1$H NMR (500 MHz, DMSO-d6) δ 0.07 (s, 9 H), 0.92 (m, 2 H), 1.41 (s, 12 H), 3.66 (m, 2 H), 5.78 (s, 2 H), 7.38-7.42 (m, 3 H), 8.02 (s, 1 H), 8.56 (s, 1 H). MS: m/z 521.2 (M + H$^+$).

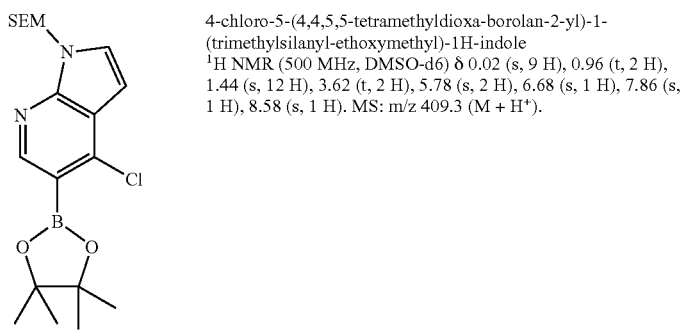

4-chloro-5-(4,4,5,5-tetramethyldioxa-borolan-2-yl)-1-(trimethylsilanyl-ethoxymethyl)-1H-indole
$^1$H NMR (500 MHz, DMSO-d6) δ 0.02 (s, 9 H), 0.96 (t, 2 H), 1.44 (s, 12 H), 3.62 (t, 2 H), 5.78 (s, 2 H), 6.68 (s, 1 H), 7.86 (s, 1 H), 8.58 (s, 1 H). MS: m/z 409.3 (M + H$^+$).

Method 44

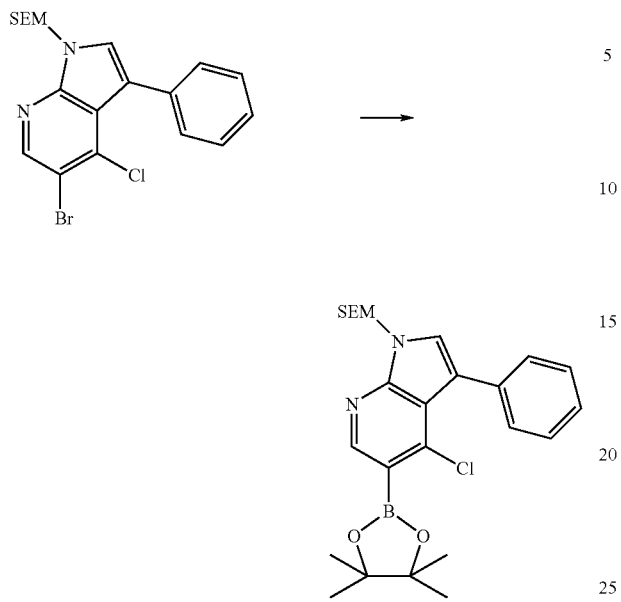

Synthesis of 4-chloro-3-phenyl-5-(4,4,5,5-tetramethyl-[1,3,2]dioxaborolan-2-yl)-1-(2-trimethylsilanyl-ethoxymethyl)-1H-pyrrolo[2,3-b]pyridine A mixture of 5-bromo-4-chloro-3-phenyl-1-(2-trimethylsilanyl-ethoxymethyl)-1H-pyrrolo 2,3,b]-pyridine (2.0 g, 4.5 mmol), bis(pinacolato)diboron (2.3 g, 9.1 mmol), dichloro[1,1'-bis(diphenylphosphino)ferrocene]palladium(II) dichloromethane adduct (166 mg, 0.2 mmol), and sodium acetate (1.1, 13.6 mmol) in DMF (20 ml) was stirred at 95° C. overnight. The mixture was allowed to cool down to room temperature and then extracted with ethyl acetate (3×). The combined organic layers were extracted with brine, dried with $Na_2SO_4$, decanted, and concentrated to dryness. Silica chromatography of the crude using a gradient of ethyl acetate and hexane afforded 4-chloro-3-phenyl-5-(4,4,5,5-tetramethyl-[1,3,2]dioxaborolan-2-yl)-1-(2-trimethylsilanyl-ethoxymethyl)-1H-pyrrolo-[2,3-b]pyridine (0.9 g, 42% yield). $^1$H NMR (500 MHz, DMSO-d6) δ 0.02 (s, 9H), 0.98 (m, 2H), 3.64 (m, 2H), 5.78 (s, 2H), 7.58 (m, 5H), 8.02 (s, 1H), 8.64 (s, 1H). MS: m/z 485.1 (M+H$^+$).

Method 45

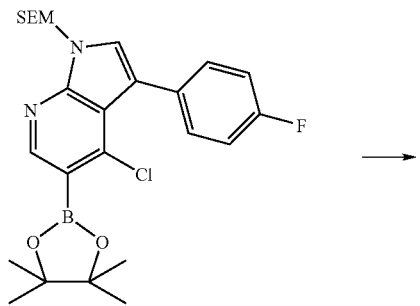

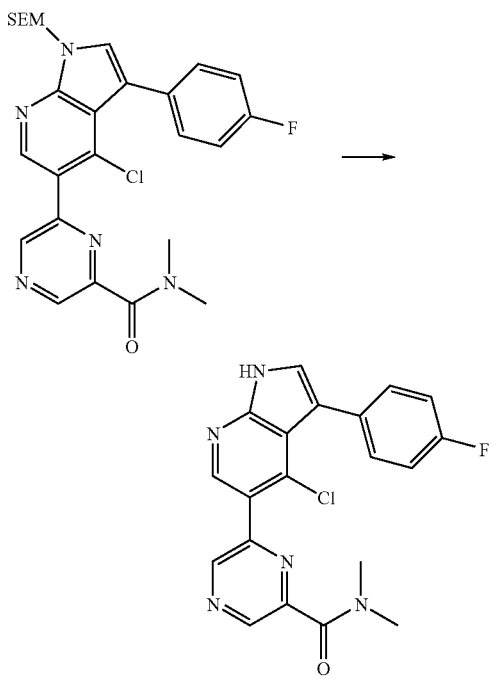

Synthesis of 6-[4-Chloro-3-(4-fluoro-phenyl)-1H-pyrrolo[2,3-b]pyridin-5-yl]-pyrazine-2-carboxylic acid dimethylamide 45 mg (84 mmol) of 4-chloro-3-(4-fluoro-phenyl)-5-(4,4,5,5-tetramethyl-[1,3,2]dioxaborolan-2-yl)-1-(2-trimethylsilanyl-ethoxymethyl)-1H-pyrrolo[2,3-b]pyridine, 5 mg (6 μmol) of (1,1'-bis(diphenylphosphino)ferrocene palladium (II)-dichloride dichloromethane adduct and 25 mg (0.13 mmol) of 6-chloro-pyrazine-2-carboxylic acid dimethylamide were dissolved in a mixture of 1 mL of acetonitrile and 1 mL of toluene. 2 mL of a saturated aqueous solution of sodium bicarbonate was added and the resulting mixture heated in closed vial to 110° C. for 18 h. The aqueous layer was removed and the organic phase evaporated. The residue was purified by flash chromatography on silica gel using a gradient of 10% v/v of methanol in ethyl acetate and hexanes to afford 46 mg (81 μmol, 97%) of 6-[4-chloro-3-(4-fluoro-phenyl)-1-(2-trimethylsilanyl-ethoxymethyl)-1H-pyrrolo[2,3-b]pyridin-5-yl]-pyrazine-2-carboxylic acid dimethylamide.

The material was dissolved in 3 mL of 25% v/v trifluoroacetic acid in dichloromethane and left at ambient temperature for 16 h. The mixture was evaporated and the residue dissolved in dichloromethane and 100 μL of 1,2-ethylenediamine was added. After 1 h at ambient temperature the volatiles were removed and the residue purified by mass-triggered reverse-phase HPLC to afford 12.2 mg (29 μmol, 35% over two steps) of 6-[4-chloro-3-(4-fluoro-phenyl)-1H-pyrrolo[2,3-b]pyridin-5-yl]-pyrazine-2-carboxylic acid dimethylamide as an ivory solid. $^1$H-NMR [500 MHz, d$_6$-DMSO] δ: 8.98 (s, 1H), 8.78 (s, 1H), 8.39 (s, 1H), 7.69 (s, 1H), 7.48 (dd (m), 2H), 7.17 (t (m), 2H), 2.95 (s, 6H); MS [MH$^+$] m/z: 396.

Other compound synthesized according to Method 45:

| Structure | MS: MH+ [m/z] | ¹H-NMR 500 MHz d₆-DMSO δ: |
|---|---|---|
| 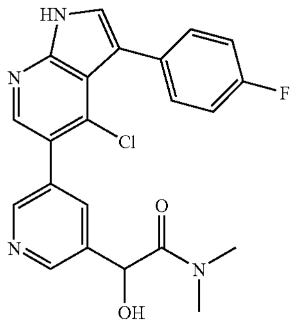 | 425 | 2-{5-[4-Chloro-3-(4-fluoro-phenyl)-1H-pyrrolo[2,3-b]pyridin-5-yl]-pyridin-3-yl}-2-hydroxy-N,N-dimethyl-acetamide 12.43(s, br., 1 H), 8.62(d, 1 H), 8.61(d, 1 H), 8.27(s, 1 H), .789(t, 1 H), 7.73(s, 1 H), 7.54(dd(m), 2 H), 7.23 (t(m), 2 H), 5.85((d), br., 1 H), 5.58(s, br., 1 H), 2.97 (s, 3 H), 2.86(s, 3 H). |
| 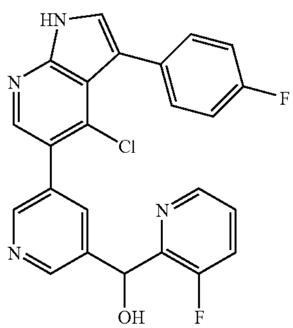 | 449 | {5-[4-Chloro-3-(4-fluoro-phenyl)-1H-pyrrolo[2,3-b]pyridin-5-yl]-pyridin-3-yl}-(3-fluoro-pyridin-2-yl)-methanol 12.35(s, br., 1 H), 8.55(d, 1 H), 8.51(d, 1 H), 8.34(dt, 1 H), 8.17(s, 1 H), 7.88(t, 1 H), 7.64(s, 1 H), 7.64(dd, 1 H), 7.46(dd(m), 2 H), 7.36(m, 1 H), 7.16(t(m), 2 H), 6.30(s, br. 1 H), 6.09(s, 1 H). |
| 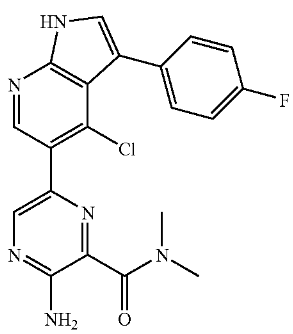 | 411 | 3-amino-6-[4-chloro-3-(4-fluoro-phenyl)-1H-pyrrolo[2,3-b]pyridin-5-yl]-pyrazine-2-carboxylic acid dimethylamide 8.27(s, 1 H), 8.25(s, 1 H), 7.62(s, 1 H), 7.46(dd(m), 2 H), 7.16(t(m), 2 H), 6.62(s, 1 H), 2.95(s, 6 H). |

Method 46

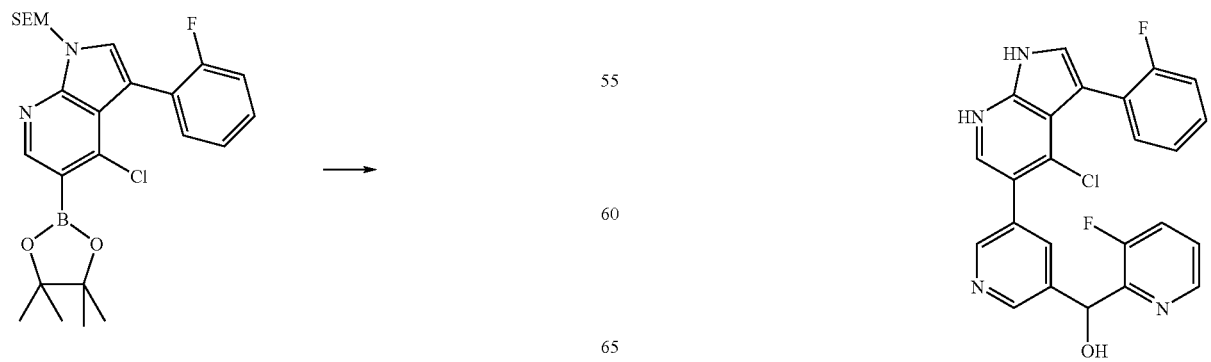

Synthesis of {5-[4-chloro-3-(fluoro-phenyl)-1H-pyrrolo[2,3-b]pyridine-5-yl]-pyridin-3-yl}-(3-fluoro-pyridin-2-yl)-methanol A mixture of 4-chloro-3-(2-fluoro-phenyl)-5-(4,4,5,5-tetramethyl[1,3,2]-dioxaborolan-2-yl)-1-(2-trimethylsilanyl-ethoxymethyl)-1H-pyrrolo[2,3-b]pyridine (100 mg, 0.2 mmol), 5-bromo-pyridin-3-yl)-(3-fluoro-pyridin-2-yl)-methanol (57 mg, 0.2 mmol), dichloro[1,1'-bis(diphenylphosphino)ferrocene]palladium(II) dichloromethane adduct (7 mg, 0.01 mmol) in THF/Acetonitrile/saturated NaHCO$_3$ (5 ml/5 ml/5 ml) was stirred at 120° C. in the microwave for 20 minutes. The mixture was allowed to cool down to room temperature and then extracted with ethyl acetate (2×). The combined organic layers were extracted with brine, dried with Na$_2$SO$_4$, decanted, and concentrated to dryness. Silica chromatography of the crude using a gradient of ethyl acetate and hexane afforded {5-[4-chloro-3-(fluoro-phenyl)-1-(2-trimethylsilanyl-ethoxy-methyl)-1H-pyrrolo[2,3-b]pyridine-5-yl]-pyridin-3-yl}-(3-fluoro-pyridin-2-yl)-methanol (102 mg, 88% yield).

The material was stirred in dichloromethane/trifluoroacetate acid (1 ml/1 ml) at room temperature for 2 hours. The solvents were removed under vacuum and the crude was stirred in dichloromethane/ethylenediamine (1 ml/1 ml) for 2 hours at room temperature. Again the solvents was removed under vacuum and the crude was dissolved in DMSO, filtered and purified by reverse phase HPLC, lyophilized afforded {5-[4-chloro-3-(fluoro-phenyl)-1H-pyrrolo[2,3-b]pyridine-5-yl]-pyridin-3-yl}-(3-fluoro-pyridin-2-yl)-methanol (25 mg, 32% yield). $^1$H NMR (500 MHz, DMSO-d6) δ 6.14 (s, 1H), 6.35 (s, 1H), 7.25 (m, 2H), 7.43 (m, 3H), 7.69 (t, 1H), 7.72 (m, 1H), 7.93 (s, 1H), 8.25 (s, 1H), 8.40 (m, 1H), 8.56 (s, 1H), 8.61 (s, 1H). MS: m/z 449.1 (M+H$^+$).

Other compounds synthesized using Method 46:

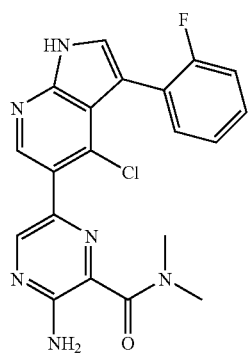

6-[4-chloro-3-(2-fluoro-phenyl)-1H-pyrrolo[2,3,b]pyridine-5-yl]-pyrazine-2-carboxylic acid dimethylamide
$^1$H NMR (500 MHz, DMSO-d6) δ 3.01 (s, H), 6.68 (s, 2 H), 7.24 (m, 2 H), 7.40 (m, 1 H), 7.45 (m, 1 H), 7.71 (s, 1 H), 8.30 (s, 1 H), 8.34 (s, 1 H). MS: m/z 411.1 (M + H$^+$).

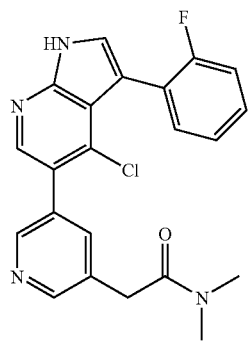

6-[4-chloro-3-(2-fluoro-phenyl)-1H-pyrrolo[2,3,b]pyridine-5-yl]-pyrazine-2-carboxylic acid dimethylamide
2.84 (s, 3 H), 3.07 (s, 3 H), 3.82 (s, 2 H), 7.23-7.28 (m, 2 H), 7.39-7.44 (m, 1 H), 7.46-7.49 (m, 1 H), 7.75-7.76 (m, 2 H), 8.26 (s, 1 H), 8.45 (d, 1 H), 8.53 (d, 1 H), 12.48 (s, 1 H). MS: m/z 409.1 (M + H$^+$).

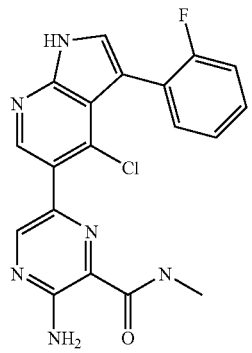

6-[4-chloro-3-(2-fluoro-phenyl)-1H-pyrrolo[2,3,b]pyridine-5-yl]-pyrazine-2-carboxylic acid methylamide
2.79 (m, 3 H), 7.23-7.28 (m, 2 H), 7.40-7.49 (m, 2 H), 7.72 (d, 1 H), 8.49 (s, 1 H), 8.52 (s, 1 H), 8.63-8.66 (m, 1 H), 12.42 (s, 1 H). MS: m/z 397.1 (M + H$^+$).

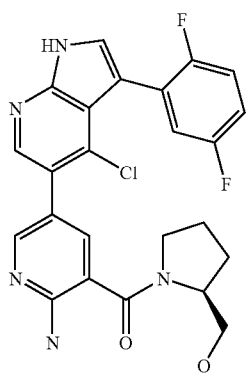

{2-Amino-5-[4-chloro-3-(2,5-difluoro-phenyl)-1H-pyrrolo[2,3-b]pyridin-5-yl]-pyridin-3-yl}-(2-hydroxymethyl-pyrrolidin-1-yl)-methanone
$^1$H NMR (500 MHz, DMSO-d6) δ 1.69 (s, 1 H), 1.86-1.98 (m, 4 H), 3.33-3.62 (m, 10 H), 4.14 (s, 1 H), 4.78 (s, 1 H), 6.29 (s, 2 H), 7.22-7.35 (m, 3 H), 7.62 (s, 1 H), 7.76 (s, 1 H), 8.08 (m, 1 H), 8.24 (s, 1 H). MS: m/z 484.1 (M + H$^+$)

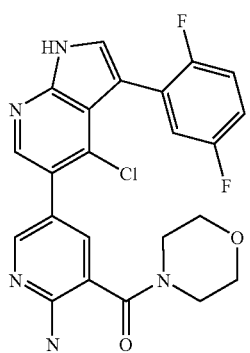

{2-Amino-5-[4-chloro-3-(2,5-difluoro-phenyl)-1H-pyrrolo[2,3-b]pyridin-5-yl]-pyridin-3-yl}-morpholin-4-yl-methanone
$^1$H NMR (500 MHz, DMSO-d6) δ 3.4-3.6 (m, 8 H), 6.22 (s, 2 H), 7.22-7.36 (m, 3 H), 7.52 (d, 1 H), 7.76 (s, 1 H), 8.10 (d, 1 H), 8.43 (s, 1 H). MS: m/z 470.1 (M + H$^+$).

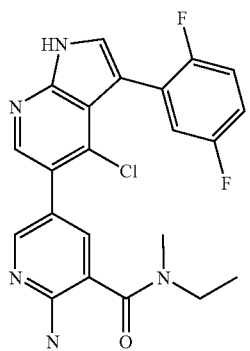

2-Amino-5-[4-chloro-3-(2,5-difluoro-phenyl)-1H-pyrrolo[2,3-b]pyridin-5-yl]-N-ethyl-N-methyl-nicotinamide
$^1$H NMR (500 MHz, DMSO-d6) δ 1.10 (s, 3 H), 2.94 (s, 3 H), 3.32 (bs, 2 H), 6.16 (s, 2 H), 7.22-7.26 (m, 1 H), 7.28-7.35 (m, 2 H), 7.46 (s, 1 H), 7.76 (s, 1 H), 8.08 (d, 1 H), 8.44 (s, 1 H). MS: m/z 442.1 (M + H$^+$).

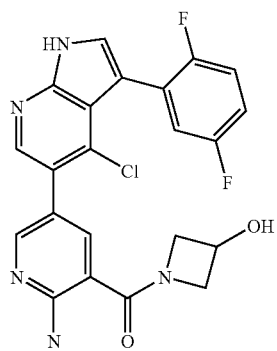

{2-Amino-5-[4-chloro-3-(2,5-difluoro-phenyl)-1H-pyrrolo[2,3-b]pyridin-5-yl]-pyridin-3-yl}-(3-hydroxy-azetidin-1-yl)-methanone
$^1$H NMR (500 MHz, DMSO-d6) δ 3.79-4.46 (m, 5 H), 5.74 (s, 1 H), 6.91 (s, 1 H), 7.22-7.27 (m, 1 H), 7.29-7.36 (m, 2 H), 7.67 (d, 1 H), 7.77 (s, 1 H), 8.14 (d, 1 H), 8.25 (s, 1 H). MS: m/z 456.1 (M + H$^+$).

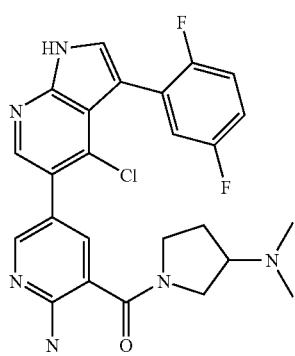

{2-Amino-5-[4-chloro-3-(2,5-difluoro-phenyl)-1H-pyrrolo[2,3-b]pyridin-5-yl]-pyridin-3-yl}-(3-dimethylamino-pyrrolidin-1-yl)-methanone
$^1$H NMR (500 MHz, DMSO-d6) δ 1.71 (m, 1 H), 2.0-2.16 (m, 7 H), 2.63 (m, 1 H), 3.21-3.70 (m, 5 H), 6.33-6.38 (d, 2 H), 7.22-7.35 (m, 3 H), 7.60-7.65 (d, 1 H), 7.76 (s, 1 H), 8.09 (d, 1 H), 8.25 (s, 1 H). MS: m/z 497.1 (M + H$^+$).

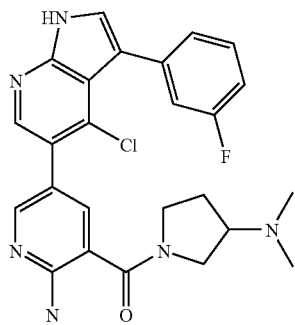

{2-Amino-5-[4-chloro-3-(3-fluoro-phenyl)-1H-pyrrolo[2,3-b]pyridin-5-yl]-pyridin-3-yl}-(3-dimethylamino-pyrrolidin-1-yl)-methanone
$^1$H NMR (500 MHz, DMSO-d6) δ 1.71 (m, 1 H), 2.0-2.16 (m, 7 H), 2.63-2.68 (m, 1 H), 3.21-3.71 (m, 4 H), 6.34 (d, 2 H), 7.14 (t, 1 H), 7.35 (t, 2 H), 7.42 (m, 1 H), 7.63-7.70 (d, 1 H), 7.74 (s, 1 H), 8.10 (d, 1 H), 8.24 (s, 1 H). MS: m/z 479.1 (M + H$^+$).

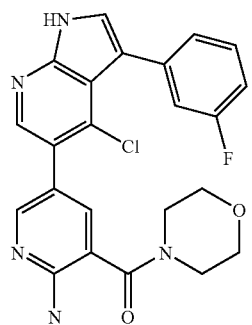

{2-Amino-5-[4-chloro-3-(3-fluoro-phenyl)-1H-pyrrolo[2,3-b]pyridin-5-yl]-pyridin-3-yl}-morpholin-4-yl-methanone
$^1$H NMR (500 Mhz, DMSO-d$_6$) δ 3.49 (s, 4 H), 3.61 (s, 4 H), 7.12-7.16 (t, 1 H), 7.31-7.36 (t, 2 H), 7.40-7.45 (m, 1 H), 7.54 (d, 1 H), 7.74 (s, 1 H), 8.12 (d, 1 H), 8.24 (s, 1 H). MS: m/z 452.1 (M + H$^+$).

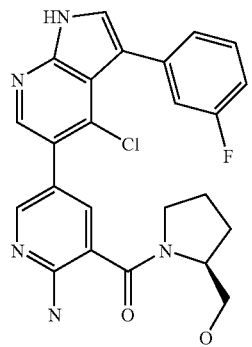

{2-Amino-5-[4-chloro-3-(3-fluoro-phenyl)-1H-pyrrolo[2,3-b]pyridin-5-yl]-pyridin-3-yl}-(2-hydroxymethyl-pyrrolidin-1-yl)-methanone
$^1$H NMR (500 MHz, DMSO-d6) δ 1.70 (s, 1 H), 1.89-1.97 (m, 4 H), 3.41-3.62 (m, 4 H), 4.15 (s, 1 H), 4.79 (s, 1 H), 6.28 (s, 2 H), 7.14 (t, 1 H), 7.31-7.36 (m, 2 H), 7.40-7.45 (m, 1 H), 7.64 (s, 1 H), 7.74 (s, 1 H), 8.10 (d, 1 H), 8.23 (s, 1 H). MS: m/z 466.1 (M + H$^+$).

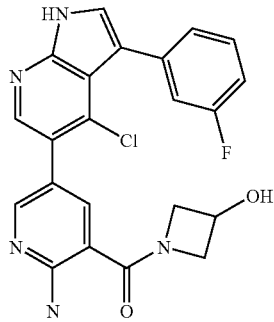

{2-Amino-5-[4-chloro-3-(3-fluoro-phenyl)-1H-pyrrolo[2,3-b]pyridin-5-yl]-pyridin-3-yl}-(3-hydroxy-azetidin-1-yl)-methanone
¹H NMR (500 MHz, DMSO-d6) δ 3.79-4.48 (m, 4 H), 5.73 (s, 1 H), 6.90 (s, 2 H), 7.14 (t, 1 H), 7.32-7.37 (t, 2 H), 7.40-7.45 (m, 1 H), 7.70 (d, 1 H), 7.74 (s, 1 H), 8.16 (d, 1 H), 8.23 (s, 1 H). MS: m/z 438.1 (M + H⁺).

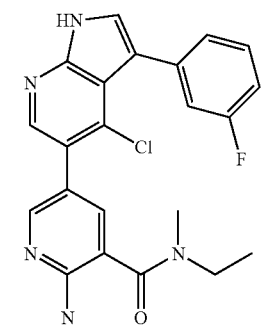

2-Amino-5-[4-chloro-3-(3-fluoro-phenyl)-1H-pyrrolo[2,3-b]pyridin-5-yl]-N-ethyl-N-methyl-nicotinamide
¹H NMR (500 MHz, DMSO-d6) δ 1.09 (s, 3 H), 2.94 (s, 3 H), 6.11 (s, 2 H), 7.14 (t, 1 H), 7.31-7.36 (t, 2 H), 7.40-7.44 (m, 1 H), 7.51 (s, 1 H), 7.74 (s, 1 H), 8.09 (d, 1 H), 8.33 (s, 1 H). MS: m/z 424.1 (M + H⁺).

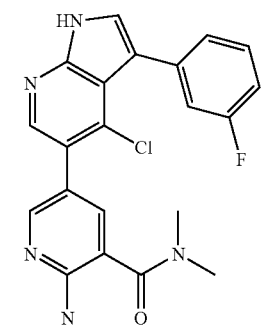

2-Amino-5-[4-chloro-3-(3-fluoro-phenyl)-1H-pyrrolo[2,3-b]pyridin-5-yl]-N,N-dimethyl-nicotinamide
¹H NMR (500 MHz, DMSO-d6) δ 2.96 (s, 6 H), 6.18 (s, 2 H), 7.14 (t, 1 H), 7.31-7.35 (t, 2 H), 7.36-7.44 (m, 1 H), 7.54 (d, 1 H), 7.74 (s, 1 H), 8.09 (d, 1 H), 8.23 (s, 1 H). MS: m/z 410.1 (M + H⁺).

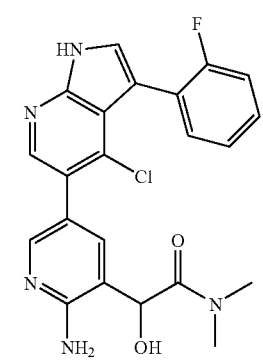

2-{2-Amino-5-[4-chloro-3-(2-fluoro-phenyl)-1-(2-trimethylsilanyl-ethoxymethyl)-1H-pyrrolo[2,3-b]pyridin-5-yl]-pyridin-3-yl}-2-hydroxy-N,N-dimethyl-acetamide.
¹H NMR (500 MHz, DMSO-d6) δ 5.39 (s, 1 H), 6.11 (br s, 2 H), 7.23 (br q, 2 H), 7.41 (m, 1 H), 7.44 (dt, 1 H), 7.48 (d, 1 H), 7.67 (s, 1 H), 7.96 (d, 1 H), 8.18 (s, 1 H). MS: m/z 440 (M + H⁺).

-continued

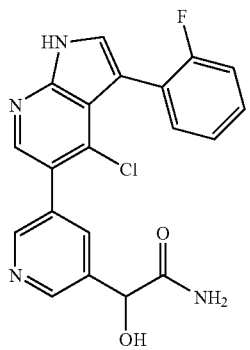

2-{5-[4-chloro-3-(2-fluoro-phenyl)-1H-pyrrolo[2,3-b]pyridin-5-yl]-pyridin-3-yl}-2-hydroxy-acetamide.
N-benzhydryl-2-(5-bromo-pyridin-3-yl)-2-hydroxy-acetamide was used as the starting material
Anisole was added to the deprotection reaction (1%)
$^1$H NMR (500 MHz, DMSO-d6) δ 5.0 (s, 1 H), 7.25 (q, 2 H), 7.30 (br d, 1 H), 7.41 (m, 1 H), 7.47 (m, 1 H), 7.55 (br d, 1 H), 7.75 (s, 1 H), 7.92 (br t, 1 H), 8.25 (s, 1 H), 8.57 (d, 1 H), 8.64 (d, 1 H). MS: m/z 397 (M + H$^+$).

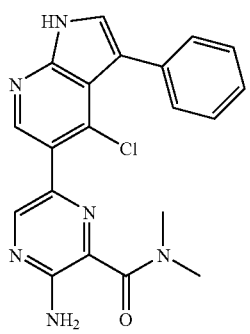

3-Amino-6-(4-chloro-3-phenyl-1H-pyrrolo[2,3-b]pyridin-5-yl)-pyrazine-2-carboxylic acid dimethylamide
$^1$H NMR (500 MHz, DMSO-d6) δ 3.02 (s, 6 H), 6.69 (s, 2 H), 7.32 (m, 1 H), 7.40 (m, 2 H), 7.51 (m, 2 H), 7.68 (s, 1 H), 8.32 (s, 1 H), 8.34 (s, 1 H), 12.38 (s, 1 H). MS: m/z 393.0 (M + H$^+$).

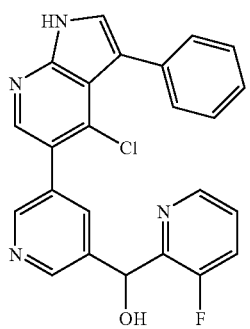

[5-(4-Chloro-3-phenyl-1H-pyrrolo[2,3-b]pyridin-5-yl)-pyridin-3-yl]-(3-fluoro-pyridin-2-yl)-methanol
$^1$H NMR (500 MHz, DMSO-d6) δ 6.15 (s, 1 H), 6.32 (s, 1 H), 7.32 (t, 1 H), 7.38-7.45 (m, 3 H), 7.50 (d, 2 H), 6.69-7.72 (m, 2 H), 7.95 (s, 1 H), 8.23 (s, 1 H), 8.40 (m, 2 H), 8.58 (d, 1 H), 8.62 (d, 1 H). MS: m/z 431.0 (M + H$^+$).

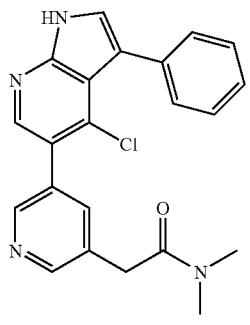

2-[5-(4-Chloro-3-phenyl-1H-pyrrolo[2,3-b]pyridin-5-yl)-pyridin-3-yl]-N,N-dimethyl-acetamide $^1$H NMR (500 MHz, DMSO-d6) δ 2.85 (m, 3 H), 3.07 (m, 3 H), 3.82 (m, 2 H), 7.26-7.33 (t, 1 H), 7.50-7.52 (d, 1 H), 7.71 (s, 1 H), 7.77 (m, 1 H), 8.45 (m, 2 H), 8.55 (d, 1 H), 12.40 (s, 1 H). MS: m/z 390.87 (M + H$^+$).

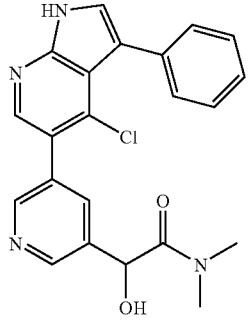

2-[5-(4-Chloro-3-phenyl-1H-pyrrolo[2,3-b]pyridin-5-yl)-pyridin-3-yl]-2-hydroxy-N,N-dimethyl-acetamide
$^1$H NMR (500 MHz, DMSO-d6) δ 3.02 (s, 6 H), 6.69 (s, 2 H), 7.30-7.33 (t, 1 H), 7.38-7.41 (t, 2 H), 7.50-7.52 (d, 2 H), 7.67 (s, 1 H), 8.32 (s, 1 H), 8.34 (s, 1 H), 12.40 (s, 1 H). MS: m/z 407.0 (M + H$^+$).

Method 47

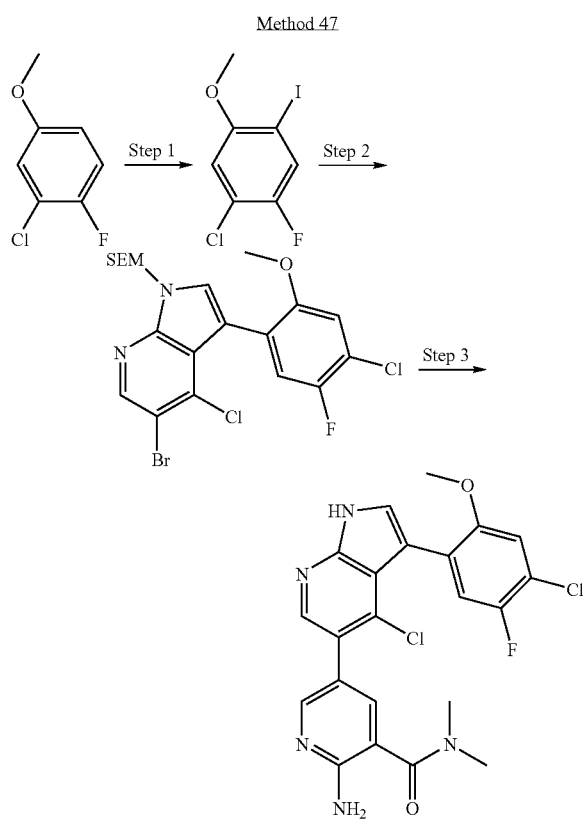

Synthesis of 2-amino-5-[4-chloro-5-fluoro-2-methoxy-phenyl)-1H-pyrrolo-[2,3,b]pyridine-5-yl]-N,N-dimethyl-nicotinamide Step 1: Synthesis of 1-chloro-2-fluoro-4-iodo-5-methoxy-benzene Silver trifluoroacetate (23.2 g, 105.0 mmol) was added to a solution of 2-chloro-1-fluoro-4-methoxy-benzene (5 g, 29.2 mmols) in chloroform (250 ml), followed by iodine (15.8 g, 62.2 mmol) in several portions. The mixture was stirred at room temperature for 2 hours and filtered through Celite. The filtrate was washed with water, brine, dried with Na₂SO₄, decanted, and concentrated to dryness. Silica chromatography of the crude using a gradient of ethyl acetate and hexane afforded 1-chloro-2-fluoro-4-iodo-5-methoxy-benzene (6.8 g, 81% yield). ¹H NMR (500 MHz, DMSO-d6) δ 3.83 (s, 3H), 7.22 (d, 1H), 7.88 (d, 1H).

Step 2: Synthesis of 5-bromo-4-chloro-3-(4-chloro-5-fluoro-2-methoxy-phenyl)-1-(2-trimethylsilanyl-ethoxymethyl)-1H-indole Isopropyl magnesium chloride/Li—Cl complex (20.4 ml, 20.6 mmol-14% in THF) was added dropwise to a solution of 1-chloro-2-fluoro-4-iodo-5-methoxy-benzene (2.9 g, 10.3 mmol) under nitrogen in THF at 40° C. The reaction was allowed to proceed at −40° C. for another 2 hours. Then 2-methoxy-4,4,5,5-tetramethyl-1,3,2-dioxaborane (4.2 ml, 25.8 mmol) in THF (20 ml) was added dropwise and the reaction was continued at −40° C. and then at room temperature overnight. The solvent was removed under vacuum. Silica chromatography of the crude using a gradient of ethyl acetate and hexane afforded 2-(4-chloro-5-fluoro-2-methoxy-phenyl)-4,4,5,5-tetramethyl-[1,3,2]dioxaborolane.

A mixture of 2-(4-chloro-5-fluoro-2-methoxy-phenyl)-4,4,5,5-tetramethyl-[1,3,2]dioxaborolane (0.3 g, 1.0 mmol), 5-bromo-4-chloro-3-iodo-1-(2-trimethylsilanyl-ethoxyethyl)-1H-pyrrolo[2,3b]pyridine (0.5 g, 1.0 mmol), and dichloro[1,1'-bis(diphenylphosphino)-ferrocene]palladium (II) dichloromethane adduct (43 mg, 0.05 mmol) in THF/Acetonitrile/saturated NaHCO₃ (5 ml/5 ml/5 ml) was stirred at 60° C. overnight. The mixture was allowed to cool down to room temperature and then extracted with ethyl acetate (2×). The combined organic layers were extracted with brine, dried with Na₂SO₄, decanted, and concentrated to dryness. Silica chromatography of the crude using a gradient of ethyl acetate and hexane afforded 5-bromo-4-chloro-3-(4-chloro-5-fluoro-2-methoxy-phenyl)-1-(2-trimethylsilanyl-ethoxymethyl)-1H-indole (0.3 g, 58% yield).

Step 3: Synthesis of 2-amino-5-[4-chloro-5-fluoro-2-methoxy-phenyl)-1H-pyrrolo-[2,3,b]pyridine-5-yl]-N,N-dimethyl-nicotinamide A mixture of 5-bromo-4-chloro-3-(4-chloro-5-fluoro-2-methoxy-phenyl)-1-(2-trimethylsilanyl-ethoxymethyl)-1H-indole (317 mg, 0.6 mmol), 2-amino-N,N-dimethyl-5-(4,4,5,5-tetramethyl-[1,3,2]dioxaborolan-2-yl-nicotinamide (523 mg, 1.8 mmol), dichloro[1,1'-bis(diphenylphosphino)ferrocene]palladium(II) dichloromethane adduct (25 mg, 0.03 mmol) in THF/Acetonitrile/saturated NaHCO₃ (5 ml/5 ml/5 ml) was stirred at 120° C. in the microwave for 20 minutes. The mixture was allowed to cool down to room temperature and then extracted with ethyl acetate (2×). The combined organic layers were extracted with brine, dried with Na₂SO₄, decanted, and concentrated to dryness. Silica chromatography of the crude using a gradient of ethyl acetate and hexane gave 2-amino-5-[4-chloro-3-(4-chloro-5-fluoro-2-methoxy-phenyl)-1-(2-trimethylsilanyl-ethoxymethyl)-1H-pyrrolo[2,3-b]pyridine-5-yl]-N,N-dimethyl-nicotinamide which was stirred in dichloromethane/trifluoroacetate acid (1 ml/1 ml) at room temperature for 2 hours. The solvents were removed under vacuum and the crude was stirred in dichloromethane/ethylenediamine (1 ml/1 ml) for 2 hours at room temperature. Again the solvents was removed under vacuum and the crude was dissolved in DMSO, filtered and purified by reverse phase HPLC, lyophilized afforded 2-amino-5-[4-chloro-3-(4-chloro-5-fluoro-2-methoxy-phenyl)-1H-pyrrolo[2,3-b]pyridine-5-yl]-N,N-dimethyl-nicotinamide (27 mg, 9% yield). ¹H NMR (500 MHz, DMSO-d6) δ 2.96 (s, 6H), 3.72 (s, 3H), 6.17 (s, 2H), 7.21 (d, 1H), 7.35 (d, 1H), 7.49 (d, 1H), 7.60 (s, 1H), 8.07 (d, 1H), 8.19 (s, 1H). MS: m/z 474.0 (M+H⁺).

Method 48

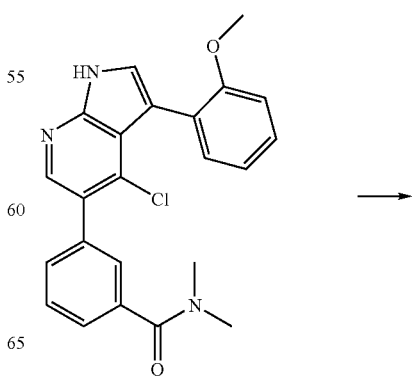

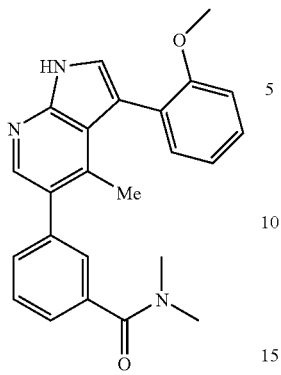

Synthesis of 3-[3-(2-Methoxy-phenyl)-4-methyl-1H-pyrrolo[2,3-b]pyridin-5-yl]-N,N-dimethyl-benzamide Into a 5 mL Personal Chemistry microwave reaction vial were added 3-[4-Chloro-3-(2-methoxy-phenyl)-1H-pyrrolo[2,3-b]pyridin-5-yl]-N,N-dimethyl-benzamide (37 mg, 0.09 mmol), trimethylboroxine (15 μL, 0.11 mmol), tetrakis(triphenylphosphine)palladium (7 mg, 0.009 mmol), potassium carbonate (52 mg, 0.27 mmol), and dioxane (1 mL). The vial was purged with nitrogen, sealed, and irradiated in a Personal Chemistry Optimizer at 140° C. for 60 min. The reaction mixture was diluted with ethylacetate, filtered over Celite and concentrated. The crude product was purified by mass triggered reverse phase HPLC to afford the title compound (2.4 mg, 0.006 mmol, 7% yield). $^1$H NMR (500 MHz, DMSO-d6) δ 11.74 (d, J=2 Hz, 1H), 8.32 (s, 1H), 8.04 (s, 1H), 7.50 (t, J=8 Hz, 1H), 7.41 (dt, $J_1$=9.5 Hz, $J_2$=1.5 Hz, 1H), 7.37 (dt, J=7.5 Hz, $J_2$=1.5 Hz, 1H), 7.33 (m, 4H), 7.26 (dd, $J_1$=7 Hz, $J_2$=2 Hz, 1H), 7.04 (d, J=7.5 Hz, 1H), 6.97 (td, J=7.5 Hz, $J_2$=1 Hz, 1H), 3.70 (s, 3H), 2.97 (bs, 3H), 2.93 (bs, 3H), 2.04 (s, 3H). MS: m/z 386.2 (M+H$^+$).

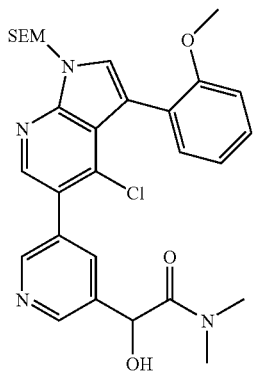

Synthesis of 2-{5-[4-Chloro-3-(2-methoxy-phenyl)-1-(2-trimethylsilanyl-ethoxymethyl)-1H-pyrrolo[2,3-b]pyridin-5-yl]-pyridin-3-yl}-2-hydroxy-N,N-dimethyl-acetamide 2-{5-[4-Chloro-3-(2-methoxy-phenyl)-1-(2-trimethylsilanyl-ethoxymethyl)-1H-pyrrolo[2,3-b]pyridin-5-yl]-pyridin-3-yl}-N,N-dimethyl-2-oxo-acetamide (57 mg, 0.129 mmol) was dissolved in methanol (7 mL), and hydrochloric acid solution was added (774 μL, 0.774 mmol, 1.0 M solution in water). The flask was purged with nitrogen gas before and after addition of Palladium hydroxide (1.8 mg, 0.013 mmol, 20 weight % on carbon, wet) The flask was purged with hydrogen gas and allowed to stir for 15 hours at 23° C. under 1 atm of hydrogen gas. The reaction mixture was filtered through Celite® and concentrated to afford 2-{5-[4-Chloro-3-(2-methoxy-phenyl)-1-(2-trimethylsilanyl-ethoxymethyl)-1H-pyrrolo[2,3-b]pyridin-5-yl]-pyridin-3-yl}-2-hydroxy-N,N-dimethyl-acetamide (79 mg, quantitative yield) as an orange-brown oil. MS [MH$^+$] m/z: 573.0

Method 49

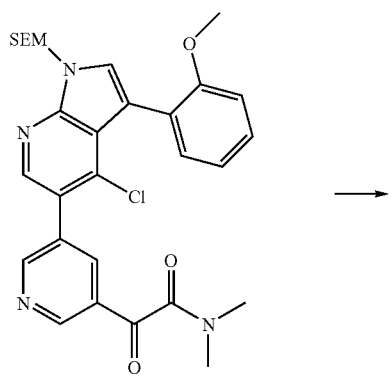

Method 50

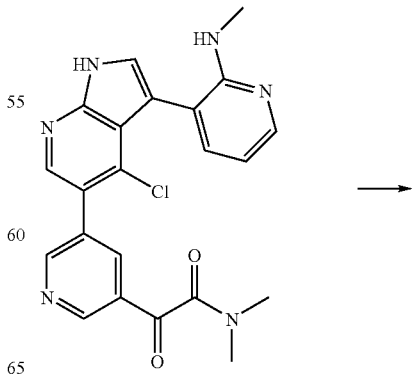

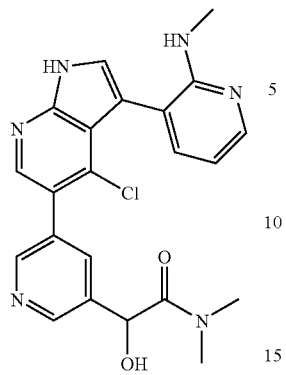

Synthesis of 2-{5-[4-chloro-3-(2-methylamino-pyridin-3-yl)-1H-pyrrolo[2,3-b]pyridin-5-yl]-pyridin-3-yl}-2-hydroxy-N,N-dimethyl-acetamide A mixture of 2-{5-[4-chloro-3-(2-methylamino-pyridin-3-yl)-1H-pyrrolo[2,3-b]pyridin-5-yl]-pyridin-3-yl}-N,N-dimethyl-2-oxo-acetamide (35 mg, 0.08 mmol), 9-BBN-dimer (98 mg, 0.4 mmol) in toluene (5 ml) was stirred at 60° C. overnight. The solvent was removed under vacuum and the crude was dissolved in DMSO, filtered and purified by reverse phase HPLC, lyophilized afforded 2-{5-[4-chloro-3-(2-methylamino-pyridin-3-yl)-1H-pyrrolo[2,3-b]-pyridin-5-yl]-pyridin-3-yl]-2-hydroxy-N,N-dimethyl-acetamide (18 mg, 50% yield). $^1$H NMR (500 MHz, DMSO-d6) δ 2.74 (d, 3H), 2.85 (s, 3H), 2.96 (s, 3H), 5.68 (m, 1H), 5.82 (s, 1H), 6.53 (d, 1H), 7.28 (d, 1H), 7.62 (s, 1H), 7.84 (m, 1H), 8.02 (d, 1H), 8.24 (s, 1H), 8.58 (m, 2H), 12.26 (s, 1H). MS: m/z 437.3 (M+H$^+$).

Method 51

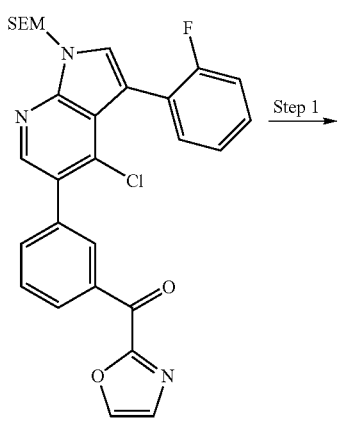

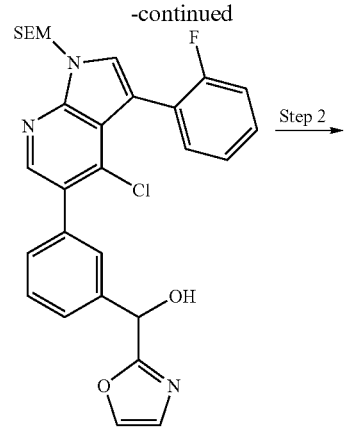

Step 1: Synthesis of {3-[4-chloro-3-(2-fluoro-phenyl)-1-(2-trimethylsilanyl-ethoxymethyl)-1H-pyrazolo[3,4-b]pyridin-5-yl]-phenyl}-oxazol-2-yl-methanol A solution of {3-[4-chloro-3-(2-fluoro-phenyl)-1-(2-trimethylsilanyl-ethoxymethyl)-1H-pyrrolo[2,3-b]pyridin-5-yl]-phenyl}-oxazol-2-yl-methanone (22 mg, 0.040 mmol) in MeOH (0.25 mL) was added to a cold suspension (0° C.) of NaBH$_4$ (1.59 mg, 0.042 mmol) in MeOH (0.25 mL). After 1 h, the mixture was quenched by addition of saturated ammonium chloride and the solution was concentrated to a solid. The residue was triturated with ethyl acetate to afford {3-[4-chloro-3-(2-fluoro-phenyl)-1-(2-trimethylsilanyl-ethoxymethyl)-1H-pyrrolo[2,3-b]pyridin-5-yl]-phenyl}-oxazol-2-yl-methanol (16 mg, 72.82%). MS: m/z 550 (M+H$^+$).

Step 2: Synthesis of {3-[4-chloro-3-(2-fluoro-phenyl)-1H-pyrrolo[2,3-b]pyridin-5-yl]-phenyl}-oxazol-2-yl-methanol {3-[4-Chloro-3-(2-fluoro-phenyl)-1-(2-trimethylsilanyl-ethoxymethyl)-1H-pyrrolo[2,3-b]pyridin-5-yl]-phenyl}-oxazol-2-yl-methanol (0.040 mmol) was treated with 1 mL neat TFA. After 1 h, the TFA was removed in vacuo. The residue was treated with ethylene diamine (0.5 mL) and THF (1 mL) for 20 min. The mixture was concentrated and purified by preparative LCMS to afford {3-[4-chloro-3-(2-fluoro-phenyl)-1H-pyrrolo[2,3-b]pyridin-5-yl]-phenyl}-oxazol-2-yl-methanol (2.7 mg, 16%) MS: m/z 420 (M+H$^+$). $^1$H NMR (500 MHz, DMSO-d6) δ 5.88 (d, 1H), 6.48 (d, 1H), 7.15 (d, 1H), 7.23 (m, 2H), 7.38-7.46 (m, 5H), 7.52 (br s, 1H), 7.71 (s, 1H), 8.04 (s, 1H), 8.19 (s, 1H).

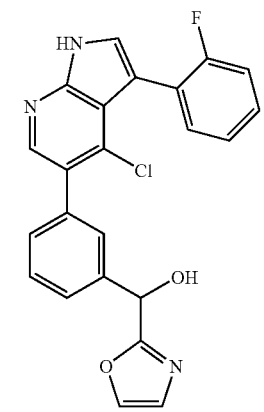

Other compounds synthesized using Method 51:

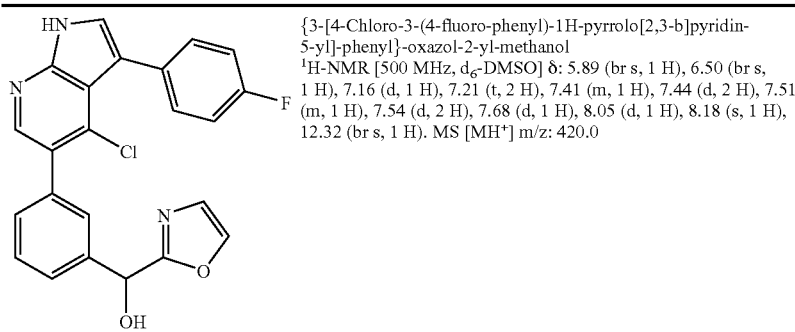

{3-[4-Chloro-3-(4-fluoro-phenyl)-1H-pyrrolo[2,3-b]pyridin-5-yl]-phenyl}-oxazol-2-yl-methanol
$^1$H-NMR [500 MHz, d$_6$-DMSO] δ: 5.89 (br s, 1 H), 6.50 (br s, 1 H), 7.16 (d, 1 H), 7.21 (t, 2 H), 7.41 (m, 1 H), 7.44 (d, 2 H), 7.51 (m, 1 H), 7.54 (d, 2 H), 7.68 (d, 1 H), 8.05 (d, 1 H), 8.18 (s, 1 H), 12.32 (br s, 1 H). MS [MH$^+$] m/z: 420.0

Method 52

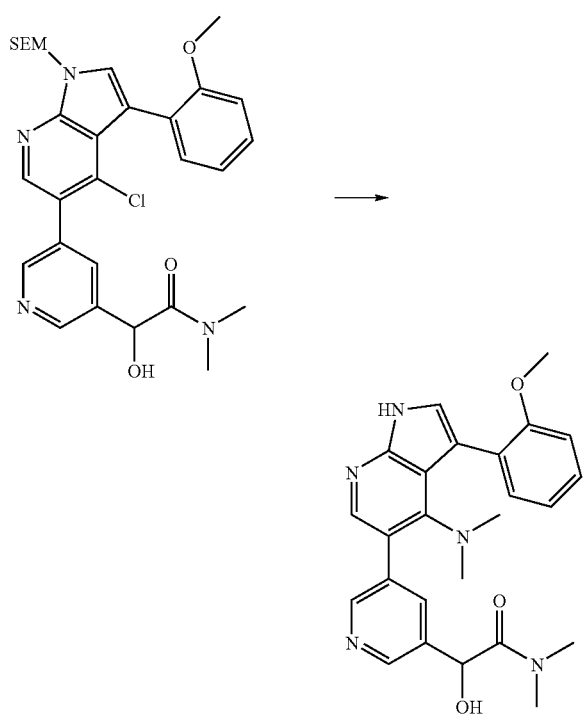

Synthesis of 2-{5-[4-Dimethylamino-3-(2-methoxy-phenyl)-1H-pyrrolo[2,3-b]pyridin-5-yl]-pyridin-3-yl}-2-hydroxy-N,N-dimethyl-acetamide 2-{5-[4-Chloro-3-(2-methoxy-phenyl)-1-(2-trimethylsilanyl-ethoxymethyl)-1H-pyrrolo[2,3-b]pyridin-5-yl]-pyridin-3-yl}-2-hydroxy-N,N-dimethyl-acetamide (18 mg, 0.317 mmol) was dissolved in a solution of dimethyl amine (2 mL, 17.7 mmol) and 1,4 dioxane (1 mL). The mixture was heated for at 150° C. for 15 hours in a sealed vessel and concentrated under in vacuo. To the residue were added O-(7-Azabenzotriazol-1-yl)-N,N,N',N'-tetramethyluronium hexafluorophosphate (14.5 mg, 0.0381 mmol), dimethylamine hydrochloride salt (12 mg, 0.147 mmol), N,N-dimethylformaldehyde and N,N-Diisopropylethylamine (33 μL, 0.317 mmol). After stirring at 23° C. for 1 hour, the mixture was concentrated. The crude product was dissolved in 1 mL TFA and stirred at 23° C. for 1 hour. The solvent was evaporated and the resulting oil was dissolved in 1 mL DMSO and 50 μL ethylenediamine and purified by mass triggered reverse phase HPLC to afford 2-{5-[4-Dimethylamino-3-(2-methoxy-phenyl)-1H-pyrrolo[2,3-b]pyridin-5-yl]-pyridin-3-yl}-2-hydroxy-N,N-dimethyl-acetamide (1.60 mg, 0.00359 mmol, 1.1% yield). $^1$H-NMR [500 MHz, d$_6$-DMSO] δ: 8.56 (d, 2H), 7.99 (s, 1H), 7.63 (s, 1H), 7.32 (m, 1H), 7.24 (dd, 1H), 7.04 (d, 1H), 6.97 (t, 1H), 5.57 (s, 1H) 3.68 (s, 4H), 2.95 (s, 4H), 2.82 (s, 3H), 2.18 (s, 6H); MS [MH$^+$] m/z: 446.

Other compounds synthesized using Method 52:

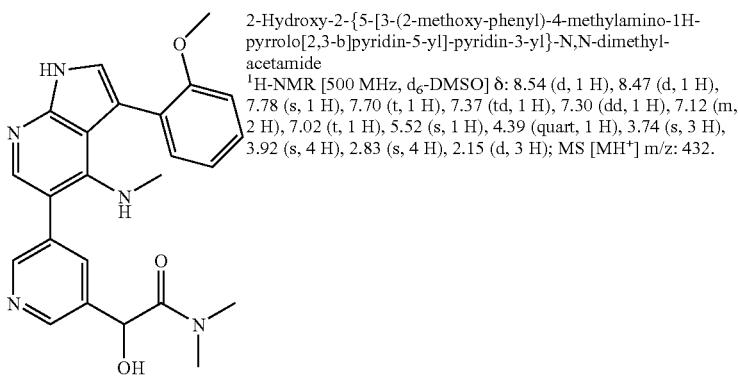

2-Hydroxy-2-{5-[3-(2-methoxy-phenyl)-4-methylamino-1H-pyrrolo[2,3-b]pyridin-5-yl]-pyridin-3-yl}-N,N-dimethyl-acetamide
$^1$H-NMR [500 MHz, d$_6$-DMSO] δ: 8.54 (d, 1 H), 8.47 (d, 1 H), 7.78 (s, 1 H), 7.70 (t, 1 H), 7.37 (td, 1 H), 7.30 (dd, 1 H), 7.12 (m, 2 H), 7.02 (t, 1 H), 5.52 (s, 1 H), 4.39 (quart, 1 H), 3.74 (s, 3 H), 3.92 (s, 4 H), 2.83 (s, 4 H), 2.15 (d, 3 H); MS [MH$^+$] m/z: 432.

Method 53

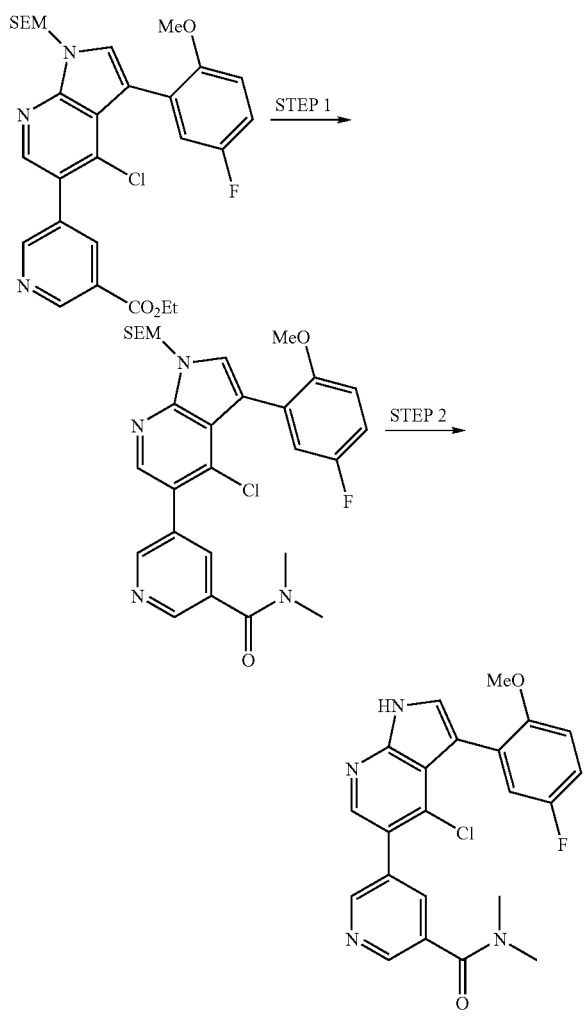

Synthesis of 5-[4-chloro-3-(5-fluoro-2-methoxy-phenyl)-1H-pyrrolo[2,3-b]pyridin-5-yl]-N,N-dimethyl-nicotinamide

Step 1: Synthesis of 5-[4-chloro-3-(5-fluoro-2-methoxy-phenyl)-1-(2-trimethylsilanyl-ethoxymethyl)-1H-pyrrolo[2,3-b]pyridin-5-yl]-N,N-dimethyl-nicotinamide 68 mg (0.12 mmol) of 5-[4-chloro-3-(5-fluoro-2-methoxy-phenyl)-1-(2-trimethylsilanyl-ethoxymethyl)-1H-pyrrolo[2,3-b]pyridin-5-yl]-nicotinic acid ethyl ester was dissolved in methanol and 100 μL of 50% w/v of potassium hydroxide in water was added. The resulting mixture was left at room temperature for 8 h. The mixture was adjusted to pH 3 by addition of 100 μL of concentrated aqueous hydrochloric acid and the solvent completely evaporated. The residue was dissolved in 50 mL of 50% v/v methanol in diethyl ether. The insoluble residue was filtered off and the filtrate evaporated. The resulting material was dissolved in 10 mL of 50% v/v acetonitrile in dichloromethane. 100 μL (0.57 mmol) of di-iso-propylethylamine was added, followed by 92 mg (0.24 mmol) of O-(7-azabenzotriazol-1-yl)-N,N,N',N'-tetramethyluronium hexafluorophosphate. The resulting suspension was sonicated until a homogeneous solution was obtained. 0.5 mL (1 mmol) of a 2 M solution of dimethylamine in anhydrous THF was added and the resulting mixture left at ambient temperature for 24 h. The resulting solution was distributed between dichloromethane and 10% w/v aqueous citric acid solution. The organic phase was dried over sodium sulfate and evaporated to afford 24 mg (45 μmol, 37%) of 5-[4-chloro-3-(5-fluoro-2-methoxy-phenyl)-1-(2-trimethylsilanyl-ethoxymethyl)-1H-pyrrolo[2,3-b]pyridin-5-yl]-N,N-dimethyl-nicotinamide. $^1$H-NMR [500 MHz, d$_6$-DMSO] δ: 8.75 (d, 1H), 8.71 (d, 1H), 8.27 (s, 1H), 7.89 (t, 1H), 7.42 (s, 1H), 7.27 (s, 1H), 7.09-7.03 (m, 2H), 6.86 (dd, 1H), 5.74 (s, 2H), 3.74 (s, 3H), 3.64 (t, 2H), 3.15 (s, 3H), 3.08 (s, 3H), 0.97 (t, 2H), −0.2 (s, 9H); MS [MH$^+$] m/z: 555.2.

Step 2: Synthesis of 5-[4-chloro-3-(5-fluoro-2-methoxy-phenyl)-1H-pyrrolo[2,3-b]pyridin-5-yl]-N,N-dimethyl-nicotinamide The material obtained was dissolved in a solution of 7% v/v trifluoroacetic acid in dichloromethane and left at ambient temperature for 24 h. The volatiles were removed and 150 μL (2.24 mmol) of ethylenediamine in dichloromethane was added. The resulting solution was left at ambient temperature for 24 h. The solvent was removed and the resulting residue purified by mass-triggered reverse-phase HPLC affording 8 mg (19 μmol, 16%) of 5-[4-chloro-3-(5-fluoro-2-methoxy-phenyl)-1H-pyrrolo[2,3-b]pyridin-5-yl]-N,N-dimethyl-nicotinamide as a colorless solid. $^1$H-NMR [500 MHz, d$_6$-DMSO] δ: 12.36 (s, br., 1H), 8.73 (d, 1H), 8.65 (d, 1H), 8.28 (s, 1H), 7.96 ((m), 1H), 7.64 (s, 1H), 7.19-7.13 (m, 2H), 7.02 (dd, 1H), 3.69 (s, 3H), 3.02 (s, 3H), 2.98 (s, 3H); MS [MH$^+$] m/z: 425.1.

Method 54

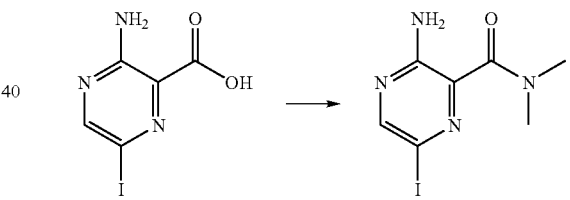

Synthesis of 3-amino-6-iodo-pyrazine-2-carboxylic acid dimethylamide 534 mg (2.02 mmol) of 3-amino-6-iodo-pyrazine-2-carboxylic acid were dissolved in 20 mL of 50% v/v acetonitrile in dichloromethane containing 350 μL (2.01 mmol) of di-iso-propyl-ethylamine. 818 mg (2.18 mmol) of N,N,N',N',-tetramethyl-O-(7-azabenzotriazol-1-yl)uronium hexafluorophosphate were added. Upon stirring for 3 minutes at ambient temperature 2.5 mL (5 mmol) of 2.0 M dimethylamine in anhydrous THF was added and stirring was continued for 23 h. The resulting solution was distributed between dichloromethane and 10% w/v aqueous citric acid solution. The organic phase was dried over sodium sulfate and evaporated. The resulting crude was purified by flash chromatography on silica gel using a gradient of ethyl acetate and hexanes to afford 363 mg (1.24 mmol, 62%) of 3-amino-6-iodo-pyrazine-2-carboxylic acid dimethylamide as a pale yellow crystalline solid. $^1$H-NMR [500 MHz, d$_6$-DMSO] δ: 8.25 (s, 1H), 6.71 (s, hr., 2H), 2.98 (s, 3H), 2.92 (s, 3H); MS [MH$^+$] m/z: 293.

Method 55

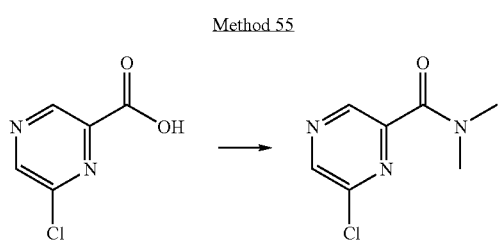

Synthesis of 6-chloro-pyrazine-2-carboxylic acid dimethylamide 1.000 g (6.31 mmol) of 6-chloro-pyrazine-2-carboxylic acid were dissolved in 75 mL of 50% v/v acetonitrile in dichloromethane containing. 2.810 g (7.48 mmol) of N,N,N',N'-tetramethyl-O-(7-azabenzotriazol-1-yl)uronium hexafluorophosphate were added, then 8.0 mL (16 mmol) of 2 M dimethylamine in anhydrous THF was added and stirring was continued for 18 h. The resulting solution was distributed between ethyl acetate and a 2 M aqueous solution of sodium carbonate. The organic phase was washed with brine, dried over sodium sulfate and evaporated. The resulting crude was purified by flash chromatography on silica gel using a gradient of ethyl acetate and hexanes to afford 695 mg (3.74 mmol, 59%) of 6-chloro-pyrazine-2-carboxylic acid dimethylamide as a pale yellow oil. $^1$H-NMR [500 MHz, $d_6$-DMSO] δ: 8.91 (s, 1H), 8.84 (s, 1H), 3.04 (s, 3H), 2.98 (s, 3H); MS [MH$^+$] m/z: 186.

Method 56

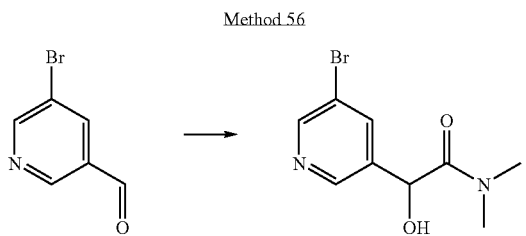

Synthesis of 2-(5-Bromo-pyridin-3-yl)-2-hydroxy-N,N-dimethyl-acetamide

5-Bromo-pyridine-3-carbaldehyde (10 g, 53 mmol) and zinc iodide (16.9 g, 53 mmol) were suspended in DCM (212 mL). Trimethylsilylcyanide (8.6 mL, 64 mmol) was added and the resulting mixture was stirred for 30 min at 23° C. The reaction mixture was concentrated and 10 mL concentrated HCl was added and the mixture was stirred at 80° C. for 1 h. The mixture was cooled and poured into 100 mL of water. The pH was adjusted to pH 3 with 4N potassium hydroxide and the resulting precipitate was filtered and washed with water and isopropanol to afford 10.2 g of a yellow solid.

Part of the solid (3.4 g) was suspended in 100 mL THF and 11 mL dimethylamine solution (2M in THF, 22 mmol), diisopropylethylamine (7.65 mL, 44 mmol), and O-(7-Azabenzotriazol-1-yl)-N,N,N',N'-tetramethyluronium hexafluorophosphate (6.6 g, 17.6 mmol) were added. The solution was stirred at 60° C. for 1 h. The solution was concentrated and redissolved in ethyl acetate and saturated sodium bicarbonate solution. The layers were separated and the aqueous layer was extracted with ethyl acetate. The combined organic fractions were washed with brine, dried over sodium sulfate and concentrated. The crude product was purified by cyano-modified silica gel chromatography using a gradient of ethyl acetate in hexanes to afford the title compound (1.39 g, 5.4 mmol, 30% yield). $^1$H NMR (500 MHz, DMSO-d6) δ 8.62 (d, J=2 Hz, 1H), 8.54 (d, J=2 Hz, 1H), 7.96 (t, J=2 Hz, 1H), 5.99 (d, J=7 Hz, 1H), 5.53 (d, J=7 Hz, 1H), 2.98 (s, 3H), 2.84 (s, 3H). MS: m/z 259.1 (M+H$^+$).

Method 57

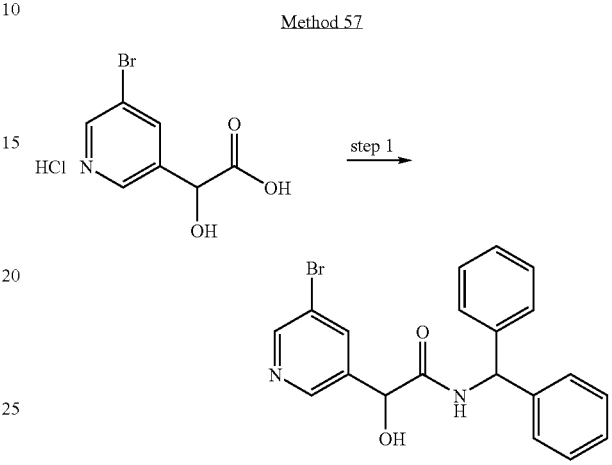

Step 1: Synthesis of N-benzhydryl-2-(5-bromo-pyridin-3-yl)-2-hydroxy-acetamide (5-Bromo-pyridin-3-yl)-hydroxy-acetic acid HCl salt (1.19 g, 4.47 mmol), diphenylmethylamine (1.3 g, 5.36 mmol), HOAT (2.0 g, 5.36 mmol) and DIEA (1.94 mL, 11.17 mmol) were all combined in THF (43.0 mL) and heated in a closed vial for 20 min at 60° C. The solution was diluted with ethyl acetate and washed with saturated sodium bicarbonate (1×) and brine (1×). The material was purified by silica gel chromatography using a gradient of hexanes and ethyl acetate (0-100%) to afford N-benzhydryl-2-(5-bromo-pyridin-3-yl)-2-hydroxy-acetamide (1.5 g, 73.5%) as a waxy white solid. MS: m/z 397 (M+H$^+$).

Method 58

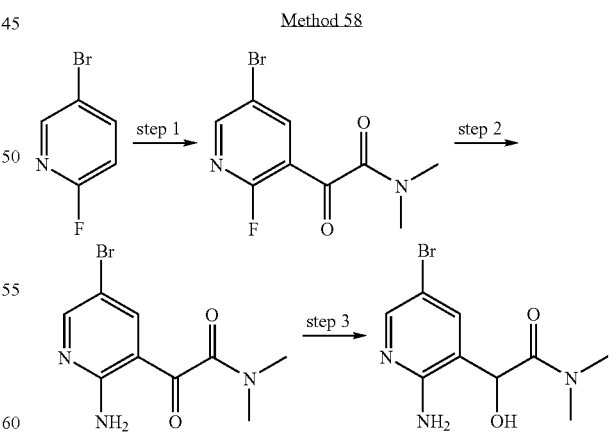

Step 1: Synthesis of 2-(5-bromo-2-fluoro-pyridin-3-yl)-N,N-dimethyl-2-oxo-acetamide 5-Bromo-2-fluoro-pyridine (1 g, 5.68 mmol) in THF (1 mL) was added dropwise to a freshly prepared solution of lithium N,N-diisopropylamide (6.81 mmol) in THF at −78° C. The mixture was stirred 2 h at −78° C. The orange suspension was quickly added via cannula to a cold (−78° C.) solution of N,N-dimethyl-oxalamic acid ethyl ester (925.6 uL 6.81 mmol). After 1.5 h at −78° C., the reaction was quenched by addition of saturated NH₄Cl solution and was allowed to warm to room temperature. The mixture was extracted with diethyl ether and the product was purified by silica gel chromatography using hexanes and ethyl acetate (0-100% gradient) to afford 2-(5-bromo-2-fluoro-pyridin-3-yl)-N,N-dimethyl-2-oxo-acetamide (1.01 g, 65.1%). ¹H NMR (500 MHz, DMSO-d6) δ 3.0 (d, 6H), 8.6 (dd, 1H), 8.78 (dd, 1H) MS: m/z 275 (M+H⁺).

Step 2: Synthesis of 2-(2-amino-5-bromo-pyridin-3-yl)-N,N-dimethyl-2-oxo-acetamide 2-(5-Bromo-2-fluoro-pyridin-3-yl)-N,N-dimethyl-2-oxo-acetamide (948 mg, 3.45 mmol) was treated with saturated ammonia solution in ethyl alcohol (10 mL) in a sealed vial at 50° C. for 1 h. The reaction was complete and the mixture was dried in vacuo and used crude in the next step. MS: m/z 272 (M+H⁺).

Step 3: Synthesis of 2-(2-amino-5-bromo-pyridin-3-yl)-2-hydroxy-N,N-dimethyl-acetamide Sodium borohydride (85.5 mg, 2.25 mmol) was added to methanol (5 mL) at 0° C. After 5 min, 2-(2-amino-5-bromo-pyridin-3-yl)-N,N-dimethyl-2-oxo-acetamide (408 mg, 1.50 mmol) in MeOH (15 mL) was added. After 1 h, the reaction was quenched by addition of saturated NH₄Cl and the mixture was concentrated in vacuo. The residue was extracted with ethyl acetate, dried over Na₂SO₄ and purified by silica gel chromatography using DCM and MeOH to afford 2-(2-amino-5-bromo-pyridin-3-yl)-2-hydroxy-N,N-dimethyl-acetamide (234 mg, 57.1%) as a brown oily solid. The material was used in the next step. MS: m/z 274 (M+H⁺).

Method 59

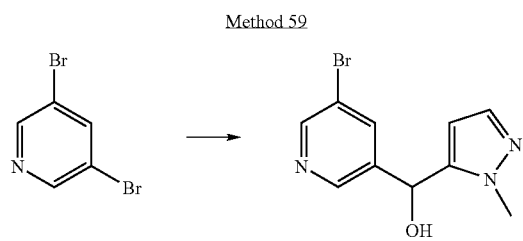

Synthesis of (5-bromo-pyridin-3-yl)-(2-methyl-2H-pyrazol-3-yl)-methanol

Commercial 3,5-dibromopyridine (500 mg, 2.10 mmol) was dissolved in 10 mL THF and cooled to 0° C. in an ice water bath. Commercial isopropylmagnesium chloride lithium chloride solution (1M, 2.1 mL) was added drop wise. After 20 min at 0° C., a solution of 2-methyl-2H-pyrazole-3-carbaldehyde (232 mg, 2.10 mmol) in 10 mL THF was added. A precipitate formed on addition of the aldehyde. After 1 hr, the reaction was quenched by addition of saturated aqueous ammonium chloride. The solution was extracted with diethyl ether (2×) and the combined organic layers were dried over Na₂SO₄, filtered and concentrated in vacuo to an oil. The crude (5-bromo-pyridin-3-yl)-(2-methyl-2H-pyrazol-3-yl)-methanol was used in the following reaction. MS: m/z 268 (M+H⁺).

Other compounds synthesized using Method 59:

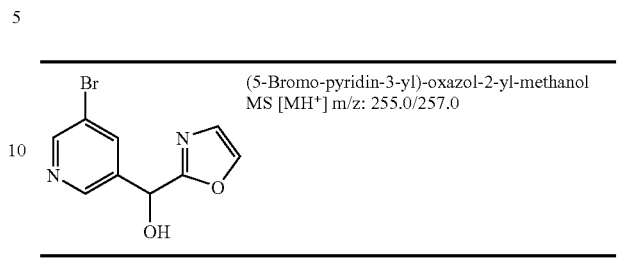

(5-Bromo-pyridin-3-yl)-oxazol-2-yl-methanol
MS [MH⁺] m/z: 255.0/257.0

Method 60

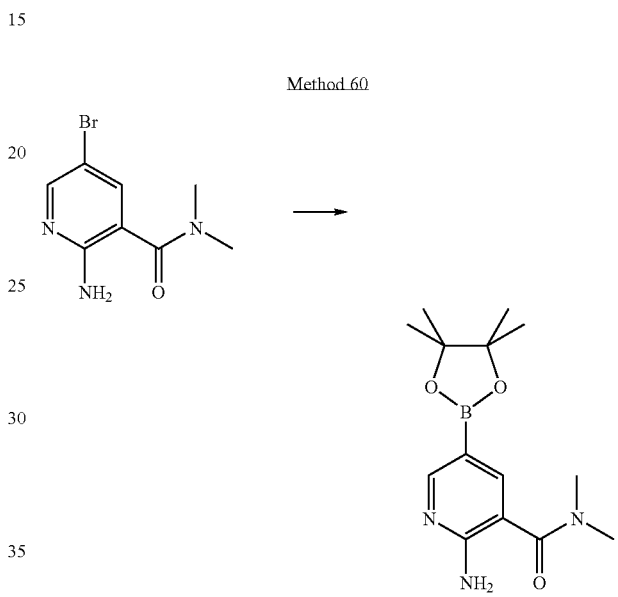

Synthesis of 2-Amino-N,N-dimethyl-5-(4,4,5,5-tetramethyl-[1,3,2]dioxaborolan-2-yl)-nicotinamide 2-Amino-5-bromo-N,N-dimethyl-nicotinamide (7.0 g, 28.6 mmol) was combined with bis(pinacolato)diboron (8.74 g, 34.4 mmol) bis(diphenylphosphino)ferrocenepalladium (II)-dichloride dichloromethane adduct (1.77 g, 1.43 mmol) and potassium acetate (8.42 g, 85.8 mmol) were combined in N,N-dimethylformaldehyde (56 mL) under nitrogen gas into four separate 20 mL microwave vials. The vials were purged with nitrogen, sealed, and irradiated in a Personal Chemistry Optimizer at 110° C. for 20 minutes. The reaction mixtures were concentrated in vacuo. The crude was sonicated in diethyl ether (300 mL) and resulting slurry was filtered over Celite®. The cake was rinsed with ethyl acetate (100 mL) followed by dichloromethane (200 mL). The fitrate obtained during the dichloromethane rinse was concentrated in vacuo to obtain 2-Amino-N,N-dimethyl-5-(4,4,5,5-tetramethyl-[1,3,2]dioxaborolan-2-yl)-nicotinamide (5.39 g, 18.5 mmol, 65% yield) as a brown-black powder. ¹H-NMR [500 MHz, d₆-DMSO] δ: 8.21 (s, 1H), 7.47 (s, 1H), 6.39 (s, 2H), 2.788 (s, 6H), 1.25 (s, 13H); MS [MH⁺] m/z: 210.

Example 2

Bioassays

Kinase assays known to those of skill in the art may be used to assay the inhibitory activities of the compounds and compositions of the present invention. Kinase assays include, but are not limited to, the following examples.

Although the first of these examples uses the kinase domain of a mutant form of Abl T315I ("Abl T315I KD"), the kinase assays may use various forms of mutant and wild type enzymes, including, for example, the entire protein, the kinase domain, or a portion thereof (e.g. Abl Y393F). The kinases used in the assays may also be of varying phosphorylation states. In the c-Abl example, a mutant kinase at a zero phosphorylation state was used.

c-Abl Pyruvate Kinase/Lactate Dehydrogenase Coupled Enzyme Assay

In the c-Abl Pyruvate Kinase (PK)/Lactate Dehydrogenase (LDH) Coupled Assay the protein kinase dependant phosphorylation of a substrate peptide was coupled to the oxidation of NADH. The oxidation of NADH to NAD+ was detected by monitoring a decrease in absorbance at 340 nm.

Materials: Abl substrate peptide=EAIYAAPFAKKK-OH (SEQ ID NO: 1) (Biopeptide, San Diego, Calif.); □NADH (Sigma Cat#N-8129, FW=709.4); 2M $MgCl_2$; 1M HEPES buffer, pH 7.5; Phosphoenolpyruvate (PEP) (Sigma Cat#P-7002, FW=234); Lactate dehydrogenase (LDH) (Worthington Biochemical Cat#2756); Pyruvate Kinase (PK) (Sigma Cat#P-9136); ATP (Sigma Cat#A-3377, FW=551); Greiner 384-well UV star plate; and purified and unphosphorylated T315I Abl kinase domain.

Stock Solutions: 10 mM NADH (7.09 mg/ml in $miliQH_2O$) made fresh daily; 10 mM Abl substrate peptide (13.4 mg/ml in $miliQH_2O$) stored at −20° C.; 100 mM HEPES buffer, pH 7.5 (5 ml 1M stock+45 ml $miliQH_2O$); 100mM $MgCl_2$ (5 ml 2M $MgCl_2$+95 ml $dH_2O$); 100 mM PEP (23.4 mg/ml in $dH_2O$) stored at −20° C.; 10mM ATP (5.51 mg/ml in $dH_2O$) stored at −20° C. (diluted 50 µl into total of 10 ml $miliQH_2O$ daily=50 µM ATP working stock); 1000 U/ml PK (U/mg varies with lot) flash-frozen under liquid $N_2$ and stored at −80° C.; and 1000 U/ml LDH (U/mg varies with lot) flash-frozen under liquid $N_2$ and stored at −80° C.

Standard Assay Setup for 384-well format (50 µl reaction): 300 µM NADH; 10 mM $MgCl_2$; 2 mM PEP; 45 U/ml PK; 60 U/ml LDH; 200 µM Abl substrate peptide; 2.5 µl test compound (in DMSO); 2 µg/ml Abl kinase domain; 10 µM ATP; 100 mM HEPES buffer. Positive controls contained DMSO with no test compound. Negative controls contained 5 µl of 0.5M EDTA (50 mM in the assay). The dephosphorylated form of the c-Abl T315I mutant was used in the biochemical screening assays. The kinase reaction was initiated at time t=0 by the addition of ATP.

Activity was measured by following the time-dependent loss of NADH by absorbance spectroscopy at 340 nm. The linear portion of the resulting progress curve was then analyzed by linear regression to get the activity in absorbance units/time, reported as the slope of that best fit line (moles/unit time can be calculated from using molar extinction coefficient for NADH at 340 nm, $6250 M^{-1} cm^{-1}$).

Screening data was evaluated using the equation: $Z'=1-[3*(\sigma_+ + \sigma_-)/|\mu_+ - \mu_-|]$ (Zhang, et al., 1999 J Biomol Screening 4(2) 67-73), where µ denotes the mean and σ the standard deviation. The subscript designates positive or negative controls. The Z' score for a robust screening assay should be ≧0.50. The typical threshold=$\mu_+ - 3*\sigma_+$. Any value that falls below the threshold was designated a "hit".

Dose response was analyzed using the equation: $y = min + \{(max-min)/(1+10^{[compound]-logIC50})\}$, where y is the observed initial slope, max=the slope in the absence of inhibitor, min=the slope at infinite inhibitor, and the $IC_{50}$ is the [compound] that corresponds to ½ the total observed amplitude (Amplitude=max−min).

To measure modulation, activation, or inhibition of Abl KD, a test compound was added to the assay at a range of concentrations. Inhibitors may inhibit Abl KD activity at an $IC_{50}$ in the micromolar range, the nanomolar range, or, for example, in the subnanomolar range.

Additional Kinase Assays

In addition to the c-Abl PK/LDH coupled assay (above), homogeneous luminescence-based inhibitor screening assays were developed for c-Abl, MET, AurA, and PDK1 kinases (among others). Each of these assays made use of an ATP depletion assay (Kinase-Glo™, Promega Corporation, Madison, Wis.) to quantitate kinase activity. The Kinase-Glo™ format uses a thermostable luciferase to generate luminescent signal from ATP remaining in solution following the kinase reaction. The luminescent signal is inversely correlated with the amount of kinase activity.

cAbl Luminescence-Based Enzyme Assay

Materials: Abl substrate peptide=EAIYAAPFAKKK-OH (SEQ ID NO: 1) (Biopeptide, San Diego, Calif.), ATP (Sigma Cat#A-3377, FW=551), HEPES buffer, pH 7.5, Bovine serum albumin (BSA) (Roche 92423420), $MgCl_2$, Staurosporine (*Streptomyces* sp. Sigma Cat#85660-1MG), white Costar 384-well flat-bottom plate (VWR Cat#29444-088), Abl kinase (see below), Kinase-Glo™ (Promega Cat#V6712).

Stock Solutions: 10 mM Abl substrate peptide (13.4 mg/ml in $miliQH_2O$) stored at −20° C.; 100 mM HEPES buffer, pH 7.5 (5 ml 1M stock+45 ml $miliQH_2O$); 10 mM ATP (5.51 mg/ml in $dH_2O$) stored at −20° C. (diluted 50 µl into total of 10 ml $miliQH_2O$ daily=50 µM ATP working stock); 1% BSA (1 g BSA in 100 ml 0.1 M HEPES, pH 7.5, stored at −20° C.), 100 mM $MgCl_2$; 200 µM Staurosporine, 2× Kinase-Glom reagent (made fresh or stored at −20° C.).

Standard Assay Setup for 384-well format (20 µl kinase reaction, 40 µl detection reaction): 10 mM $MgCl_2$; 100 µM Abl substrate peptide; 0.1% BSA; 1 µl test compound (in DMSO); 0.4 µg/ml Abl kinase domain; 10 µM ATP; 100 mM HEPES buffer. Positive controls contained DMSO with no test compound. Negative controls contained 10 µM staurosporine. The kinase reactions were initiated at time t=0 by the addition of ATP.ABl Kinase reactions were incubated at 21° C. for 30 min, then 20 µl of Kinase-Glo™ reagent were added to each well to quench the kinase reaction and initiate the luminescence reaction. After a 20 min incubation at 21° C., the luminescence was detected in a plate-reading luminometer.

Protein Kinase Expression

An open-reading frame for c-Abl was amplified from a *Mus musculus* (mouse) cDNA library prepared from freshly harvested mouse liver using a commercially available kit (Invitrogen) by PCR using the following primers:

```
Forward primer: GACAAGTGGGAAATGGAGC  (SEQ ID NO: 2)

Reverse primer: CGCCTCGTTTCCCCAGCTC. (SEQ ID NO: 3)
```

The PCR product (846 base pairs expected) was purified from the PCR reaction mixture using a PCR cleanup kit (Qiagen). The purified DNA was ligated for 5 minutes at room temperature with topoisomerase into pSGX3-TOPO. The vector pSGX3-TOPO is a topoisomerase-activated, modified version of pET26b (Novagen, Madison, Wis.) wherein the following sequence has been inserted into the NdeI site: CATATGTCCCTT (SEQ ID NO: 4) and the following sequence inserted into the BamnHI site: AAGGGCATCATCACCATCACCACTGATCC (SEQ ID NO: 5). The sequence of the resulting plasmid, from the Shine-Dalgarno sequence through the stop site and the BamHI, site is as follows: AAGGAGGA GATATACATAT-GTC CCTT (SEQ ID NO: 6) [ORF]AAGGGCATCAT CAC-CATCACCACTGATCC (SEQ ID NO: 7). The c-Abl expressed using this vector had three amino acids added to its N-terminus (Met Ser Leu) and 8 amino acids added to its C-terminus (GluGlyHisHisHisHisHisHis) (SEQ ID NO: 8).

A c-Abl/phosphatase co expression plasmid was then created by subcloning the phosphatase from the Aurora co-expression plasmid of Example 1 into the above plasmid. Both the Aurora co-expression plasmid and the Abl non-co-expression plasmid were digested 3 hrs with restriction enzymes EcoRI and NotI. The DNA fragments were gel purified and the phosphatase gene from the Aurora plasmid was ligated with the digested c-Abl plasmid for 8 h at 16° C. and transformed into Top10 cells. The presence of the phosphatase gene in the resulting construct was confirmed by restriction digestion analysis.

This plasmid codes for c-Abl and lambda phosphatase co expression. It has the additional advantage of two unique restriction sites, XbaI and NdeI, upstream of the target gene that can be used for subcloning of other target proteins into this phosphatase co-expressing plasmid.

The plasmid for Abl T315I was prepared by modifying the Abl plasmid using the Quick Change mutagenesis kit (Stratagene) with the manufacturer's suggested procedure and the following oligonucleotides:

```
Mm05582dS4
                                     (SEQ ID NO: 9)
5'-CCACCATTCTACATAATCATTGAGTTCATGACCTATGGG-3'

Mm05582dA4
                                     (SEQ ID NO: 10)
5'-CCCATAGGTCATGAACTCAATGATTATGTAGAATGGTGG-3'.
```

Protein from the phosphatase co-expression plasmids was purified as follows. The non-co-expression plasmid was transformed into chemically competent BL21 (DE3)Codon+ RIL (Stratagene) cells and the co-expression plasmid was transformed into BL21(DE3) pSA0145 (a strain that expresses the lytic genes of lambda phage and lyses upon freezing and thawing (Crabtree S, Cronan J E Jr. J Bacteriol 1984 April; 158(1):354-6)) and plated onto petri dishes containing LB agar with kanamycin. Isolated single colonies were grown to mid-log phase and stored at −80° C. in LB containing 15% glycerol. This glycerol stock was streaked on LB agar plates with kanamycin and a single colony was used to inoculate 10 ml cultures of LB with kanamycin and chloramphenicol, which was incubated at 30° C. overnight with shaking. This culture was used to inoculate a 2 L flask containing 500 ml of LB with kanamycin and chloramphenicol, which was grown to mind-log phase at 37° C. and induced by the addition of IPTG to 0.5 mM final concentration. After induction flasks were incubated at 21° C. for 18 h with shaking.

The c-Abl T315I KD (kinase domain) was purified as follows. Cells were collected by centrifugation, lysed in diluted cracking buffer (50 mM Tris HCl, pH 7.5, 500mM KCl, 0.1% Tween 20, 20 mM Imidazole, with sonication, and centrifuged to remove cell debris. The soluble fraction was purified over an IMAC column charged with nickel (Pharmacia, Uppsala, Sweden), and eluted under native conditions with a gradient of 20 mM to 500 mM imidazole in 50 mM Tris, pH7.8, 500mM NaCl, 10mM methionine, 10% glycerol.

The protein was then further purified by gel filtration using a Superdex 75 preparative grade column equilibrated in GF5 buffer (10 mM HEPES, pH7.5, 10 mM methionine, 500mM NaCl, 5 mM DTT, and 10% glycerol). Fractions containing the purified c-Abl T315I KD kinase domain were pooled. The protein obtained was 98% pure as judged by electrophoresis on SDS polyacrylamide gels. Mass spectroscopic analysis of the purified protein showed that it was predominantly singly phosphorylated. The protein was then dephosphorylated with Shrimp Alkaline Phosphatase (MBI Fermentas, Burlington, Canada) under the following conditions: 100 U Shrimp Alkaline Phosphatase/mg of c-Abl T315I KD, 100 mM $MgCl_2$, and 250mM additional NaCl. The reaction was run overnight at 23° C. The protein was determined to be unphosphorylated by Mass spectroscopic analysis. Any precipitate was spun out and the soluble fraction was separated from reactants by gel filtration using a Superdex 75 preparative grade column equilibrated in GF4 buffer (10 mM HEPES, pH7.5, 10 mM methionine, 150 mM NaCl, 5 mM DTT, and 10% glycerol).

Example 3

Cell Assays

MV4-11 and THP cells were maintained in Iscove's Modified Dulbecco's Medium supplemented with 10% fetal bovine serum (FBS) and penicillin/streptomycin, Ba/F3 cells were maintained in RPMI 1640 supplemented with 10% FBS, penicillin/streptomycin and 5 ng/ml recombinant mouse IL-3.

Cell Survival Assays

Compounds were tested in the following assays in duplicate.

96-well XTT assay: Cells (e.g. BaF3 315I, M351I, or E255K cells) were grown in growth media containing various concentrations of compounds (duplicates) on a 96-well plate for 72 hours at 37° C. The starting cell number was 5000-8000 cells per well and volume was 120 µl. At the end of the 72-hour incubation, 40 µl of XTT labeling mixture (50:1 solution of sodium 3'-[1-(phenylamino-carbonyl)-3,4-tetrazolium]-bis(4-methoxy-6-nitro) benzene sulfonic acid hydrate and Electron-coupling reagent: PMS (N-methyl dibenzopyrazine methyl sulfate) were added to each well of the plate. After an additional 2-6 hours of incubation at 37° C., the absorbance reading at 405 nm with background correction at 650 nm was measured with a spectrophotometer.

384-well AlamarBlue assay: 90 µl of cell suspension were plated onto each well of a 384-well plate preprinted with 0.5 µl of compound in DMSO or DMSO only. The starting cell number was 4000 cells per well. After a 72-hour incubation, 10 µl of AlamarBlue solution (440 µM resazurin in PBS) were then added to each well of the plate. After an additional 2-hour incubation at 37° C., fluorescence was measured using a TECAN plate reading fluorometer with excitation at 535 nm and emission at 591 nm.

BCR-ABL Phospho-ELISA Assay

The following table shows the reagents that were typically used in the BCR-ABL phospho-ELISA ("P-ELISA") assay.

TABLE 76

BCR-ABL phospho-ELISA(p-ELISA) Typical Reagent List

| Description | Vendor | Catalog # |
|---|---|---|
| RPMI 1640 | Invitrogen | 11875-135 |
| 10% Fetal Bovine Serum, characterized, heat inactivated | VWR | 16777-014 |
| Human Plasma, Anticoagulant = EDTA | Bioreclamation Inc. | HMPLEDTA |
| c-Abl (Ab-3) monoclonal antibody | VWR | 80001-286 |
| Recombinant Mouse Interleukin-3 | Chemicon | IL015 |
| Adhesive Plate Seals | | |

TABLE 76-continued

BCR-ABL phospho-ELISA(p-ELISA) Typical Reagent List

| Description | Vendor | Catalog # |
|---|---|---|
| 96well PP 325 µl round bottom plate w/ lid TC | Thompson Instrument Co | 932465 |
| 96well Nunc Maxisorp plate (for colorimetric assay) | Fisher Scientific | 12-565-136 |
| 96well white flat-bottom plate (for luminescent assay) | Matrix | 4923 |
| Lysis buffer components | | |
| Tris-Cl pH7.4 (20 mM) | | |
| NP-40 (1%) | | |
| EDTA (5 mM) | | |
| Sodium pyrophosphate (NaPP; 5 mM) | | |
| NaF (5 mM) | | |
| NaCl (150 mM) | | |
| Protease Inhibitor Cocktail | Sigma | P2714 |
| PMSF (1 mM) | | |
| Sodium vanadate (NaVO$_4$; 2 mM) | | |
| PBS, ice cold | | |
| Anti-Phosphotyrosine (4G10 ™), HRP conjugate or unconjugated | Upstate | 16-105 or 05-321 |
| Goat Anti-Mouse IgG, HRP conjugate (if unconjugated 4G10 is used) | Upstate | 12-349 |
| BD OptEIA Reagent Set B | BD Biosciences | 550534 |
| Coating Buffer (0.1M Na-carbonate, pH 9.5) | | |
| Assay Diluent | | |
| Wash buffer (.05% Tween/PBS) | | |
| Stop Solution (2N sulfuric acid) | | |
| Substrate Reagents A&B | | |
| SuperSignal ELISA Pico Chemiluminescent Substrate (may be used instead of Substrate Reagents A&B) | Pierce | 37070 |

Cells (Ba/F$_3$ cells transfected with WT BCR-ABL, other kinases, or T315I, Y253F, M351T, E255K, or other mutant forms of BCR-ABL) were grown in the absence of IL-3 at least ½ week before the assay. The day before assay, the cells were fed with fresh media so that at the time of assay the cells were in log phase. Ba/F3 cells that had been grown in the absence of IL-3 for at least ½ week were resuspended in RPMI 1640 so that each well of a 96-well plate would contain approximately 200,000 cells. Cells were distributed in a 96-well plate containing serially diluted concentrations of test compounds. Cells were typically incubated with or without test compounds for 60-120 minutes at 5% $CO_2$, 37° C. The incubation was performed with or without other additives such as 10% FCS or 50% human plasma. After incubation of compounds, lysis buffer was added and incubated for 10-15 minutes; the lysate was cleared by centrifugation.

To make the ELISA plate, commercially available Anti-ABL antibodies (e.g. (Ab-3, Calbiochem OP20) were prepared at a concentration of 0.125 µg/ml in coating buffer (0.1M Na-carbonate, pH 9.5), and plated at 10 ml per plate (12.5 µl 100 µg/ml Ab/10 ml). In a high binding multi-well plate, 100 µl Ab in coating buffer were added to each well, and each plate was covered with a plate seal and incubated overnight at 4° C.

Excess antibody was removed and the ELISA plate was washed 3-4 times with 200 µl of wash buffer (0.05% Tween in PBS, pH 7.4). 150 µl of lysate (see above) were transferred to the ELISA plate. Plates were sealed and incubated 2 hours at room temperature. The detection antibody (e.g. HRP conjugated anti-pTyr or unconjugated □p-Y 4G10, Upstate) was prepared in assay diluent. The antibody was diluted 1:1000 (stock=2 µg/µl, 200 µg in 100 µl; f.c.=2 µg/ml) in assay diluent and 10 ml of diluted antibody per plate were added. The lysate was removed from the ELISA plates, and wells were washed four times with 200 µl of wash buffer per well. 100 µl of detection antibody was added to each well; the plate was covered, and incubated 1 hr at room temperature (21° C.). Excess detection antibody was removed from the ELISA plates, and the wells were washed four times with 200 µl of wash buffer per well.

If necessary, (i.e. for unconjugated anti-pTyr antibody) secondary antibody (goat anti-rabbit HRP) was diluted 1:3000 in assay diluent (3.33 µl per 10 ml diluent) and added at 10 ml of diluted antibody per plate. Excess secondary antibody was removed from the ELISA plate, and the plate was washed four times with 200 µl per well of wash buffer.

Substrate Reagent A and Substrate Reagent B (Pierce Cat#37070 SuperSignal ELISA Pico Chemiluminescent Substrate) were added immediately before use (10 ml resultant solution per plate). 100 µl substrate were added per well, mixed for 1 minute, and chemiluminescent signal was measured with a luminometer.

The biological activity of compounds prepared by the methods described herein and evaluated as described above is shown in the Table below. Ranges for $IC_{50}$ determinations given in the Table—A: >1.0 µM; B: 1.0-0.1 µM; C: 0.1-0.01 µM; D: <0.01 µM; ND: not determined.

| Name | ABL_T315I_0P (IC50) | CELL BIO ABL P210WT BAF3 XTT (IC50) | CELL BIO ABL T315I BAF3 XTT (IC50) |
|---|---|---|---|
| 3-[4-Chloro-3-(2-methoxy-phenyl)-1H-pyrrolo[2,3-b]pyridin-5-yl]-N,N-dimethyl-benzamide | D | C | C |

| Name | ABL_T315I_0P (IC50) | CELL BIO ABL P210WT BAF3 XTT (IC50) | CELL BIO ABL T315I BAF3 XTT (IC50) |
|---|---|---|---|
| 2-Amino-5-[4-chloro-3-(2-methoxy-phenyl)-1H-pyrrolo[2,3-b]pyridin-5-yl]-N,N-dimethyl-benzamide | D | D | D |
| 3-[3-(2-Methoxy-phenyl)-4-methyl-1H-pyrrolo[2,3-b]pyridin-5-yl]-N,N-dimethyl-benzamide | D | C | C |
| 2-{5-[4-Chloro-3-(2-methoxy-phenyl)-1H-pyrrolo[2,3-b]pyridin-5-yl]-pyridin-3-yl}-2-hydroxy-N,N-dimethyl-acetamide | D | D | D |
| 3-amino-6-[4-chloro-3-(4-fluoro-phenyl)-1H-pyrrolo[2,3-b]pyridin-5-yl]-pyrazine-2-carboxylic acid dimethylamide | C | B | B |
| 2-{5-[4-Chloro-3-(4-fluoro-phenyl)-1H-pyrrolo[2,3-b]pyridin-5-yl]-pyridin-3-yl}-2-hydroxy-N,N-dimethyl-acetamide | C | B | A |
| 5-[4-Chloro-3-(4-fluoro-phenyl)-1H-pyrrolo[2,3-b]pyridin-5-yl]-N,N-dimethyl-nicotinamide | C | B | A |
| 5-[4-Chloro-3-(5-fluoro-2-methoxy-phenyl)-1H-pyrrolo[2,3-b]pyridin-5-yl]-N,N-dimethyl-nicotinamide | D | D | C |
| {3-[4-Chloro-3-(4-fluoro-phenyl)-1H-pyrrolo[2,3-b]pyridin-5-yl]-phenyl}-oxazol-2-yl-methanol | C | A | A |
| 2-{5-[4-Chloro-3-(4-fluoro-phenyl)-1H-pyrrolo[2,3-b]pyridin-5-yl]-pyridin-3-yl}-N,N-dimethyl-2-oxo-acetamide | B | ND | ND |
| 5-Bromo-3-iodo-4-methylsulfanyl-1H-pyrrolo[2,3-b]pyridine | A | ND | ND |
| 5-Bromo-2H,7H-6-oxa-2,3-diaza-dibenzo[cd,h]azulene | A | ND | ND |
| 5-Bromo-2H,7H-6-oxa-2,3-diaza-dibenzo[cd,h]azulene | B | ND | ND |
| 2-Hydroxy-2-{5-[4-methoxy-3-(2-methoxy-phenyl)-1H-pyrrolo[2,3-b]pyridin-5-yl]-pyridin-3-yl}-N,N-dimethyl-acetamide | D | C | C |
| 2-{5-[4-Methoxy-3-(2-methoxy-phenyl)-1H-pyrrolo[2,3-b]pyridin-5-yl]-pyridin-3-yl}-N,N-dimethyl-2-oxo-acetamide | D | B | C |
| Benzooxocine derivative A of Method 32 | C | A | A |
| 5-Bromo-3-(2-methoxy-phenyl)-4-methylsulfanyl-1H-pyrrolo[2,3b]pyridine | B | A | A |
| 5-Bromo-4-chloro-3-(2-methoxy-phenyl)-1H-pyrrolo[2,3-b]pyridine | C | ND | ND |
| 2-{5-[4-Chloro-3-(2-methoxy-phenyl)-1H-pyrrolo[2,3-b]pyridin-5-yl]-pyridin-3-yl}-N,N-dimethyl-acetamide | D | C | C |
| 6-[4-Chloro-3-(5-fluoro-2-methoxy-phenyl)-1H-pyrrolo[2,3-b]pyridin-5-yl]-pyrazine-2-carboxylic acid dimethylamide | D | C | C |
| 2-Hydroxy-2-{5-[3-(2-methoxy-phenyl)-4-methyl-1H-pyrrolo[2,3-b]pyridin-5-yl]-pyridin-3-yl}-N,N-dimethyl-acetamide | D | C | C |
| 2-Hydroxy-2-{5-[3-(2-methoxy-phenyl)-4-methylsulfanyl-1H-pyrrolo[2,3-b]pyridin-5-yl]-pyridin-3-yl}-N,N-dimethyl-acetamide | D | B | C |
| 3-amino-6-[4-chloro-3-(5-fluoro-2-methoxy-phenyl)-1H-pyrrolo[2,3-b]pyridin-5-yl]-pyrazine-2-carboxylic acid dimethylamide | D | D | C |
| {5-[4-Chloro-3-(5-fluoro-2-methoxy-phenyl)-1H-pyrrolo[2,3-b]pyridin-5-yl]-pyridin-3-yl}-(3-fluoro-pyridin-2-yl)-methanol | D | D | C |
| 6-[4-Chloro-3-(4-fluoro-phenyl)-1H-pyrrolo[2,3-b]pyridin-5-yl]-pyrazine-2-carboxylic acid dimethylamide | D | B | A |
| {5-[4-Chloro-3-(4-fluoro-phenyl)-1H-pyrrolo[2,3-b]pyridin-5-yl]-pyridin-3-yl}-(3-fluoro-pyridin-2-yl)-methanol | C | A | A |
| 3-(2-Methoxy-phenyl)-5-(1-methyl-1H-pyrazol-4-yl)-1H-pyrrolo[2,3-b]pyridin-4-ylamine | B | ND | ND |
| 2-Amino-5-[4-chloro-3-(2-oxo-2,3-dihydro-1H-indol-5-yl)-1H-pyrrolo[2,3-b]pyridin-5-yl]-N,N-dimethyl-nicotinamide | D | B | A |
| 2-Amino-5-[4-chloro-3-(2,3-difluoro-phenyl)-1H-pyrrolo[2,3-b]pyridin-5-yl]-N,N-dimethyl-nicotinamide | D | B | B |
| 2-Hydroxy-2-{5-[3-(2-methoxy-phenyl)-4-trifluoromethyl-1H-pyrrolo[2,3-b]pyridin-5-yl]-pyridin-3-yl}-N,N-dimethyl-acetamide | D | C | C |
| {2-Amino-5-[4-chloro-3-(2-methoxy-phenyl)-1H-pyrrolo[2,3-b]pyridin-5-yl]-pyridin-3-yl}-morpholin-4-yl-methanone | D | B | B |
| {2-Amino-5-[4-chloro-3-(2,5-difluoro-phenyl)-1H-pyrrolo[2,3-b]pyridin-5-yl]-pyridin-3-yl}-(3-hydroxy-azetidin-1-yl)-methanone | D | B | B |
| 6-[4-chloro-3-(2-fluoro-phenyl)-1H-pyrrolo[2,3,b]pyridine-5-yl]-pyrazine-2-carboxylic acid dimethylamide | D | B | B |
| {5-[4-Chloro-3-(2,3-difluoro-phenyl)-1H-pyrrolo[2,3-b]pyridin-5-yl]-pyridin-3-yl}-cyclopropyl-methanol | D | B | B |
| {5-[4-Chloro-3-(2-fluoro-phenyl)-1H-pyrrolo[2,3-b]pyridin-5-yl]-pyridin-3-yl}-(2-methyl-2H-pyrazol-3-yl)-methanol | D | A | A |
| 2-Amino-5-[4-chloro-3-(2-fluoro-phenyl)-1H-pyrrolo[2,3-b]pyridin-5-yl]-N,N-dimethyl-nicotinamide | D | B | B |
| {5-[4-Chloro-3-(2-fluoro-phenyl)-1H-pyrrolo[2,3-b]pyridin-5-yl]-pyridin-3-yl}-oxazol-2-yl-methanol | D | B | B |
| 2-Amino-5-[4-chloro-3-(4-fluoro-2-methoxy-phenyl)-1H-pyrrolo[2,3-b]pyridin-5-yl]-N,N-dimethyl-nicotinamide | D | C | C |
| 5-Bromo-3-(2-methoxy-phenyl)-1H-pyrrolo[2,3-b]pyridin-4-ylamine | C | A | A |
| 2-Hydroxy-2-{5-[4-hydroxy-3-(2-methoxy-phenyl)-1H-pyrrolo[2,3-b]pyridin-5-yl]-pyridin-3-yl}-N,N-dimethyl-acetamide | C | A | A |
| {2-Amino-5-[4-chloro-3-(3-fluoro-phenyl)-1H-pyrrolo[2,3-b]pyridin-5-yl]-pyridin-3-yl}-(3-dimethylamino-pyrrolidin-1-yl)-methanone | D | B | B |
| 2-{5-[4-chloro-3-(2-fluoro-phenyl)-1H-pyrrolo[2,3-b]pyridin-5-yl]-pyridin-3-yl}-2-hydroxy-acetamide. | D | A | A |

| Name | ABL_T315I_0P (IC50) | CELL BIO ABL P210WT BAF3 XTT (IC50) | CELL BIO ABL T315I BAF3 XTT (IC50) |
|---|---|---|---|
| 2-Amino-5-[4-chloro-3-(2-methoxy-5-trifluoromethyl-phenyl)-1H-pyrrolo[2,3-b]pyridin-5-yl]-N,N-dimethyl-nicotinamide | D | B | B |
| 2-{5-[4-Cyano-3-(2-methoxy-phenyl)-1H-pyrrolo[2,3-b]pyridin-5-yl]-pyridin-3-yl}-2-hydroxy-N,N-dimethyl-acetamide | D | A | A |
| 2-amino-5-[4-chloro-5-fluoro-2-methoxy-phenyl)-1H-pyrrolo[2,3,b]pyridine-5-yl]-N,N-dimethyl-nicotinamide. | D | D | C |
| 2-{5-[4-Amino-3-(2-methoxy-phenyl)-1H-pyrrolo[2,3-b]pyridin-5-yl]-pyridin-3-yl}-2-hydroxy-N,N-dimethyl-acetamide | D | B | B |
| 2-{5-[4-Chloro-3-(4-isopropyl-pyrimidin-5-yl)-1H-pyrrolo[2,3-b]pyridin-5-yl]-pyridin-3-yl}-2-hydroxy-N,N-dimethyl-acetamide | B | ND | ND |
| 2-Amino-5-[4-chloro-3-(2,5-difluoro-phenyl)-1H-pyrrolo[2,3-b]pyridin-5-yl]-N,N-dimethyl-nicotinamide | D | C | B |
| 2-Amino-5-[4-chloro-3-(2,5-difluoro-phenyl)-1H-pyrrolo[2,3-b]pyridin-5-yl]-N-ethyl-N-methyl-nicotinamide | D | B | B |
| {5-[4-Chloro-3-(2,3-difluoro-phenyl)-1H-pyrrolo[2,3-b]pyridin-5-yl]-pyridin-3-yl}-(3-fluoro-pyridin-2-yl)-methanol | D | B | B |
| 2-[5-(4-Chloro-3-phenyl-1H-pyrazolo[3,4-b]pyridin-5-yl)-pyridin-3-yl]-2-hydroxy-N,N-dimethyl-acetamide | B | ND | ND |
| 6-[4-chloro-3-(2-fluoro-phenyl)-1H-pyrrolo[2,3,b]pyridine-5-yl]-pyrazine-2-carboxylic acid methylamide | C | A | A |
| 2-{[5-Bromo-3-(2-methoxy-phenyl)-1H-pyrrolo[2,3-b]pyridin-4-yl]-methyl-amino}-ethanol | C | A | A |
| 2-Amino-5-[4-chloro-3-(1H-pyrazol-3-yl)-1H-pyrrolo[2,3-b]pyridin-5-yl]-N,N-dimethyl-nicotinamide | C | A | A |
| 5-[4-Chloro-3-(2-chloro-phenyl)-1H-pyrrolo[2,3-b]pyridin-5-yl]-N,N-dimethyl-nicotinamide | D | B | A |
| 2-[5-(4-Chloro-3-phenyl-1H-pyrrolo[2,3-b]pyridin-5-yl)-pyridin-3-yl]-N,N-dimethyl-acetamide | D | A | A |
| 2-Amino-5-[4-chloro-3-(5-fluoro-2-methoxy-phenyl)-1H-pyrrolo[2,3-b]pyridin-5-yl]-N,N-dimethyl-nicotinamide | D | D | D |
| 2-{2-Amino-5-[4-chloro-3-(2-fluoro-phenyl)-1H-pyrrolo[2,3-b]pyridin-5-yl]-pyridin-3-yl}-2-hydroxy-N,N-dimethyl-acetamide | D | B | C |
| 5-(4-Chloro-3-phenyl-1H-pyrazolo[3,4-b]pyridin-5-yl)-N,N-dimethyl-nicotinamide | B | A | A |
| 2-{5-[4-Chloro-3-(2-fluoro-phenyl)-1H-pyrrolo[2,3-b]pyridin-5-yl]-pyridin-3-yl}-2-hydroxy-N,N-dimethyl-acetamide | D | B | B |
| 5-[4-Chloro-3-(2,4-difluoro-phenyl)-1H-pyrrolo[2,3-b]pyridin-5-yl]-N,N-dimethyl-nicotinamide | C | A | A |
| {5-[4-chloro-3-(fluoro-phenyl)-1H-pyrrolo[2,3-b]pyridine-5-yl]-pyridin-3-yl}-(3-fluoro-pyridn-2-yl)-methanol | D | B | B |
| 2-Hydroxy-2-{5-[3-(2-methoxy-phenyl)-4-methylamino-1H-pyrrolo[2,3-b]pyridin-5-yl]-pyridin-3-yl}-N,N-dimethyl-acetamide | D | B | B |
| {2-Amino-5-[4-chloro-3-(2,5-difluoro-phenyl)-1H-pyrrolo[2,3-b]pyridin-5-yl]-pyridin-3-yl}-morpholin-4-yl-methanone | D | B | B |
| [5-(4-Chloro-3-phenyl-1H-pyrrolo[2,3-b]pyridin-5-yl)-pyridin-3-yl]-(3-fluoro-pyridin-2-yl)-methanol | D | B | B |
| 2-{5-[4-Chloro-3-(2,3-difluoro-phenyl)-1H-pyrrolo[2,3-b]pyridin-5-yl]-pyridin-3-yl}-N,N-dimethyl-2-oxo-acetamide | C | A | A |
| 2-Amino-5-[4-chloro-3-(2-methoxy-phenyl)-1H-pyrrolo[2,3-b]pyridin-5-yl]-N,N-dimethyl-nicotinamide | D | D | D |
| 2-{5-[4-Chloro-3-(2-chloro-phenyl)-1H-pyrrolo[2,3-b]pyridin-5-yl]-pyridin-3-yl}-2-hydroxy-N,N-dimethyl-acetamide | D | B | B |
| 2-{5-[4-Chloro-3-(2-methoxy-phenyl)-1H-pyrazolo[3,4-b]pyridin-5-yl]-pyridin-3-yl}-2-hydroxy-N,N-dimethyl-acetamide | C | B | B |
| 6-[4-chloro-3-(2-fluoro-phenyl)-1H-pyrrolo[2,3,b]pyridine-5-yl]-pyrazine-2-carboxylic acid dimethylamide | D | B | B |
| 2-{5-[4-Chloro-3-(4-methoxy-pyridin-3-yl)-1H-pyrrolo[2,3-b]pyridin-5-yl]-pyridin-3-yl}-2-hydroxy-N,N-dimethyl-acetamide | D | B | B |
| 5-[4-Chloro-3-(2,3-difluoro-phenyl)-1H-pyrrolo[2,3-b]pyridin-5-yl]-N,N-dimethyl-nicotinamide | D | B | B |
| 2-{5-[4-Chloro-3-(2-fluoro-phenyl)-1H-pyrazolo[3,4-b]pyridin-5-yl]-pyridin-3-yl}-2-hydroxy-N,N-dimethyl-acetamide | B | ND | ND |
| 3-Amino-6-(4-chloro-3-phenyl-1H-pyrrolo[2,3-b]pyridin-5-yl)-pyrazine-2-carboxylic acid dimethylamide | D | B | B |
| 2-[5-Bromo-3-(2-methoxy-phenyl)-1H-pyrrolo[2,3-b]pyridin-4-ylamino]-ethanol | B | ND | ND |
| 6-[4-Chloro-3-(2,3-difluoro-phenyl)-1H-pyrrolo[2,3-b]pyridin-5-yl]-pyrazine-2-carboxylic acid dimethylamide | D | B | B |
| 2-{5-[4-chloro-3-(2-methylamino-pyridin-3-yl)-1H-pyrrolo[2,3-b]pyridin-5-yl]-pyridin-3-yl}-2-hydroxy-N,N-dimethyl-acetamide. | C | A | A |
| 5-[4-Chloro-3--(2-fluoro-phenyl)-1H-pyrrolo[2,3-b]pyridin-5-yl]-N,N-dimethyl-nicotinamide | D | B | B |
| [5-Bromo-3-(2-methoxy-phenyl)-1H-pyrrolo[2,3-b]pyridin-4-yl]-methyl-amine | C | A | A |

| Name | ABL_T315I_0P (IC50) | CELL BIO ABL P210WT BAF3 XTT (IC50) | CELL BIO ABL T315I BAF3 XTT (IC50) |
|---|---|---|---|
| 2-Amino-5-[4-chloro-3-(3-fluoro-phenyl)-1H-pyrrolo[2,3-b]pyridin-5-yl]-N,N-dimethyl-nicotinamide | D | B | B |
| 5-[4-Chloro-3-(3,5-dimethyl-isoxazol-4-yl)-1H-pyrrolo[2,3-b]pyridin-5-yl]-N,N-dimethyl-nicotinamide | B | A | A |
| 2-{5-[4-Chloro-3-(2-methoxy-pyridin-3-yl)-1H-pyrrolo[2,3-b]pyridin-5-yl]-pyridin-3-yl}-2-hydroxy-N,N-dimethyl-acetamide | D | C | B |
| {2-Amino-5-[4-chloro-3-(3-fluoro-phenyl)-1H-pyrrolo[2,3-b]pyridin-5-yl]-pyridin-3-yl}-(3-hydroxy-azetidin-1-yl)-methanone | D | B | B |
| 5-[4-Chloro-3-(2-methylsulfanyl-phenyl)-1H-pyrrolo[2,3-b]pyridin-5-yl]-N,N-dimethyl-nicotinamide | D | A | A |
| {2-Amino-5-[4-chloro-3-(2,5-difluoro-phenyl)-1H-pyrrolo[2,3-b]pyridin-5-yl]-pyridin-3-yl}-(3-dimethylamino-pyrrolidin-1-yl)-methanone | D | B | B |
| {2-Amino-5-[4-chloro-3-(2,5-difluoro-phenyl)-1H-pyrrolo[2,3-b]pyridin-5-yl]-pyridin-3-yl}-(2-hydroxymethyl-pyrrolidin-1-yl)-methanone | D | B | B |
| {2-Amino-5-[4-chloro-3-(3-fluoro-phenyl)-1H-pyrrolo[2,3-b]pyridin-5-yl]-pyridin-3-yl}-morpholin-4-yl-methanone | D | C | C |
| 2-{5-[4-Chloro-3-(3-methoxy-pyridin-4-yl)-1H-pyrrolo[2,3-b]pyridin-5-yl]-pyridin-3-yl}-2-hydroxy-N,N-dimethyl-acetamide | D | A | A |
| 2-[5-(4-Chloro-3-phenyl-1H-pyrrolo[2,3-b]pyridin-5-yl)-pyridin-3-yl]-2-hydroxy-N,N-dimethyl-acetamide | D | B | B |
| 2-Amino-5-[4-chloro-3-(2-methoxy-pyridin-3-yl)-1H-pyrrolo[2,3-b]pyridin-5-yl]-N,N-dimethyl-nicotinamide | D | C | C |
| 2-Amino-5-[4-chloro-3-(4,5-difluoro-2-methoxy-phenyl)-1H-pyrrolo[2,3-b]pyridin-5-yl]-N,N-dimethyl-nicotinamide | D | C | C |
| 2-{5-[4-Ethyl-3-(2-methoxy-phenyl)-1H-pyrrolo[2,3-b]pyridin-5-yl]-pyridin-3-yl}-2-hydroxy-N,N-dimethyl-acetamide | D | B | B |
| 5-[4-Chloro-3-(2-fluoro-phenyl)-1H-pyrrolo[2,3-b]pyridin-5-yl]-N-methyl-nicotinamide | C | A | A |
| 6-[4-Chloro-3-(2-fluoro-phenyl)-1H-pyrrolo[2,3-b]pyridin-5-yl]-pyrazine-2-carboxylic acid dimethylamide | D | A | A |
| {3-[4-Chloro-3-(2-fluoro-phenyl)-1H-pyrrolo[2,3-b]pyridin-5-yl]-phenyl}-oxazol-2-yl-methanol | D | A | A |
| 2-{5-[4-Dimethylamino-3-(2-methoxy-phenyl)-1H-pyrrolo[2,3-b]pyridin-5-yl]-pyridin-3-yl}-2-hydroxy-N,N-dimethyl-acetamide | B | ND | ND |
| 2-Amino-5-[4-chloro-3-(2-chloro-5-fluoro-phenyl)-1H-pyrrolo[2,3-b]pyridin-5-yl]-N,N-dimethyl-nicotinamide | D | B | B |
| 2-{5-[4-Chloro-3-(2,3-difluoro-phenyl)-1H-pyrrolo[2,3-b]pyridin-5-yl]-pyridin-3-yl}-N,N-dimethyl-acetamide | D | B | B |
| 2-Amino-5-[4-chloro-3-(4-cyano-2-methoxy-phenyl)-1H-pyrrolo[2,3-b]pyridin-5-yl]-N,N-dimethyl-nicotinamide | C | ND | ND |
| 2-Amino-5-[4-chloro-3-(4-chloro-2-methoxy-phenyl)-1H-pyrrolo[2,3-b]pyridin-5-yl]-N,N-dimethyl-nicotinamide | D | C | C |
| 5-(4-Chloro-3-phenyl-1H-pyrrolo[2,3-b]pyridin-5-yl)-N,N-dimethyl-nicotinamide | D | A | A |
| 2-Amino-5-[4-chloro-3-(3-fluoro-phenyl)-1H-pyrrolo[2,3-b]pyridin-5-yl]-N-ethyl-N-methyl-nicotinamide | D | C | C |
| 2-{5-[4-Chloro-3-(2,3-difluoro-phenyl)-1H-pyrrolo[2,3-b]pyridin-5-yl]-pyridin-3-yl}-2-hydroxy-N,N-dimethyl-acetamide | D | B | B |
| {2-Amino-5-[4-chloro-3-(3-fluoro-phenyl)-1H-pyrrolo[2,3-b]pyridin-5-yl]-pyridin-3-yl}-(2-hydroxymethyl-pyrrolidin-1-yl)-methanone | D | B | B |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A compound having the formula:

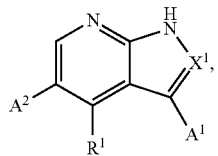

or an enantiomer, diastereomer, racemate, or pharmaceutically acceptable salt thereof, wherein:

$A^1$ is independently halogen, cyano, nitro, hydroxyl, substituted or unsubstituted alkyl, substituted or unsubstituted alkene, substituted or unsubstituted alkyne, substituted or unsubstituted haloalkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, —$(CH_2)_jC(=Z)R^3$, —$(CH_2)_jOR^3$, —$(CH_2)_jC(O)R^3$, —$(CH_2)_jC(O)OR^3$, —$(CH_2)_jNR^4R^5$, —$(CH_2)_jC(O)NR^4R^5$, —$(CH_2)_jOC(O)NR^4R^5$, —$(CH_2)_jNR^6C(O)R^3$, —$(CH_2)_jNR^6C(O)OR^3$, —$(CH_2)_jNR^6C(O)NR^4R^5$, —$(CH_2)_jS(O)_mR^7$, —$(CH_2)_j NR^6S(O)_2R^7$, or —$(CH_2)_jS(O)_2NR^4R^5$; wherein each j is independently an integer from 0 to 6; and m is independently an integer from 0 to 2 and Z is O, S or $NR^8$; with the proviso when $A^1$ is —$S(O)_mR^7$, m is not 2;

$X^1$ is —CH—;

$A^2$ is independently nitro, hydroxyl, haloalkyl, substituted or unsubstituted alkyl, substituted or unsubstituted alkene, substituted or unsubstituted alkyne, substituted or unsubstituted cycloalkyl, substituted or unsubstituted heteroalkyl, substituted or unsubstituted heterocycloalkyl, substituted or unsubstituted aryl, substituted or unsubstituted aralkyl, substituted or unsubstituted heteroaryl; substituted or unsubstituted heteroaralkyl; —$(CH_2)_jC(=Z)R^3$, —$(CH_2)_jOR^3$, —$(CH_2)_jC(O)R^3$, —$(CH_2)_jC(O)OR^3$, —$(CH_2)_jNR^4R^5$, —$(CH_2)_jC(O) NR^4R^5$, —$(CH_2)_jOC(O)NR^4R^5$, —$(CH_2)_jNR^6C(O)R^3$, —$(CH_2)_jNR^6C(O)OR^3$, —$(CH_2)_jNR^6C(O)NR^4R^5$, —$(CH_2)_jS(O)_mR^7$, —$(CH_2)_jNR^6S(O)_2R^7$, or —$(CH_2)_j S(O)_2NR^4R^5$; wherein each j is independently an integer from 0 to 6; and m is independently an integer from 0 to 2; and Z is O, S or $NR^8$; with the proviso that when $A^1$ is methyl, $A^2$ is not heteroaryl, —C(O)OEt, or —C(O) phenyl; and with the proviso that $A^2$ is not —C(O)H, —$C(O)NH_2$, or —C(O)NHMe;

$R^1$ is independently halogen, cyano, nitro, hydroxyl, substituted or unsubstituted alkyl, substituted or unsubstituted haloalkyl, substituted or unsubstituted cycloalkyl, substituted or unsubstituted heteroalkyl, substituted or unsubstituted heterocycloalkyl, substituted or unsubstituted aryl, substituted or unsubstituted heteroaryl, —$(CH_2)_jC(=Z)R^3$, —$(CH_2)_jOR^3$, —$(CH_2)_jC(O)R^3$, —$(CH_2)_jC(O)OR^3$, —$(CH_2)_jNR^4R^5$, —$(CH_2)_jC(O) NR^4R^5$, —$(CH_2)_jOC(O)NR^4R^5$, —$(CH_2)_jNR^6C(O)R^3$, —$(CH_2)_jNR^6C(O)OR^3$, —$(CH_2)_jNR^6C(O)NR^4R^5$, —$(CH_2)_jS(O)_mR^7$, —$(CH_2)_jN^6RS(O)_2R^7$, or —$(CH_2)_j S(O)_2NR^4R^5$; wherein each j is independently an integer from 0 to 6; and m is independently an integer from 0 to 2; and Z is O, S or $NR^8$; or $R^2$ is independently hydrogen, bromine, chlorine, fluorine, cyano, nitro, substituted or unsubstituted alkyl, or substituted or unsubstituted haloalkyl;

$R^3$ is independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^4$, $R^5$, $R^6$ and $R^7$ are each independently hydrogen, substituted or unsubstituted alkyl, substituted or unsubstituted alkyl-$NR^9R^{10}$, substituted or unsubstituted alkyl-$CONR^9R^{10}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl, substituted or unsubstituted aralkyl, substituted or unsubstituted hetero aralkyl, or $R^4$ and $R^5$ are joined together with the nitrogen to which they are attached, to form substituted or unsubstituted 3- to 7-membered heterocycloalkyl, or substituted or unsubstituted 5-membered heteroaryl;

$R^8$ is independently hydrogen, substituted or unsubstituted alkyl, substituted or unsubstituted haloalkyl, substituted or unsubstituted heteroalkyl, substituted or unsubstituted aryl, substituted or unsubstituted heteroaryl, substituted or unsubstituted heterocycloalkyl, or substituted or unsubstituted cycloalkyl;

$R^9$ and $R^{10}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or $R^9$ and $R^{10}$ are joined together with the nitrogen to which they are attached, to form substituted or unsubstituted 3- to 7-membered heterocycloalkyl, or substituted or unsubstituted 5-membered heteroaryl;

where any of the groups listed for $R^1$, $R^2$, $R^3$, $R^4$, $R^5$, $R^6$, $R^7$, $R^8$, $R^9$ and $R^{10}$ in are each optionally independently substituted with 1 to 3 groups, each group independently selected from halogen, hydroxyl, amino, aminomonoalkyl, aminodialkyl, cyano, nitro, haloalkyl, alkyl, heteroalkyl, oxo, —O-alkyl, and —S-alkyl.

2. The compound of claim 1, wherein:

$A^1$ is an aryl or heteroaryl group each optionally substituted with 1 to 5 $R^{11}$ groups;

each $R^{11}$ is independently hydrogen, halogen, cyano, nitro, hydroxyl, perfluoroalkyl, difluoromethyl, substituted or unsubstituted alkyl, substituted or unsubstituted heteroalkyl, substituted or unsubstituted heterocycloalkyl, substituted or unsubstituted aryl, substituted or unsubstituted heteroaryl, —(CH$_2$)$_j$C(=Z)R$^{12}$, —(CH$_2$)$_j$OR$^{12}$, —(CH$_2$)$_j$C(O)R$^{12}$, —(CH$_2$)$_j$C(O)OR$^{12}$, —(CH$_2$)$_j$NR$^{13}$R$^{14}$, —(CH$_2$)$_j$C(O)NR$^{13}$R$^{14}$, (CH$_2$)$_j$OC(O)NR$^{13}$R$^{14}$, —(CH$_2$)$_j$NR$^{15}$C(O)R$^{12}$, —(CH$_2$)$_j$NR$^{15}$C(O)OR$^{12}$, —(CH$_2$)$_j$NR$^{15}$C(O)NR$^{13}$R$^{15}$, —(CH$_2$)$_j$S(O)$_m$ R$^{16}$, —(CH$_2$)NR$^{15}$S(O)$_2$R$^{16}$, or —(CH$_2$)$_j$S(O)$_2$NR$^{13}$R$^{14}$, wherein each j is independently an integer from 0 to 6; m is independently an integer from 0 to 2; and Z is O, S or NR$^{17}$;

$R^{12}$ is independently hydrogen, substituted or unsubstituted haloalkyl, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{13}$, $R^{14}$, $R^{15}$ and $R^{16}$ are each independently hydrogen, substituted or unsubstituted substituted or unsubstituted alkyl-NR$^{18}$R$^{19}$, substituted or unsubstituted alkyl-CONR$^{18}$R$^{19}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or $R^{13}$ and $R^{14}$ are joined together with the nitrogen to which they are attached, to form substituted or unsubstituted 3- to 7-membered heterocycloalkyl, or substituted or unsubstituted 5-membered heteroaryl;

$R^{17}$ is independently hydrogen, substituted or unsubstituted alkyl, substituted or unsubstituted heteroalkyl, substituted or substituted aryl, substituted or unsubstituted heteroaryl, substituted or unsubstituted heterocycloalkyl, or substituted or unsubstituted cycloalkyl;

$R^{18}$ and $R^{19}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or $R^{18}$ and $R^{19}$ are joined together with the nitrogen to which they are attached, to form substituted or unsubstituted 3- to 7-membered heterocycloalkyl, or substituted or unsubstituted 5-membered heteroaryl; and wherein any of the groups listed for $R^{11}$, $R^{12}$, $R^{13}$, $R^{14}$, $R^{15}$, $R^{16}$, $R^{17}$, $R^{18}$, and $R^{19}$ are each optionally independently substituted with 1 to 3 groups, each group independently selected from halogen, hydroxyl, amino, aminomonoalkyl, aminodialkyl, cyano, nitro, haloalkyl, heteroalkyl, oxo, alkyl, —O-alkyl, and —S-alkyl.

3. The compound of claim 1, wherein:

$A^2$ is an aryl or heteroaryl group each optionally substituted with 1 to 5 —(CR$^{20}$R$^{21}$)$_n$R$^{22}$ groups;

n is an integer from 0 to 2;

$R^{20}$, $R^{21}$ and $R^{22}$ are each independently hydrogen, halogen, cyano, nitro, hydroxyl, substituted or unsubstituted haloalkyl, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —(CH$_2$)$_j$C(Z)R$^{23}$, —(CH$_2$)$_3$OR$^{23}$, —(CH$_2$)$_j$C(O)R$^{23}$, —(CH$_2$)$_j$C(O)OR$^{23}$, —(CH$_2$)$_j$ NR$^{24}$R$^{25}$, —(CH$_2$)$_j$C(O)NR$^{24}$R$^{25}$, —(CH$_2$)$_j$OC(O)NR$^{24}$R$^{25}$, —(CH$_2$)$_j$NR$^{26}$C(O)R$^{23}$, —(CH$_2$)$_j$NR$^{26}$C(O)OR$^{23}$, —(CH$_2$)$_j$NR$^{26}$C(O)NR$^{24}$R$^{25}$, —(CH$_2$)$_j$S(O)$_m$ R$^{27}$, —(CH$_2$)$_j$NR$^{26}$S(O)$_2$R$^{27}$, or —(CH$_2$)$_j$S(O)$_2$ NR$^{24}$R$^{25}$, wherein each j is independently an integer from 0 to 6; m is independently an integer from 0 to 2; and Z is O, S or NR$^{28}$; or $R^{20}$ and $R^{21}$ together form oxo, or $R^{21}$ and $R^{22}$ are joined together to form substituted or unsubstituted cycloalkyl or substituted or unsubstituted heterocycloalkyl;

$R^{23}$ is independently hydrogen, substituted or unsubstituted haloalkyl, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or substituted heteroaryl;

$R^{24}$, $R^{25}$, $R^{26}$ and $R^{27}$ are each independently hydrogen, substituted or unsubstituted alkyl, substituted or unsubstituted alkyl-NR$^{29}$R$^{30}$, substituted or unsubstituted alkyl-CONR$^{29}$R$^{30}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or $R^{24}$ and $R^{25}$ are joined together with the nitrogen to which they are attached, to form substituted or unsubstituted 3- to 7-membered heterocycloalkyl, or substituted or unsubstituted 5-membered heteroaryl;

$R^{28}$ is independently hydrogen, substituted or unsubstituted alkyl, or substituted or unsubstituted heteroalkyl, substituted or unsubstituted aryl, substituted or unsubstituted heteroaryl, substituted or unsubstituted heterocycloalkyl, or substituted or unsubstituted cycloalkyl;

$R^{29}$ and $R^{30}$ are each independently hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or $R^{29}$ and $R^{30}$ are joined together with the nitrogen to which they are attached, to form substituted or unsubstituted 3- to 7-membered heterocycloalkyl, or substituted or unsubstituted 5-membered heteroaryl; and wherein any of the groups listed for $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are each optionally independently substituted with 1 to 3 groups, each group independently selected from halogen, hydroxyl, amino, aminomonoalkyl, aminodialkyl, cyano, nitro, haloalkyl, heteroalkyl, oxo, alkyl, —O-alkyl, and —S-alkyl.

4. The compound of claim 2, wherein:

$A^2$ is an aryl or heteroaryl group each optionally substituted with 1 to 5 —$(CR^{20}R^{21})_n R^{22}$ groups;

n is an integer from 0 to 2;

$R^{20}$, $R^{21}$ and $R^{22}$ are each independently hydrogen, halogen, cyano, nitro, hydroxyl, substituted or unsubstituted haloalkyl, substituted or unsubstituted alkyl, substituted or unsubstituted heteroalkyl, substituted or unsubstituted cycloalkyl, substituted or unsubstituted heterocycloalkyl, substituted or unsubstituted aryl, substituted or unsubstituted heteroaryl, —$(CH_2)_j C(Z)R^{23}$, —$(CH_2)_j OR^{23}$, —$(CH_2)_j C(O)R^{23}$, —$(CH_2)_j C(O)OR^{23}$, —$(CH_2)_j NR^{24}R^{25}$, —$(CH_2)_j C(O)NR^{24}R^{25}$, —$(CH_2)_j OC(O)NR^{24}R^{25}$, —$(CH_2)_j NR^{26}OC(O)R^{23}$, —$(CH_2)_j NR^{26}C(O)R^{23}$, —$(CH_2)_j NR^{26}C(O)NR^{24}R^{25}$, —$(CH_2)_j NR^{26}C(O)OR^{23}$, —$(CH_2)_j S(O)_m R^{27}$, —$(CH_2)_j NR^{26}S(O)_2 R^{27}$, or —$(CH_2)_j S(O)_2 NR^{24}R^{25}$, wherein each j is independently an integer from 0 to 6; m is independently an integer from 0 to 2; and Z is O, S or $NR^{28}$; or $R^{20}$ and $R^{21}$ together form oxo, or $R^{21}$ and $R^{22}$ are joined together to form substituted or unsubstituted cycloalkyl or substituted or unsubstituted heterocycloalkyl;

$R^{23}$ is independently hydrogen, substituted or unsubstituted haloalkyl, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^{24}$, $R^{25}$, $R^{26}$ and $R^{27}$ are each independently hydrogen, substituted or unsubstituted alkyl, substituted or substituted alkyl-$NR^{29}R^{30}$, substituted or unsubstituted alkyl-$CONR^{29}R^{30}$, substituted or unsubstituted heteroalkyl, substituted or unsubstituted cycloalkyl, substituted or unsubstituted heterocycloalkyl, substituted or unsubstituted aryl, or substituted or unsubstituted heteroaryl, or $R^{24}$ and $R^{25}$ are joined together with the nitrogen to which they are attached, to form substituted or unsubstituted 3- to 7-membered heterocycloalkyl, or substituted or substituted 5-membered heteroaryl;

$R^{28}$ is independently hydrogen, substituted or unsubstituted alkyl, or substituted or unsubstituted heteroalkyl, substituted or unsubstituted aryl, substituted or unsubstituted heteroaryl, substituted or unsubstituted heterocycloalkyl, or substituted or unsubstituted cycloalkyl;

$R^{29}$ and $R^{30}$ are each independently hydrogen, substituted or unsubstituted alkyl, substituted or substituted heteroalkyl, substituted or unsubstituted cycloalkyl, substituted or unsubstituted heterocycloalkyl, substituted or unsubstituted aryl, or substituted or unsubstituted heteroaryl, or $R^{29}$ and $R^{30}$ are joined together with the nitrogen to which they are attached, to form substituted or unsubstituted 3- to 7-membered heterocycloalkyl, or substituted or unsubstituted 5-membered heteroaryl; and wherein any of the groups listed for $R^{20}$, $R^{21}$, $R^{22}$, $R^{23}$, $R^{24}$, $R^{25}$, $R^{26}$, $R^{27}$, $R^{28}$, $R^{29}$, and $R^{30}$ are each optionally independently substituted with 1 to 3 groups, each group independently selected from halogen, hydroxyl, amino, aminomonoalkyl, aminodialkyl, cyano, nitro, haloalkyl, heteroalkyl, oxo, alkyl, —O-alkyl, and —S-alkyl.

5. The compound of claim 4, wherein $A^1$ is substituted 6-membered aryl, substituted 6-membered heteroaryl, or substituted 5-membered heteroaryl.

6. The compound of claim 4, wherein $A^1$ is:

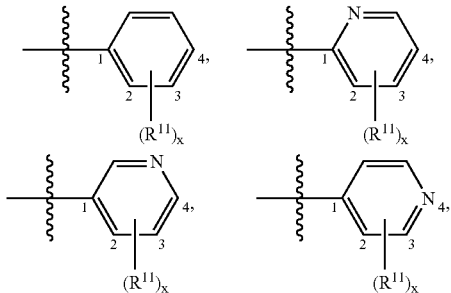

wherein x is independently an integer from 1 to 3.

7. The compound of claim 6, wherein two $R^{11}$ groups are combined to form a substituted or unsubstituted ring with the carbons to which they are attached, wherein the substituted or unsubstituted ring is substituted or unsubstituted heterocycloalkyl or substituted or unsubstituted heteroaryl.

8. The compound of claim 6, wherein $R^{11}$ is independently halogen, —$OR^{12}$, —$NR^{13}R^{14}$, substituted or substituted alkyl, substituted or substituted haloalkyl, or substituted or substituted heteroalkyl; wherein $R^{12}$, $R^{13}$ and $R^{14}$ are each independently hydrogen, substituted or substituted alkyl, substituted or substituted haloalkyl, substituted or substituted heteroalkyl, substituted or substituted cycloalkyl, substituted or unsubstituted heterocycloalkyl, substituted or unsubstituted aryl, or substituted or substituted heteroaryl.

9. The compound of claim 8, wherein $R^{12}$, $R^{13}$ and $R^{14}$ are each independently hydrogen, unsubstituted $(C_1$-$C_6)$alkyl, or unsubstituted $(C_1$-$C_6)$haloalkyl.

10. The compound of claim 6, wherein x is 1 or 2 and $R^{11}$ is attached at position 2 or position 3.

11. The compound of claim 4, wherein $A^2$ is:

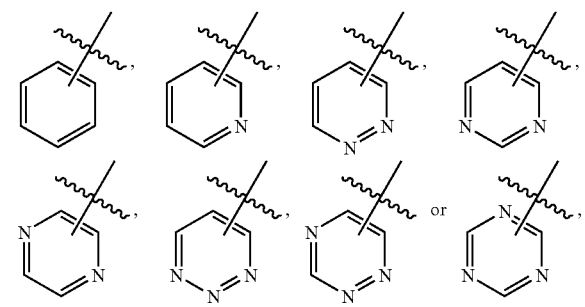

wherein any of the above groups are each independently optionally substituted with 1 to 5 —$R^{22}$ groups.

12. The compound of claim 11, wherein:

$R^{22}$ is substituted or substituted haloalkyl, substituted or unsubstituted alkyl, —$(C_0$-$C_3)OR^{23}$, —$NR^{24}R^{25}$, —$(C_0$-$C_3)C(O)C(O)NR^{24}R^{25}$, —$(C_0$-$C_3)CH(OH)C(O)NR^{24}R^{25}$, or —$(C_0$-$C_3)C(O)NR^{24}R^{25}$; wherein $R^{23}$, $R^{24}$ and $R^{25}$ are each independently hydrogen, $(C_1$-$C_6)$alkoxy, or $(C_1$-$C_6)$alkyl; or where $R^{24}$ and $R^{25}$ cyclize with the nitrogen they are attached to form a 3- to 7-membered heterocycloalkyl, or substituted or substituted 5-to 6-membered heteroaryl.

13. The compound of claim 11, wherein $R^{22}$ is —$(C_0-C_3)$C(O)C(O)$R^{23}$, —$(C_0-C_3)$CH(OH)$R^{23}$, —$(C_0-C_3)$CH(OH)C(O)$R^{23}$, or —$(C_0-C_3)$C(O)$R^{23}$; wherein $R^{23}$ is substituted or substituted cycloalkyl, substituted or substituted heterocycloalkyl, substituted or substituted aryl, or substituted or unsubstituted heteroaryl.

14. The compound of claim 4, wherein:

n is 1;

$R^{29}$ is hydrogen; and $R^{21}$ is —$OR^{23}$, wherein $R^{23}$ is hydrogen or substituted or unsubstituted alkyl.

15. The compound of claim 14, wherein:

$R^{22}$ is independently substituted or unsubstituted heterocycloalkyl, substituted or unsubstituted cycloalkyl, substituted or unsubstituted aryl, substituted or unsubstituted heteroaryl, —$OR^{23}$, —$NR^{24}R^{25}$ or —$C(O)NR^{24}R^{25}$; wherein $R^{24}$ and $R^{25}$ are each independently hydrogen, substituted or unsubstituted alkyl, substituted or unsubstituted alkyl-$NR^{29}R^{30}$, substituted or unsubstituted alkyl-$C(O)NR^{29}R^{30}$, wherein $R^{29}$ and $R^{30}$ are each independently hydrogen or substituted or unsubstituted alkyl.

16. The compound of claim 3, having formulae:

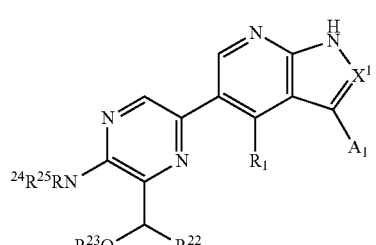

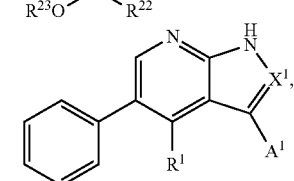

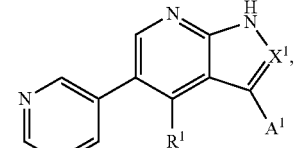

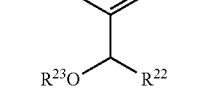 or

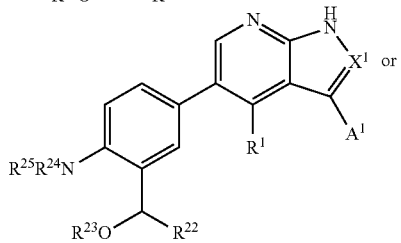

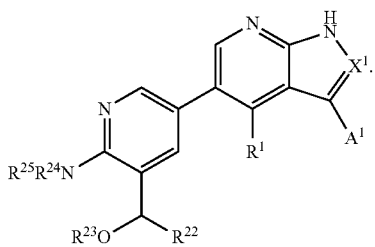.

17. The compound of claim 3, having formulae:

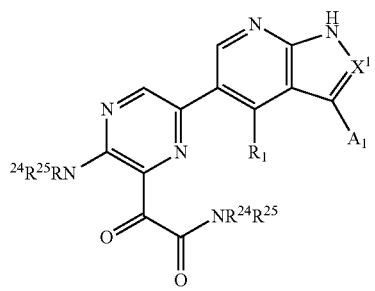

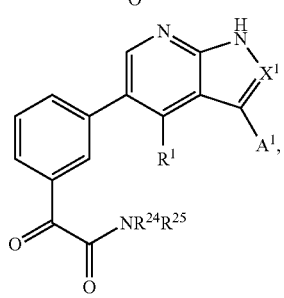,

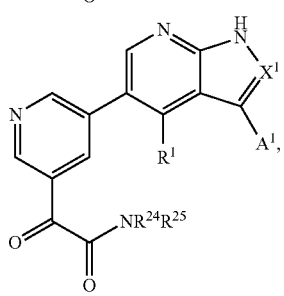,

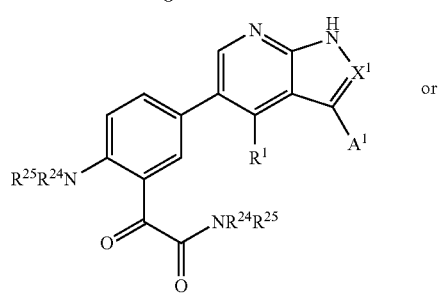 or

-continued

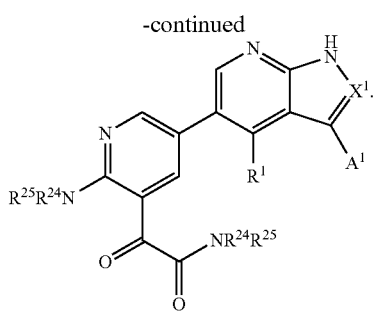

18. The compound of claim 3, having formulae:

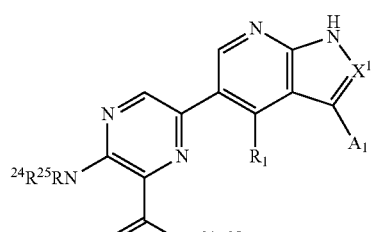

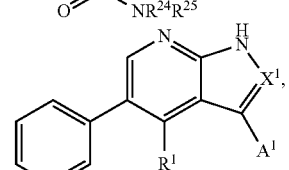

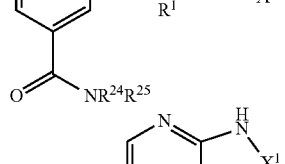

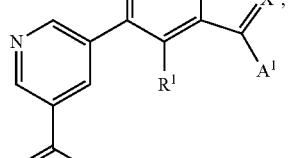

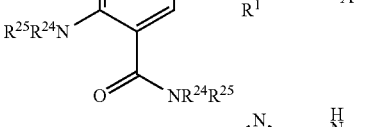

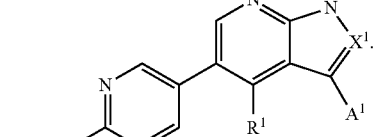

19. The compound of claim 4, wherein $R^1$ is chlorine, —($C_0$-$C_3$)alkylCN —($C_1$-$C_3$)alkyl, —($C_1$-$C_3$)haloalkyl, —($C_1$-$C_3$)alkene, —($C_1$-$C_3$)alkyne, —($C_0$-$C_3$)$NH_2$, —($C_0$-$C_3$)OH, —($C_0$-$C_3$)SH, —($C_0$-$C_3$)NH($C_1$-$C_3$)alkyl, —($C_0$-$C_3$)N($C_1$-$C_3$)$_2$alkyl, —($C_0$-$C_3$)O($C_1$-$C_3$)alkyl, —($C_0$-$C_3$)S($C_1$-$C_3$)alkyl, —($C_0$-$C_3$)NH($C_1$-$C_3$)haloalkyl, —($C_0$-$C_3$)N($C_1$-$C_3$)$_2$haloalkyl, —($C_0$-$C_3$)O($C_1$-$C_3$)haloalkyl, —($C_0$-$C_3$)S($C_1$-$C_3$)haloalkyl.

20. The compound of claim 4, having formulae:

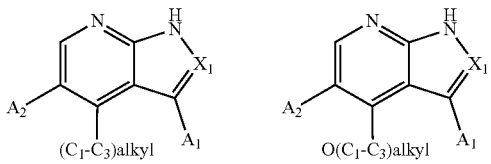

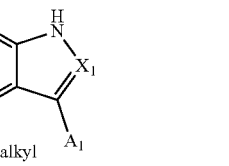

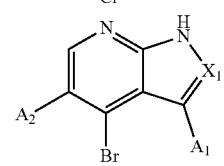

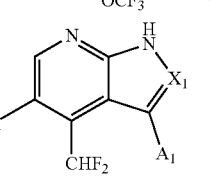

wherein S is optionally substituted with one or two oxygen atoms.

21. The compound of claim 19 or 20, wherein $A^1$ is substituted 6-membered aryl, substituted 6-membered heteroaryl, or substituted 5-membered heteroaryl.

22. The compound of claim 21, wherein $A^1$ is

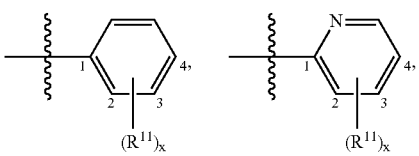

-continued

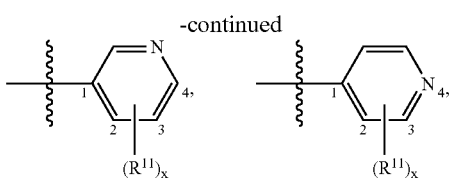

wherein x is independently an integer from 1 to 3.

23. The compound of claim 22, wherein two $R^{11}$ groups are combined to form a substituted or unsubstituted ring with the carbons to which they are attached, wherein the substituted or unsubstituted ring is substituted or unsubstituted heterocycloalkyl or substituted or unsubstituted heteroaryl.

24. The compound of claim 22, wherein $R^{11}$ is independently halogen, $-OR^{12}$, $-NR^{13}R^{14}$, substituted or unsubstituted alkyl, substituted or unsubstituted haloalkyl, or substituted or unsubstituted heteroalkyl; wherein $R^{12}$, $R^{13}$ and $R^{14}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

25. The compound of claim 24, wherein $R^{12}$, $R^{13}$ and $R^{14}$ are each independently hydrogen, unsubstituted ($C_1$-$C_6$) alkyl, or unsubstituted ($C_1$-$C_6$)haloalkyl.

26. The compound of claim 22, wherein $A^2$ is:

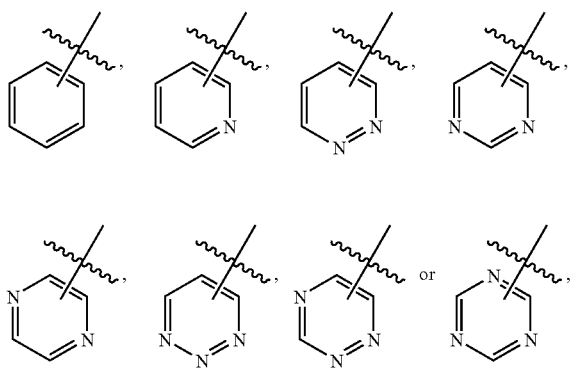

wherein any of the above groups are each independently optionally substituted with 1 to 5—$R^{22}$ groups.

27. The compound of claim 26, wherein: $R^{22}$ is substituted or unsubstituted haloalkyl, substituted or unsubstituted alkyl, $-(C_0$-$C_3)OR^{23}$, $-NR^{24}R^{25}$, $-(C_0$-$C_3)C(O)C(O)NR^{24}R^{25}$, $-(C_0$-$C_3)CH(OH)C(O)NR^{24}R^{25}$, or $-(C_0$-$C_3)C(O)NR^{24}R^{25}$; wherein $R^{23}$, $R^{24}$ and $R^{25}$ are each independently hydrogen, ($C_1$-$C_6$)alkoxy, or ($C_1$-$C_6$)alkyl; or where $R^{24}$ and $R^{25}$ cyclize with the nitrogen they are attached to form a 3- to 7-membered heterocycloalkyl, or substituted or unsubstituted 5- to 6-membered heteroaryl.

28. The compound of claim 26, wherein $R^{22}$ is $-(C_0$-$C_3)OR^{23}$, $-(C_0$-$C_3)C(O)C(O)R^{23}$, $-(C_0$-$C_3)CH(OH)R^{23}$, $-(C_0$-$C_3)CH(OH)C(O)R^{23}$, or $-(C_0$-$C_3)C(O)R^{23}$; wherein $R^{23}$ is substituted or unsubstituted cycloalkyl, substituted or unsubstituted heterocycloalkyl, substituted or unsubstituted aryl, or substituted or unsubstituted heteroaryl.

29. The compound of claim 26, wherein: $R^{22}$ is independently substituted or unsubstituted heterocycloalkyl, substituted or unsubstituted cycloalkyl, substituted or unsubstituted aryl, substituted or unsubstituted heteroaryl, $-OR^{23}$, $-NR^{24}R^{25}$ or $-C(O)NR^{24}R^{25}$; wherein $R^{24}$ and $R^{25}$ are each independently hydrogen, substituted or unsubstituted alkyl, substituted or unsubstituted alkyl-$NR^{29}R^{30}$, substituted or unsubstituted alkyl-$C(O)NR^{29}R^{30}$, wherein $R^{29}$ and $R^{30}$ are each independently hydrogen or substituted or unsubstituted alkyl.

30. The compound of claim 4, having the formula:

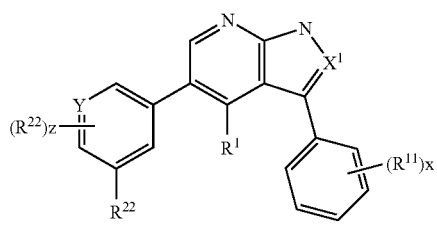

wherein:
$X^1$ is $-CH$;
Y is N or CH;
each $R^{11}$ is independently halogen, $-OR^{12}$, $-NR^{13}R^{14}$, substituted or unsubstituted alkyl, substituted or unsubstituted haloalkyl, or substituted or unsubstituted heteroalkyl; wherein $R^{12}$, $R^{13}$ and $R^{14}$ are each independently hydrogen, substituted or unsubstituted alkyl, substituted or unsubstituted haloalkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; and x is a whole integer between 1 and 3; and
each $R^{22}$ is substituted or unsubstituted haloalkyl, substituted or unsubstituted alkyl, $-(C_0$-$C_3)OR^{23}$, $-NR^{24}R^{25}$, $-(C_0$-$C_3)C(O)C(O)NR^{24}R^{25}$, $-(C_0$-$C_3)CH(OH)C(O)NR^{24}R^{25}$, or $-(C_0$-$C_3)C(O)NR^{24}R^{25}$;
$R^{23}$, $R^{24}$ and $R^{25}$ are each independently hydrogen, ($C_1$-$C_6$)alkoxy, or ($C_1$-$C_6$)alkyl; or where $R^{24}$ and $R^{25}$ cyclize with the nitrogen they are attached to form a 3- to 7-membered heterocycloalkyl, or substituted or unsubstituted 5- to 6-membered heteroaryl; and z is a whole integer between 0 and 2.

31. The compound of claim 30, wherein $R^1$ is chlorine, $-(C_0$-$C_3)$alkylCN $-(C_1$-$C_3)$haloalkyl, $-(C_1$-$C_3)$alkene, $-(C_1$-$C_3)$alkyne, $-(C_0$-$C_3)NH_2$, $-(C_0$-$C_3)OH$, $-(C_0$-$C_3)SH$, $-(C_0$-$C_3)NH(C_1$-$C_3)$alkyl, $-(C_0$-$C_3)N(C_1$-$C_3)_2$alkyl, $-(C_0$-$C_3)O(C_1$-$C_3)$alkyl, $-(C_0$-$C_3)S(C_1$-$C_3)$alkyl, $-(C_0$-$C_3)NH(C_1$-$C_3)$haloalkyl, $-(C_0$-$C_3)N(C_1$-$C_3)_2$haloalkyl, $-(C_0$-$C_3)O(C_1$-$C_3)$haloalkyl, $-(C_0$-$C_3)S(C_1$-$C_3)$haloalkyl.

32. The compound of claim 31, wherein each $R^{22}$ is independently $-(C_0$-$C_3)OR^{23}$, $-(C_0$-$C_3)C(O)C(O)R^{23}$, $-(C_0$-$C_3)CH(OH)R^{23}$, $-(C_0$-$C_3)CH(OH)C(O)R^{23}$, or $-(C_0$-$C_3)C(O)R^{23}$; wherein $R^{23}$ is substituted or unsubstituted cycloalkyl, substituted or unsubstituted heterocycloalkyl, substituted or unsubstituted aryl, or substituted or unsubstituted heteroaryl.

33. The compound of claim 31, wherein each $R^{22}$ is independently substituted or unsubstituted heterocycloalkyl, substituted or unsubstituted cycloalkyl, substituted or unsubstituted aryl, substituted or unsubstituted heteroaryl, $-OR^{23}$, $-NR^{24}R^{25}$ or $-C(O)NR^{24}R^{25}$; wherein $R^{24}$ and $R^{25}$ are each independently hydrogen, substituted or unsubstituted alkyl, substituted or unsubstituted alkyl-$NR^{29}R^{30}$, substituted or unsubstituted alkyl-C(O)NR$^{29}$R$^{30}$, wherein R$^{29}$ and R$^{30}$ are each independently hydrogen or substituted or unsubstituted alkyl.

34. The compound of claim 30, wherein R$^{12}$, R$^{13}$ and R$^{14}$ are each independently hydrogen, unsubstituted (C$_1$-C$_6$) alkyl, or unsubstituted (C$_1$-C$_6$)haloalkyl.

35. A pharmaceutical composition comprising a therapeutically effective amount of a compound of claim 1.

* * * * *

SEQUENCE LISTING

```
<160> NUMBER OF SEQ ID NOS: 11

<210> SEQ ID NO 1
<211> LENGTH: 12
<212> TYPE: PRT
<213> ORGANISM: Artificial Sequence
<220> FEATURE:
<223> OTHER INFORMATION: Synthetic construct - AB1 substrate peptide
```

<400> SEQUENCE: 1

Glu Ala Ile Tyr Ala Ala Pro Phe Ala Lys Lys Lys
1               5                   10

<210> SEQ ID NO 2
<211> LENGTH: 19
<212> TYPE: DNA
<213> ORGANISM: Artificial Sequence
<220> FEATURE:
<223> OTHER INFORMATION: Forward primer

<400> SEQUENCE: 2
gacaagtggg aaatggagc                                              19

<210> SEQ ID NO 3
<211> LENGTH: 19
<212> TYPE: DNA
<213> ORGANISM: Artificial Sequence
<220> FEATURE:
<223> OTHER INFORMATION: Reverse primer

<400> SEQUENCE: 3
cgcctcgttt ccccagctc                                              19

<210> SEQ ID NO 4
<211> LENGTH: 12
<212> TYPE: DNA
<213> ORGANISM: Artificial Sequence
<220> FEATURE:
<223> OTHER INFORMATION: Synthetic construct - sequence inserted into
      NdeI site of vector pSGX3-TOPO

<400> SEQUENCE: 4
catatgtccc tt                                                     12

<210> SEQ ID NO 5
<211> LENGTH: 29
<212> TYPE: DNA
<213> ORGANISM: Artificial Sequence
<220> FEATURE:
<223> OTHER INFORMATION: Synthetic construct - sequence inserted into
      the BamHI site of vector pSGX3-TOPO

<400> SEQUENCE: 5
aagggcatca tcaccatcac cactgatcc                                   29

<210> SEQ ID NO 6
<211> LENGTH: 26
<212> TYPE: DNA
<213> ORGANISM: Artificial Sequence
<220> FEATURE:
<223> OTHER INFORMATION: Synthetic construct - portion of resulting
      plasmid sequence upstream of ORF

<400> SEQUENCE: 6
aaggaggaga tatacatatg tccctt                                      26

<210> SEQ ID NO 7
<211> LENGTH: 29
<212> TYPE: DNA
<213> ORGANISM: Artificial Sequence
<220> FEATURE:
<223> OTHER INFORMATION: Synthetic construct - portion of resulting
      plasmid sequence downstream of ORF

<400> SEQUENCE: 7
aagggcatca tcaccatcac cactgatcc                                            29

<210> SEQ ID NO 8
<211> LENGTH: 8
<212> TYPE: PRT
<213> ORGANISM: Artificial Sequence
<220> FEATURE:
<223> OTHER INFORMATION: Synthetic construct - amino acids added to
      C-terminus of expressed c-ABl

<400> SEQUENCE: 8

Glu Gly His His His His His His
1               5

<210> SEQ ID NO 9
<211> LENGTH: 39
<212> TYPE: DNA
<213> ORGANISM: Artificial Sequence
<220> FEATURE:
<223> OTHER INFORMATION: Synthetic construct - Mm05582dS4
      oligonucleotide used to modify Abl plasmid

<400> SEQUENCE: 9
ccaccattct acataatcat tgagttcatg acctatggg                                 39

<210> SEQ ID NO 10
<211> LENGTH: 39
<212> TYPE: DNA
<213> ORGANISM: Artificial Sequence
<220> FEATURE:
<223> OTHER INFORMATION: Synthetic construct - Mm05582dA4
      oligonucleotide used to modify Abl plasmid

<400> SEQUENCE: 10
cccataggtc atgaactcaa tgattatgta gaatggtgg                                 39

<210> SEQ ID NO 11
<211> LENGTH: 1130
<212> TYPE: PRT
<213> ORGANISM: Homo sapiens

<400> SEQUENCE: 11

Met Leu Glu Ile Cys Leu Lys Leu Val Gly Cys Lys Ser Lys Lys Gly
1               5                   10                  15

Leu Ser Ser Ser Ser Ser Cys Tyr Leu Glu Glu Ala Leu Gln Arg Pro
            20                  25                  30

Val Ala Ser Asp Phe Glu Pro Gln Gly Leu Ser Glu Ala Ala Arg Trp
        35                  40                  45

Asn Ser Lys Glu Asn Leu Leu Ala Gly Pro Ser Glu Asn Asp Pro Asn
    50                  55                  60

Leu Phe Val Ala Leu Tyr Asp Phe Val Ala Ser Gly Asp Asn Thr Leu
65                  70                  75                  80

Ser Ile Thr Lys Gly Glu Lys Leu Arg Val Leu Gly Tyr Asn His Asn
                85                  90                  95

Gly Glu Trp Cys Glu Ala Gln Thr Lys Asn Gly Gln Gly Trp Val Pro
            100                 105                 110

Ser Asn Tyr Ile Thr Pro Val Asn Ser Leu Glu Lys His Ser Trp Tyr
        115                 120                 125

His Gly Pro Val Ser Arg Asn Ala Ala Glu Tyr Leu Leu Ser Ser Gly
    130                 135                 140

Ile Asn Gly Ser Phe Leu Val Arg Glu Ser Glu Ser Ser Pro Gly Gln
145                 150                 155                 160

-continued

```
Arg Ser Ile Ser Leu Arg Tyr Glu Gly Arg Val Tyr His Tyr Arg Ile
                165                 170                 175

Asn Thr Ala Ser Asp Gly Lys Leu Tyr Val Ser Ser Glu Ser Arg Phe
            180                 185                 190

Asn Thr Leu Ala Glu Leu Val His His Ser Thr Val Ala Asp Gly
            195                 200                 205

Leu Ile Thr Thr Leu His Tyr Pro Ala Pro Lys Arg Asn Lys Pro Thr
            210                 215                 220

Val Tyr Gly Val Ser Pro Asn Tyr Asp Lys Trp Glu Met Glu Arg Thr
225                 230                 235                 240

Asp Ile Thr Met Lys His Lys Leu Gly Gly Gln Tyr Gly Glu Val
                245                 250                 255

Tyr Glu Gly Val Trp Lys Lys Tyr Ser Leu Thr Val Ala Val Lys Thr
                260                 265                 270

Leu Lys Glu Asp Thr Met Glu Val Glu Glu Phe Leu Lys Glu Ala Ala
            275                 280                 285

Val Met Lys Glu Ile Lys His Pro Asn Leu Val Gln Leu Leu Gly Val
            290                 295                 300

Cys Thr Arg Glu Pro Pro Phe Tyr Ile Ile Thr Glu Phe Met Thr Tyr
305                 310                 315                 320

Gly Asn Leu Leu Asp Tyr Leu Arg Glu Cys Asn Arg Gln Glu Val Asn
                325                 330                 335

Ala Val Val Leu Leu Tyr Met Ala Thr Gln Ile Ser Ser Ala Met Glu
                340                 345                 350

Tyr Leu Glu Lys Lys Asn Phe Ile His Arg Asp Leu Ala Ala Arg Asn
            355                 360                 365

Cys Leu Val Gly Glu Asn His Leu Val Lys Val Ala Asp Phe Gly Leu
370                 375                 380

Ser Arg Leu Met Thr Gly Asp Thr Tyr Thr Ala His Ala Gly Ala Lys
385                 390                 395                 400

Phe Pro Ile Lys Trp Thr Ala Pro Glu Ser Leu Ala Tyr Asn Lys Phe
            405                 410                 415

Ser Ile Lys Ser Asp Val Trp Ala Phe Gly Val Leu Leu Trp Glu Ile
            420                 425                 430

Ala Thr Tyr Gly Met Ser Pro Tyr Pro Gly Ile Asp Leu Ser Gln Val
            435                 440                 445

Tyr Glu Leu Leu Glu Lys Asp Tyr Arg Met Glu Arg Pro Glu Gly Cys
450                 455                 460

Pro Glu Lys Val Tyr Glu Leu Met Arg Ala Cys Trp Gln Trp Asn Pro
465                 470                 475                 480

Ser Asp Arg Pro Ser Phe Ala Glu Ile His Gln Ala Phe Glu Thr Met
            485                 490                 495

Phe Gln Glu Ser Ser Ile Ser Asp Glu Val Glu Lys Glu Leu Gly Lys
            500                 505                 510

Gln Gly Val Arg Gly Ala Val Ser Thr Leu Leu Gln Ala Pro Glu Leu
            515                 520                 525

Pro Thr Lys Thr Arg Thr Ser Arg Arg Ala Ala Glu His Arg Asp Thr
            530                 535                 540

Thr Asp Val Pro Glu Met Pro His Ser Lys Gly Gln Gly Glu Ser Asp
545                 550                 555                 560

Pro Leu Asp His Glu Pro Ala Val Ser Pro Leu Leu Pro Arg Lys Glu
                565                 570                 575

Arg Gly Pro Pro Glu Gly Gly Leu Asn Glu Asp Glu Arg Leu Leu Pro
            580                 585                 590
```

```
Lys Asp Lys Lys Thr Asn Leu Phe Ser Ala Leu Ile Lys Lys Lys
            595                 600                 605

Lys Thr Ala Pro Thr Pro Lys Arg Ser Ser Phe Arg Glu Met
        610                 615                 620

Asp Gly Gln Pro Glu Arg Arg Gly Ala Gly Glu Glu Gly Arg Asp
625                 630                 635                 640

Ile Ser Asn Gly Ala Leu Ala Phe Thr Pro Leu Asp Thr Ala Asp Pro
                645                 650                 655

Ala Lys Ser Pro Lys Pro Ser Asn Gly Ala Gly Val Pro Asn Gly Ala
                660                 665                 670

Leu Arg Glu Ser Gly Gly Ser Gly Phe Arg Ser Pro His Leu Trp Lys
        675                 680                 685

Lys Ser Ser Thr Leu Thr Ser Ser Arg Leu Ala Thr Gly Glu Glu Glu
        690                 695                 700

Gly Gly Gly Ser Ser Lys Arg Phe Leu Arg Ser Cys Ser Ala Ser
705                 710                 715                 720

Cys Val Pro His Gly Ala Lys Asp Thr Glu Trp Arg Ser Val Thr Leu
                725                 730                 735

Pro Arg Asp Leu Gln Ser Thr Gly Arg Gln Phe Asp Ser Ser Thr Phe
                740                 745                 750

Gly Gly His Lys Ser Glu Lys Pro Ala Leu Pro Arg Lys Arg Ala Gly
        755                 760                 765

Glu Asn Arg Ser Asp Gln Val Thr Arg Gly Thr Val Thr Pro Pro Pro
770                 775                 780

Arg Leu Val Lys Lys Asn Glu Glu Ala Ala Asp Glu Val Phe Lys Asp
785                 790                 795                 800

Ile Met Glu Ser Ser Pro Gly Ser Ser Pro Pro Asn Leu Thr Pro Lys
                805                 810                 815

Pro Leu Arg Arg Gln Val Thr Val Ala Pro Ala Ser Gly Leu Pro His
                820                 825                 830

Lys Glu Glu Ala Glu Lys Gly Ser Ala Leu Gly Thr Pro Ala Ala Ala
        835                 840                 845

Glu Pro Val Thr Pro Thr Ser Lys Ala Gly Ser Gly Ala Pro Gly Gly
        850                 855                 860

Thr Ser Lys Gly Pro Ala Glu Glu Ser Arg Val Arg Arg His Lys His
865                 870                 875                 880

Ser Ser Glu Ser Pro Gly Arg Asp Lys Gly Lys Leu Ser Arg Leu Lys
                885                 890                 895

Pro Ala Pro Pro Pro Pro Ala Ala Ser Ala Gly Lys Ala Gly Gly
                900                 905                 910

Lys Pro Ser Gln Ser Pro Ser Gln Glu Ala Ala Gly Glu Ala Val Leu
        915                 920                 925

Gly Ala Lys Thr Lys Ala Thr Ser Leu Val Asp Ala Val Asn Ser Asp
        930                 935                 940

Ala Ala Lys Pro Ser Gln Pro Gly Glu Gly Leu Lys Lys Pro Val Leu
945                 950                 955                 960

Pro Ala Thr Pro Lys Pro Gln Ser Ala Lys Pro Ser Gly Thr Pro Ile
                965                 970                 975

Ser Pro Ala Pro Val Pro Ser Thr Leu Pro Ser Ala Ser Ala Leu
                980                 985                 990

Ala Gly Asp Gln Pro Ser Ser Thr Ala Phe Ile Pro Leu Ile Ser Thr
        995                 1000                1005

Arg Val Ser Leu Arg Lys Thr Arg Gln Pro Pro Glu Arg Ile Ala
```

-continued

```
            1010                1015                1020
Ser Gly Ala Ile Thr Lys Gly Val Val Leu Asp Ser Thr Glu Ala
            1025                1030                1035

Leu Cys Leu Ala Ile Ser Arg Asn Ser Glu Gln Met Ala Ser His
            1040                1045                1050

Ser Ala Val Leu Glu Ala Gly Lys Asn Leu Tyr Thr Phe Cys Val
            1055                1060                1065

Ser Tyr Val Asp Ser Ile Gln Gln Met Arg Asn Lys Phe Ala Phe
            1070                1075                1080

Arg Glu Ala Ile Asn Lys Leu Glu Asn Asn Leu Arg Glu Leu Gln
            1085                1090                1095

Ile Cys Pro Ala Thr Ala Gly Ser Gly Pro Ala Ala Thr Gln Asp
            1100                1105                1110

Phe Ser Lys Leu Leu Ser Ser Val Lys Glu Ile Ser Asp Ile Val
            1115                1120                1125

Gln Arg
            1130
```